United States Patent
Ding et al.

(10) Patent No.: US 7,300,946 B2
(45) Date of Patent: Nov. 27, 2007

(54) N-(SUBSTITUTED ARYLMETHYL)-4-(DISUBSTITUTED METHYL) PIPERIDINES AND PYRIDINES

(75) Inventors: Ping Ding, Lawrenceville, NJ (US); Robert N. Henrie, II, Pennington, NJ (US); Daniel H. Cohen, Princeton, NJ (US); John W. Lyga, Basking Ridge, NJ (US); David S. Rosen, Kendall Park, NJ (US); George Theodoridis, Princeton, NJ (US); Qun Zhang, Princeton, NJ (US); Walter H. Yeager, Yardley, PA (US); Stephen F. Donovan, Revere, PA (US); Steven Shunxiang Zhang, Plainsboro, NJ (US); Inna Shulman, Langhorne, PA (US); Seong Jae Yu, Pennington, NJ (US); Guozhi Wang, Freshmeadow, NJ (US); Y. Larry Zhang, Kendall Park, NJ (US); Ariamala Gopalsamy, Mahwah, NJ (US); Dennis L. Warkentin, East Windsor, NJ (US); Paul E. Rensner, Yardley, PA (US); Ian R. Silverman, Morrestown, NJ (US); Thomas G. Cullen, Milltown, NJ (US)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/538,998

(22) PCT Filed: Dec. 8, 2003

(86) PCT No.: PCT/US03/38878

§ 371 (c)(1),
(2), (4) Date: Dec. 16, 2005

(87) PCT Pub. No.: WO2004/060371

PCT Pub. Date: Jul. 22, 2004

(65) Prior Publication Data
US 2006/0135504 A1    Jun. 22, 2006

Related U.S. Application Data

(60) Provisional application No. 60/495,059, filed on Aug. 14, 2003, provisional application No. 60/434,718, filed on Dec. 18, 2002.

(51) Int. Cl.
| | |
|---|---|
| A61K 31/44 | (2006.01) |
| A61K 31/445 | (2006.01) |
| A61K 31/4422 | (2006.01) |
| C07D 211/06 | (2006.01) |
| C07D 211/08 | (2006.01) |
| C07D 211/70 | (2006.01) |
| C07D 211/82 | (2006.01) |

(52) U.S. Cl. ............ 514/317; 514/331; 546/229; 546/237

(58) Field of Classification Search ............ 514/318, 514/345, 317, 331; 546/194, 216, 229, 237; 548/250
See application file for complete search history.

(56) References Cited

U.S. PATENT DOCUMENTS

| | | | |
|---|---|---|---|
| 3,100,775 A | * | 8/1963 | Rorig ................. 546/342 |
| 5,639,763 A | | 6/1997 | Silverman et al. |
| 5,795,901 A | | 8/1998 | Szczepanski |
| 5,939,438 A | | 8/1999 | Yeager et al. |
| 6,017,931 A | | 1/2000 | Silverman et al. |

FOREIGN PATENT DOCUMENTS

| | | |
|---|---|---|
| WO | 94/27966 A1 | 12/1994 |
| WO | 01/17964 A1 | 3/2001 |
| WO | 02/068392 A1 | 9/2002 |

OTHER PUBLICATIONS

Copy of Search Report for Taiwanese Patent Application No. 092135801, completed on Jan. 15, 2007, Taiwan Patent Office.

* cited by examiner

*Primary Examiner*—Kamal A. Saeed
*Assistant Examiner*—Yong Chu
(74) *Attorney, Agent, or Firm*—Sterne, Kessler, Goldstein & Fox, PLLC

(57) ABSTRACT

It has now been found that certain novel N-(substituted aryl)-4(disubstituted methyl)piperidine and pyridine derivatives have provided unexpected insecticidal activity. These compounds are represented by formula (I): wherein m, n, q, r, and s are independently selected from 0 or 1; and p is 0, 1, 2, or 3; A is C or CH; and B, D, E, R, $R^1$, $R^2$, $R^3$, $R^4$, $R^5$, $R^6$, $R^7$ and $R^8$ are fully described herein. In addition, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present

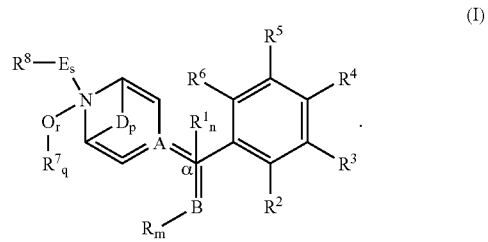

(I)

30 Claims, No Drawings

N-(SUBSTITUTED ARYLMETHYL)-4-(DISUBSTITUTED METHYL) PIPERIDINES AND PYRIDINES

This application is a National Stage of International Application No. PCT/US03/38878, filed Dec. 8, 2003, which claims the benefit of priority of U.S. Provisional Appl. No. 60/434,718, filed Dec. 18, 2002 and U.S. Provisional Appl. No. 60/495,059, filed Aug. 14, 2003.

FIELD OF THE INVENTION

The present invention generally relates to insecticidal compounds and their use in controlling insects. In particular, it pertains to insecticidal N-(substituted aryl)-4-(disubstituted methyl)piperidines and pyridine derivatives, N-oxides, and agriculturally acceptable salts thereof, compositions of these insecticides, and methods for their use in controlling insects.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Thus, there is a continuing demand for new insecticides that are safer, more effective, and less costly. Insecticides are useful for controlling insects which may otherwise cause significant damage to crops such as wheat, corn, soybeans, potatoes, and cotton to name a few. For crop protection, insecticides are desired which can control the insects without damaging the crops, and which have no deleterious effects to mammals and other living organisms.

A number of patents disclose a variety of insecticidally active substituted piperidine and piperazine derivatives. For example, as set forth in U.S. Pat. No. 5,569,664, compounds of the following structure are reported to be insecticidally active:

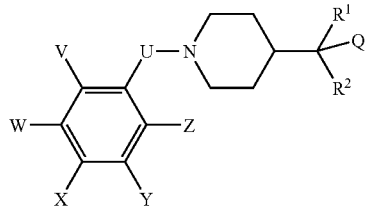

where U is selected from —(CH$_2$)$_n$— and ethylidine, where n is 1, 2, or 3; Q is selected from hydrogen, hydroxy, sulfhydryl, and fluorine; V is selected from hydrogen, halogen, alkyl, haloalkyl, alkoxy, alkylthio, alkylsulfinyl, alkylsilyloxy, dialkylamino, cyano, nitro, hydroxy, and phenyl; W is selected from hydrogen, halogen, alkyl, haloalkyl, alkoxy, nitro, amino, phenoxy, and phenylalkoxy; X is selected from hydrogen, hydroxy, halogen, alkyl, alkoxyalkyl, alkoxy, cycloalkylalkoxy, haloalkoxy, alkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkoxycarbonylamino, alkylcarbonyl, alkoxycarbonyl, alkylaminocarbonyl, aminocarbonyloxy, phenyl, phenylalkoxy, phenoxy, and phenoxyalkyl; Y and Z are independently selected from hydrogen and alkoxy; R$^1$ and R$^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and the corresponding N-oxides and agriculturally acceptable salts.

As set forth in U.S. Pat. No. 5,639,763 compounds of the following structure are reported to be insecticidally active:

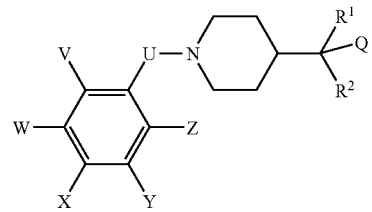

where U is selected from —(CH$_2$)$_n$— and ethylidine, where n is 1, 2, or 3; Q is selected from hydrogen, hydroxy, sulfhydryl, and fluorine; V is selected from hydrogen, halogen, alkyl, haloalkyl, alkoxy, alkylthio, alkylsulfinyl, alkylsilyloxy, dialkylamino, cyano, nitro, hydroxy, and phenyl; Y and Z are independently selected from hydrogen and alkoxy; W and X taken together is —OCH$_2$CH$_2$O—, —CH$_2$C(CH$_3$)$_2$O—, —OC(CH$_3$)$_2$O—, or —N═C(C$_2$H$_5$)O—; R$^1$ and R$^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and the corresponding N-oxides and agriculturally acceptable salts.

As set forth in U.S. Pat. No. 5,795,901 compounds of the following structure are reported to be insecticidally active:

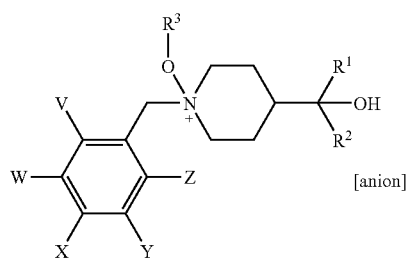

where V, W, Y, and Z are hydrogen; X is alkoxy, cycloalkoxy, alkoxycarbonyl, alkoxycarbonylamino, or a five- or six-membered heteroaryl or heteroaryloxy, each heteroaryl optionally substituted with halogen, cyano, alkyl, haloalkyl, alkoxy, haloalkoxy, alkoxyalkyl, or haloalkoxyalkyl; R$^1$ and R$^2$ are independently selected from haloalkyl, phenyl substituted with halogen, halothio, haloalkyl, or haloalkoxy; or a five- or six-membered heteroaryl substituted with halogen or alkyl; R$^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, arylcarbonyl, sulfonato, or sulfonatoalkyl, and may bear a negative charge resulting in an inner salt, and a separate anion is chloride, bromide, iodide, or a phenyl, or alkyl sulfate or sulfonate.

As set forth in U.S. Pat. No. 5,939,438 compounds of the following structure are reported to be insecticidally active:

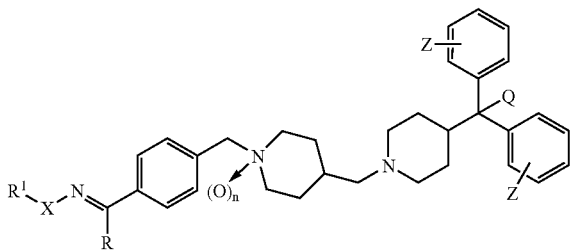

where R is hydrogen, halogen, alkyl, alkoxy, or dialkylamino; $R^1$ is hydrogen, alkyl, haloalkyl, alkoxyalkyl, alkylcarbonyl, or alkylaminocarbonyl; Q is fluoro or hydroxy; X is oxygen or $NR^2$; Z is halogen, haloalkyl, haloalkoxy, pentahalothio, haloalkylthio, haloalkylsulfinyl, haloalkylsulfonyl, or —$OCF_2O$— attached to two adjacent carbon atoms of the phenyl ring; n is 0 or 1; and, when X is $NR^2$, $R^2$ is hydrogen, alkyl, alkylcarbonyl, alkoxycarbonyl, or $R^1$ and $R^2$ taken together may be —$C_mH_{2m}$—, or —$C_2H_4OC_2H_4$—, where m is 3–9; and their agriculturally acceptable salts.

As set forth in U.S. Pat. No. 6,017,931 compounds of the following structure are reported to be insecticidally active:

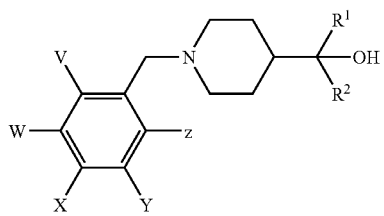

where V, W, and Z are hydrogen; X is selected from alkoxy, haloalkoxy, alkoxyalkyl, cycloalkylalkoxyl, halocycloalkylalkoxy, alkoxycarbonyl, haloalkoxycarbonyl, cycloalkylalkoxylcarbonyl, halocycloalkylalkoxylcarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, and phenoxycarbonyl, each cycloalkyl moiety or phenyl ring optionally substituted with halogen; Y is selected from hydrogen or halogen; $R^1$ and $R^2$ are independently selected from phenyl or pyridyl, each substituted with haloalkyl, haloalkoxy, or alkylthio, and the corresponding N-oxides and agriculturally acceptable salts.

As set forth in U.S. Pat. No. 6,030,987 compounds of the following structure are reported to be insecticidally active:

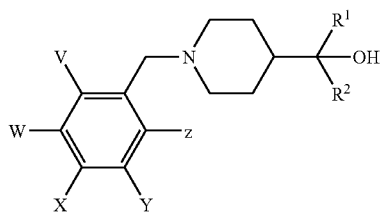

where V, W, Y and Z are hydrogen; X is a five- or six-membered heterocycle optionally substituted with halogen, alkyl, alkoxy, alkoxyalkyl, cyano, aminocarbonyl, haloalkyl, haloalkoxy, or haloalkoxyalkyl; and the heterocycle is optionally connected to the phenyl ring through a —O—, —S—, —$(CH_2)_p$—, —C(O)—, or —$O(CR^3R^4)_q$— linkage; $R^1$ and $R^2$ are independently selected from phenyl or pyridyl, each substituted with haloalkyl, or haloalkoxy; $R^3$ and $R^4$ are independently selected from hydrogen and methyl; n and p are independently 1, 2, or 3; and q is 1 or 2, and the corresponding N-oxides and agriculturally acceptable salts.

As set forth in U.S. Pat. No. 6,184,234 compounds of the following structure are reported to be insecticidally active:

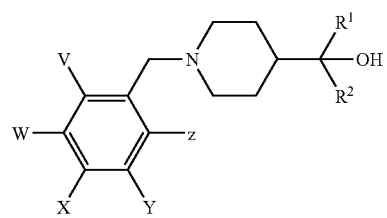

where V, W, Y and Z are hydrogen; X is a five- or six-membered heterocycle optionally substituted with bromine, chlorine, fluorine, alkyl, alkoxy, alkoxyalkyl, cyano, aminocarbonyl, haloalkyl, haloalkoxy, or haloalkoxyalkyl; and the heterocycle is optionally connected to the phenyl ring through a —O—, —S—, —$(CH_2)_p$—, —C(O)—, or —$O(CR^3R^4)_q$— linkage; $R^1$ and $R^2$ are independently selected from i) phenyl or pyridyl, each substituted with pentahalothio, haloalkylthio, haloalkylsulfinyl, or haloalkylsulfonyl; ii) phenyl substituted with —$OC(M)_2O$—, where M is bromine, chlorine, or fluorine to provide a dihalobenzodioxolyl fused ring; or iii) pyridyl substituted with —OC$(M)_2$—, to provide a dihalodioxoleneopyridyl fused ring; $R^3$ and $R^4$ are independently selected from hydrogen and methyl; n and p are independently 1, 2, or 3; and q is 1 or 2, and the corresponding N-oxides and agriculturally acceptable salts.

As set forth in United States Statutory Invention Registration H1,838 compounds of the following structure are reported to be insecticidally active:

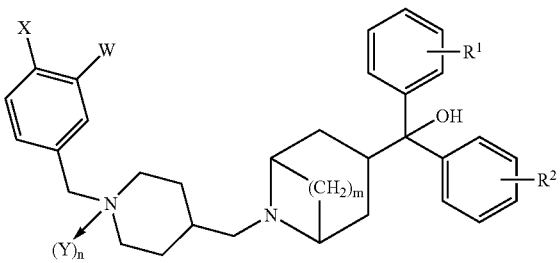

where m is 2 or 3; n is 0 or 1; X is hydrogen, alkoxy, cycloalkylalkoxy, haloalkoxyimino, or a five- or six-membered heteroaryl or heteroaryloxy in which one or more hetero atoms may be optionally substituted with alkyl; $R^1$ and $R^2$ are independently selected from hydrogen, haloalkyl, halothio, or haloalkoxy; and when n is 1, Y represents (a) an N-oxide of the ring nitrogen; or (b) an agriculturally acceptable anionic salt of the ring nitrogen; or (c) forms an $OR^3$ linkage in which R³ is selected from hydrogen, alkyl, alkoxycarbonylalkyl, hydroxycarbonylethyl in association with an agriculturally acceptable anion resulting in an ionic salt, or R³ is an oxycarbonylalkyl group bearing a negative charge resulting in an inner salt.

As set forth in United States Statutory Invention Registration H1,996 photostable, agriculturally acceptable acid salts of an organic or inorganic acid of the following structure are reported to be insecticidally active:

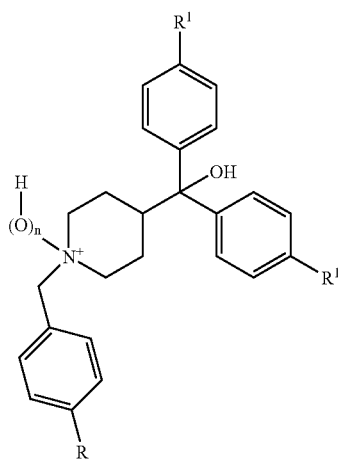

where R is alkoxycarbonyl, alkoxycarbonylamino, cycloalkylalkoxy, 2-alkyl-2H-tetrazol-5-yl, or 2-haloalkyl-2H-tetrazol-5-yl; R¹ is trihaloalkyl, or trihaloalkoxy; n is 0, or 1; and said salt is at least 2.5 times more photostable than its non-ionic parent and is derived from hydrochloric acid, hydrobromic acid, boric acid, phosphoric acid, maleic acid, fumaric acid, phthalic acid, D-glucuronic acid; the sulfonic acid R²SO₃H where R² is alkyl, haloalkyl, hydroxyalkyl, D-10-camphoryl, or phenyl optionally substituted with alkyl or halogen; the carboxylic acid R³CO₂H where R³ is hydrogen, alkyl, trihaloalkyl, carboxyl, phenyl optionally substituted with alkyl or halogen, or pyridyl; the boronic acid R⁴B(OH)₂ where R⁴ is alkyl or phenyl optionally substituted with alkyl or halogen; the phosphonic acid R⁵PO₃H₂ where R⁵ is alkyl, haloalkenyl, or phenyl optionally substituted with alkyl or halogen; the sulfuric acid R⁶OSO₃H where R⁶ is hydrogen or alkyl; or the alkanoic acid X—(CH₂)$_q$CO₂H where q is 0 to 11, X is halogen, trihaloalkyl, haloalkenyl, cyano, aminocarbonyl, or CO₂R⁷ where R⁷ is hydrogen or alkyl.

As set forth in United States Statutory Invention Registration H2,007 compounds of the following structures are reported to be insecticidally active:

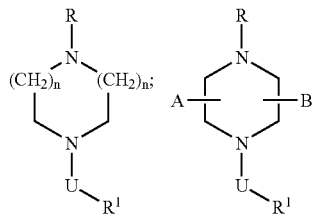

where A and B are independently selected from lower alkyl; U is selected from lower alkylidene, lower alkenylidene, and CH-Z, where Z is selected from hydrogen, lower alkyl, lower cycloalkyl, or phenyl; R is —CHR³R⁴ where R³ and R⁴ are are independently selected from phenyl, optionally substituted with halogen, lower alkyl, lower haloalkyl, lower alkoxy, lower haloalkoxy, lower alkenyl, or phenyl; R¹ is phenyl, naphthyl, tetrazolylphenyl, phenylcyclopropyl, phenoxyphenyl, benzyloxyphenyl, pyridylphenyl, pyridyloxyphenyl, or thiadiazolyloxyphenyl, each optionally substituted with halogen, cyano, hydroxy, lower alkyl, lower haloalkyl, lower alkoxy, amino, lower dialkylamino, nitro, lower haloalkylsulfonyloxy, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic R¹ groups; m is 2 or 3; and n is 1, 2, or 3.

As set forth in unexamined Japanese Patent Application 2002-220372 compounds of the following structures are reported to be insecticidally active:

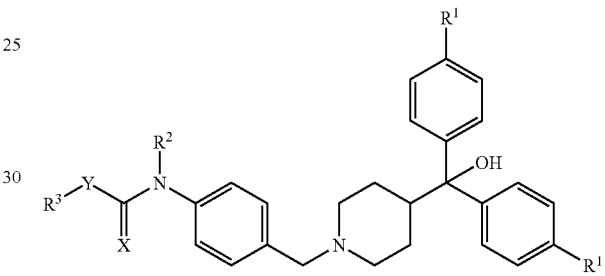

where R¹ and R² are independently selected from hydrogen, halogen, lower alkyl, lower haloalkyl, lower alkoxy, lower haloalkoxy, or lower alkylsulfonyloxy; R² is selected from hydrogen, lower alkyl, lower alkenyl, lower alkoxyalkyl, or lower alkylcarbonyl; X and Y are independently oxygen or sulfur; R³ is selected from lower alkenyl, or lower alkynyl, which are optionally substituted with hydroxy, halogen, lower alkoxy, lower haloalkoxy, lower alkylthio, lower alkylsulfinyl, lower alkylsulfonyl, lower cycloalkyl, lower alkoxyalkoxy, amino, lower alkylamino, lower dialkylamino, lower alkoxycarbonyl, nitro, cyano, trimethylsilyl, phenyl, or lower cycloalkenyl; and the corresponding N-oxides and salts.

As set forth in PCT Publication WO 02/068392A1 compounds of the following structures are reported to be insecticidally active:

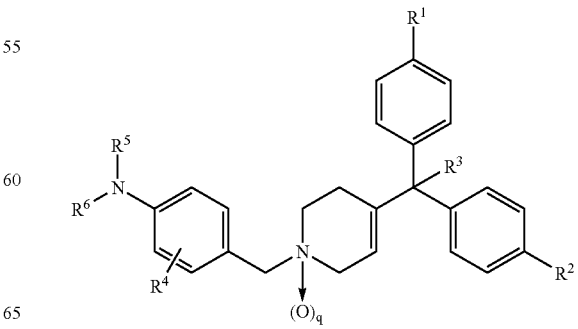

where $R^1$ and $R^2$ are independently selected from halogen, $C_1$–$C_6$alkyl, halo$C_1$–$C_6$alkyl, $C_1$–$C_6$alkoxy, halo$C_1$–$C_6$alkoxy, —S(=O)$_p$—$R^9$, or SF$_5$; $R^3$ is hydrogen, hydroxy, $C_1$–$C_6$alkoxy, or —OC(=O)—$C_1$–$C_6$alkyl; $R^4$ is hydrogen, halogen, $C_1$–$C_6$alkyl, halo$C_1$–$C_6$alkyl, $C_1$–$C_6$alkoxy, halo$C_1$–$C_6$alkoxy, or —S(=O)$_p$—$R^9$, or —SCN; $R^5$ and $R^6$ are independently selected from $C_1$–$C_{12}$alkyl, halo$C_1$–$C_{12}$alkyl, $C_2$–$C_{12}$alkenyl, halo$C_2$–$C_{12}$alkenyl, $C_2$–$C_{12}$alkynyl, halo$C_2$–$C_{12}$alkynyl, $C_3$–$C_8$cycloalkyl, —C(=O)—OR$^7$, —C(=S)—OR$^8$, —C(=Y)-ZR$^8$, —S(=O)$_p$—R$^9$, aryl, aryl$C_1$–$C_6$alkyl, heterocycle, heterocycle$C_1$–$C_6$alkyl, each substituted in the ring from one to five times independently of one another by halogen, hydroxy, cyano, nitro, $C_1$–$C_6$alkyl, halo$C_1$–$C_6$alkyl, $C_1$–$C_6$alkoxy, halo$C_1$–$C_6$alkoxy; or in common together with the nitrogen atom to which they are attached to form a heterocyclic ring which is substituted or unsubstituted; Y is oxygen or sulfur; X is a bond, —NR$^{10}$—, or sulfur; $R^7$ is $C_1$–$C_6$alkoxy-$C_1$–$C_6$alkyl, $C_1$–$C_6$alkylthio-$C_1$–$C_6$alkyl, $C_1$–$C_6$alkylamino-$C_1$–$C_6$alkyl, $C_3$–$C_6$alkynyl, $C_1$–$C_6$alkyl-S(=O)$_p$—$C_1$–$C_6$alkyl, $C_3$–$C_8$cycloalkyl, aryl, aryl-$C_1$–$C_6$alkyl, heterocyclyl, or heterocyclyl-$C_1$–$C_6$alkyl each substituted in the ring from one to five times independently of one another by halogen, cyano, nitro, $C_1$–$C_6$alkyl, halo$C_1$–$C_6$alkyl, $C_1$–$C_6$alkoxy, or halo$C_1$–$C_6$alkoxy; $R^8$ is $C_1$–$C_6$alkyl, halo$C_1$–$C_6$alkyl, $C_1$–$C_6$alkoxy-$C_1$–$C_6$alkyl, $C_1$–$C_6$alkylthio-$C_1$–$C_6$alkyl, $C_2$–$C_6$alkenyl, $C_3$–$C_6$alkynyl, $C_1$–$C_6$alkyl-S(=O)$_p$—$C_1$–$C_6$alkyl, $C_3$–$C_8$cycloalkyl, aryl, aryl-$C_1$–$C_6$alkyl, heterocyclyl, or heterocyclyl-$C_1$–$C_6$alkyl, or is $C_3$–$C_8$cycloalkyl, aryl, aryl-$C_1$–$C_6$alkyl, heterocyclyl, or heterocyclyl-$C_1$–$C_6$alkyl each substituted in the ring from one to five times independently of one another by halogen, cyano, nitro, $C_1$–$C_6$alkyl, halo$C_1$–$C_6$alkyl, $C_1$–$C_6$alkoxy, or halo$C_1$–$C_6$alkoxy; $R^9$ is $C_1$–$C_6$alkyl, $C_3$–$C_8$cycloalkyl, halo$C_1$–$C_6$alkyl, or benzyl; $R^{10}$ is hydrogen, $C_1$–$C_6$alkyl, $C_3$–$C_8$cycloalkyl, halo$C_1$–$C_6$alkyl, or benzyl; p is 0, 1, or 2; q is 0 or 1; and, where appropriate, E/Z isomers, E/Z isomer mixtures and/or toutomers, each in free form or in salt form.

As set forth in PCT Publication WO 200020409A1 compounds of the following structures are reported to be insecticidally active:

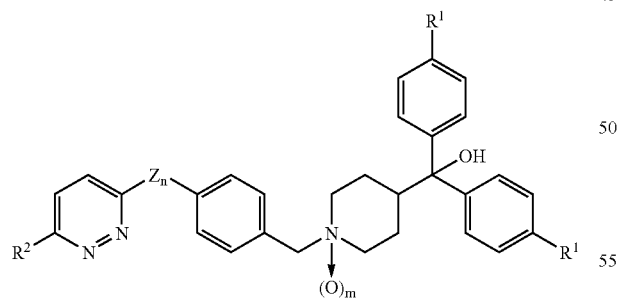

where $R^1$ is halo, $C_1$–$C_4$alkyl, $C_1$–$C_4$alkoxy, $C_1$–$C_4$haloalkyl, $C_1$–$C_4$haloalkoxy; $R^2$ is hydrogen, hydroxyl, halo, $C_1$–$C_4$alkyl, $C_1$–$C_4$alkoxy, $C_1$–$C_4$alkoxycarbonyl, $C_1$–$C_4$alkylthio, $C_1$–$C_4$alkylsulfonyl, optionally substituted phenyl or carbarnoyl; Z is 0 or S(O)$_p$, p is 0 or 2; and m and n are 0 or 1.

As set forth in PCT Publication WO 03/022808A1 compounds of the following structures are reported to be pesticidally active:

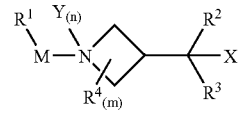

where $R^1$ represents aryl or heteroaryl that is optionally identically or differently substituted once or several times; $R^2$ and $R^3$ are identical of different and represent arylor heteroaryl that is optionally identically or differently substituted once or several times, whereby both groups can also be bridged by a common substituent; M is optionally substituted (CH$_2$)$_l$, where l is 1, 2, or 3, CO, or —HN—C(O); X represents H, OH, halogen, OR4 or CN; Y represents (O), H, OH, OR$^4$, R$^4$; (in the last four groups, in which nitrogen has a positive charge, in combination with a corresponding anion); R$^4$ is identical or different and represents (C$_1$–C$_4$) alkyl, (C$_1$–C$_4$)alkanoyl, (C$_1$–C$_4$)haloalkyl; m is 0, 1, 2, 3; and n 0 or 1.

As set forth in published Japanese Patent Application JP 62,145,018, the following compound is disclosed as being an antiallergy pharmaceutical agent:

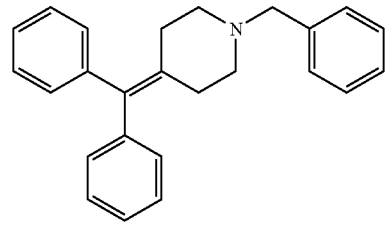

There is no disclosure or suggestion in any of the citations set forth above of the piperidine or pyridine derivatives of the present invention.

SUMMARY OF THE INVENTION

In accordance with the present invention, it has now been found that certain N-(substituted arylmethyl)-4-(disubstituted methyl)piperidine and pyridine derivatives, (hereinafter termed "compounds of formula"), N-oxides, and agriculturally acceptable salts thereof are surprisingly active when used in the insecticidal compositions and methods of this invention. The compounds of formula I are represented by the following general formula I:

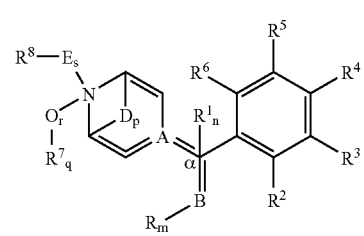

wherein;

m, n, q, r, and s are independently selected from 0 or 1; and p is 0, 1, 2, or 3;

A is selected from C and CH, forming a six-membered azine ring selected from piperidine, 1,4-dihydropyridine, and 1,2,5,6-tetrahydropyridine;

$R^2$, $R^3$, $R^4$, $R^5$, and $R^6$ are independently selected from hydrogen, halogen, alkyl, haloalkyl, hydroxyl, alkoxy, haloalkoxy, pentahalothio, alkylthio, cyano, nitro, alkylcarbonyl, alkoxycarbonyl, aryl, or aryloxy, provided that at least one of $R^2$, $R^3$, $R^4$, $R^5$, and $R^6$ are other than hydrogen; and, wherein either of $R^2$ and $R^3$, or $R^3$ and $R^4$ are taken together with —OCF$_2$O—, —OCF$_2$CF$_2$—, —CF$_2$CF$_2$O—, or —CH=CHCH=CH—, forming a benzo-fused ring;

And when,
(a) m and n are 0;
a double bond between methyl carbon (a) and the 4-position of the six-membered azine ring is formed,

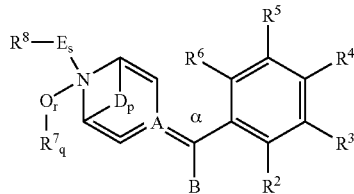

where
B is phenyl substituted with $R^9$, $R^{10}$, $R^{11}$, $R^{12}$, and $R^{13}$,

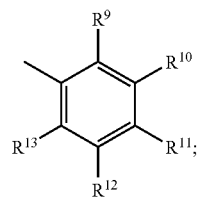

where
$R^9$, $R^{10}$, $R^{11}$, $R^{12}$, and $R^{13}$ are independently selected from hydrogen, halogen, alkyl, haloalkyl, hydroxyl, alkoxy, haloalkoxy, mercapto, and alkylthio, cyano, alkylcarbonyl, alkoxycarbonyl, or aryloxy; and, wherein either of $R^9$ and $R^{10}$, or $R^{10}$ and $R^{11}$ may be taken together with —OCF$_2$O—, —OCF$_2$CF$_2$—, or —CF$_2$CF$_2$O—, forming a benzo-fused ring, providing that at least one of $R^9$, $R^{10}$, $R^{11}$, $R^{12}$, and $R^{13}$ is other than hydrogen;
and when
(b) m is 1, and n is 0;
a double bond between methyl carbon (a) and the 4-position of the six-membered azine ring is formed,

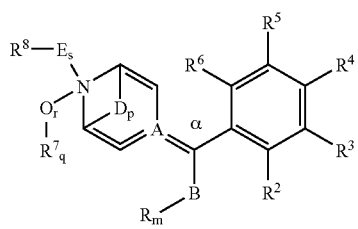

where
B is a bridging group from methyl carbon (a) to R;
where
B is selected from O, S, *CH$_2$O, *OCH$_2$, OC(=O)O, *OC(=O)NR$^{15}$, *NR$^{15}$C(=O)O, *OC(=S)NR$^{15}$, *NR$^{15}$C(=S)O, *OCH$_2$C(=O)NR$^{15}$, *NR$^{15}$C(=O)CH$_2$O, *CH$_2$OC(=O)NR$^{15}$, *NR$^{15}$C(=O)OCH$_2$, *NR$^{15}$CH$_2$, *CH$_2$NR$^{15}$, *NR$^{15}$C(=O), *C(=O)NR$^{15}$, *NR$^{15}$SO$_2$, *SO$_2$NR$^{15}$, *NR$^{15}$NHSO$_2$, *SO$_2$NHNR$^{15}$, *OC(=O)NR$^{15}$SO$_2$, *SO$_2$NR$^{15}$C(=O)O, *OC(=O)NR$^{15}$CHR$^{16}$, *CHR$^{16}$NR$^{15}$C(=O)O, *NR$^{15}$C(=O)NR$^{16}$; 1,4-dioxycyclohexyl, or 4-oxypiperidin-1-yl, where the asterisk denotes attachment to the methyl carbon (a);
where
$R^{15}$ and $R^{16}$ are independently selected from hydrogen, alkyl, alkylaminocarbonyl, and arylcarbonyl wherein the aryl is optionally substituted with halogen, alkyl, alkoxy, haloalkyl, haloalkoxy, or nitro;
where
R is alkyl, cycloalkyl, alkenyl, or alkoxycarbonyl;
or
R is phenyl substituted with $R^{17}$, $R^{18}$, $R^{19}$, $R^{20}$, and $R^{21}$;

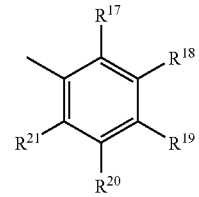

or,
R is pyrid-2-yl substituted with $R^{18}$, $R^{19}$, $R^{20}$, and $R^{21}$,

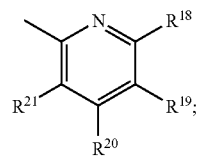

or
pyrid-3-yl substituted with $R^{17}$, $R^{19}$, $R^{20}$, and $R^{21}$,

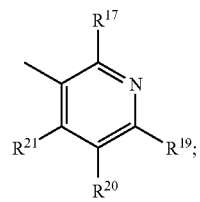

or
pyrid4-yl substituted with $R^{17}$, $R^{18}$, $R^{20}$, and $R^{21}$,

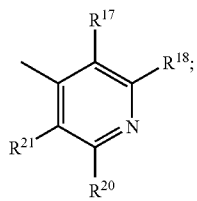

or
pyridazin-3-yl substituted with $R^{19}$, $R^{20}$ and $R^{21}$,

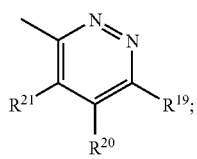

where
$R^{17}$, $R^{18}$, $R^{19}$, $R^{20}$, and $R^{21}$ are independently selected from hydrogen, halogen, alkyl, haloalkyl, alkoxy, haloalkoxy, alkylthio, haloalkylthio, cyano, nitro, alkylcarbonyl, alkoxycarbonyl, alkoxycarbonylamino, aryl, aryloxy, and 2-alkyl-2H-tetrazole, and, wherein either of $R^{17}$ and $R^{18}$, or $R^{18}$ and $R^{19}$ may be taken together with —CH$_2$CH=CHCH$_2$O—, —OCF$_2$—, —OCF$_2$CF$_2$—, or —CF$_2$CF$_2$O—, to form benzo-fused rings;
and when
(c) m and n are 1;
a single bond between methyl carbon (a) and the 4-position of the six-membered azine ring is formed;

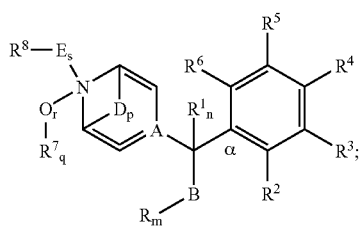

where
B is a bridging group from methyl carbon (a) to R;
where
B is selected from O, S, *CH$_2$O, *OCH$_2$, OC(=O)O, *OC(=O)NR$^{15}$, *NR$^{15}$C(=O)O, *OC(=S)NR$^{15}$, *NR$^{15}$C(=S)O, *OCH$_2$C(=O)NR$^{15}$, *NR$^{15}$C(=O)CH$_2$O, *CH$_2$OC(=O)NR$^{15}$, *NR$^{15}$C(=O)OCH$_2$, *NR$^{15}$CH$_2$, *CH$_2$NR$^{15}$, *NR$^{15}$C(=O), *C(=O)NR$^{15}$, *NR$^{15}$SO$_2$, *SO$_2$NR$^{15}$, *NR$^{15}$NHSO$_2$, *SO$_2$NHNR$^{15}$, *OC(=O)NR$^{15}$SO$_2$, *SO$_2$NR$^{15}$C(=O)O, *OC(=O)NR$^{15}$CHR$^{16}$, *CHR$^{16}$NR$^{15}$C(=O)O, *NR$^{15}$C(=O)NR$^{16}$; 1,4-dioxycyclohexyl, or 4-oxypiperidin-1-yl, where the asterisk denotes attachment to the methyl carbon (a); where $R^{15}$ and $R^{16}$ are described above;
and,
R is alkyl, cycloalkyl, alkenyl, or alkoxycarbonyl;
or
R is phenyl substituted with $R^{17}$, $R^{18}$, $R^{19}$, $R^{20}$, and $R^{21}$; pyrid-2-yl substituted with $R^{18}$, $R^{19}$, $R^{20}$, and $R^{21}$; pyrid-3-yl substituted with $R^{17}$, $R^{19}$, $R^{20}$, and $R^{21}$; pyrid-4-yl substituted with $R^{17}$, $R^{18}$, $R^{20}$, and $R^{21}$; or pyridazin-3-yl substituted with $R^{19}$, $R^{20}$ and $R^{21}$; where $R^{17}$, $R^{18}$, $R^{19}$, $R^{20}$, and $R^{21}$ are described above;

$R^1$ is selected from hydrogen, alkyl, alkoxyalkyl, or aryl;
when p is 1, 2, or 3;
D is —CH$_2$—, and an azabicyclo derivative of the six-membered azine ring is formed;
when q is 0, and r is 1, an N-oxide derivative of the six-membered azine ring nitrogen is formed;
when q is 1 and r is 0 or 1;
$R^7$ is selected from alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, arylalkyl, arylcarbonyl, sulfonato, or sulfonatoalkyl, and may bear a negative charge resulting in an inner salt; and a separate ion is chloride, bromide, iodide, or an alkyl or phenyl sulfate or sulfonate;
when s is 0 or 1;
$R^8$ is selected from hydrogen, alkyl, cycloalkyl, cycloalkylalkyl, alkoxy, alkoxyalkyl, amino, morpholinyl, optionally substituted indolyl, piperidinyl, optionally substituted (pyridyl)alkenyl, optionally substituted 1,2,3,4-tetrahydronaphthylenyl, optionally substituted arylpyrazolyl, benzo[b]thiophenyl, 5-hydropyridino[1,2a]pyrimidinonyl, optionally substituted 4-hydro-1,3-thiazolino[3,2a]pyrimidinonyl, 1,2,3,4-tetrahydroquinolinyl, 2-thioxo-1,3-dihydroquinazolinonyl, 1,3-dihydroquinazolindionyl, or benzo[c]azolindionyl, wherein the optional substituent is selected from halogen, alkyl, alkoxy, and nitro;
or
$R^8$ is phenyl substituted with $R^{22}$, $R^{23}$, $R^{24}$, $R^{25}$, and $R^{26}$,

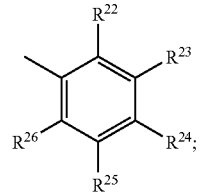

or
pyrid-2-yl substituted with $R^{23}$, $R^{24}$, $R^{25}$, and $R^{26}$,

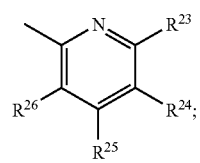

or
pyrid-3-yl substituted with $R^{22}$, $R^{24}$, $R^{25}$, and $R^{26}$,

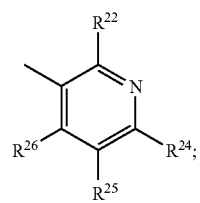

or
pyrid-4-yl substituted with $R^{22}$, $R^{23}$, $R^{25}$, and $R^{26}$,

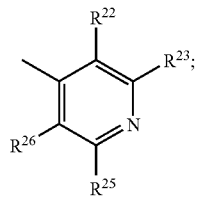

where
R²², R²³, R²⁴, R²⁵, and R²⁶ are independently selected from hydrogen, halogen, alkyl, hydroxy, alkoxy, alkoxyalkyl, dialkoxyalkyl, trialkoxyalkyl, alkoxyiminoalkyl, alkenyloxyiminoalkyl, alkynyloxyiminoalkyl, cycloalkylalkoxy, alkoxyalkoxy, alkylthio, dithioalkoxyalkyl, trithioalkoxyalkyl, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted -arylalkoxy, cyano, nitro, amino, alkylamino, alkylcarbonylamino, alkoxycarbonylamino, alkenyloxycarbonylamino, alkynyloxycarbonylamino, haloalkylcarbonylamino, alkoxyalkoxycarbonylamino, (alkyl)(alkoxycarbonyl)amino, alkylsulfonylamino, optionally substituted (heteroaryl)(alkoxycarbonyl)amino, optionally substituted arylcarbonylamino, formyl, optionally substituted 1,3-dioxolan-2-yl, optionally substituted 1,3-dioxan-2-yl, optionally substituted 1,3-oxazolidin-2-yl, optionally substituted 1,3-oxazaperhydroin-2-yl, optionally substituted 1,3-dithiolan-2-yl, optionally substituted 1,3-dithian-2-yl, alkoxycarbonyl, alkylaminocarbonyloxy, alkylaminocarbonylamino, dialkylaminocarbonylamino, alkylamino(thiocarbonyl)amino, dialkylphosphoroureidyl, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted heteroaryl, optionally substituted heteroaryloxy, optionally substituted pyrrolyl, optionally substituted pyrazolyl, optionally substituted pyrazinyloxy, optionally substituted 1,3-oxazolinyl, optionally substituted 1,3-oxazolinyloxy, optionally substituted 1,3-oxazolinylamino, optionally substituted 1,2,4-triazolyl, optionally substituted 1,2,3-thiadiazolyl, optionally substituted 1,2,5-thiadiazolyl, optionally substituted 1,2,5-thiadiazolyloxy, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahydropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, dialkoxyalkyl, dithioalkoxyalkyl, cyano, nitro, amino, or alkoxycarbonylamino, provided that at least one of R²², R²³, R²⁴, R²⁵, and R²⁶ is other than hydrogen;

when s is 1;
E is a bridging group selected from (CR²⁷R²⁸)$_x$—(CR²⁹R³⁰)$_y$, (CR²⁷R²⁸)$_x$—(CR²⁹R³⁰)$_y$O*, C₃H₆, C₄H₈, C(=O), C(=O)C₂H₄*, C₂H₄C(=O)*, C₃H₆C(=O)*, C₄H₈NHC(=O), or C(=S)NH*, where the asterisk denotes attachment at R⁸,
where
x is 1; y is 0, or 1;
and,
where R²⁷, R²⁸, R²⁹, and R³⁰ are independently selected from hydrogen, alkyl, and aryl optionally substituted with alkoxy;

N-oxides;
and
agriculturally-acceptable salts thereof.

The present invention is also directed to compositions containing an insecticidally effective amount of at least one of a compound of formula I, and optionally, an effective amount of at least one of a second compound, with at least one agriculturally acceptable extender or adjuvant.

The present invention is also directed to methods of controlling insects, where control is desired, which comprise applying an insecticidally effective amount of the above composition to the locus of crops, or other areas where insects are present or are expected to be present. Other aspects of the present invention will become apparent.

DETAILED DESCRIPTION OF THE INVENTION

One aspect of the present invention relates to certain new and useful compounds, namely certain novel N-(substituted arylmethyl)-4-(disubstituted methyl)piperidine and pyridine derivatives as depicted in general formula I:

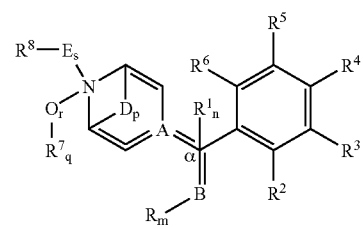

wherein;
m, n, q, r, and s are independently selected from 0 or 1; and
p is 0, 1, 2, or 3;
A is selected from C and CH, forming a six-membered azine ring selected from piperidine, 1,4-dihydropyridine, and 1,2,5,6-tetrahydropyridine;
R², R³, R⁴, R⁵, and R⁶ are independently selected from hydrogen, halogen, alkyl, haloalkyl, hydroxyl, alkoxy, haloalkoxy, pentahalothio, alkylthio, cyano, nitro, alkylcarbonyl, alkoxycarbonyl, aryl, or aryloxy, provided that at least one of R², R³, R⁴, R⁵, and R⁶ are other than hydrogen; and, wherein either of R² and R³, or R³ and R⁴ are taken together with —OCF₂O—, —OCF₂CF₂—, —CF₂CF₂O—, or —CH=CHCH=CH—, forming a benzo-fused ring;
and when,
(a) m and n are 0;
a double bond between methyl carbon (a) and the 4-position of the six-membered azine ring is formed,

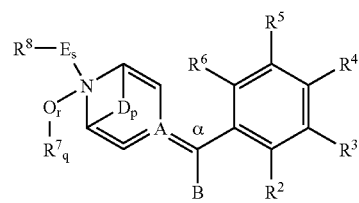

where
B is phenyl substituted with R⁹, R¹⁰, R¹¹, R¹², and R¹³,

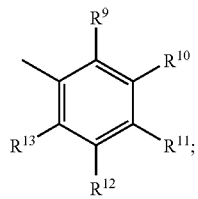

where $R^9$, $R^{10}$, $R^{11}$, $R^{12}$, and $R^{13}$ are independently selected from hydrogen, halogen, alkyl, haloakyl, hydroxyl, alkoxy, haloalkoxy, mercapto, and alkylthio, cyano, alkylcarbonyl, alkoxycarbonyl, or aryloxy; and, wherein either of $R^9$ and $R^{10}$, or $R^{10}$ and $R^{11}$ may be taken together with —OCF$_2$O—, —OCF$_2$CF$_2$—, or —CF$_2$CF$_2$O—, forming a benzo-fused ring, and;

and when (b) m is 1, and n is 0;

a double bond between methyl carbon (a) and the 4-position of the six-membered azine ring is formed,

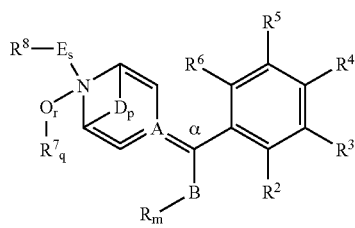

where

B is a bridging group from methyl carbon (a) to R;

where

B is selected from O, S, *CH$_2$O, *OCH$_2$, OC(=O)O, *OC(=O)NR$^{15}$, *NR$^{15}$C(=O)O, *OC(=S)NR$^{15}$, *NR$^{15}$C(=S)O, *OCH$_2$C(=O)NR$^{15}$, *NR$^{15}$C(=O)CH$_2$O, *CH$_2$OC(=O)NR$^{15}$, *NR$^{15}$C(=O)OCH$_2$, *NR$^{15}$CH$_2$, *CH$_2$NR$^{15}$, *NR$^{15}$C(=O), *C(=O)NR$^{15}$, *NR$^{15}$SO$_2$, *SO$_2$NR$^{15}$, *NR$^{15}$NHSO$_2$, *SO$_2$NHNR$^{15}$, *OC(=O)NR$^{15}$SO$_2$, *SO$_2$NR$^{15}$C(=O)O, *OC(=O)NR$^{15}$CHR$^{16}$, *CHR$^{16}$NR$^{15}$C(=O)O, *NR$^{15}$C(=O)NR$^{16}$; 1,4-dioxycyclohexyl, or 4-oxypiperidin-1-yl, where the asterisk denotes attachment to the methyl carbon (a);

where $R^{15}$ and $R^{16}$ are independently selected from hydrogen, alkyl, alkylaminocarbonyl, and arylcarbonyl wherein the aryl is optionally substituted with halogen, alkyl, alkoxy, haloalkyl, haloalkoxy, or nitro;

where

R is alkyl, cycloalkyl, alkenyl, or alkoxycarbonyl;

or

R is phenyl substituted with $R^{17}$, $R^{18}$, $R^{19}$, $R^{20}$, and $R^{21}$;

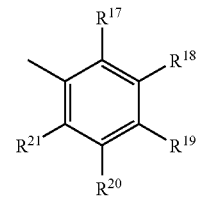

or,

R is pyrid-2-yl substituted with $R^{18}$, $R^{19}$, $R^{20}$, and $R^{21}$,

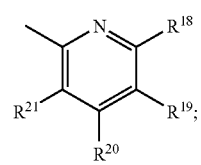

or pyrid-3-yl substituted with $R^{17}$, $R^{19}$, $R^{20}$, and $R^{21}$,

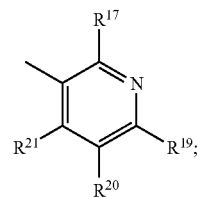

or pyrid-4-yl substituted with $R^{17}$, $R^{18}$, $R^{20}$, and $R^{21}$,

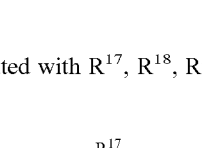

or pyridazin-3-yl substituted with $R^{19}$, $R^{20}$ and $R^{21}$,

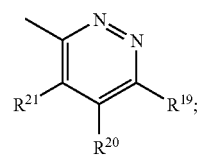

where $R^{17}$, $R^{18}$, $R^{19}$, $R^{20}$, and $R^{21}$ are independently selected from hydrogen, halogen, alkyl, haloalkyl, alkoxy, haloalkoxy, alkylthio, haloalkylthio, cyano, nitro, alkylcarbonyl, alkoxycarbonyl, alkoxycarbonylamino, aryl, aryloxy, and 2-alkyl-2H-tetrazole, and, wherein either of $R^{17}$ and $R^{18}$, or $R^{18}$ and $R^{19}$ may be taken together with —CH$_2$CH=CHCH$_2$—, —OCF$_2$O—, —OCF$_2$CF$_2$—, or —CF$_2$CF$_2$O—, to form benzo-fused rings;

and when (c) m and n are 1;

a single bond between methyl carbon (a) and the 4-position of the six-membered azine ring is formed;

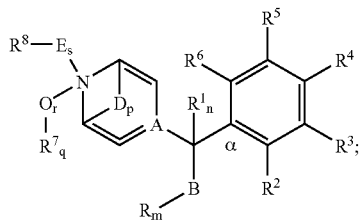

where

B is a bridging group from methyl carbon (a) to R;

where

B is selected from O, S, *CH$_2$O, *OCH$_2$, OC(=O)O, *OC(=O)NR$^{15}$, *NR$^{15}$C(=O)O, *OC(=S)NR$^{15}$, *NR$^{15}$C(=S)O, *OCH$_2$C(=O)NR$^{15}$, *NR$^{15}$C(=O)CH$_2$O, *CH$_2$OC(=O)NR$^{15}$, *NR$^{15}$C(=O)OCH$_2$, *NR$^{15}$CH$_2$, *CH$_2$NR$^{15}$, *NR$^{15}$C(=O), *C(=O)NR$^{15}$, *NR$^{15}$SO$_2$, *SO$_2$NR$^{15}$, *NR$^{15}$NHSO$_2$, *SO$_2$NHNR$^{15}$, *OC(=O)NR$^{15}$SO$_2$, *SO$_2$NR$^{15}$C(=O)O, *OC(=O)NR$^{15}$CHR$^{16}$, *CHR$^{16}$NR$^{15}$C(=O)O, *NR$^{15}$C(=O)NR$^{16}$; 1,4-dioxycyclohexyl, or 4-oxypiperidin-1-yl, where the asterisk denotes attachment to the methyl carbon (a); where R$^{15}$ and R$^{16}$ are described above;

and,

R is alkyl, cycloalkyl, alkenyl, or alkoxycarbonyl;

or

R is phenyl substituted with R$^{17}$, R$^{18}$, R$^{19}$, R$^{20}$, and R$^{21}$; pyrid-2-yl substituted with R$^{18}$, R$^{19}$, R$^{20}$, and R$^{21}$; pyrid-3-yl substituted with R$^{17}$, R$^{19}$, R$^{20}$, and R$^{21}$; pyrid-4-yl substituted with R$^{17}$, R$^{18}$, R$^{20}$, and R$^{21}$; or pyridazin-3-yl substituted with R$^{19}$, R$^{20}$ and R$^{21}$; where R$^{17}$, R$^{18}$, R$^{19}$, R$^{20}$, and R$^{21}$ are described above;

R$^1$ is selected from hydrogen, alkyl, alkoxyalkyl, or aryl;

when p is 1, 2, or 3;

D is —CH$_2$—, and an azabicyclo derivative of the six-membered azine ring is formed;

when q is 0, and r is 1, an N-oxide derivative of the six-membered azine ring nitrogen is formed;

when q is 1 and r is 0 or 1;

R$^7$ is selected from alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, arylalkyl, arylcarbonyl, sulfonato, or sulfonatoalkyl, and may bear a negative charge resulting in an inner salt; and a separate ion is chloride, bromide, iodide, or an alkyl or phenyl sulfate or sulfonate;

when s is 0 or 1;

R$^8$ is selected from hydrogen, alkyl, cycloalkyl, cycloalkylalkyl, alkoxy, alkoxyalkyl, amino, morpholinyl, optionally substituted indolyl. piperidinyl, optionally substituted (pyridyl)alkenyl, optionally substituted 1,2,3,4-tetrahydronaphthylenyl, optionally substituted arylpyrazolyl, benzo[b]thiophenyl, 5-hydropyridino[1,2a]pyrimidinonyl, optionally substituted 4-hydro-1,3-thiazolino[3,2a] pyrimidinonyl, 1,2,3,4-tetrahydroquinolinyl, 2-thioxo-1,3-dihydroquinazolinonyl, 1,3-dihydroquinazolindionyl, or benzo[c]azolindionyl, wherein the optional substituent is selected from halogen, alkyl, alkoxy, and nitro;

or

R$^8$ is phenyl substituted with R$^{22}$, R$^{23}$, R$^{24}$, R$^{25}$, and R$^{26}$,

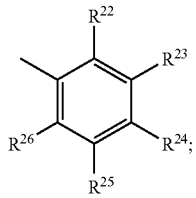

or pyrid-2-yl substituted with R$^{23}$, R$^{24}$, R$^{25}$ and R$^{26}$,

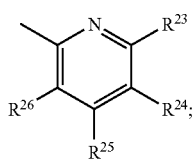

or pyrid-3-yl substituted with R$^{22}$, R$^{24}$, R$^{25}$, and R$^{26}$,

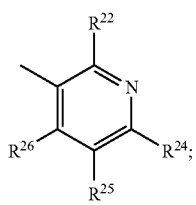

or pyrid-4-yl substituted with R$^{22}$, R$^{23}$, R$^{25}$, and R$^{26}$,

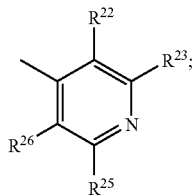

where

R$^{22}$, R$^{23}$, R$^{24}$, R$^{25}$, and R$^{26}$ are independently selected from hydrogen, halogen, alkyl, hydroxy, alkoxy, alkoxyalkyl, dialkoxyalkyl, trialkoxyalkyl, alkoxyiminoalkyl, alkenyloxyiminoalkyl, alkynyloxyiminoalkyl, cycloalkylalkoxy, alkoxyalkoxy, alkylthio, dithioalkoxyalkyl, trithioalkoxyalkyl, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted arylalkoxy, cyano, nitro, amino, alkylamino, alkylcarbonylamino, alkoxycarbonylamino, alkenyloxycarbonylamino, alkynyloxycarbonylamino, haloalkylcarbonylamino, alkoxyalkoxycarbonylamino, (alkyl)(alkoxycarbonyl)amino, alkylsulfonylamino, optionally substituted (heteroaryl)(alkoxycarbonyl)amino, optionally substituted arylcarbonylamino, formyl, optionally substituted 1,3-dioxolan-2-yl, optionally substituted 1,3-dioxan-2-yl, optionally substituted 1,3-oxazolidin-2-yl, optionally substituted 1,3-oxazaperhydroin-2-yl, optionally substituted 1,3-dithiolan-2-yl, optionally substituted 1,3-dithian-2-yl, alkoxycarbonyl, alkylaminocarbonyloxy, alkylaminocarbonylamino, dialkylaminocarbonylamino, alkylamino(thiocarbonyl)amino, dialkylphosphoroureidyl, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted heteroaryl, optionally substituted heteroaryloxy, optionally substituted pyrrolyl, optionally substituted pyrazolyl, optionally substituted pyrazinyloxy. optionally substituted 1,3-oxazolinyl, optionally substituted 1,3-oxazolinyloxy, optionally substituted 1,3-oxazolinylamino, optionally substituted 1,2,4-triazolyl, optionally substituted 1,2,3-thiadiazolyl, optionally substituted 1,2,5-thiadiazolyl, optionally substituted 1,2,5-thiadiazolyloxy, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahydropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, dialkoxyalkyl, dithioalkoxyalkyl, cyano, nitro, amino, or alkoxycarbonylamino, provided that at least one of $R^{22}$, $R^{23}$, $R^{24}$, $R^{25}$, and $R^{26}$ is other than hydrogen; when s is 1;

E is a bridging group selected from $(CR^{27}R^{28})_x$—$(CR^{29}R^{30})_y$, $(CR^{27}R^{28})_x$—$(CR^{29}R^{30})_yO^*$, $C_3H_6$, $C_4H_8$, $C(=O)$, $C(=O)C_2H_4^*$, $C_2H_4C(=O)^*$, $C_3H_6C(=O)^*$, $C_4H_8NHC(=O)^*$, or $C(=S)NH^*$, where the asterisk denotes attachment at $R^8$, where x is 1; y is 0 or 1;

and, where $R^{27}$, $R^{28}$, $R^{29}$, and $R^{30}$ are independently selected from hydrogen, alkyl, and aryl optionally substituted with alkoxy;

N-oxides;

and agriculturally-acceptable salts thereof.

Compounds within the scope of the present invention that are of particular interest are those where p and q are 0; r is 0 or 1; and s is 1; $R^2$, $R^3$, $R^4$, $R^5$, and $R^6$ are independently selected from hydrogen, halogen, alkyl, haloalkyl, hydroxyl, alkoxy, haloalkoxy, pentahalothio, alkylthio, nitro, aryl, and aryloxy; E is the bridging group —$(CR^{27}R^{28})_x$—$(CR^{29}R^{30})_y$—, where x is 1 and y is 0, $R^{27}$ and $R^{28}$ are hydrogen; and $R^8$ is phenyl substituted with $R^{22}$, $R^{23}$, $R^{24}$, $R^{25}$, and $R^{26}$, where $R^{22}$, $R^{23}$, $R^{24}$, $R^{25}$, and $R^{26}$ are independently selected from hydrogen, alkoxy, dialkoxyalkyl, dithioalkoxyalkyl, alkoxyiminoalkyl, alkenyloxyiminoalkyl, alkynyloxyiminoalkyl, alkoxycarbonylamino, optionally substituted arylcarbonylamino, alkoxycarbonyl, alkylaminocarbonyloxy, optionally substituted 1,3-dioxolane-2-yl, optionally substituted 1,3-dioxan-2-yl, optionally substituted 1,3-dithiolan-2-yl, optionally substituted aryl, optionally substituted 1,3-dithian-2-yl, optionally substituted aryl, optionally substituted aryloxy, optionally substituted 2H-tetrazole, optionally substituted pyridyl, optionally substituted pyridyloxy, optionally substituted pyrimidinyl, optionally substituted pyrimidinyloxy, and optionally substituted pyridazinyloxy.

In one aspect of the present invention, preferred compounds of the present invention are those where A is C, forming the piperidine ring; m is (a) 0 or (b) 1, and n is 0, forming a double bond between methyl carbon (a) and the 4-position of said piperidine ring;

and when (a) m and n are 0;

B is phenyl substituted with $R^9$, $R^{10}$, $R^{11}$, $R^{12}$, and $R^{13}$, where $R^9$, $R^{10}$, $R^{11}$, $R^{12}$, and $R^{13}$ are independently selected from hydrogen, halogen, alkyl, haloalkyl, hydroxyl, alkoxy, haloalkoxy, mercapto, and alkylthio;

or when (b) m is 1, and n is 0;

B is the bridging group selected from O, $*OC(=O)NR^{15}$, and $*SO_2NR^{15}$, where $R^{15}$ is hydrogen;

and,

R is phenyl substituted with $R^{17}$, $R^{18}$, $R^{19}$, $R^{20}$, and $R^{21}$ where $R^{17}$, $R^{18}$, $R^{19}$, $R^{20}$, and $R^{21}$ are independently selected from hydrogen, halogen, alkyl, haloalkyl, alkoxy, haloalkoxy, nitro, aryl, aryloxy, and 2-alkyl-2H-tetrazole. More preferred are those compounds where $R^2$, $R^3$, $R^4$, $R^5$, and $R^6$ are independently selected from hydrogen, halogen, haloalkyl, and haloalkoxy; and $R^{22}$, $R^{23}$, $R^{24}$, $R^{25}$, and $R^{26}$ are independently selected from hydrogen, dialkoxyalkyl, dithioalkoxyalkyl, alkoxyiminoalkyl, alkylaminocarbonyloxy, optionally substituted 1,3-dioxolan-2-yl, optionally substituted 1,3-dioxan-2-yl, optionally substituted aryloxy, optionally substituted 2H-tetrazole, optionally substituted pyridyloxy, optionally substituted pyrimidinyl, optionally substituted pyrimidinyloxy, and optionally substituted pyridazinyloxy.

Particularly preferred are those compounds i) where (a) m and n are 0; and $R^9$, $R^{10}$, $R^{11}$, $R^{12}$, and $R^{13}$ are independently selected from hydrogen, halogen, haloalkyl, and haloalkoxy; more particularly where $R^2$, $R^3$, $R^5$, $R^6$, $R^9$, $R^{10}$, $R^{12}$, $R^{13}$, $R^{22}$, $R^{23}$, $R^{25}$, and $R^{26}$ are hydrogen; $R^4$ and $R^{11}$ are difluoromethyl, trifluoromethyl or trifluoromethoxy; and $R^{24}$ is pyrid-2-yloxy or pyrimidin-2-yloxy.

Other particularly preferred are those compounds ii) where (b) m is 1, and n is 0; B is the bridging group O or $*OC(=O)NR^{15}$; and $R^{17}$, $R^{18}$, $R^{19}$, $R^{20}$, and $R^{21}$ are independently selected from hydrogen, halogen, haloalkyl, and haloalkoxy; more particularly where $R^2$, $R^3$, $R^5$, $R^6$, $R^{17}$, $R^{18}$, $R^{20}$, $R^{21}$, $R^{22}$, $R^{23}$, $R^{25}$, and $R^{26}$ are hydrogen; $R^4$ and $R^{19}$ are difluoromethyl, trifluoromethyl or trifluoromethoxy; and $R^{24}$ is pyrid-2-yloxy or pyrimidin-2-yloxy.

In another aspect of the present invention, preferred compounds of the present invention are those where A is CH, forming the piperidine ring;

(c) m and n are 1, forming a single bond between methyl carbon (a) and the 4-position of said rings;

$R^1$ is hydrogen;

B is the bridging group selected from O, $*OC(=O)NR^{15}$, and $*SO_2NR^{15}$, where $R^{15}$ is hydrogen;

and

R is phenyl substituted with $R^{17}$, $R^{18}$, $R^{19}$, $R^{20}$, and $R^{21}$ where $R^{17}$, $R^{18}$, $R^{19}$, $R^{20}$, and $R^{21}$ are independently selected from hydrogen, halogen, alkyl, haloalkyl, alkoxy, haloalkoxy, nitro, aryl, aryloxy, and 2-alkyl-2H-tetrazole. More preferred are those compounds where $R^2$, $R^3$, $R^4$, $R^5$, and $R^6$ are independently selected from hydrogen, halogen, haloalkyl, and haloalkoxy; and $R^{22}$, $R^{23}$, $R^{24}$, $R^{25}$, and $R^{26}$ are independently selected from hydrogen, dialkoxyalkyl, dithioalkoxyalkyl, alkoxyiminoalkyl, alkylaminocarbonyloxy, optionally substituted 1,3-dioxolan-2-yl, optionally substituted 1,3-dioxan-2-yl, optionally substituted aryloxy, optionally substituted 2H-tetrazole, optionally substituted pyridyloxy, optionally substituted pyrimidinyl, optionally substituted pyrimidinyloxy, and optionally substituted pyridazinyloxy.

Particularly preferred are those compounds where B is the bridging group O or * O C(=O)NR$^{15}$; R$^{17}$, R$^{18}$, R$^{19}$, R$^{20}$, and R$^{21}$ are independently selected from hydrogen, halogen, haloalkyl, and haloalkoxy; more particularly where R$^2$, R$^3$, R$^5$, R$^6$, R$^{17}$, R$^{18}$, R$^{20}$, R$^{21}$, R$^{22}$, R$^{23}$, R$^{25}$ and R$^{26}$ are hydrogen; R$^4$ and R$^{19}$ are difluoromethyl, trifluoromethyl or trifluoromethoxy; and R$^{24}$ is pyrid-2-yloxy or pyrimidin-2-yloxy.

In certain cases the compounds within the scope of formula I may possess asymmetric centers, which can give rise to optical enantiomorphs and diastereomers. Compounds within the scope of formula I may exist in two or more forms, i.e., polymorphs, which are significantly different in physical and chemical properties. Compounds within the scope of formula I may also exist as tautomers, which are in equilibrium. Compounds within the scope of formula I may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I, and, optionally, an effective amount of at least one second compound, with at least one agriculturally acceptable extender or adjuvant.

Another aspect of the present invention relates to methods of controlling insects by applying an insecticidally effective amount of a composition set forth above to a locus of crops such as, without limitation, cereals, cotton, vegetables, and fruits, other areas where insects are present or are expected to be present, or adjacent to areas where insects are present or are expected to be present.

The present invention also includes the use of the compounds and compositions set forth herein for control of non-agricultural insect species, for example, ants, dry wood termites and subterranean termites as well as other insects; and also for use as pharmaceutical agents and compositions thereof.

In the field of veterinary medicine, the compounds of the present invention are expected to be effective against certain endo- and ecto-parasites, such as insects and worms, which prey on animals. Examples of such animal parasites include, without limitation, *Gaytrophilus* spp., *Stomoxys* spp., *Trichodectes* sp., *Rhodnius* spp., *Ctenocephalides canis*, and other species.

As used in this specification and unless otherwise indicated the substituent terms "alkyl", "alkenyl", "alkynyl", "alkoxy", "alkenyloxy", and "alkynyloxy" used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms, wherein "alkenyl" has at least one carbon to carbon double bond, and "alkynyl" has at least one carbon to carbon triple bond. The term "aryl" refers to an aromatic ring structure, including fused rings, having four to ten carbon atoms, for example, phenyl and naphthyl. The term "heteroaryl" refers to an aromatic ring structure, including fused rings, having four to ten carbon atoms, and in which one or more of the atoms in the ring is other than carbon, for example, sulfur, oxygen, or nitrogen. The term "THF" refers to tetrahydrofuran. The term "DMSO" refers to methyl sulfoxide. The term "DMF" refers to N,N-dimethylformamide. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The compounds of formula I of the present invention can be synthesized by methods that are individually known to one skilled in the art from intermediate compounds readily available in commerce.

Scheme 1 below illustrates a general procedure for synthesizing those compounds of formula I, where A is C, forming a piperidine ring; n is 0, forming a double bond between the methyl carbon (a) and the 4-position of the piperidine ring; m, p, and q are 0; r is 1, forming an N-oxide; and s is 1; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; B is phenyl substituted with R$^9$, R$^{10}$, R$^{11}$, R$^{12}$, and R$^{13}$, where R$^{27}$ and R$^{28}$ are hydrogen:

Scheme 1

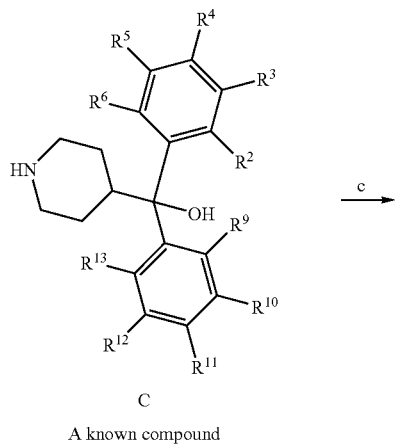

C

A known compound

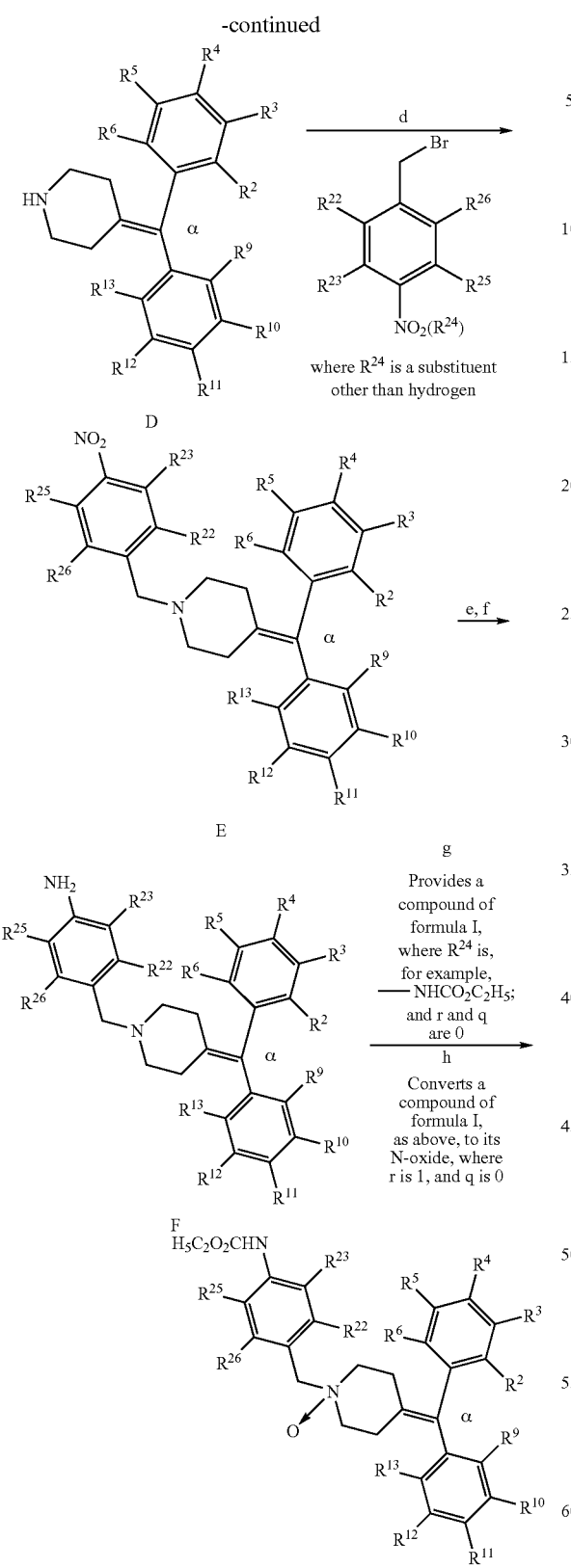

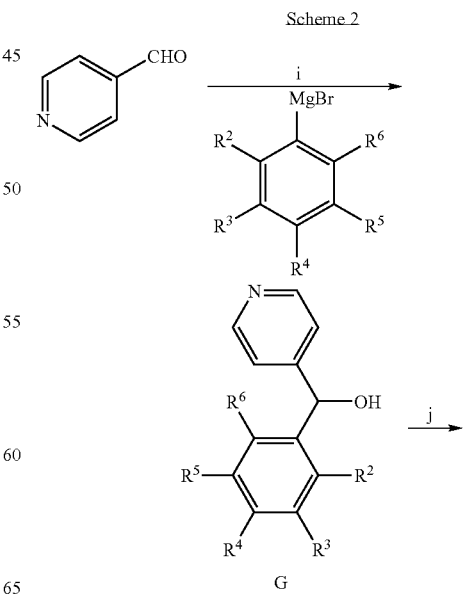

In a first step as set forth in Scheme 1, an appropriately substituted methanol (C), for example, 4-{bis[4-(trifluoromethyl)phenyl]hydroxymethyl}piperidine, was treated with trifluoroacetic acid at reduced temperature, yielding the corresponding unsaturated methylene derivative (D), for example, 4-{bis[4-(trifluoromethyl)phenyl]methylene}piperidine. Intermediate (D) was then reacted with an appropriately substituted phenyl bromide, for example, 4-nitrophenylmethyl bromide, under basic conditions in an appropriate solvent, providing the 1-substituted pyridyl derivative (E), for example, 4-{bis[4-(trifluoromethyl)phenyl]methylene}-1-[(4-nitrophenyl)methyl]piperidine. Intermediate (E) was then hydrogenated in the presence of a catalyst, for example, 5% palladium on carbon, at elevated temperature thereby reducing the nitro group to the amino group, providing 4-[(4-{bis(trifluoromethyl)phenyl]methylene}piperidyl)methyl]phenylamine (F). Intermediate (F) was in turn reacted with an alkyl haloformate, for example, ethyl chloroformate, under basic conditions in an appropriate solvent, affording the corresponding alkyl carboxamide, for example N-{4-[(4-{bis[4-(trifluoromethyl)phenyl]methylene}-piperidyl)methyl]phenyl}ethoxycarboxamide, a compound of formula I. The so-prepared carboxamide was then converted to the corresponding 1-oxypiperidyl derivative (an N-oxide) by treating it with, for example, 30% hydrogen peroxide in methanol, to provide additional compounds of formula I. Example 1, set forth below provides a detailed procedure for this synthesis.

Scheme 2 below illustrates a general procedure for synthesizing those compounds of formula I where A is CH, forming a piperidine ring; n is 1, forming single bonds from the methyl carbon (a) and its substituents; p, q, and r are 0; m and s are 1; B is a bridging group from the methyl carbon to R; E is $-(CR^{27}R^{28})_x-(CR^{29}R^{30})_y-$, where x is 1, and y is 0; $R^8$ is phenyl substituted with $R^{22}$, $R^{23}$, $R^{24}$, $R^{25}$, and $R^{26}$; and R is phenyl substituted with $R^{17}$, $R^{18}$, $R^{19}$, $R^{20}$, and $R^{21}$, where $R^{27}$ and $R^{28}$ are hydrogen:

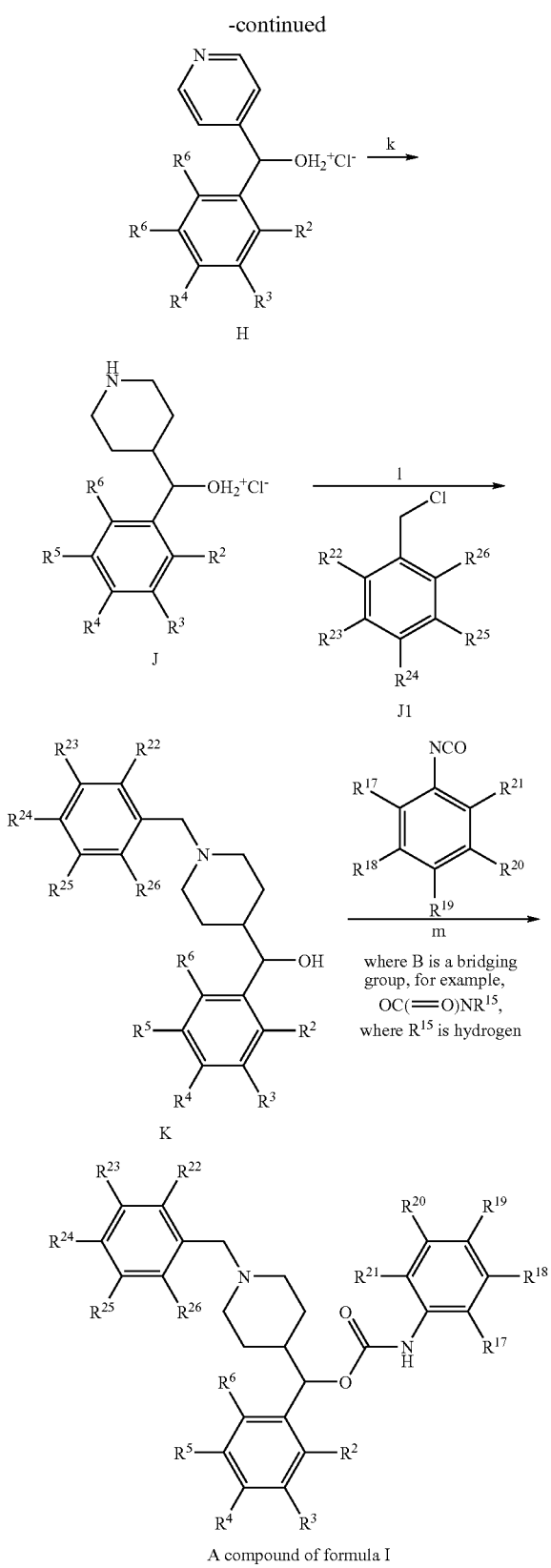

A compound of formula I i) Mg/I₂/THF/≤40° C.; j) HCl (g)/EtOAc; k) H₂/PtO₂/MeOH; l) N,N-diisopropylethylamine/DMSO; m) Et₃N/CH₂Cl₂/35° C.

In one syntheses, as depicted in Scheme 2, Intermediate (J1) was first prepared by reacting an appropriate formaldehyde, for example (4-(2-pyridyloxy)phenyl)formaldehyde, with sodium borohydride at reduced temperature in an appropriate solvent, yielding the corresponding substituted methanol derivative, for example, (4-(2-pyridyloxy)phenyl)methanol; which was in turn reacted with thionyl chloride in the presence of a catalytic amount of pyridine, at reduced temperature in an appropriate solvent, yielding, for example, (4-(2-pyridyloxy)phenyl)methyl chloride (J1). In a second syntheses, as depicted in Scheme 2, an appropriate carboxaldehyde, for example, 4-pyridinecarboxaldehyde, was reacted with a Grignard Reagent, for example, 4-trifluoromethylphenylmagnesium bromide, at an elevated temperature in an appropriate solvent, yielding the corresponding pyridylmethanol, for example, 4-(trifluoromethylphenyl)-4-pyridylmethanol (G). Intermediate (G) was then converted to its hydrochloride salt (H) by treating it with hydrogen chloride gas in an appropriate solvent. The so-formed salt (H) was then hydrogenated in the presence of platinum oxide, affording the corresponding piperidylmethanol, for example, the hydrochloride salt of 4-(trifluoromethylphenyl)-4-piperidylmethanol (J). To substitute the 1-position of the piperidine ring, intermediate (J) was reacted with intermediate (J1) under basic conditions in an appropriate solvent, providing the corresponding methanol derivative (K), for example, {1-[(4-(2-pyridyloxy)phenyl)methyl](4-piperidyl)}[4-(trifluoromethyl)phenyl]methanol. Intermediate (K) was then reacted with an appropriate isocyanate, for example, 4-chlorophenylisocyanate, under basic conditions in an appropriate solvent, affording the corresponding compound, for example, N-(4-chlorophenyl)({1-[(4-(2-pyridyloxy)phenyl)methyl](4-piperidyl)}[4-(trifluoromethyl)phenyl]methoxy)carboxamide, a compound of formula I. Example 2, set forth below provides a detailed procedure for this synthesis. The so-prepared carboxamide set forth in Example 2 was converted to the corresponding 1-oxypiperidyl derivative (an N-oxide) by treating it with, for example, 50% hydrogen peroxide in an appropriate solvent. Example 6, set forth below provides a detailed procedure for this synthesis. A similar procedure as depicted in Scheme 2 was used to prepare analogous compounds where A is C, forming a 1,2,5,6-tetrahydropyridine ring. Example 5, set forth below provides a detailed procedure for this synthesis.

Scheme 3 below illustrates a general procedure for synthesizing those compounds of formula I where A is CH, forming a piperidine ring; n is 1, forming single bonds from the methyl carbon (a) and its substituents; p, q, and r are 0; m and s are 1; B is a bridging group from the methyl carbon to R; E is $-(CR^{27}R^{28})_x-(CR^{29}R^{30})_y-$, where x is 1, and y is 0; and $R^8$ is phenyl substituted with $R^{22}$, $R^{23}$, $R^{24}$, $R^{25}$, and $R^{26}$; where $R^{27}$ and $R^{28}$ are hydrogen:

Scheme 3
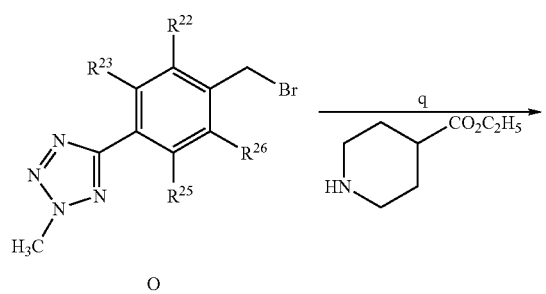
O
A known compound where $R^{22}$, $R^{23}$, $R^{25}$ and $R^{26}$ are hydrogen; See Example 19 of U.S. Pat. No. 5,639,763
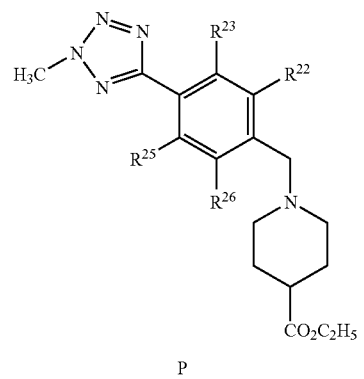
P
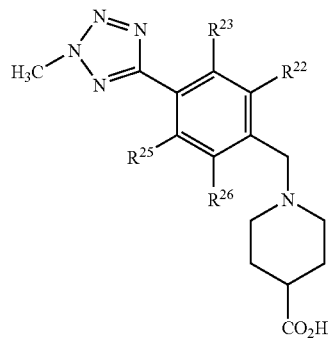
Q
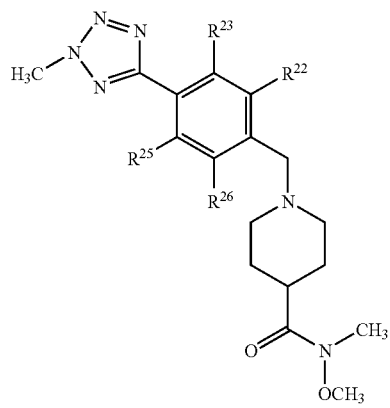
R
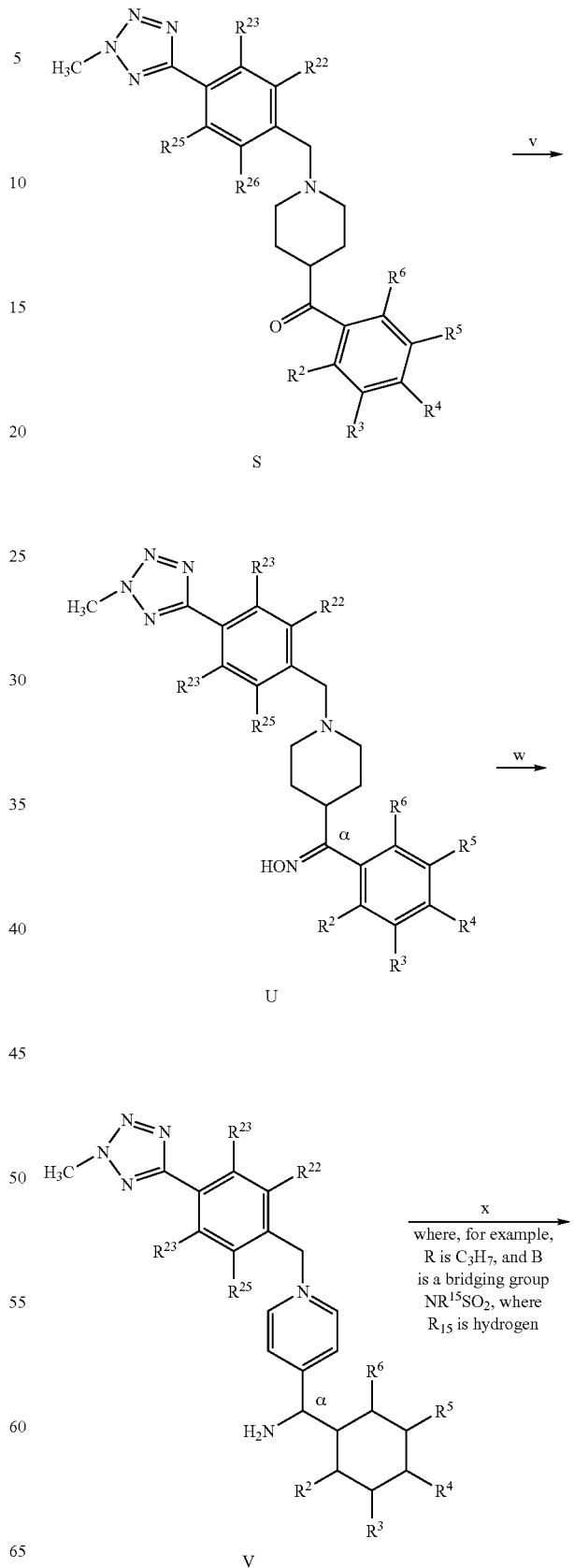
S
U
V
where, for example, R is $C_3H_7$, and B is a bridging group $NR^{15}SO_2$, where $R_{15}$ is hydrogen

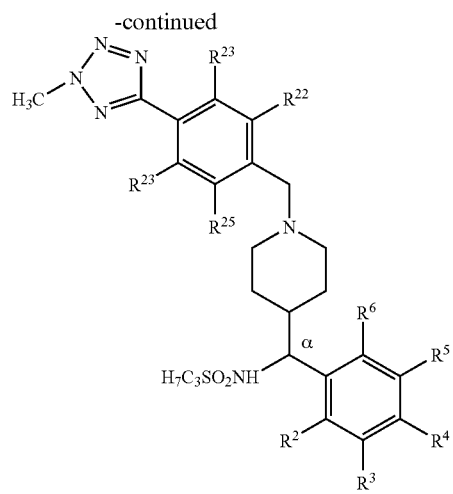

A compound of formula I q) N,N-diisopropylethylamine/DMSO; r) NaOH/H₂O/MeOH/THF; s) (EtO)₂P(O)CN/HN(OCH₃)(CH₃):HCl/DMF/0° C.; t) Mg/THF/RT-60° C.; v) H₂NOH:HCl/Et₃N/EtOH/Reflux; w) LiAlH₄/THF/RT-65° C.; x) C₃H₇SO₂Cl/Et₃N/CH₂Cl₂

As depicted in Scheme 3, the known compound, for example, 5-[4-(bromomethyl)phenyl]-2-methyl-1,2,3,4-tetraazole (O) was reacted with ethyl isonipecotate under basic conditions in an appropriate solvent, providing the corresponding ester (P), for example, ethyl 1-{[4-(2-methyl-1,2,3,4-tetraazol-5-yl)phenyl]methyl}piperidine-4-carboxylate, which was in turn converted to its piperidinecarboxylic acid (Q) by reacting it with aqueous sodium hydroxide in an appropriate solvent, affording, for example, 1-{[4-(2-methyl-1,2,3,4-tetraazol-5-yl)phenyl]methyl}piperidinecarboxylic acid. Intermediate (Q) was then reacted with, for example, N,O-dimethylhydroxylamine hydrochloride and diethylcyanophosphonate, under basic conditions at reduced temperature in an appropriate solvent, yielding the corresponding piperidine carboxamine (R), for example, 1-{[4-(2-methyl(1,2,3,4-tetraazol-5-yl))phenyl]methyl}(4-piperidyl)-N-methoxy-N-methylcarboxamide. Intermediate (R) was reacted with a Grignard Reagent, for example, 4-trifluoromethoxyphenylmagnesium bromide, in an appropriate solvent, affording the corresponding ketone (T), for example, 1-{[4-(2-methyl(1,2,3,4-tetraazol-5-yl))phenyl]methyl}(4-piperidyl)4-(trifluoromethoxy)phenyl ketone. Intermediate (T) was in turn reacted with hydroxylamine hydrochloride at an elevated temperature under basic conditions in an appropriate solvent, yielding the corresponding hydroxyimino (U) intermediate, for example, (hydroxyimino)(1-[[4-(2-methyl(1,2,3,4-tetraazol-5-yl))phenyl]methyl}(4-piperidyl)[4-(trifluoromethoxy)phenyl]methane. Intermediate (U) was then reacted with, for example, lithium aluminum hydride, then with ammonium chloride in an appropriate solvent, affording the corresponding amine (V) derivative, for example, 1-[[4-(2-methyl(1,2,3,4-tetraazol-5-yl)phenyl]methyl}(4-piperidyl))[4-(trifluoromethoxy)phenyl]methylamine. The amine (V) was in turn reacted with an appropriate halide, such as 1-propanesulfonyl chloride, under basic conditions in an appropriate solvent, affording a compound of formula I, for example, [(1-{[4-(2-methyl(1,2,3,4-tetraazol-5-yl))phenyl]methyl}(4-piperidyl))[4-(trifluoromethoxy)-phenyl]methyl]propylsulfonylamide. Example 3, set forth below provides a detailed procedure for this synthesis.

Scheme 4 below illustrates another general procedure for synthesizing those compounds of formula I where A is CH, forming a piperidine ring; n is 1, forming single bonds from the methyl carbon (a) and its substituents; p, q, and r are 0; m and s are 1; B is a bridging group from the methyl carbon to R; E is —(CR²⁷R²⁸)ₓ—(CR²⁹R³⁰)ᵧ—, where x is 1, and y is 0; and R⁸ is phenyl substituted with R²², R²³, R²⁴, R²⁵, and R²⁶; where R²⁷ and R²⁸ are hydrogen:

Scheme 4

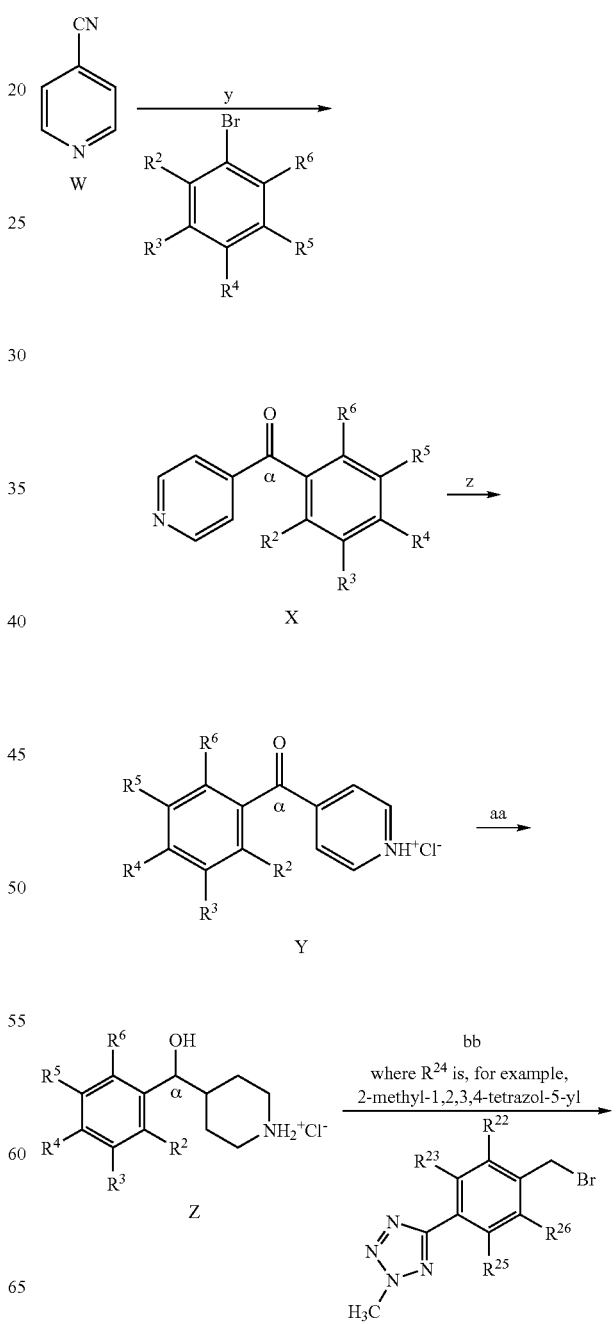

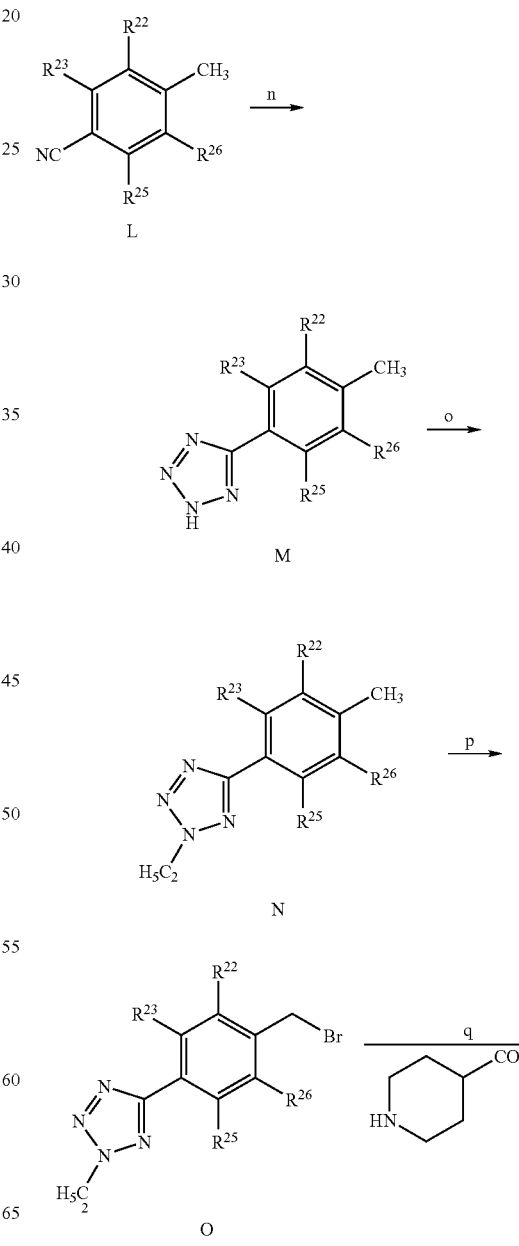

2-fluoro-5-trifluoromethylpyridine, affording a pyridine derivative, for example, 2-[(1-{[4-(2-methyl(1,2,3,4-tetraazol-5-yl))phenyl]methyl}(4-piperidyl))[4-(trifluoromethoxy)phenyl]methoxy]-5-(trifluoromethyl)pyridine, a compound of formula I. Example 4, set forth below provides a detailed procedure for this synthesis.

Scheme 5 below illustrates a general procedure for synthesizing those compounds of formula I where A is C, forming a piperidine ring; n is 0, forming a double bond between the methyl carbon (a) and the 4-position of the piperidine ring, where B is a bridging group from the methyl carbon to R; p, q, and r are 0; m and s are 1; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; and R is phenyl substituted with R$^{17}$, R$^{18}$, R$^{19}$, R$^{20}$, and R$^{21}$; where R$^{27}$, and R$^{28}$ are hydrogen:

A compound of formula I
y) Mg/THF/40° C.; z) HCl (g)/Et$_2$O; aa) H$_2$/PtO$_2$/MeOH; bb) N,N-diisopropylethylamine/DMSO; cc) NaH/DMSO/85–90° C.

As depicted in Scheme 4, a cyanopyridine (W), for example 4-cyanopyridine, was reacted with a Grignard Reagent, for example, 4-trifluoromethoxyphenylmagnesium bromide, in an appropriate solvent, affording the corresponding ketone (X), for example, 4-pyridyl 4-(trifluoromethoxy)phenyl ketone, which was, in turn converted to its hydrochloride salt (Y), by reacting it with hydrogen chloride gas in an appropriate solvent. Intermediate (Y) was in turn hydrogenated in the presence platinum oxide and in an appropriate solvent, providing the corresponding methanol (Z), for example, 4-piperidyl[4-(trifluoromethoxy)phenyl]methanol, hydrochloride. To substitute the 1-position of the piperidine ring, intermediate (Z) was reacted with an appropriate methyl halide, for example, 5-[4-(bromomethyl)phenyl]-2-methyl-1,2,3,4-tetraazole, under basic conditions in an appropriate solvent, affording the corresponding methanol (AA) derivative, for example, {1-[(2-methyl(1,2,3,4-tetraazol-5-yl))methyl](4-piperidyl)}[4-(trifluoromethoxy)phenyl]methanol. Intermediate (AA) was in turn treated with sodium hydride at elevated temperature, and then it was reacted with an appropriate halide, for example,

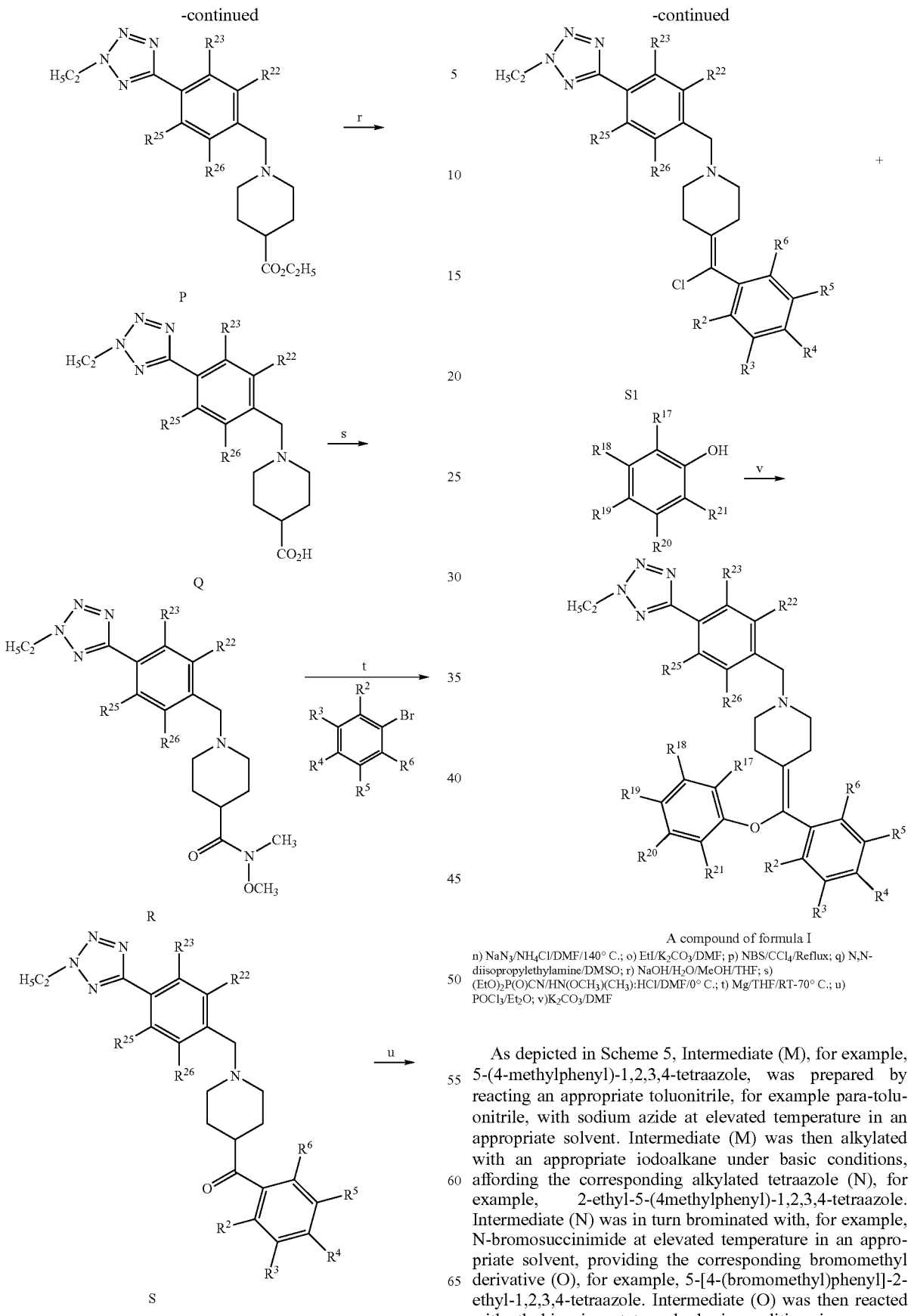

A compound of formula I n) NaN₃/NH₄Cl/DMF/140° C.; o) EtI/K₂CO₃/DMF; p) NBS/CCl₄/Reflux; q) N,N-diisopropylethylamine/DMSO; r) NaOH/H₂O/MeOH/THF; s) (EtO)₂P(O)CN/HN(OCH₃)(CH₃):HCl/DMF/0° C.; t) Mg/THF/RT-70° C.; u) POCl₃/Et₂O; v)K₂CO₃/DMF As depicted in Scheme 5, Intermediate (M), for example, 5-(4-methylphenyl)-1,2,3,4-tetraazole, was prepared by reacting an appropriate toluonitrile, for example para-toluonitrile, with sodium azide at elevated temperature in an appropriate solvent. Intermediate (M) was then alkylated with an appropriate iodoalkane under basic conditions, affording the corresponding alkylated tetraazole (N), for example, 2-ethyl-5-(4methylphenyl)-1,2,3,4-tetraazole. Intermediate (N) was in turn brominated with, for example, N-bromosuccinimide at elevated temperature in an appropriate solvent, providing the corresponding bromomethyl derivative (O), for example, 5-[4-(bromomethyl)phenyl]-2-ethyl-1,2,3,4-tetraazole. Intermediate (O) was then reacted with ethyl isonipecotate under basic conditions in an appropriate solvent, providing the corresponding ester (P), for example, ethyl 1-{[4-(2-ethyl-1,2,3,4-tetraazol-5-yl)phenyl] methyl}piperidine-4-carboxylate, which was in turn converted to its piperidinecarboxylic acid (Q) by reacting it with aqueous sodium hydroxide in an appropriate solvent, affording, for example, 1-{[4-(2-ethyl-1,2,3,4-tetraazol-5-yl)phenyl]methyl}piperidinecarboxylic acid. Intermediate (Q) was then reacted with, for example, N,O-dimethylhydroxylamine hydrochloride and diethylcyanophosphonate, under basic conditions at reduced temperature in an appropriate solvent, yielding the corresponding piperidine carboxamine (R), for example, 1-{[4-(2-ethyl(1,2,3,4-tetraazol-5-yl))phenyl]methyl}(4-piperidyl)-N-methoxy-N-methylcarboxamide. Intermediate (R) was reacted with a Grignard Reagent, for example, 4-trifluoromethoxyphenylmagnesium bromide, in an appropriate solvent, affording the corresponding ketone (S), for example, 1-{[4-(2-ethyl(1,2,3,4-tetraazol-5-yl))phenyl]methyl}(4-piperidyl)4-(trifluoromethoxy)-phenyl ketone. The ketone (S) is then halogenated with, for example, phosphorous oxychloride in an appropriate solvent, yielding the corresponding halogen compound (S1), for example, {4-[chloro(1-{[4-(2-ethyl(1,2,3,4-tetraazol-5-yl))phenyl]methyl}(4-piperidyl))methyl] phenoxy}trifluoromethane. Intermediate (S1) is in turn reacted with, for example, an appropriate phenol, such as 4-(trifluoromethoxy)phenol in an appropriate solvent, providing the corresponding phenoxy derivative, a compound of formula I, for example, 1-[(1-[[4-(2-ethyl(1,2,3,4-tetraazol-5-yl))phenyl]methyl](4-piperidylidene))[4-(trifluoromethoxy)phenyl]methoxy]-4-(trifluoromethoxy)benzene. Example 11, set forth below provides a detailed procedure for this synthesis.

Examples 7, 8, 9, and 10, set forth below provide detailed procedures for the synthesis of other compounds of formula I, prepared by methods derived from those procedures provided in Schema 1–4 and the Examples associated with these schema.

One skilled in the art will, of course, recognize that the formulation and mode of application of a toxicant may affect the activity of the material in a given application. Thus, for agricultural use the present insecticidal compounds may be formulated as a granular of relatively large particle size (for example, ⁵⁄₁₆ or ⅜ US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may: be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile, ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sufonyl]methyl]benzoic acid ("bensulfuron"), 2-[[[[(4,6-dimethoxy-2-pyrimidinyl)amino]carbonyl]amino]sulfonyl]-1-methy-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl] benzenesulfonamide ("triasulfuron"); 2-(4-aryloxyphenoxy) alkanoic acids such as (+/−)-2[4-[(6-chloro-2-benzoxazolyl) oxyl]phenoxy]propanoic acid (fenoxaprop"), (+/−)-2-[4[[5-(trifluoromethyl)-2-pyridinyl]oxy]phenoxy]propanoic acid ("fluazifop"), (+/−)-2-[4-(6chloro-2-quinoxalinyl)oxy]phenoxy]propanoic acid ("quizalofop"), and (+/−) 2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichlioro-6-fluoro-2-pyridinyl)oxy]acetic acid ("fluroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, biphenthrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as arnitraz, clofentezine, fenpyroximate, hexythiazox, spinosad, and imidacloprid.

When the active insecticidal compounds of the present invention are used in combination with one or more of second compounds, e.g., with other pesticides such as fungicides, the fungicides include, for example: benzimidazine fungicides, such as benomyl, carbendazim, thiabendazine, and thiophanate-methyl; 1,2,4-triazine fungicides, such as epoxyconazine, cyproconazine, flusilazine, flutriafol, propiconazine, tebuconazine, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalii, prochloraz, tricyclazine, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldecarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobiuni,* and soil-borne *cyanobacteria.*

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates one protocol for the preparation of N-{4-[(4-{bis[4-(trifluoromethyl)phenyl]methylene}piperidyl)methyl]phenyl}ethoxycarboxamide, N-oxide (Compound 101 in table below)

Step A Synthesis of 4-{bis[4-(trifluoromethyl)phenyl]methylene}piperidine as an intermediate A solution of 10.0 grams (0.025 mole) of 4-{bis[4-(trifluoromethyl)phenyl]hydroxymethyl}piperidine (known compound) in 50 mL of trifluoroacetic acid was heated to 70° C. where it stirred for four hours. After this time, excess trifluoroacetic acid was removed by distillation. The residue remaining from the distillation was added drop wise to ice water. Upon completion of addition, the mixture was neutralized with an aqueous solution saturated with potassium carbonate. The mixture was then extracted with methylene chloride, and the extract was washed with an aqueous solution saturated with sodium chloride. The extract was concentrated under reduced pressure to a residue, and the residue was crystallized in hexane, yielding in two crops, 9.1 grams of the subject compound. The NMR spectrum was consistent with the proposed structure.

Step B Synthesis of 4-{bis[4-(trifluoromethyl)phenyl]methylene}-1-[(4-nitrophenyl)methyl]piperidine as an intermediate A stirred mixture of 3.8 grams (0.010 mole) of 4-{bis[4-(trifluoromethyl)phenyl]methylene}piperidine, 2.2 grams (0.010 mole) of 4-nitrophenylmethyl bromide, and 1.7 grams (0.012 mole) of potassium carbonate in about 20 mL of ethanol was warmed to 75° C., where it stirred for about 18 hours. After this time, an additional 0.2 gram (0.001 mole) of 4-nitrophenylmethyl bromide and an additional 0.2 gram (0.001 mole) of potassium carbonate was added to the reaction mixture. The reaction mixture was again heated to 75° C., where it stirred for about eight hours. After this time, the reaction mixture was cooled and filtered to remove excess potassium carbonate. The reaction mixture was then taken up in acetic acid, and 0.2 gram (catalyst) of 5% platinum on carbon was added to the mixture in preparation for the following hydrogenation step. A quantitative yield of the subject compound was assumed.

Step C Synthesis of 4-[(4-{bis(trifluoromethyl)phenyl]methylene}piperidyl) methyl]phenylamine as an intermediate The reaction product from Step B of this example and 5% platinum on carbon in acetic acid was stirred at 75° C. for about 18 hours while hydrogen gas was bubbled into the reaction mixture. Analysis of the reaction mixture after this time indicated that the hydrogenation had not taken place. A mixture of 1:1 ethanol:acetic acid and 3.0 grams of iron powder was added to the reaction mixture and the hydrogenation was continued at 65° C. during a one hour period. Analysis of the reaction mixture after this time indicated that the hydrogenation was complete. The reaction mixture was then cooled and filtered through diatomaceous earth. The filtrate was concentrated under reduced pressure to a residue. The residue was dissolved in methylene chloride and the solution was washed with water, and then with an aqueous solution saturated with sodium carbonate. The organic layer was concentrated under reduced pressure, yielding 4.2 grams of the subject compound. The NMR spectrum was consistent with the proposed structure.

Step D Synthesis of N-{4-[(4-{bis[4-(trifluoromethyl)phenyl]methylene}piperidyl)methyl]phenyl}ethoxycarboxamide as an intermediate (Compound 55 in table below)

A stirred solution of 0.52 gram (0.001 1 mole) of 4-[(4-{bis(trifluoromethyl)phenyl]methylene}piperidyl)methyl]phenylamine and 0.20 gram (0.0020 mole) of triethylamine in 5 mL of ethyl acetate was cooled to 0–5° C., and 0.11 gram (0.0010 mole) of ethyl chloroformate was added. Upon completion of addition, the reaction mixture was stirred for about ten minutes. After this time, the reaction mixture was washed with a saturated solution saturated with potassium carbonate and then it concentrated under reduced pressure to a residue. The residue was purified with column chromatography on silica gel using mixtures of ethyl acetate and hexane as eluants. The appropriate fractions were combined and concentrated under reduced pressure, yielding 0.12 gram of Compound 144. The NMR spectrum was consistent with the proposed structure.

Step E Synthesis of Compound 101

A solution of 0.06 gram (0.00011 mole) of Compound 144 in 3 mL of methanol was stirred, and 1.5 mL of 30% hydrogen peroxide was added. Upon completion of addition, the reaction mixture became cloudy and additional methanol was added to keep the reaction mixture clear. The reaction mixture was stirred for about three days at ambient temperature, during which time an additional 0.5 mL of 30% hydrogen peroxide was added to drive the reaction to completion. After this time, the reaction mixture was extracted with methylene chloride, and the extract was concentrated under reduced pressure, yielding 0.06 gram of Compound 101. The NMR spectrum was consistent with the proposed structure.

EXAMPLE 2

This example illustrates one protocol for the preparation of N-(4-chlorophenyl)({1-[(4-(2-pyridyloxy)phenyl)methyl](4-piperidyl)}[4-(trifluoromethyl)phenyl]methoxy)carboxamide (Compound 227 in table below)

Step A Synthesis of (4-(2-pyridyloxy)phenyl)methanol as an intermediate

A stirred solution of 15.3 grams (0.077 mole) of (4-(2-pyridyloxy))formaldehyde (a known compound) in 150 mL of methanol was cooled to 0–5° C., and 3.2 grams (0.085 mole) of sodium borohydride was added portion wise. Upon completion of addition, the reaction mixture was allowed to warm to ambient temperature where it stirred for 30 minutes. After this time, the reaction mixture was cooled to 5° C. and 150 mL of water was carefully added to destroy excess sodium borohydride. The mixture was cooled to 0° C. and neutralized with concentrated hydrochloric acid. Excess acid was added causing the mixture to be acidic. The mixture was brought to neutrality by the addition of solid sodium bicarbonate. The mixture was concentrated under reduced pressure to remove some of the methanol. The concentrate was taken up in ethyl acetate and washed with an aqueous solution saturated with sodium chloride. The organic layer was dried with sodium sulfate, filtered, and concentrated under reduced pressure, yielding 12.6 grams of the subject compound. The NMR spectrum was consistent with the proposed structure.

Step B Synthesis of (4-(2-pyridyloxy)phenyl)methyl chloride as an intermediate A stirred solution of 4.4 gram (0.037 mole) of thionyl chloride in 75 mL of dry methylene chloride was cooled to 0° C., and 0.07 gram (catalyst) of pyridine was added. A solution of 5.0 grams (0.025 mole) of (4-(2-pyridyloxy)phenyl)methanol in 25 mL of methylene chloride was then added drop wise. Upon completion addition of addition, the reaction mixture was allowed to warm to 22° C. where it stirred for 30 minutes. After this time an aliquot of the reaction mixture was taken up in ethyl acetate and treated with solid sodium bicarbonate. The organic layer was dried with sodium sulfate, filtered, and concentrated under reduced pressure to a residue. The NMR spectrum was consistent with the proposed structure. Inasmuch as this compound is unstable, it was used without further purification. The yield was estimated at about 5.0 grams.

Step C Synthesis of 4-(trifluoromethylphenyl)-4-pyridylmethanol as an intermediate A solution of 4-bromobenzotrifluoride in 62 mL of THF was carefully added to a mixture of 1.9 grams (0.079 mole) of magnesium turnings and an iodine crystal (catalyst), during a period of 60 minutes while maintaining the reaction mixture at a temperature of no higher than 40° C. After this time, the reaction mixture was stirred and a solution of 5.0 grams (0.047 mole) of 4-pyridinecarboxaldehyde in 45 mL of THF was added dropwise. Upon completion of addition, the reaction mixture was stirred at ambient temperature for about 16 hours. The reaction mixture was then cooled to 0° C. and a sufficient amount of an aqueous solution saturated with ammonium chloride was added to quench the reaction. The mixture was then extracted with ethyl acetate, and the extract was washed with an aqueous solution saturated with sodium chloride. The extract was dried with sodium sulfate, filtered, and concentrated under reduced pressure, yielding about 15.2 grams of crude product.

Step D Synthesis of 4-(trifluoromethylphenyl)-4-piperidylmethanol, hydrochloride Salt as an intermediate A solution of 6.4 grams (0.020 mole) of 4-(trifluoromethylphenyl)-4-pyridylmethanol in 80 mL of ethyl acetate was stirred, and dry hydrogen chloride gas was bubbled through the solution, thereby forming the hydrochloride salt of the pyridylmethanol intermediate. The salt was collected by filtration and washed with a small amount of ethyl acetate. The damp solid was then dissolved in 100 mL of methanol and placed in a Parr hydrogenation bottle, along with 0.5 gram (catalyst) of platinum oxide. The mixture was then hydrogenated at 45 pounds per square inch (psi) for about 75 minutes, using a Parr Hydrogenator. An NMR taken of the reaction mixture indicated that the reaction was about 90% complete. An additional 0.25 gram of platinum oxide catalyst was added to the reaction mixture, and the hydrogenation at 45 psi was continued for an additional 60 minutes. After this time, the reaction mixture was filtered through diatomaceous earth. The filter cake was washed with methylene chloride and the combined wash and filtrate was concentrated under reduced pressure, yielding 5.2 grams of subject compound. The NMR spectrum was consistent with the proposed structure. The reaction was repeated.

Step E Synthesis of {1-[(4-(2-pyridyloxy)phenyl)methyl](4-piperidyl)}[4-(trifluoromethyl)phenyl]methanol as an intermediate A solution of 6.1 grams (0.021 mole) of 4-(trifluoromethylphenyl)-4-piperidylmethanol, hydrochloride salt in 31 mL of DMSO was stirred, and 10.7 grams (0.083 mole) of N,N-diisopropylethylamine was added. Upon completion of addition, the reaction mixture was stirred for 10 minutes, and was then added to the 5.0 grams (0.023 mole) of (4-(2-pyridyloxy)phenyl)methyl chloride that was prepared in Step B of this Example. Upon completion of addition, the reaction mixture was stirred at ambient temperature for 16 hours. After this time, the reaction mixture was treated with aqueous 10% sodium carbonate and extracted with ethyl acetate. The ethyl acetate layer was washed with water, then with an aqueous solution saturated with sodium chloride. The ethyl acetate layer was dried with sodium sulfate, filtered, and concentrated under reduced pressure to a residue. The residue was purified with column chromatography on silica gel using mixtures of acetone and methylene chloride as eluants. The appropriate fractions were combined and concentrated under reduced pressure, yielding 4.2 grams of the subject compound. The NMR spectrum was consistent with the proposed structure.

Step F Synthesis of Compound 227

A 0.06 gram (0.0004 mole) sample of 4-chlorophenylisocyanate was weighed into a two-dram vial, followed in turn by 1.2 mL of methylene chloride, 0.18 gram (0.0004 mole) of {1-[(4-(2-pyridyloxy)phenyl)methyl](4-piperidyl)}[4-(trifluoromethyl)phenyl]methanol, and 0.06 mL of triethylamine. The vial was tightly capped and gently shaken at 35° C. for 16 hours using a vortex mixer. After this time, the methylene chloride was removed under a nitrogen stream to provide a residue. The residue was purified with column chromatography on silica gel using mixtures of acetone and methylene chloride as eluants. The appropriate fractions were combined and concentrated under reduced pressure, yielding 0.2 gram of Compound 227. The NMR spectrum was consistent with the proposed structure.

EXAMPLE 3

This example illustrates one protocol for the preparation of [(1-{[4-(2-methyl(1,2,3,4-tetraazol-5-yl))phenyl]methyl}(4-piperidyl))[4-(trifluoromethoxy)phenyl]methyl]propylsulfonylamide (Compound 433 in table below)

Step A Synthesis of ethyl 1-{[4-(2-methyl-1,2,3,4-tetraazol-5-yl)phenyl]methyl}piperidine-4-carboxylate as an intermediate A solution of 30.0 grams (0.191 mole) of ethyl isonipecotate in 75 mL of DMSO and 99 mL of methanol was stirred and 61.7 grams (0.477 mole) of N,N-diisopropylethylamine, followed by 40.2 grams (0.159 mole) of 5-[4-(bromomethyl)phenyl]-2-methyl-1,2,3,4-tetraazole (known compound-U.S. Pat. No. 5,639,763) were added. Upon completion of addition the reaction mixture was stirred at ambient temperature for about 72 hours. The reaction mixture was then diluted with 175 mL of ethyl acetate and washed with 175 mL of a solution comprised of one part of an aqueous solution saturated with sodium chloride and one part of water. The organic layer was concentrated under reduced pressure to a residue. NMR analysis of the residue indicated the presence of some of the starting ethyl isonipecotate. The residue was dissolved in 370 mL of methanol and water was added to precipitate a solid material. After standing for about 20 minutes, the solid was collected by filtration and was washed with a cold solution of one part methanol and one part of water. The solid was dried, yielding 32.9 grams of the subject compound. A second crop of solid was collected from the filtrate, yielding an additional 11.0 grams of the subject compound. The NMR spectra were consistent with the proposed structure.

Step B Synthesis of 1-{[4-(2-methyl-1,2,3,4-tetraazol-5-yl)phenyl]methyl}piperidinecarboxylic acid as an intermediate A solution of 51.6 grams (0.157 mole) of ethyl 1-{[4-(2-methyl-1,2,3,4-tetraazol-5-yl)phenyl]methyl}piperidine-4-carboxylate in 264 mL of THF was stirred, and a solution of 6.9 grams (0.172 mole) of sodium hydroxide in 186 mL of water, followed by 160 mL of methanol were added. Upon completion of addition, the reaction mixture was stirred at ambient temperature for two hours. After this time, the reaction mixture was concentrated under reduced pressure to a residue. The residue was dissolved in 250 mL of water and the solution was cooled to about 4° C. The solution was then neutralized with concentrated hydrochloric acid, yielding a solid. The water was removed under a stream of nitrogen during about a 60 hour period. The resultant solid was dried in a vacuum oven, yielding 53.4 grams of the subject compound. The NMR spectrum was consistent with the proposed structure.

Step C Synthesis of 1-{[4-(2-methyl(1,2,3,4-tetraazol-5-yl))phenyl]methyl}(4-piperidyl)-N-methoxy-N-methylcarboxamide as an intermediate A solution of 47.2 grams (0.157 mole) of 1-{[4-(2-methyl-1,2,3,4-tetraazol-5-yl)phenyl]methyl}piperidinecarboxylic acid in 675 mL of DMF was stirred, and 18.3 grams (0.188 mole) of N,O-dimethylhydroxylamine hydrochloride was added. The reaction mixture was cooled to 0° C., and 30.7 grams (0.188 mole) of diethyl cyanophosphonate, followed by 34.9 grams (0.345 mole) of triethylamine were added. Upon completion of addition, the reaction mixture was allowed to warm to ambient temperature as it stirred for two hours. The reaction mixture was then diluted with ethyl acetate and a 1:1 solution of an aqueous solution saturated with sodium chloride and water. The aqueous layer was separated from the organic layer and washed with ethyl acetate. The wash was then combined with the organic layer, and the combination was washed with one portion of water, and then with four 150 mL portions of an aqueous solution saturated with sodium chloride. The mixture was dried with sodium sulfate, filtered, and concentrated under reduced pressure, yielding 44.1 grams of the subject compound. The NMR spectrum was consistent with the proposed structure.

Step D Synthesis of 1-{[4-(2-methyl(1,2,3,4-tetraazol-5-yl))phenyl]methyl}(4-piperidyl)-4-(trifluoromethoxy)phenyl ketone as an intermediate To a Grignard Reagent prepared from 46.2 grams (0.192 mole) of 1-bromo-4-trifluoromethoxybenzene and 5.0 grams (0.205 gram-atom) of magnesium metal in 133 mL of THF was added a solution of 44.1 grams (0.128 mole) of 1-{[4-(2-methyl(1,2,3,4-tetraazol-5-yl))phenyl]methyl}(4-piperidyl)-N-methoxy-N-methylcarboxamide in 65 mL of THF. Upon completion of addition, the reaction mixture was warmed to 60° C., where it stirred for an additional 60 minutes. After this time, the reaction mixture was poured into a cold solution of 15.5 mL of concentrated hydrochloric acid in 101.5 mL of ethanol, and stirred for five minutes. The mixture was diluted methylene chloride and washed with an aqueous solution saturated with sodium bicarbonate. The organic layer was washed with an aqueous solution saturated with sodium chloride, dried with sodium sulfate and filtered. The filtrate was concentrated under reduced pressure to a residue, yielding 58.5 grams of the subject compound. The NMR spectrum was consistent with the proposed structure.

Step E Synthesis of (hydroxyimino)(1-[[4-(2-methyl(1,2,3,4-tetraazol-5-yl))phenyl]methyl]}(4-piperidyl)[4-(trifluoromethoxy)phenyl]methane as an intermediate A solution of 40.0 grams (0.090 mole) of 1-{[4-(2-methyl(1,2,3,4-tetraazol-5-yl))phenyl]methyl}(4-piperidyl)-4-(trifluoromethoxy)phenyl ketone in 641 mL of ethanol was stirred and 6.3 grams (0.091 mole) of hydroxylamine hydrochloride, followed by 9.1 grams (0.090 mole) of triethylamine were added. Upon completion of addition, the reaction mixture was warmed to reflux where it stirred 16 hours. After this time an additional 0.1 equivalent each of hydroxylamine hydrochloride and triethylamine were added to the reaction mixture, and heating under reflux was continued for another three hours. The reaction mixture was then cooled and concentrated under reduced pressure to a residue. The residue was dissolved in methylene chloride and washed in turn with an aqueous solution saturated with sodium bicarbonate and an aqueous solution saturated with sodium chloride. The organic layer was concentrated under reduced pressure to a residue. The residue was dried under reduced pressure, yielding 39.9 grams of the subject compound. The NMR spectrum was consistent with the proposed structure.

Step F Synthesis of 1-[[4-(2-methyl(1,2,3,4-tetraazol-5-yl)phenyl]methyl}(4-piperidyl))[4-(trifluoromethoxy)phenyl]methylamine as an intermediate A stirred solution of 39.9 grams (0.087 mole) of (hydroxyimino)(1-[[4-(2-methyl(1,2,3,4-tetraazol-5-yl))phenyl]methyl]}(4-piperidyl)[4-(trifluoromethoxy)phenyl]methane in 100 mL of THF was cooled to −10° C., and 19.1 mL (0.191 mole-1M in THF) of lithium aluminum hydride was added. Upon completion of addition, the reaction mixture was warmed to 65° C. where it stirred for 2.5 hours. After this time, the reaction mixture was cooled to about ambient temperature and added by cannulation to a cold, stirred aqueous solution saturated with ammonium chloride. The mixture was then extracted ethyl acetate, in which the extracts were separated from the aqueous layer by cannulation. The combined extracts were concentrated under reduced pressure to a residue. The residue was dried, yielding 36.1 grams of the subject compound. The NMR spectrum was consistent with the proposed structure.

Step G Synthesis of Compound 433

A solution of 0.30 gram (0.0007 mole) of 1-[[4-(2-methyl(1,2,3,4-tetraazol-5-yl)phenyl]methyl}(4-piperidyl))[4-(trifluoromethoxy)phenyl]methylamine, 0.10 gram (0.0007 mole) of 1-propanesulfonyl chloride, and 0.11 gram (0.0011 mole) of triethylamine in 7 mL of methylene chloride was stirred at ambient temperature for about 18 hours. After this time, the reaction mixture was concentrated under reduced pressure to a residue. The residue was purified with column chromatography on silica gel using hexane, ethyl acetate, and mixtures thereof as eluants. The appropriate fractions were combined and concentrated under reduced pressure, yielding 0.07 gram of Compound 433. The NMR spectrum was consistent with the proposed structure.

EXAMPLE 4

This example illustrates one protocol for the preparation of 2-[(1-{[4-(2-methyl(1,2,3,4-tetraazol-5-yl))phenyl]methyl}(4-piperidyl))[4-(trifluoromethoxy)phenyl]methoxy]-5-(trifluoromethyl)pyridine (Compound 434 in table below)

Step A Synthesis of 4-pyridyl 4-(trifluoromethoxy)phenyl ketone as an intermediate To a Grignard Reagent prepared from 21.3 grams (0.088 mole) of 1-bromo-4-trifluoromethoxybenzene and 2.5 grams (0.102 gram-atom) of magnesium metal was added a solution of 7.1 grams (0.068 mole) of 4-cyanopyridine in 50 mL of THF. Upon completion of addition, the reaction mixture was stirred at 40° C. for 18 hours. After this time, the reaction mixture was poured into an aqueous dilute solution of ammonium chloride, and was acidified to a pH of 3 with aqueous 10% hydrochloric acid. The mixture was extracted with methylene chloride and the combined extracts were dried with sodium sulfate. The mixture was filtered, and the filtrate was concentrated under reduced pressure to a residue. The residue was purified with column chromatography on silica gel using acetone, methylene chloride, and mixtures thereof as eluants. The appropriate fractions were combined and concentrated under reduced pressure, yielding the subject compound. The NMR spectrum was consistent with the proposed structure.

Step B Synthesis of 4-pyridyl 4-(trifluoromethoxy)phenyl ketone hydrochloride as an intermediate A solution of 20.0 grams (0.075 mole) of 4-pyridyl 4-(trifluoromethoxy)phenyl ketone in 350 mL of ethanol was stirred as hydrogen chloride gas was bubbled through during a five minute period. Upon completion of addition, the reaction mixture was stirred for one hour, and then it was filtered to collect a solid. The solid was washed with three portions of diethyl ether, and dried in a vacuum oven, yielding about 22.0 grams of the subject compound. The NMR spectrum was consistent with the proposed structure.

Step C Synthesis of 4-piperidyl[4-(trifluoromethoxy)phenyl]methanol, hydrochloride as an intermediate Platinum oxide, 1.0 gram (catalyst) was added to a 2000 mL Parr hydrogenation bottle, and the bottle was purged with dry nitrogen. To the bottle was then added 1.0 gram of platinum oxide and a solution of 22.0 grams (0.072 mole) of 4-(trifluoromethoxy)phenyl ketone hydrochloride in 750 mL of ethanol. The bottle was placed in a Parr hydrogenator, and the contents of the bottle were subjected to hydrogenation conditions. When the theoretical amount of hydrogen gas was taken up, the bottle was removed from the hydrogenator, and the contents filtered through diatomaceous earth. The filter cake was washed with methylene chloride, and the combined filtrate and washes were concentrated under reduced pressure, yielding the subject compound. The NMR spectrum was consistent with the proposed structure.

Step D Synthesis of {1-[(2-methyl(1,2,3,4-tetraazol-5-yl))methyl](4-piperidyl)}[4-(trifluoromethoxy)phenyl]methanol as an intermediate This compound was prepared in a manner analogous to that of Step E of Example 3, using 7.0 grams (0.026 mole) of 4-piperidyl[4-(trifluoromethoxy)phenyl]methanol, hydrochloride, 6.8 grams (0.026 mole) of 5-[4-(bromomethyl) phenyl]-2-methyl-1,2,3,4-tetraazole (prepared in a manner analogous to that of Steps A–C of Example 4), and 9.9 grams (0.077 mole) of N,N-diisopropylethylamine in about 40 mL of DMSO. The NMR spectrum was consistent with the proposed structure.

Step E Synthesis of Compound 434

A stirred mixture of 0.89 gram (0.002 mole) of {1-[(2-methyl(1,2,3,4-tetraazol-5-yl))methyl](4-piperidyl)}[4-(trifluoromethoxy)phenyl]methanol, 0.36 gram (0.002 mole) of 2-fluoro-5-trifluoromethylpyridine, and 0.08 gram (0.002 mole) of 60% sodium hydride (in mineral oil) in about 10 mL of DMSO was heated at 85–90° C. for three hours. After this time, the reaction mixture was allowed to cool to ambient temperature, and then it was poured into water. The mixture was extracted with diethyl ether and the combined extracts were dried with magnesium sulfate. The mixture was filtered and the filtrate was concentrated under reduced pressure to a residue. The residue was purified with column chromatography on silica gel using mixtures of methylene chloride and methanol eluants. The appropriate fractions were combined and concentrated under reduced pressure, yielding 0.63 gram of Compound 434. The NMR spectrum was consistent with the proposed structure.

EXAMPLE 5

This example illustrates one protocol for the preparation of N-(3,5-difluorophenyl)({1-[(4-pyrimidin-2-yloxyphenyl)methyl](4-1,2,5,6-tetrahydropyridyl)}[4-(trifluoromethyl)phenyl]methoxy)carboxamide (Compound 786 in table below)

Step A Synthesis of
2-[4-(chloromethyl)phenoxy]pyrimidine as an intermediate

A stirred solution of 4.0 grams (0.02 mole) of (4-pyrimidin-2-yloxyphenyl)methanol (known compound) and seven drops of pyridine in 35 mL of methylene chloride was cooled in an ice-water bath and a solution of 2.0 mL (0.027 mole) of thionyl chloride was added dropwise. Upon completion of addition the reaction mixture was stirred at about 10° C. to 20° C. during a three-hour period. After this time, the reaction mixture was poured into a cold aqueous solution of sodium bicarbonate. The mixture was then stirred for 30 minutes and the organic layer was separated. The aqueous layer was extracted with one 50 mL portion of methylene chloride. The extract was combined with the organic layer, and the combination was passed through silicone-coated filter paper to remove traces of water. The filtrate was concentrated under reduced pressure, yielding grams of the subject compound. The NMR spectrum was consistent with the proposed structure.

Step B Synthesis of
4-pyridyl[4-(trifluoromethyl)phenyl]methanol as an intermediate Under a dry nitrogen atmosphere, an appropriate amount of freshly cut magnesium chips was suspended in 150 mL of THF. To this was added about 5% of a solution of 22.5 grams (0.100 mole) of 4-bromobenzotrifluoride in 75 mL of THF. The reaction mixture was then warmed to about 30° C. to initiate the reaction. Once the reaction was proceeding, the remainder of the solution of 4-bromobenzotrifluoride was added during a one hour period, at a rate to maintain the reaction mixture temperature at about 34° C. to about 38° C. Upon completion of addition, the reaction mixture was stirred during a one hour period, as it cooled to ambient temperature. After this time a solution of 8.5 grams (0.075 mole) of 4-pyridinecarboxaldehyde in 75 mL of THF was added portion wise while maintaining the reaction mixture temperature below 30° C. Upon completion of addition the reaction mixture was stirred at ambient temperature for about 18 hours. With vigorous stirring the reaction mixture was then poured into 600 mL of aqueous 10% ammonium chloride. The mixture was extracted with two 300 mL portions of ethyl acetate. The combined extracts were washed with 250 mL of an aqueous solution saturated with sodium chloride, then dried with magnesium sulfate. The mixture was filtered and the filtrate was concentrated under reduced pressure, yielding 21.2 grams of the subject compound. The product was used without purification in the following reaction.

Step C Synthesis of
4-pyridyl[4-(trifluoromethyl)phenyl]methanol hydrochloride salt as an intermediate A solution of 21.2 grams (0.070 mole) of 4-pyridyl[4-(trifluoromethyl)phenyl]methanol in 500 mL of ethyl acetate was stirred vigorously and anhydrous hydrogen chloride gas was slowly added during a 15 minute period, below the surface of the solution. The reaction mixture was then stirred for an additional 15 minutes, and a solid was collected by filtration. The solid was washed with ethyl acetate and dried, yielding 11.4 grams of the subject compound. The NMR spectrum was consistent with the proposed structure.

Step D Synthesis of {1-[(4-pyrimidin-2-yloxyphenyl)methyl](4-pyridyl)}[4-(trifluoromethyl)phenyl]methanol, hydrochloride salt as an intermediate A 3.3 gram (0.0113 mole) aliquot of 4-pyridyl[4-(trifluoromethyl)phenyl]methanol, hydrochloride salt was partitioned between diethyl ether and an aqueous solution of sodium bicarbonate. The ether layer was separated and dried with magnesium sulfate. The mixture was filtered and the filtrate was concentrated under reduced pressure to a residue. The residue was dissolved in 100 mL of acetone, and 2.5 grams (0.0113 mole) of 2-[4-(chloromethyl)phenoxy]pyrimidine and 0.2 gram (0.0012 mole) of potassium iodide were added. Upon completion of addition, the reaction mixture was warmed to 50° C. where it stirred for about 18 hours. The reaction mixture was then concentrated under reduced pressure to a residue, and the residue was triturated with 150 mL of diethyl ether, yielding when dried, 5.2 grams of solid product. The NMR spectrum was consistent with the proposed structure.

Step E Synthesis of {1-[(4-pyrimidin-2-yloxyphenyl)methyl](4-1,2,5,6-tetrahydropyridyl)}[4-(trifluoromethyl)phenyl]methanol as an intermediate A stirred solution of 1.0 gram (0.0021 mole) of {1-[(4-pyrimidin-2-yloxyphenyl)methyl](4-pyridyl)}[4-(trifluoromethyl)phenyl]methanol, hydrochloride salt in 30 mL of ethanol was cooled in an ice-water bath, and 0.1 gram (0.0026 mole) of sodium borohydride was added in one portion. Upon completion of addition, the reaction mixture was stirred at about 10° C. to 20° C. during a three-hour period. After this time the reaction mixture was diluted with 100 mL of water and extracted with two 75 mL portions of ethyl acetate. The combined extracts were washed with one 75 mL portion of aqueous 10% lithium chloride, and the combination was dried with sodium sulfate. The mixture was then filtered and the filtrate was concentrated under reduced pressure to a residue. The residue was purified with column chromatography on neutral alumina (6% water) using 1% to 2% methanol/methylene chloride mixtures as eluants. The appropriate fractions were combined and concentrated under reduced pressure, yielding 0.44 gram of the subject compound. The NMR spectrum was consistent with the proposed structure.

Step F Synthesis of Compound 786

This compound was prepared in a manner analogous to that of Step F of Example 2, using 0.44 gram (0.0010 mole) of {1-[(4-pyrimidin-2-yloxyphenyl)methyl](4-1,2,5,6-tetrahydropyridyl)}[4-(trifluoromethyl)phenyl]methanol, 0.21 gram (0.0014 mole) of 3,5-difluorophenylisocyanate, 0.14 gram (0.0014 mole) of triethylamine, and 0.05 gram (catalyst) of 4-dimethylaminopyridine in 15 mL of methylene chloride. The reaction product was purified with column chromatography on silica gel using 10% to 25% acetone/methylene chloride mixtures as eluants. The appropriate fractions were combined and concentrated under reduced pressure, yielding 0.18 gram of Compound 786, mp 85–92° C. The NMR spectrum was consistent with the proposed structure.

EXAMPLE 6

This example illustrates one protocol for the preparation of N-(4-chlorophenyl)({1-[(4-(2-pyridyloxy)phenyl)methyl](4-(1-oxypiperidyl))}[4-(trifluoromethyl)phenyl]methoxy)carboxamide (Compound 395 in table below)

A solution of 12.9 grams (0.0216 mole) of Compound 227 (prepared by the method of Example 2) and 390 grams of methanol was stirred, and 117.7 grams (1.7315 moles) of aqueous 50% hydrogen peroxide was added. Upon completion of addition, the reaction mixture was stirred during a 48 hour period as it was being monitored by high pressure liquid chromatography and NMR analyses for completion of reaction. After this time the reaction mixture was concentrated under reduced pressure to remove the methanol, and then the concentrate was extracted with methylene chloride. The methylene chloride was removed under reduced pressure, leaving a residue. The residue was purified with column chromatography on neutral alumina (6% water) using 1% to 2% methanol/methylene chloride mixtures as eluants. The appropriate fractions were combined and concentrated under reduced pressure, yielding 9.2 grams of Compound 395. The NMR spectrum was consistent with the proposed structure.

EXAMPLE 7

This example illustrates one protocol for the preparation of N-(4-chlorophenyl)({1-ethoxy-1-[(4-(2-pyridyloxy)phenyl)methyl](4-piperidyl)}[4-(trifluoromethyl)phenyl]methoxy)carboxamide, ethyl sulfate salt (Compound 860 in table below)

A stirred solution of 0.5 gram (0.0008 mole) of Compound 493 (prepared in Example 6) and 0.25 gram (0.0016 mole) of diethyl sulfate in 10 mL of chloroform was heated at reflux during a 24 hour period. After this time the reaction mixture was concentrated under reduced pressure to a residue. The residue was triturated with diethyl ether during a 24 hour period, then washed with fresh diethyl ether. The residue was dried under reduced pressure at 60° C., yielding 0.57 gram of solid material. The solid was dissolved in one mL of chloroform, and re-precipitated with about 10 mL of diethyl ether. The chloroform was decanted and the remaining solid was dried under reduced pressure at 60° C., yielding 0.45 gram of Compound 860. The NMR spectrum was consistent with the proposed structure.

EXAMPLE 8

This example illustrates one protocol for the preparation of 2-{4-[{bis[4-(trifluoromethyl)phenyl]methylene}piperidyl)methyl]phenoxy}pyrimidine (Compound 824 in table below) as an intermediate This compound was prepared in a manner analogous to that of Step B of Example 1, using 26.0 grams (0.1011 mole) of 2-[4-(chloromethyl)phenoxy]pyrimidine hydrochloride (prepared in a manner analogous to Step A of Example 7) and 34.0 grams (0.0882 mole) of 4-{bis[4-(trifluoromethyl)phenyl]methylene}piperidine (prepared in Step A of Example 2), 36.0 grams (0.2604 mole) of potassium carbonate in 200 grams of DMF. The yield of Compound 824 was 41.0 grams. The NMR spectrum was consistent with the proposed structure.

EXAMPLE 9

This example illustrates one protocol for the preparation of 2-{4-[{bis[4-(trifluoromethyl)phenyl]methylene}1-oxypiperidyl)methyl]phenoxy}pyrimidine (Compound 854 in table below)

This compound was prepared in a manner analogous to that of Step E of Example 1, using 40.0 grams (0.0702 mole) of Compound 824 (prepared in Example 8) and 50 grams of 30% hydrogen peroxide in 140 mL of methanol. The yield of Compound 854 was 35.0 grams. The NMR spectrum was consistent with the proposed structure.

EXAMPLE 10

This example illustrates one protocol for the preparation of 2-{4-[(9-aza-3-{bis[4-(trifluoromethyl)phenyl]methylene}bicyclo[3.3.1]non-9-yl)methyl]phenoxy}pyridine (Compound 117 in table below)

This compound was prepared in a manner analogous to that of Step A of Example 1, using 0.18 gram (0.00025 mole) of {9-aza-9-[(4-(2-pyridyloxy)phenyl)nethyl]bicyclo[3.3.1]non-3-yl}bis[4-(trifluoromethyl)phenyl]methanol (known compound-disclosed in US Statutory Invention Registration H1,838) in trifluoroacetic acid, yielding Compound 117. The NMR spectrum was consistent with the proposed structure.

EXAMPLE 11

This example illustrates one protocol for the preparation of 1-[(1-[[4-(2-ethyl(1,2,3,4-tetraazol-5-yl))phenyl]methyl}(4-piperidylidene))[4-(trifluoromethoxy)phenyl]methoxy]-4-(trifluoromethoxy)benzene (Compound 137 in table below)

Step A Synthesis of 5-(4-methylphenyl)-1,2,3,4-tetraazole as an intermediate A solution of 10.0 grams (0.085 mole) of para-toluonitrile in 160 mL of DMF was stirred and 5.6 grams (0.085 mole) of sodium azide was added. Upon completion of addition, the reaction mixture was warmed to 135° C. where it stirred for three hours. The reaction mixture was then cooled and poured into 200 mL of stirred, cold aqueous 1N hydrochloric acid. Upon completion of addition, the mixture was stirred for five minutes and filtered to collect a white solid. The solid was dried for 16 hours in a vacuum oven at 35–40° C., yielding 7.1 grams of the subject compound. The reaction was repeated.

Step B Synthesis of 2-ethyl-5-(4-methylphenyl)-1,2,3,4-tetraazole as an intermediate A solution of 20.0 grams (0.125 mole) of 5-(4-methylphenyl)-1,2,3,4-tetraazole in 230 mL of acetonitrile was stirred and 48.7 grams (0.312 mole) of iodoethane, followed by 17.3 grams (0.125 mole) of potassium carbonate were added. Upon completion of addition, the reaction mixture was warmed to reflux, where it stirred for two hours. After this time, the reaction mixture was concentrated under reduced pressure to a residue. The residue was taken up in ethyl acetate and filtered. The filtrate was concentrated under reduced pressure to a residue. The residue was purified with column chromatography on silica gel using 1:4 ethyl acetate:hexane as an eluant. The appropriate fractions were combined and concentrated under reduced pressure, yielding 18.8 grams of the subject compound. The NMR spectrum was consistent with the proposed structure.

Step C Synthesis of 5-[4-(bromomethyl)phenyl]-2-ethyl-1,2,3,4-tetraazole as an intermediate A solution of 18.8 grams (0.100 mole) of 2-ethyl-5-(4-methylphenyl)-1,2,3,4-tetraazole in 156 mL of carbon tetrachloride was stirred, and 19.6 grams (0.110 mole) of N-bromosuccinimide, followed by 0.24 gram (0.001 mole) of benzoyl peroxide were added. Upon completion of addition, the reaction mixture was heated to reflux where it stirred for 90 minutes. After this time the reaction mixture was cooled and filtered. The filtrate was concentrated under reduced pressure, yielding 27.7 grams of the subject compound. The NMR spectrum was consistent with the proposed structure.

Step D Synthesis of ethyl 1-{[4-(2-ethyl-1,2,3,4-tetraazol-5-yl)phenyl]methyl}piperidine-4-carboxylate as an intermediate A solution of 16.0 grams (0.102 mole) of ethyl isonipecotate in 50 mL of DMSO and 66 mL of methanol was stirred, and 44 mL (0.256 mole) of N,N-diisopropylethylamine, followed by 22.8 grams (0.085 mole) of 5-[4-(bromomethyl)phenyl]-2-ethyl-1,2,3,4-tetraazole were added. Upon completion of addition, the reaction mixture was stirred at ambient temperature for about 72 hours. After this time, the reaction mixture was diluted with 130 mL of ethyl acetate, and washed with a 1:1 solution of an aqueous solution saturated with sodium chloride and water. The organic layer was then washed with an aqueous solution saturated with sodium chloride and water, dried with sodium sulfate, and filtered. The filtrate was concentrated under reduced pressure to a residue. The residue was purified with column chromatography on silica gel using mixtures of methylene chloride and acetone. The appropriate fractions were combined and concentrated under reduced pressure, yielding 20.9 grams of the subject compound. The NMR spectrum was consistent with the proposed structure.

Step E Synthesis of 1-{[4-(2-ethyl-1,2,3,4-tetraazol-5-yl)phenyl]methyl}piperidinecarboxylic acid as an intermediate A solution of 20.9 grams (0.078 mole) of ethyl 1-{[4-(2-ethyl-1,2,3,4-tetraazol-5-yl)phenyl]methyl}piperidine-4-carboxylate in 132 mL of THF was stirred, and a solution of 3.4 grams (0.086 mole) of sodium hydroxide in 93 mL of water, followed by 80 mL of methanol were added. Upon completion of addition, the reaction mixture was stirred at ambient temperature for two hours. After this time, the reaction mixture was concentrated under reduced pressure to a residue. The residue was taken up in toluene and concentrated under reduced pressure to remove any remaining solvents. The residue was dissolved in 100 mL of water and extracted with diethyl ether. The aqueous layer was cooled to about −2° C., and was brought to a pH of 7 with concentrated hydrochloric acid. The resultant solid was collected by filtration, washed with water, and dried, yielding 18.2 grams of the subject compound. The NMR spectrum was consistent with the proposed structure.

Step F Synthesis of 1-{[4-(2-ethyl(1,2,3,4-tetraazol-5-yl))phenyl]methyl}(4piperidyl)-N-methoxy-N-methylcarboxamide as an intermediate A solution of 18.2 grams (0.058 mole) of 1-{[4-(2-ethyl-1,2,3,4-tetraazol-5-yl)phenyl]methyl}piperidinecarboxylic acid in 240 mL of DMF was stirred, and 6.8 grams (0.070 mole) of N,O-dimethylhydroxylamine hydrochloride was added. The reaction mixture was cooled to 0° C., and 11.3 grams (0.070 mole) of diethyl cyanophosphonate, followed by 17.8 mL (0.127 mole) of triethylamine were added. Upon completion of addition, the reaction mixture was stirred for two hours, and then it was diluted with ethyl acetate and a 1:1 solution of an aqueous solution saturated with sodium chloride and water. To aid in separating the organic layer from the aqueous layer, hexane and solid sodium chloride were added to the reaction mixture. The organic layer was organic layer was separated and washed with water, and then with an aqueous solution saturated with sodium chloride. The mixture was dried with sodium sulfate, filtered, and concentrated under reduced pressure, yielding 18.5 grams of the subject compound. The NMR spectrum was consistent with the proposed structure.

Step G Synthesis of 1-{[4-(2-ethyl(1,2,3,4-tetraazol-5-yl))phenyl]methyl}(4-piperidyl)-4-(trifluoromethoxy)phenyl ketone as an intermediate To a Grignard Reagent prepared from 9.3 grams (0.039 mole) of 1-bromo-4-trifluoromethoxybenzene and 1.0 gram (0.041 gram-atom) of magnesium metal in 27 mL of THF was added a solution of 9.3 grams (0.026 mole) of 1-{[4-(2-ethyl(1,2,3,4-tetraazol-5-yl))phenyl]methyl}(4-piperidyl)-N-methoxy-N-methylcarboxamide in 13 mL of THF. Upon completion of addition, the reaction mixture was stirred at ambient temperature for 90 minutes, and then it was warmed to 70° C., where it stirred for an additional 60 minutes. After this time, the reaction mixture was poured into a cold solution of 13 mL of concentrated hydrochloric acid in 93 mL of ethanol, and stirred for ten minutes. The mixture was diluted methylene chloride and washed with an aqueous dilute solution of sodium bicarbonate. The organic layer was dried with sodium sulfate and filtered. The filtrate was concentrated under reduced pressure to a residue, yielding 10.2 grams of the subject compound. The NMR spectrum was consistent with the proposed structure.

Step H Synthesis of {4-[chloro(1-{[4-(2-ethyl(1,2,3,4-tetraazol-5-yl))phenyl]methyl}(4-piperidyl))methyl]phenoxy}trifluoromethane as an intermediate A solution of 1-{[4-(2-ethyl(1,2,3,4-tetraazol-5-yl))phenyl]methyl}(4-piperidyl)-4-(trifluoromethoxy)phenyl ketone and phosphorous oxychloride in diethyl ether is heated under reflux for about two hours. After this time, the reaction mixture is concentrated under reduced pressure to yield the subject compound.

Step I Synthesis of Compound 137

A solution of {4-[chloro(1-{[4-(2-ethyl(1,2,3,4-tetraazol-5-yl))phenyl]methyl}(4-piperidyl))methyl]phenoxy}trifluoromethane, 4-(trifluoromethoxy)phenol and potassium carbonate in DMF is stirred at ambient temperature for about two hours. After this time the reaction mixture is poured into water and the mixture is extracted with ethyl acetate. The extract is dried with magnesium sulfate and filtered. The filtrate is concentrated under reduced pressure, yielding compound 137.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

TABLE 1

Insecticidal N-substituted-4-(substituted arylmethyl)piperidines and Pyridines

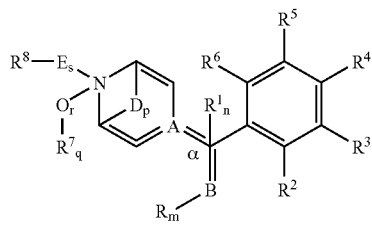

I

Compounds of the formula I where A is C, forming a piperidine ring; m, p, q, r and s are 0; n is 0, forming a double bond between the methyl carbon (α) and the 4-position of the piperidine ring; and B is phenyl substituted with $R^9$, $R^{10}$, $R^{11}$, $R^{12}$, and $R^{13}$; where $R^2$, $R^5$, $R^6$, $R^9$, $R^{10}$, $R^{12}$, and $R^{13}$ are hydrogen:

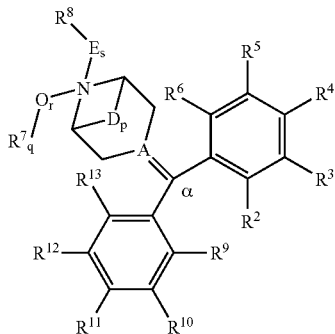

I

| Cmpd. No. | $R^3$ | $R^4$ | $R^8$ | $R^{11}$ |
|---|---|---|---|---|
| 1 | H | H | H | H |
| 2[1] | H | H | H | H |
| 3[4] | H | H | H | H |
| 4[1] | Cl | H | H | H |
| 5[1] | H | Cl | H | H |
| 6[1] | F | H | H | H |
| 7[6] | H | F | H | F |
| 8 | H | $CF_3$ | H | $CF_3$ |
| 9 | H | $OCF_3$ | H | $OCF_3$ |
| 10 | H | $C_2H_5$ | H | $C_2H_5$ |
| 11 | H | Cl | $CH_3$ | H |
| 12 | H | $OCF_3$ | $CH_3$ | $OCF_3$ |

TABLE 1-continued

Compounds of formula I where A is C, forming a piperidine ring; m, p, q, and r are 0; s is 1; n is 0, forming a double bond between the methyl carbon (α) and the 4-position of the piperidine ring; B is phenyl substituted with $R^9$, $R^{10}$, $R^{11}$, $R^{12}$, and $R^{13}$; where $R^2$, $R^5$, $R^6$, $R^9$, $R^{12}$, and $R^{13}$ are hydrogen:

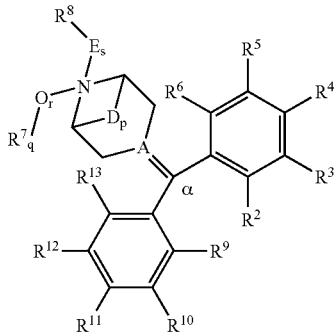

I

| Cmpd. No | $R^3$ | $R^4$ | E | x | $R^{27}/R^{28}$ | y | $R^{29}/R^{30}$ | $R^8$ | $R^{10}$ | $R^{11}$ |
|---|---|---|---|---|---|---|---|---|---|---|
| 13 | H | $C_2H_5$ | $(CR^{27}R^{28})_x$—$(CR^{29}R^{30})_y$ | 1 | H H | 0 | — | 4-fluoroindol-3-yl | H | $C_2H_5$ |
| 14 | H | H | $(CR^{27}R^{28})_x$—$(CR^{29}R^{30})_y$ | 1 | H H | 1 | H H | indol-3-yl | H | H |
| 15 | H | F | $(CR^{27}R^{28})_x$—$(CR^{29}R^{30})_y$ | 1 | H H | 1 | H H | 2-thioxo-1,3-dihydroquinolin-4-on-3-yl | H | F |
| 16 | H | F | $(CR^{27}R^{28})_x$—$(CR^{29}R^{30})_y$ | 1 | H H | 1 | H H | 7-methyl-4-hydro-1,3-thiazolino[3,2-a]pyrimidin-5-on-6-yl | H | H |
| 17 | H | F | $(CR^{27}R^{28})_x$—$(CR^{29}R^{30})_y$ | 1 | H H | 1 | H H | 7-methyl-4-hydro-1,3-thiazolino[3,2-a]pyrimidin-5-on-6-yl | H | F |
| 18[1] | $CF_3$ | H | $C_3H_6$ | — | — | — | — | piperidin-1-yl | $CF_3$ | H |
| 19[7] | H | H | $C_3H_6$ | — | — | — | — | 1,2,3,4-tetrahydro-quinolin-1-yl | H | H |
| 20 | H | H | $C_4H_8$ | — | — | — | — | $NH_2$ | H | H |
| 21 | H | H | $C_4H_8$ | — | — | — | — | benzo[c]azoline-1,3-dion-2-yl | H | H |
| 22 | H | H | $C(=O)C_2H_4$ | — | — | — | — | morpholin-1-yl | H | H |
| 23 | H | $SCH_3$ | $C(=O)$ | — | — | — | — | $OC(CH_3)_3$ | H | $SCH_3$ |
| 24[1] | H | H | $C_3H_6C(=O)$ | — | — | — | — | $OC(CH_3)_3$ | H | H |
| 25 | H | H | $C_4H_3NHC(=O)$ | — | — | — | — | 2-(pyrid-3-yl)-ethenyl | H | H |
| 26 | H | H | $C_4H_8NHC(=O)$ | — | — | — | — | 2-(2-methylpyrid-5-yl)ethenyl | H | H |
| 27 | H | H | $C(=S)NH$ | — | — | — | — | $CH_3$ | H | H |

Compounds of formula I where A is C, forming a piperidine ring; m, p, q, and r are 0; s is 1; n is 0, forming a double bond between the methyl carbon (α) and the 4-position of the piperidine ring; E is, unless otherwise noted, —$(CR^{27}R^{28})_x$—$(CR^{29}R^{30})_y$ where x is 1 and y is 0; $R^8$ is phenyl substituted with $R^{22}$, $R^{23}$, $R^{24}$, $R^{25}$ and $R^{26}$; B is phenyl substituted with $R^9$, $R^{10}$, $R^{11}$, $R^{12}$, and $R^{13}$; where $R^2$, $R^5$, $R^6$, $R^9$, $R^{12}$ $R^{13}$, $R^{25}$, $R^{26}$, $R^{27}$ and $R^{28}$ are hydrogen;

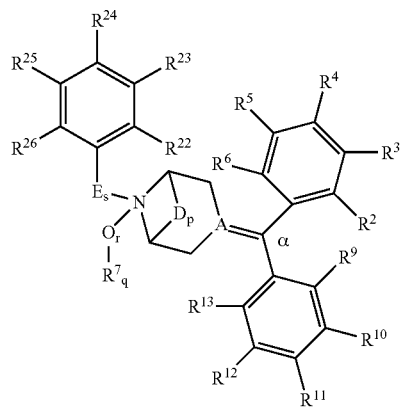

I

| Cmpd. No. | $R^3/R^4$ | $R^{22}$ | $R^{23}$ | $R^{24}$ | $R^{10}/R^{11}$ |
|---|---|---|---|---|---|
| 28 | H/F | H | H | H | H Cl |

TABLE 1-continued

| | | | | | |
|---|---|---|---|---|---|
| 29 | H/F | H | H | H | H F |
| 30 | H/CF₃ | H | H | H | H H |
| 31 | H/CF₃ | H | H | H | H F |
| 32 | H/OCF₃ | H | H | H | H H |
| 33 | H/CF₃ | H | H | Br | H CF₃ |
| 34 | H/CF₃ | H | H | F | H H |
| 35 | H/OCF₃ | H | H | F | H H |
| 36 | H/Cl | H | F | F | H H |
| 37 | H/F | H | F | F | H H |
| 38 | H/CF₃ | H | F | F | H H |
| 39 | H/Cl | H | H | OCH₃ | H H |
| 40 | H/F | H | H | OCH₃ | H H |
| 41 | H/CF₃ | H | H | OCH₃ | H H |
| 42 | H/OCF₃ | H | H | OCH₃ | H OCF₃ |
| 43 | H/C₂H₅ | H | H | OCH₃ | H C₂H₅ |
| 44 | H/OH | H | H | OC₃H₇ | H OH |
| 45 | CF₃/H | H | H | OC₃H₇ | CF₃ H |
| 46 | H/CF₃ | H | H | OC₃H₇ | H CF₃ |
| 47 | OCF₃/H | H | H | OC₃H₇ | OCF₃ H |
| 48 | H/OCF₃ | H | H | OC₃H₇ | H OCF₃ |
| 49 | H/OCF₃ | OCH₃ | H | OC₃H₇ | H OCF₃ |
| 50 | H/CF₃ | H | H | CO₂C₂H₅ | H CF₃ |
| 51 | H/CF₃ | H | H | CO₂CH(CH₃)₂ | H CF₃ |
| 52 | H/CF₃ | H | H | NHC(=O)CH₃ | H CF₃ |
| 53 | H/CF₃ | H | H | NHC(=O)CF₃ | H CF₃ |
| 54 | H/CF₃ | H | H | NHCO₂CH₃ | H CF₃ |
| 55 | H/CF₃ | H | H | NHCO₂C₂H₅ | H CF₃ |
| 56 | H/CF₃ | H | H | N(CH₃)CO₂C₂H₅ | H CF₃ |
| 57 | H/CF₃ | H | H | NHCO₂C₃H₇ | H CF₃ |
| 58 | H/CF₃ | H | H | NHCO₂CH(CH₃)₂ | H CF₃ |
| 59 | H/CF₃ | H | H | NHCO₂CH₂CH(CH₃)₂ | H CF₃ |
| 60 | H/CF₃ | H | H | CH=NOC₂H₅ | H CF₃ |
| 61 | H/CF₃ | H | H | 1,3-thiazol-2-ylmethoxy | H CF₃ |
| 62 | H/CF₃ | H | H | pyrid-2-yl | H CF₃ |
| 63 | H/CF₃ | H | H | 3-chloropyrid-2-yl | H CF₃ |
| 64 | H/OCF₃ | H | H | 3-chloropyrid-2-yl | H OCF₃ |
| 65 | H/CF₃ | H | H | 5-chloropyrid-2-yl | H CF₃ |
| 66 | H/CF₃ | H | H | 6-chloropyrid-2-yl | H CF₃ |
| 67 | H/CF₃ | H | H | 3-trifluoromethylpyrid-2-yl | H CF₃ |

TABLE 1-continued

| | | | | | | |
|---|---|---|---|---|---|---|
| 68 | H/OCF$_3$ | H | H | 3-trifluoromethylpyrid-2-yl | H | OCF$_3$ |
| 69 | H/CF$_3$ | H | H | 5-trifluoromethylpyrid-2-yl | H | CF$_3$ |
| 70 | H/CF$_3$ | H | H | 3-cyanopyrid-2-yl | H | CF$_3$ |
| 71 | H/CF$_3$ | H | H | 5-cyanopyrid-2-yl | H | CF$_3$ |
| 72 | H/CF$_3$ | H | H | 3-nitropyrid-2-yl | H | CF$_3$ |
| 73 | H/CF$_3$ | H | H | 3-(methoxycarbonylamino)-pyrid-2-yl | H | CF$_3$ |
| 74 | H/CF$_3$ | H | H | 2-methyl-2H-tetrazol-5-yl | H | Cl |
| 75 | H/CF$_3$ | H | H | 2-methyl-2H-tetrazol-5-yl | H | CF$_3$ |
| 76 | H/Cl | H | H | 2-ethyl-2H-tetrazol-5-yl | H | H |
| 77 | H/Cl | H | H | 2-ethyl-2H-tetrazol-5-yl | H | Cl |
| 78 | H/F | H | H | 2-ethyl-2H-tetrazol-5-yl | H | F |
| 79 | H/F | H | H | 2-ethyl-2H-tetrazol-5-yl | H | Cl |
| 80 | H/CF$_3$ | H | H | 2-ethyl-2H-tetrazol-5-yl | H | H |
| 81 | H/CF$_3$ | H | H | 2-ethyl-2H-tetrazol-5-yl | H | F |
| 82 | H/CF$_3$ | H | H | 2-ethyl-2H-tetrazol-5-yl | H | CF$_3$ |
| 83[a] | —OCF$_2$O— | H | H | 2-ethyl-2H-tetrazol-5-yl | —OCF$_2$O— | |
| 84 | H/H | CH$_3$ | Cl | H | H | H |
| 85 | H/H | H | H | H | H | H |

[a]In Cmpd 83, R$^3$ and R$^4$, and R$^{10}$ and R$^{11}$ are taken together with —OCF$_2$O— to form 2,2-difluoro[d]1,3-benzodioxolane rings. In Cmpd. 84, E is C(=S)NH, and in Cmpd. 85, E is C$_2$H$_4$C(=O).

Compounds of formula I where A is C, forming a piperidine ring; n is 0, forming a double bond between the methyl carbon (α) and the 4-position of the piperidine ring; m and p are 0; q is 0 and r is 1, forming an N-oxide; and s is 1; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; B is phenyl substituted with R$^9$, R$^{10}$, R$^{11}$, R$^{12}$, and R$^{13}$; where R$^2$, R$^5$, R$^6$, R$^9$, R$^{12}$, R$^{13}$, R$^{25}$, R$^{26}$, R$^{27}$, and R$^{28}$ are hydrogen:

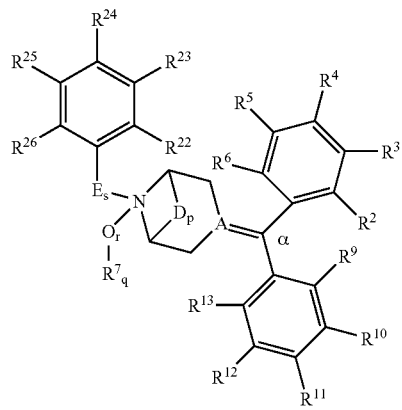

I

| Cmpd. No. | R$^3$ | R$^4$ | R$^{22}$ | R$^{23}$ | R$^{24}$ | R$^{10}$ | R$^{11}$ |
|---|---|---|---|---|---|---|---|
| 86 | H | CF$_3$ | H | H | Br | H | CF$_3$ |
| 87 | H | CF$_3$ | F | H | Br | H | CF$_3$ |

TABLE 1-continued

| | | | | | | | |
|---|---|---|---|---|---|---|---|
| 88 | H | Cl | F | F | | H | H |
| 89 | H | F | F | F | | H | H |
| 90 | H | $CF_3$ | F | F | | H | H |
| 91 | H | Cl | H | $OCH_3$ | | H | H |
| 92 | H | F | H | $OCH_3$ | | H | H |
| 93 | H | $CF_3$ | H | $OCH_3$ | | H | H |
| 94 | H | $CF_3$ | H | $OC_2H_5$ | | H | $CF_3$ |
| 95 | H | $CF_3$ | H | $OC_3H_7$ | | H | $CF_3$ |
| 96 | H | $OCF_3$ | H | $OC_3H_7$ | | H | $OCF_3$ |
| 97[b] | *—$OCF_2CF_2$— | | H | H | $OC_3H_7$ | | *—$OCF_2CF_2$— |
| 98 | H | $CF_3$ | H | H | cyclopropylmethoxy | H | $CF_3$ |
| 99 | H | $CF_3$ | H | H | $CO_2C_2H_5$ | H | $CF_3$ |
| 100 | H | $CF_3$ | H | H | $CO_2CH(CH_3)_2$ | H | $CF_3$ |
| 101 | H | $CF_3$ | H | H | $NHCO_2C_2H_5$ | H | $CF_3$ |
| 102 | H | $CF_3$ | H | H | $NHCO_2C_3H_7$ | H | $CF_3$ |
| 103 | H | $CF_3$ | H | H | $NHCO_2CH(CH_3)_2$ | H | $CF_3$ |
| 104 | H | $CF_3$ | H | H | $NHCO_2CH_2CH(CH_3)_2$ | H | $CF_3$ |
| 105 | H | $CF_3$ | H | H | 1,3-thiazol-2-ylmethoxy | H | $CF_3$ |
| 106 | H | $CF_3$ | H | H | pyrid-2-yloxy | H | $CF_3$ |
| 107 | H | $CF_3$ | H | H | 5-chloropyrid-2-yloxy | H | $CF_3$ |
| 108 | H | $CF_3$ | H | H | 6-chloropyrid-2-yloxy | H | $CF_3$ |
| 109 | H | $CF_3$ | H | H | 3-trifluoromethylpyrid-2-yloxy | H | $CF_3$ |
| 110 | H | $CF_3$ | H | H | 5-trifluoromethylpyrid-2-yloxy | H | $CF_3$ |
| 111 | H | $CF_3$ | H | H | 5-cyanopyrid-2-yloxy | H | $CF_3$ |
| 112 | H | $CF_3$ | H | H | 2-methyl-2H-tetrazol-5-yl | H | $CF_3$ |
| 113 | H | Cl | H | H | 2-ethyl-2H-tetrazol-5-yl | H | $CF_3$ |
| 114 | H | $CF_3$ | H | H | 2-ethyl-2H-tetrazol-5-yl | H | Cl |
| 115[c] | —$OCF_2O$— | | H | H | 2-ethyl-2H-tetrazol-5-yl | | —$OCF_2O$— |

[b]In Cmpd 97, $R^3$ and $R^4$, and $R^{10}$ and $R^{11}$ are taken together with —$OCF_2CF_2$— to form 2,2,3,3-tetra-fluoro-2,3-dihydrobenzo[b]furan rings, where the asterisk denotes connection at $R^3$ and at $R^{10}$.

[c]In Cmpd 115, $R^3$ and $R^4$, and $R^{10}$ and $R^{11}$ are taken together with —$OCF_2O$— to form a 2,2-di-fluoro[d]1,3-benzodioxolane rings.

Compounds of formula I where A is C, forming a piperidine ring; n is 0, forming a double bond between the methyl carbon (α) and the 4-position of the piperidine ring; m and p are 0; r is 0, and q is 1, forming an N-disubstituted derivative; and s is 1; E is —$(CR^{27}R^{28})_x$—$(CR^{29}R^{30})_y$—, where x is 1, and y is 0; $R^8$ is phenyl substituted with $R^{22}$, $R^{23}$, $R^{24}$, $R^{25}$, and $R^{26}$; B is phenyl substituted with $R^9$, $R^{10}$, $R^{11}$, $R^{12}$, and $R^{13}$; where $R^2$, $R^3$, $R^5$, $R^6$, $R^9$, $R^{10}$, $R^{12}$, $R^{13}$, $R^{22}$, $R^{23}$, $R^{25}$, $R^{26}$, $R^{27}$, and $R^{28}$ are hydrogen:

I

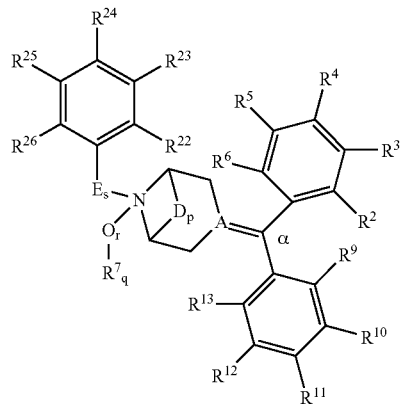

| Comp. No. | $R^4$ | $R^7$ | $R^{11}$ | $R^{24}$ |
|---|---|---|---|---|
| 116[5] | $OCHF_2$ | 4-$(C_3H_7O)PhCH_2$ | $OCHF_2$ | $OC_3H_7$ |

TABLE 1-continued

Compounds of formula I where A is C, forming a piperidine ring; n is 0, forming a double bond between the methyl carbon (α) and the 4-position of the piperidine ring; m, q and r are 0; s is 1; p is other than 0, forming an azabicyclo derivative; $R^8$ is phenyl substituted with $R^{22}$, $R^{23}$, $R^{24}$, $R^{25}$, and $R^{26}$; E is —$(CR^{27}R^{28})_x$—$(CR^{29}R^{30})_y$—, where x is 1, and y is 0; B is phenyl substituted with $R^9$, $R^{10}$, $R^{11}$, $R^{12}$, and $R^{13}$; where $R^2$, $R^3$, $R^5$, $R^6$, $R^9$, $R^{10}$, $R^{12}$, $R^{13}$, $R^{22}$, $R^{23}$, $R^{25}$, $R^{26}$, $R^{27}$, and $R^{28}$ are hydrogen:

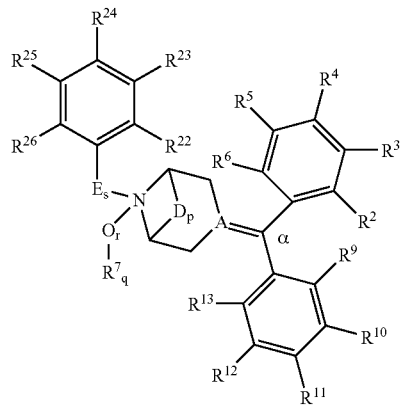

I

| Cmpd. No. | $R^4$ | D | p | $R^{11}$ | $R^{24}$ |
|---|---|---|---|---|---|
| 117 | CF$_3$ | CH$_2$ | 3 | CF$_3$ | pyrid-2-yloxy |

Compounds of formula I where A is C, forming a piperidine ring; n is 0, forming a double bond between the methyl carbon (α) and the 4-position of the piperidine ring; m is 0; q and r are 1, forming a N-substituted oxy derivative; p is other than 0, forming an azabicyclo derivative; s is 1; $R^8$ is phenyl substituted with $R^{22}$, $R^{23}$, $R^{24}$, $R^{25}$, and $R^{26}$; B is phenyl substituted with $R^9$, $R^{10}$, $R^{11}$, $R^{12}$, and $R^{13}$; and E is —$(CR^{27}R^{28})_x$—$(CR^{29}R^{30})_y$—, where x is 1, and y is 0; where $R^2$, $R^3$, $R^5$, $R^6$, $R^9$, $R^{10}$, $R^{12}$, $R^{13}$, $R^{22}$, $R^{23}$, $R^{25}$, $R^{26}$, $R^{27}$, and $R^{28}$ are hydrogen:

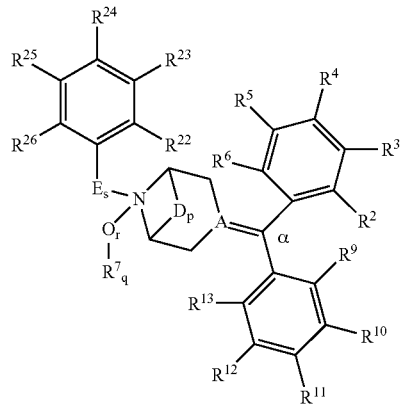

I

| Cmpd. No. | $R^4$ | $R^7$ | D | p | $R^{11}$ | $R^{24}$ |
|---|---|---|---|---|---|---|
| 118[5] | CF$_3$ | C$_2$H$_4$CO$_2$C$_2$H$_5$ | —CH$_2$— | 3 | CF$_3$ | pyrid-2-yloxy |

TABLE 1-continued

Compounds of formula I where A is C, forming a piperidine ring; m, p, q, and r are 0; s is 1; n is 0, forming a double bond between the methyl carbon (α) and the 4-position of the piperidine ring; $R^8$ is pyrid-3-yl substituted with $R^{22}$, $R^{24}$, $R^{25}$, and $R^{26}$; E is —$(CR^{27}R^{28})_x$—$(CR^{29}R^{30})_y$—, where x is 1, and y is 0; B is phenyl substituted with $R^9$, $R^{10}$, $R^{11}$, $R^{12}$, and $R^{13}$; where $R^2$, $R^3$, $R^5$, $R^6$, $R^9$, $R^{10}$, $R^{12}$, $R^{13}$, $R^{22}$, $R^{25}$, $R^{26}$, $R^{27}$, and $R^{28}$ are hydrogen;

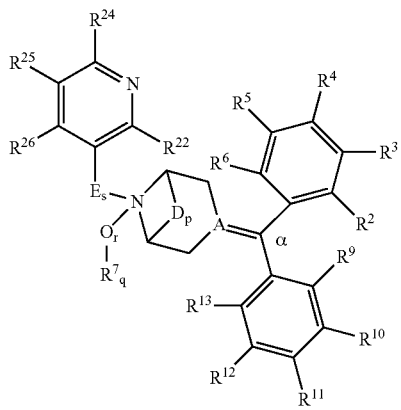

I

| Cmpd. No. | $R^4$ | $R^{11}$ | $R^{24}$ |
|---|---|---|---|
| 119 | $CF_3$ | $CF_3$ | Cl |
| 120 | $CF_3$ | $CF_3$ | $OC_3H_7$ |
| 121 | $CF_3$ | $CF_3$ | C≡N |
| 122 | $CF_3$ | $CF_3$ | $NHC_3H_7$ |
| 123 | $CF_3$ | $CF_3$ | $NHCO_2C_2H_5$ |

Compounds of formula I where A is C, forming a piperidine ring; m, p, and q, are 0; s is 1; n is 0, forming a double bond between the methyl carbon (α) and the 4-position of the piperidine ring; r is 1, forming an N-oxide; $R^8$ is pyrid-3-yl substituted with $R^{22}$, $R^{24}$, $R^{25}$, and $R^{26}$; E is —$(CR^{27}R^{28})_x$—$(CR^{29}R^{30})_y$—, where x is 1, and y is 0; B is phenyl substituted with $R^9$, $R^{10}$, $R^{11}$, $R^{12}$, and $R^{13}$; where $R^2$, $R^3$, $R^5$, $R^6$, $R^9$, $R^{10}$, $R^{12}$, $R^{13}$, $R^{22}$, $R^{25}$, $R^{26}$, $R^{27}$, and $R^{28}$ are hydrogen;

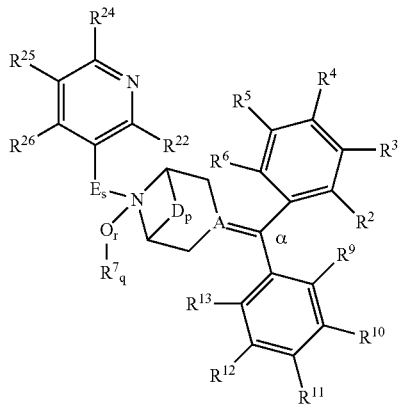

I

| Cmpd. No. | $R^4$ | $R^{11}$ | $R^{24}$ |
|---|---|---|---|
| 124 | $CF_3$ | $CF_3$ | Cl |
| 125 | $CF_3$ | $CF_3$ | $OC_3H_7$ |
| 126 | $CF_3$ | $CF_3$ | C≡N |
| 127 | $CF_3$ | $CF_3$ | $NHC_3H_7$ |
| 128 | $CF_3$ | $CF_3$ | $NHCO_2C_2H_5$ |

TABLE 1-continued

Compounds of formula I where A is C, forming a 1,4-dihydropyridine ring; m, p, q, and r are 0; s is 1; n is 0, forming a double bond between the methyl carbon (α) and the 4-position of the pyridine ring; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; B is phenyl substituted with R$^9$, R$^{10}$, R$^{11}$, R$^{12}$, and R$^{13}$; where R$^2$, R$^3$, R$^5$, R$^6$, R$^9$, R$^{10}$, R$^{12}$, R$^{13}$, R$^{22}$, R$^{23}$ R$^{25}$, R$^{26}$, R$^{27}$, and R$^{28}$ are hydrogen;

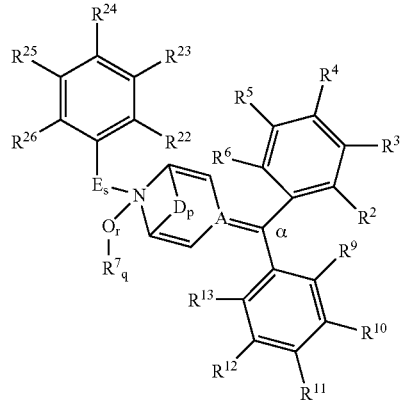

I

| Cmpd. No. | R$^4$ | R$^{11}$ | R$^{24}$ |
|---|---|---|---|
| 129 | CF$_3$ | Br | OC$_3$H$_7$ |
| 130 | CF$_3$ | F | NHCO$_2$C$_2$H$_5$ |
| 131 | CF$_3$ | CF$_3$ | CO$_2$C$_2$H$_5$ |
| 132 | CF$_3$ | CF$_3$ | pyrid-2-yloxy |
| 133 | Cl | Cl | 2-ethyl-2H-tetrazol-5-yl |
| 134 | CF$_3$ | Cl | 2-ethyl-2H-tetrazol-5-yl |
| 135 | CF$_3$ | CF$_3$ | 2-ethyl-2H-tetrazol-5-yl |
| 136 | OCF$_3$ | OCF$_3$ | 2-ethyl-2H-tetrazol-5-yl |

Compounds of formula I where A is C, forming a piperidine ring; p, q, and r are 0; m and s are 1; n is 0, forming a double bond between the methyl carbon (α) and the 4-position of the piperidine ring; E is —(CR$^{27}$R$^{28}$)$_x$—(CR$^{29}$R$^{30}$)$_y$—, where x is 1, and y is 0; B is a bridging group from the methyl carbon to R; R$^8$ is phenyl substituted with R$^{22}$, R$^{23}$, R$^{24}$, R$^{25}$, and R$^{26}$; R is phenyl substituted with R$^{17}$, R$^{18}$, R$^{19}$, R$^{20}$, and R$^{21}$; where R$^2$, R$^3$, R$^5$, R$^6$, R$^{17}$, R$^{18}$, R$^{20}$, R$^{21}$, R$^{22}$, R$^{23}$ R$^{25}$, R$^{26}$, R$^{27}$, and R$^{28}$ are hydrogen;

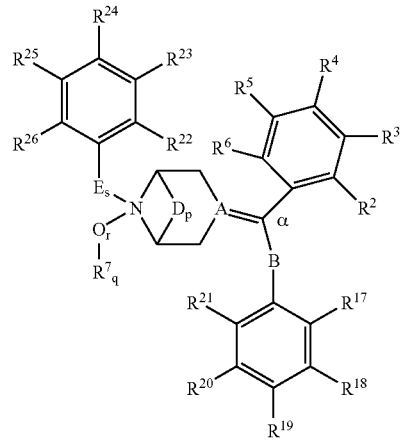

I

| Cmpd. No. | R$^4$ | B | R$^{15}$ | R$^{19}$ | R$^{24}$ |
|---|---|---|---|---|---|
| 137 | OCF$_3$ | O | — | OCF$_3$ | 2-ethyl-2H-tetrazol-5-yl |
| 138 | CF$_3$ | CH$_2$ | — | CF$_3$ | OC$_3$H$_7$ |
| 139 | CF$_3$ | CH$_2$O | — | CF$_3$ | NHCO$_2$C$_2$H$_5$ |
| 140 | CF$_3$ | OCH$_2$ | — | CF$_3$ | CH=NOC$_2$H$_5$ |
| 141 | CF$_3$ | OCH$_2$CH$_2$O | — | CF$_3$ | OC$_3$H$_7$ |
| 142 | Cl | OC(=O)NR$^{15}$ | H | Cl | pyrid-2-yloxy |
| 143 | CF$_3$ | OC(=O)NR$^{15}$ | H | Cl | pyrid-2-yloxy |

TABLE 1-continued

| | | | | | |
|---|---|---|---|---|---|
| 144 | OCF$_3$ | OC(=O)NR$^{15}$ | H | CF$_3$ | pyrid-2-yloxy |
| 145 | CF$_3$ | OC(=O)NR$^{15}$ | H | CF$_3$ | 2-ethyl-2H-tetrazol-5-yl |
| 146 | CF$_3$ | NR$^{15}$SO$_2$ | H | CF$_3$ | pyrid-2-yloxy |

Compounds of formula I where A is C, forming a 1,4-dihydropyridine ring; p, q, and r are 0; m and s are 1; n is 0, forming a double bond between the methyl carbon (α) and the 4-position of the pyridine ring; E is —(CR$^{27}$R$^{28}$)$_x$—(CR$^{29}$R$^{30}$)$_y$—, where x is 1, and y is 0; B is a bridging group from the methyl carbon to R; R$^8$ is phenyl substituted with R$^{22}$, R$^{23}$, R$^{24}$, R$^{25}$, and R$^{26}$; R is phenyl substituted with R$^{17}$, R$^{18}$, R$^{19}$, R$^{20}$, and R$^{21}$; where R$^2$, R$^3$, R$^5$, R$^6$, R$^{17}$, R$^{18}$, R$^{20}$, R$^{21}$, R$^{22}$, R$^{23}$, R$^{25}$, R$^{26}$, R$^{27}$, and R$^{28}$ are hydrogen;

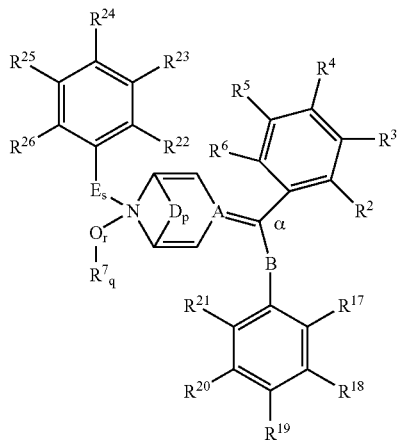

I

| Cmpd. No. | R$^4$ | B | R$^{15}$ | R$^{19}$ | R$^{24}$ |
|---|---|---|---|---|---|
| 147 | CF$_3$ | O | — | CF$_3$ | pyrid-2-yloxy |
| 148 | CF$_3$ | CH$_2$ | — | CF$_3$ | OC$_3$H$_7$ |
| 149 | CF$_3$ | CH$_2$ | — | CF$_3$ | CO$_2$C$_2$H$_5$ |
| 150 | Cl | CH$_2$ | — | Cl | NHCO$_2$C$_2$H$_5$ |
| 151 | OCF$_3$ | CH$_2$ | — | CF$_3$ | NHCO$_2$C$_2$H$_5$ |
| 152 | OCF$_3$ | CH$_2$ | — | OCF$_3$ | NHCO$_2$C$_2$H$_5$ |
| 153 | CF$_3$ | CH$_2$O | — | CF$_3$ | NHCO$_2$C$_2$H$_5$ |
| 154 | CF$_3$ | OC(=O)NR$^{15}$ | H | CF$_3$ | 2-ethyl-2H-tetrazol-5-yl |

Compounds of formula I where A is CH, forming a piperidine ring; n is 1, forming single bonds from the methyl carbon (α) and its substituents; p, q, and r are 0; m and s are 1; B is a bridging group from the methyl carbon to R; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; and R is phenyl substituted with R$^{17}$, R$^{18}$, R$^{19}$, R$^{20}$, and R$^{21}$; where R$^1$, R$^2$, R$^3$, R$^5$, R$^6$, R$^{22}$, R$^{23}$, R$^{25}$, R$^{26}$, R$^{27}$, and R$^{28}$ are hydrogen:

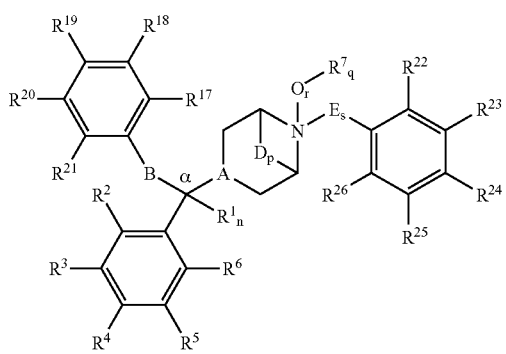

I

| Cmpd. No. | R$^4$ | R$^{24}$ | R$^{17}$/R$^{18}$ | R$^{19}$ | R$^{20}$/R$^{21}$ | B | R$^{15}$/R$^{16}$ |
|---|---|---|---|---|---|---|---|
| 155 | OCF$_3$ | OC$_3$H$_7$ | H | Cl | H | O | — |
| | | | H | | H | | |
| 156 | CF$_3$ | CO$_2$C$_2$H$_5$ | H | Cl | H | O | — |
| | | | H | | H | | |

TABLE 1-continued

| | | | | | | | |
|---|---|---|---|---|---|---|---|
| 157 | CF₃ | NHCO₂C₂H₅ | H<br>H | Cl | H<br>H | O | — |
| 158 | CF₃ | CH=NOC₂H₅ | H<br>H | Cl | H<br>H | O | — |
| 159 | CF₃ | pyrid-2-yloxy | H<br>H | Cl | H<br>H | O | — |
| 160 | CF₃ | CO₂C₂H₅ | H<br>H | Cl | H<br>H | S | — |
| 161 | CF₃ | 2-ethyl-2H-tetrazol-5-yl | H<br>H | Cl | H<br>H | SO₂ | — |
| 162 | CF₃ | 2-ethyl-2H-tetrazol-5-yl | H<br>H | Cl | H<br>H | SO₂NR¹⁵ | H |
| 163 | CF₃ | pyrid-2-yloxy | H<br>H | Cl | H<br>H | NR¹⁵SO₂ | H |
| 164 | CF₃ | 2-ethyl-2H-tetrazol-5-yl | H<br>H | Cl | H<br>H | NR¹⁵NHSO₂ | H |
| 165 | CF₃ | CH=NOC₂H₅ | H<br>H | Cl | H<br>H | OC₂H₄O | — |
| 166 | CF₃ | OC₃H₇ | H<br>H | Cl | H<br>H | —O—(cyclohexane-1,4-diyl)—O— | — |
| 167 | CF₃ | CH=NOC₂H₅ | H<br>H | Cl | H<br>H | —O—(cyclohexane-1,4-diyl)—O— | — |
| 168 | CF₃ | OC₃H₇ | H<br>H | Cl | H<br>H | —O—(1-methylpiperidin-4-yl)— | — |
| 169 | CF₃ | CH=NOC₂H₅ | H<br>H | Cl | H<br>H | —O—(1-methylpiperidin-4-yl)— | — |
| 170 | CF₃ | OC₂H₅ | H<br>H | Cl | H<br>H | OC(=O)NR¹⁵ | CH₃ |
| 171 | OCF₃ | OC₃H₇ | H<br>H | Cl | H<br>H | OC(=O)NR¹⁵ | CH₃ |
| 172 | CF₃ | OC₂H₄OCH₃ | H<br>H | Cl | H<br>H | OC(=O)NR¹⁵ | CH₃ |
| 173 | CF₃ | CO₂C₂H₅ | H<br>H | Cl | H<br>H | OC(=O)NR¹⁵ | CH₃ |
| 174 | OCF₃ | CO₂CH(CH₃)₂ | H<br>H | Cl | H<br>H | OC(=O)NR¹⁵ | CH₃ |
| 175 | CF₃ | NHCO₂C₂H₅ | H<br>H | Cl | H<br>H | OC(=O)NR¹⁵ | CH₃ |
| 176 | OCF₃ | NHCO₂CH(CH₃)₂ | H<br>H | Cl | H<br>H | OC(=O)NR¹⁵ | CH₃ |
| 177 | CF₃ | NHCO₂CH₂CH=CH₂ | H<br>H | Cl | H<br>H | OC(=O)NR¹⁵ | CH₃ |
| 178 | OCF₃ | NHCO₂CH₂C≡CH | H<br>H | Cl | H<br>H | OC(=O)NR¹⁵ | CH₃ |
| 179 | CF₃ | NHCO₂C₂H₄OCH₃ | H<br>H | Cl | H<br>H | OC(=O)NR¹⁵ | CH₃ |
| 180 | CF₃ | OC(=)NHCH(CH₃)₂ | H<br>H | Cl | H<br>H | OC(=O)NR¹⁵ | CH₃ |
| 181 | OCF₃ | 4-fluorophenylamino-carbonyloxy | H<br>H | F | H<br>H | OC(=O)NR¹⁵ | H |
| 182 | CF₃ | CH=NOC₂H₅ | H<br>H | Cl | H<br>H | OC(=O)NR¹⁵ | H |
| 183 | CF₃ | CH=NOC₂H₅ | H<br>H | Br | H<br>H | OC(=O)NR¹⁵ | H |
| 184 | CF₃ | CH=NOCH₃ | H<br>F | H | H<br>H | OC(=O)NR¹⁵ | H |
| 185 | CF₃ | CH=NOC₂H₅ | H<br>F | H | H<br>H | OC(=O)NR¹⁵ | H |
| 186 | CF₃ | CH=NOCH₃ | H<br>H | F | H<br>H | OC(=O)NR¹⁵ | H |
| 187 | CF₃ | CH=NOC₂H₅ | H<br>H | F | H<br>H | OC(=O)NR¹⁵ | H |
| 188 | CF₃ | CH=NOC₂H₅ | Cl<br>Cl | H | H<br>H | OC(=O)NR¹⁵ | H |
| 189 | CF₃ | CH=NOC₂H₅ | H<br>Cl | Cl | H<br>H | OC(=O)NR¹⁵ | H |

TABLE 1-continued

| | | | | | | | |
|---|---|---|---|---|---|---|---|
| 190 | CF$_3$ | CH=NOC$_2$H$_5$ | Cl / H | Cl | H / H | OC(=O)NR$^{15}$ | H / — |
| 191 | CF$_3$ | CH=NOC$_2$H$_5$ | Cl / H | H | Cl / H | OC(=O)NR$^{15}$ | H / — |
| 192 | CF$_3$ | CH=NOC$_2$H$_5$ | Cl / H | Cl | Cl / H | OC(=O)NR$^{15}$ | H / — |
| 193 | CF$_3$ | CH=NOC$_2$H$_5$ | F / H | F | H / H | OC(=O)NR$^{15}$ | H / — |
| 194 | OCF$_3$ | CH=NOCH$_3$ | H / F | F | H / H | OC(=O)NR$^{15}$ | H / — |
| 195 | OCF$_3$ | CH=NOC$_2$H$_5$ | H / F | F | H / H | OC(=O)NR$^{15}$ | H / — |
| 196 | CF$_3$ | CH=NOC$_2$H$_5$ | H / F | F | H / H | OC(=O)NR$^{15}$ | H / — |
| 197 | CF$_3$ | CH=NOCH(CH$_3$)$_2$ | H / F | F | H / H | OC(=O)NR$^{15}$ | H / — |
| 198 | CF$_3$ | CH=NOC$_2$H$_5$ | F / H | H | F / H | OC(=O)NR$^{15}$ | H / — |
| 199 | CF$_3$ | CH=NOC$_2$H$_5$ | F / H | H | H / F | OC(=O)NR$^{15}$ | H / — |
| 200 | CF$_3$ | CH=NOC$_2$H$_5$ | H / F | H | F / H | OC(=O)NR$^{15}$ | H / — |
| 201 | CF$_3$ | CH=NOC$_2$H$_5$ | F / F | F | H / H | OC(=O)NR$^{15}$ | H / — |
| 202 | CF$_3$ | CH=NOC$_2$H$_5$ | F / F | F | F / F | OC(=O)NR$^{15}$ | H / — |
| 203 | CF$_3$ | CH=NOC$_2$H$_5$ | CF$_3$ / H | H | H / H | OC(=O)NR$^{15}$ | H / — |
| 204 | CF$_3$ | CH=NOC$_2$H$_5$ | H / CF | H | H / H | OC(=O)NR$^{15}$ | H / — |
| 205 | CF$_3$ | CH=NOC$_2$H$_5$ | H / H | CF$_3$ | H / H | OC(=O)NR$^{15}$ | H / — |
| 206 | CF$_3$ | CH=NOC$_2$H$_5$ | CF$_3$ / H | Cl | H / H | OC(=O)NR$^{15}$ | H / — |
| 207 | CF$_3$ | CH=NOC$_2$H$_5$ | H / CF$_3$ | Cl | H / H | OC(=O)NR$^{15}$ | H / — |
| 208 | CF$_3$ | CH=NOC$_2$H$_5$ | CF$_3$ / H | Br | H / H | OC(=O)NR$^{15}$ | H / — |
| 209 | CF$_3$ | CH=NOC$_2$H$_5$ | H / H | OCH$_3$ | H / H | OC(=O)NR$^{15}$ | H / — |
| 210 | CF$_3$ | CH=NOC$_2$H$_5$ | OCH$_3$ / H | OCH$_3$ | Cl / H | OC(=O)NR$^{15}$ | H / — |
| 211 | CF$_3$ | CH=NOC$_2$H$_5$ | H / H | OCF$_3$ | H / H | OC(=O)NR$^{15}$ | H / — |
| 212 | CF$_3$ | CH=NOC$_2$H$_5$ | H / H | phenyl | H / H | OC(=O)NR$^{15}$ | H / — |
| 213 | CF$_3$ | CH=NOC$_2$H$_5$ | H / H | phenoxy | H / H | OC(=O)NR$^{15}$ | H / — |
| 214 | CF$_3$ | CH=NOC$_2$H$_5$ | —CH$_2$CHCHCH$_2$— | H | H / H | OC(=O)NR$^{28}$ | H / — |
| 215 | CF$_3$ | 4-Clpyrid-2-yl | H / H | Cl | H / H | OC(=O)NR$^{15}$ | H / — |
| 216 | CF$_3$ | 5-Clpyrid-2-yl | H / H | Cl | H / H | OC(=O)NR$^{15}$ | H / — |
| 217 | CF$_3$ | 6-Clpyrid-2-yl | H / H | Cl | H / H | OC(=O)NR$^{15}$ | H / — |
| 218 | CF$_3$ | 5-CH$_3$Opyrid-2-yl | H / H | Cl | H / H | OC(=O)NR$^{15}$ | H / — |
| 219 | CF$_3$ | 5-CF$_3$pyrid-2-yl | H / H | Cl | H / H | OC(=O)NR$^{15}$ | H / — |
| 220 | CF$_3$ | 2-(C$_3$H$_7$O)pyrid-5-yl | H / H | Cl | H / H | OC(=O)NR$^{15}$ | H / — |
| 221 | Br | pyrid-2-yloxy | H / H | Cl | H / H | OC(=O)NR$^{15}$ | H / — |
| 222 | F | pyrid-2-yloxy | H / H | Cl | H / H | OC(=O)NR$^{15}$ | H / — |
| 223 | NO$_2$ | pyrid-2-yloxy | H / H | Cl | H / H | OC(=O)NR$^{15}$ | CH$_3$ / — |
| 224 | SF$_5$ | pyrid-2-yloxy | H / H | Cl | H / H | OC(=O)NR$^{15}$ | CH$_3$ / — |
| 225 | OPh | pyrid-2-yloxy | H / H | Cl | H / H | OC(=O)NR$^{15}$ | CH$_3$ / — |
| 226 | OCF$_2$H | pyrid-2-yloxy | H / H | Cl | H / H | OC(=O)NR$^{15}$ | H / — |
| 227 | CF$_3$ | pyrid-2-yloxy | H / H | Cl | H / H | OC(=O)NR$^{15}$ | H / — |
| 228 | CF$_3$ | pyrid-2-yloxy | Cl / Cl | H | H / H | OC(=O)NR$^{15}$ | H / — |

TABLE 1-continued

| | | | | | | | |
|---|---|---|---|---|---|---|---|
| 229 | CF₃ | pyrid-2-yloxy | Cl<br>Cl | Cl | H<br>H | OC(=O)NR¹⁵ | H<br>— |
| 230 | CF₃ | pyrid-2-yloxy | H<br>Cl | Cl | H<br>H | OC(=O)NR¹⁵ | H<br>— |
| 231 | CF₃ | pyrid-2-yloxy | Cl<br>H | H | Cl<br>H | OC(=O)NR¹⁵ | H<br>— |
| 232 | CF₃ | pyrid-2-yloxy | H<br>Cl | H | Cl<br>H | OC(=O)NR¹⁵ | H<br>— |
| 233 | CF₃ | pyrid-2-yloxy | Cl<br>H | H | H<br>Cl | OC(=O)NR¹⁵ | H<br>— |
| 234 | CF₃ | pyrid-2-yloxy | Cl<br>H | Cl | Cl<br>H | OC(=O)NR¹⁵ | H<br>— |
| 235 | OCF₃ | pyrid-2-yloxy | H<br>F | H | H<br>H | OC(=O)NR¹⁵ | H<br>— |
| 236 | OCF₃ | pyrid-2-yloxy | H<br>H | F | H<br>H | OC(=O)NR¹⁵ | H<br>— |
| 237 | CF₃ | pyrid-2-yloxy | H<br>F | F | H<br>H | OC(=O)NR¹⁵ | H<br>— |
| 238 | OCF₃ | pyrid-2-yloxy | H<br>F | F | H<br>H | OC(=O)NR¹⁵ | H<br>— |
| 239 | CF₃ | pyrid-2-yloxy | F<br>H | H | F<br>H | OC(=O)NR¹⁵ | H<br>— |
| 240 | CF₃ | pyrid-2-yloxy | H<br>F | H | F<br>H | OC(=O)NR¹⁵ | H<br>— |
| 241 | CF₃ | pyrid-2-yloxy | F<br>H | H | H<br>F | OC(=O)NR¹⁵ | H<br>— |
| 242 | CF₃ | pyrid-2-yloxy | F<br>F | F | H<br>H | OC(=O)NR¹⁵ | H<br>— |
| 243 | CF₃ | pyrid-2-yloxy | F<br>F | F | F<br>F | OC(=O)NR¹⁵ | H<br>— |
| 244 | CF₃ | pyrid-2-yloxy | H<br>CF₃ | H | H<br>H | OC(=O)NR¹⁵ | H<br>— |
| 245 | CF₃ | pyrid-2-yloxy | H<br>H | CF₃ | H<br>H | OC(=O)NR¹⁵ | H<br>— |
| 246 | OCF₃ | pyrid-2-yloxy | H<br>H | CF₃ | H<br>H | OC(=O)NR¹⁵ | H<br>— |
| 247 | CF₃ | pyrid-2-yloxy | H<br>CF₃ | Cl | H<br>H | OC(=O)NR¹⁵ | H<br>— |
| 248 | CF₃ | pyrid-2-yloxy | H<br>CF₃ | H | CF₃<br>H | OC(=O)NR¹⁵ | H<br>— |
| 249 | CF₃ | pyrid-2-yloxy | H<br>H | OCF₃ | H<br>H | OC(=O)NR¹⁵ | H<br>— |
| 250 | CF₃ | pyrid-2-yloxy | H<br>H | phenyl | H<br>H | OC(=O)NR¹⁵ | H<br>— |
| 251 | CF₃ | pyrid-2-yloxy | H<br>H | phenoxy | H<br>H | OC(=O)NR¹⁵ | H<br>— |
| 252 | CF₃ | pyrimidin-2-yl | H<br>H | Cl | H<br>H | OC(=O)NR¹⁵ | H<br>— |
| 253 | CF₃ | 5-chloropyrimidin-2-yl | H<br>H | Cl | H<br>H | OC(=O)NR¹⁵ | H<br>— |
| 254 | CF₃ | 5-methoxy-pyrimidin-2-yl | H<br>H | Cl | H<br>H | OC(=O)NR¹⁵ | H<br>— |
| 255 | CF₃ | thien-3-yl | H<br>H | Cl | H<br>H | OC(=O)NR¹⁵ | H<br>— |
| 256 | CF₃ | 1-methylpyrol-3-yl | H<br>H | Cl | H<br>H | OC(=O)NR¹⁵ | H<br>— |
| 257 | CF₃ | 5-methyl-1,3-oxazol-2-yl | H<br>H | Cl | H<br>H | OC(=O)NR¹⁵ | H<br>— |
| 258 | CF₃ | 4-methoxy-1,2,5-thiadia-zol-3-yl | H<br>H | Cl | H<br>H | OC(=O)NR¹⁵ | H<br>— |
| 259 | CF₃ | 8-methoxy-1,2,3,4-tetra-hydro-naphthalen-5-yl | H<br>H | Cl | H<br>H | OC(=O)NR¹⁵ | H<br>— |
| 260 | CF₃ | 2H-tetrazol-5-yl | H<br>H | Cl | H<br>H | OC(=O)NR¹⁵ | H<br>— |
| 261 | OCF₃ | 2-ethyl-2H-tetrazol-5-yl | H<br>H | H | H<br>H | OC(=O)NR¹⁵ | H<br>— |
| 262 | OCF₃ | 2-methyl-2H-tetrazol-5-yl | Cl<br>H | H | H<br>H | OC(=O)NR¹⁵ | H<br>— |
| 263 | OCF₃ | 2-methyl-2H-tetrazol-5-yl | H<br>Cl | H | H<br>H | OC(=O)NR¹⁵ | H<br>— |
| 264 | Cl | 2-methyl-2H-tetrazol-5-yl | H<br>H | Cl | H<br>H | OC(=O)NR¹⁵ | H<br>— |
| 265 | CF₃ | 2-ethyl-2H-tetrazol-5-yl | H<br>H | Cl | H<br>H | OC(=O)NR¹⁵ | H<br>— |
| 266 | OCF₃ | 2-methyl-2H-tetrazol-5-yl | H<br>H | Cl | H<br>H | OC(=O)NR¹⁵ | H<br>— |
| 267 | OCF₃ | 2-ethyl-2H-tetrazol-5-yl | H<br>H | Cl | H<br>H | OC(=O)NR¹⁵ | H<br>— |

TABLE 1-continued

| # | | | | | | | |
|---|---|---|---|---|---|---|---|
| 268 | CF₃ | 2-ethyl-2H-tetrazol-5-yl | H<br>Br | H | H<br>H | OC(=O)NR¹⁵ | H<br>— |
| 269 | CF₃ | 2-ethyl-2H-tetrazol-5-yl | H<br>H | Br | H<br>H | OC(=O)NR¹⁵ | H<br>— |
| 270 | OCF₃ | 2-ethyl-2H-tetraozl-5-yl | H<br>H | Br | H<br>H | OC(=O)NR¹⁵ | H<br>— |
| 271 | OCF₃ | 2-ethyl-2H-tetrazol-5-yl | H<br>H | I | H<br>H | OC(=O)NR¹⁵ | H<br>— |
| 272 | OCF₃ | 2-methyl-2H-tetrazol-5-yl | F<br>H | H | H<br>H | OC(=O)NR¹⁵ | H<br>— |
| 273 | OCF₃ | 2-methyl-2H-tetrazol-5-yl | H<br>F | H | H<br>H | OC(=O)NR¹⁵ | H<br>— |
| 274 | Cl | 2-methyl-2H-tetrazol-5-yl | H<br>H | F | H<br>H | OC(=O)NR¹⁵ | H<br>— |
| 275 | OCF₃ | 2-methyl-2H-tetrazol-5-yl | H<br>H | F | H<br>H | OC(=O)NR¹⁵ | H<br>— |
| 276⁸ | OCF₃ | 2-methyl-2H-tetrazol-5-yl | H<br>H | F | H<br>H | OC(=O)NR¹⁵ | H<br>— |
| 277 | OCF₃ | 2-ethyl-2H-tetrazol-5-yl | H<br>H | F | H<br>H | OC(=O)NR¹⁵ | H<br>— |
| 278 | OCF₃ | 2-methyl-2H-tetrazol-5-yl | H<br>H | F | H<br>H | OC(=O)NR¹⁵ | H<br>— |
| 279 | CF₃ | 2-methyl-2H-tetrazol-5-yl | Cl<br>Cl | H | H<br>H | OC(=O)NR¹⁵ | H<br>— |
| 280 | CF₃ | 2-ethyl-2H-tetrazol-5-yl | Cl<br>H | Cl | H<br>H | OC(=O)NR¹⁵ | H<br>— |
| 281 | CF₃ | 2-ethyl-2H-tetrazol-5-yl | Cl<br>H | H | Cl<br>H | OC(=O)NR¹⁵ | H<br>— |
| 282 | CF₃ | 2-ethyl-2H-tetrazol-5-yl | Cl<br>H | H | H<br>Cl | OC(=O)NR¹⁵ | H<br>— |
| 283 | CF₃ | 2-ethyl-2H-tetrazol-5-yl | H<br>Cl | Cl | H<br>H | OC(=O)NR¹⁵ | H<br>— |
| 284 | CF₃ | 2-ethyl-2H-tetrazol-5-yl | H<br>Cl | H | Cl<br>H | OC(=O)NR¹⁵ | H<br>— |
| 285 | OCF₃ | 2-ethyl-2H-tetrazol-5-yl | H<br>H | CH₃ | H<br>H | OC(=O)NR¹⁵ | H<br>— |
| 286 | OCF₃ | 2-ethyl-2H-tetrazol-5-yl | H<br>H | CH(CH₃)₂ | H<br>H | OC(=O)NR¹⁵ | H<br>— |
| 287 | OCF₃ | 2-ethyl-2H-tetrazol-5-yl | H<br>H | CH₃ | H<br>H | OC(=O)NR¹⁵ | H<br>— |
| 288 | CF₃ | 2-ethyl-2H-tetrazol-5-yl | H<br>CF₃ | H | H<br>H | OC(=O)NR¹⁵ | H<br>— |
| 289 | CF₃ | 2-ethyl-2H-tetrazol-5-yl | H<br>H | CF₃ | H<br>H | OC(=O)NR¹⁵ | H<br>— |
| 290 | OCF₃ | 2-methyl-2H-tetrazol-5-yl | H<br>H | CF₃ | H<br>H | OC(=O)NR¹⁵ | H<br>— |
| 291 | OCF₃ | 2-ethyl-2H-tetrazol-5-yl | H<br>H | CF₃ | H<br>H | OC(=O)NR¹⁵ | H<br>— |
| 292 | CF₃ | 2-ethyl-2H-tetrazol-5-yl | H<br>CF₃ | Cl | H<br>H | OC(=O)NR¹⁵ | H<br>— |
| 293 | CF₃ | 2-ethyl-2H-tetrazol-5-yl | H<br>CF₃ | H | CF₃<br>H | OC(=O)NR¹⁵ | H<br>— |
| 294 | OCF₃ | 2-methyl-2H-tetrazol-5-yl | H<br>H | OCF₃ | H<br>H | OC(=O)NR¹⁵ | H<br>— |
| 295 | OCF₃ | 2-ethyl-2H-tetrazol-5-yl | H<br>H | OCF₃ | H<br>H | OC(=O)NR¹⁵ | H<br>— |
| 296 | OCF₃ | 2-ethyl-2H-tetrazol-5-yl | H<br>H | NO₂ | H<br>H | OC(=O)NR¹⁵ | H<br>— |
| 297 | CF₃ | 2-ethyl-2H-tetrazol-5-yl | H<br>H | phenyl | H<br>H | OC(=O)NR¹⁵ | H<br>— |
| 298 | CF₃ | 2-ethyl-2H-tetrazol-5-yl | H<br>H | phenoxy | H<br>H | OC(=O)NR¹⁵ | H<br>— |
| 299 | CF₃ | 2-ethyl-2H-tetrazol-5-yl | H<br>H | Cl | H<br>H | OC(=O)NR¹⁵CH₂ | H<br>— |
| 300 | CF₃ | 2-methyl-2H-tetrazol-5-yl | H<br>H | Cl | H<br>H | CH₂C(=O)NR¹⁵ | H<br>— |
| 301 | CF₃ | 2-methyl-2H-tetrazol-5-yl | H<br>H | Cl | H<br>H | OCH₂C(=O)NR¹⁵ | H<br>— |
| 302 | OCF₃ | 2-ethyl-2H-tetrazol-5-yl | H<br>H | CF₃ | H<br>H | OC(=S)NR¹⁵ | H<br>— |
| 303 | CF₃ | CO₂C₂H₅ | H<br>H | Cl | H<br>H | CH₂ | —<br>— |
| 304 | OCF₃ | 2-ethyl-2H-tetrazol-5-yl | H<br>H | CF₃ | H<br>H | OCH₂ | —<br>— |
| 305 | OCF₃ | 2-ethyl-2H-tetrazol-5-yl | H<br>H | OCF₃ | H<br>H | OCH₂ | —<br>— |
| 306 | OCF₃ | 2-methyl-2H-tetrazol-5-yl | H<br>H | 2-methyl-2H-tetrazol-5-yl | H<br>H | OCH₂ | —<br>— |

TABLE 1-continued

| No. | | | | | | | | |
|---|---|---|---|---|---|---|---|---|
| 307 | OCF$_3$ | 2-ethyl-2H-tetrazol-5-yl | H / H | CF$_3$ | H / H | OC(=O) | — | |
| 308 | OCF$_3$ | 2-ethyl-2H-tetrazol-5-yl | H / H | OCF$_3$ | H / H | OC(=O) | — | |
| 309 | OCF$_3$ | 2-methyl-2H-tetrazol-5-yl | Cl / H | H | H / H | NR$^{15}$CH$_2$ | H | |
| 310 | OCF$_3$ | 2-methyl-2H-tetrazol-5-yl | H / Cl | H | H / H | NR$^{15}$CH$_2$ | H | |
| 311 | OCF$_3$ | 2-methyl-2H-tetrazol-5-yl | H / H | Cl | H / H | NR$^{15}$CH$_2$ | H | |
| 312 | OCF$_3$ | 2-methyl-2H-tetrazol-5-yl | H / H | Br | H / H | NR$^{15}$CH$_2$ | H | |
| 313 | OCF$_3$ | 2-methyl-2H-tetrazol-5-yl | F / H | H | H / H | NR$^{15}$CH$_2$ | H | |
| 314 | OCF$_3$ | 2-methyl-2H-tetrazol-5-yl | H / F | H | H / H | NR$^{15}$CH$_2$ | H | |
| 315 | OCF$_3$ | 2-methyl-2H-tetrazol-5-yl | H / H | F | H / H | NR$^{15}$CH$_2$ | H | |
| 316 | OCF$_3$ | 2-methyl-2H-tetrazol-5-yl | H / H | I | H / H | NR$^{15}$CH$_2$ | H | |
| 317 | OCF$_3$ | 2-methyl-2H-tetrazol-5-yl | H / H | CH$_3$ | H / H | NR$^{15}$CH$_2$ | H | |
| 318 | OCF$_3$ | 2-methyl-2H-tetrazol-5-yl | H / H | OCH$_3$ | H / H | NR$^{15}$CH$_2$ | H | |
| 319 | OCF$_3$ | 2-methyl-2H-tetrazol-5-yl | H / H | OCF$_3$ | H / H | NR$^{15}$CH$_2$ | H | |
| 320 | OCF$_3$ | 2-methyl-2H-tetrazol-5-yl | H / H | NO$_2$ | H / H | NR$^{15}$CH$_2$ | H | |
| 321 | OCF$_3$ | 2-methyl-2H-tetrazol-5-yl | H / H | H | H / H | NR$^{15}$C(=O) | H | |
| 322 | OCF$_3$ | 2-methyl-2H-tetrazol-5-yl | Cl / H | H | H / H | NR$^{15}$C(=O) | H | |
| 323 | OCF$_3$ | 2-methyl-2H-tetrazol-5-yl | H / Cl | H | H / H | NR$^{15}$C(=O) | H | |
| 324 | OCF$_3$ | 2-methyl-2H-tetrazol-5-yl | H / H | Cl | H / H | NR$^{15}$C(=O) | H | |
| 325 | OCF$_3$ | 2-methyl-2H-tetrazol-5-yl | H / H | Br | H / H | NR$^{15}$C(=O) | H | |
| 326 | OCF$_3$ | 2-methyl-2H-tetrazol-5-yl | F / H | H | H / H | NR$^{15}$C(=O) | H | |
| 327 | OCF$_3$ | 2-methyl-2H-tetrazol-5-yl | H / F | H | H / H | NR$^{15}$C(=O) | H | |
| 328 | OCF$_3$ | 2-methyl-2H-tetrazol-5-yl | H / H | F | H / H | NR$^{15}$C(=O) | H | |
| 329 | OCF$_3$ | 2-methyl-2H-tetrazol-5-yl | H / H | I | H / H | NR$^{15}$C(=O) | H | |
| 330 | OCF$_3$ | 2-methyl-2H-tetrazol-5-yl | H / H | CH$_3$ | H / H | NR$^{15}$C(=O) | H | |
| 331 | OCF$_3$ | 2-methyl-2H-tetrazol-5-yl | H / H | OCH$_3$ | H / H | NR$^{15}$C(=O) | H | |
| 332 | OCF$_3$ | 2-methyl-2H-tetrazol-5-yl | H / H | OCF$_3$ | H / H | NR$^{15}$C(=O) | H | |
| 333 | OCF$_3$ | 2-methyl-2H-tetrazol-5-yl | H / H | NO$_2$ | H / H | NR$^{15}$C(=O) | H | |
| 334 | OCF$_3$ | 2-methyl-2H-tetrazol-5-yl | Cl / H | H | H / H | NR$^{15}$C(=O)NR$^{16}$ | H / H | |
| 335 | OCF$_3$ | 2-methyl-2H-tetrazol-5-yl | H / Cl | H | H / H | NR$^{15}$C(=O)NR$^{16}$ | H / H | |
| 336 | OCF$_3$ | 2-methyl-2H-tetrazol-5-yl | H / H | Cl | H / H | NR$^{15}$C(=O)NR$^{16}$ | H / H | |
| 337 | OCF$_3$ | 2-methyl-2H-tetrazol-5-yl | H / H | Br | H / H | NR$^{15}$C(=O)NR$^{16}$ | H / H | |
| 338 | OCF$_3$ | 2-methyl-2H-tetrazol-5-yl | F / H | H | H / H | NR$^{15}$C(=O)NR$^{16}$ | H / H | |
| 339 | OCF$_3$ | 2-methyl-2H-tetrazol-5-yl | H / F | H | H / H | NR$^{15}$C(=O)NR$^{16}$ | H / H | |
| 340 | OCF$_3$ | 2-methyl-2H-tetrazol-5-yl | H / H | F | H / H | NR$^{15}$C(=O)NR$^{16}$ | H / H | |
| 341 | OCF$_3$ | 2-methyl-2H-tetrazol-5-yl | H / H | I | H / H | NR$^{15}$C(=O)NR$^{16}$ | H / H | |
| 342 | OCF$_3$ | 2-methyl-2H-tetrazol-5-yl | H / H | CH$_3$ | H / H | NR$^{15}$C(=O)NR$^{16}$ | H / H | |
| 343 | OCF$_3$ | 2-methyl-2H-tetrazol-5-yl | H / H | OCH$_3$ | H / H | NR$^{15}$C(=O)NR$^{16}$ | H / H | |
| 344 | OCF$_3$ | 2-methyl-2H-tetrazol-5-yl | H / H | CF$_3$ | H / H | NR$^{15}$C(=O)NR$^{16}$ | H / H | |
| 345 | OCF$_3$ | 2-methyl-2H-tetrazol-5-yl | H / H | OCF$_3$ | H / H | NR$^{15}$C(=O)NR$^{16}$ | H / H | |

TABLE 1-continued

| | | | | | | | | |
|---|---|---|---|---|---|---|---|---|
| 346 | OCF$_3$ | 2-methyl-2H-tetrazol-5-yl | H<br>H | NO$_2$ | H<br>H | NR$^{15}$C(=O)NR$^{16}$ | H<br>H | |
| 347 | OCF$_3$ | 2-methyl-2H-tetrazol-5-yl | Cl<br>H | H | H<br>H | NR$^{15}$C(=O)O | H<br>— | |
| 348 | OCF$_3$ | 2-methyl-2H-tetrazol-5-yl | H<br>Cl | H | H<br>H | NR$^{15}$C(=O)O | H<br>— | |
| 349 | OCF$_3$ | 2-methyl-2H-tetrazol-5-yl | H<br>H | Cl | H<br>H | NR$^{15}$C(=O)O | H<br>— | |
| 350 | OCF$_3$ | 2-methyl-2H-tetrazol-5-yl | H<br>H | Br | H<br>H | NR$^{15}$C(=O)O | H<br>— | |
| 351 | OCF$_3$ | 2-methyl-2H-tetrazol-5-yl | F<br>H | H | H<br>H | NR$^{15}$C(=O)O | H<br>— | |
| 352 | OCF$_3$ | 2-methyl-2H-tetrazol-5-yl | H<br>F | H | H<br>H | NR$^{15}$C(=O)O | H<br>— | |
| 353 | OCF$_3$ | 2-methyl-2H-tetrazol-5-yl | H<br>H | F | H<br>H | NR$^{15}$C(=O)O | H<br>— | |
| 354 | OCF$_3$ | 2-methyl-2H-tetrazol-5-yl | H<br>H | I | H<br>H | NR$^{15}$C(=O)O | H<br>— | |
| 355 | OCF$_3$ | 2-methyl-2H-tetrazol-5-yl | H<br>H | CH$_3$ | H<br>H | NR$^{15}$C(=O)O | H<br>— | |
| 356 | OCF$_3$ | 2-methyl-2H-tetrazol-5-yl | H<br>H | OCH$_3$ | H<br>H | NR$^{15}$C(=O)O | H<br>— | |
| 357 | OCF$_3$ | 2-methyl-2H-tetrazol-5-yl | H<br>H | OCF$_3$ | H<br>H | NR$^{15}$C(=O)O | H<br>— | |
| 358 | OCF$_3$ | 2-methyl-2H-tetrazol-5-yl | H<br>H | NO$_2$ | H<br>H | NR$^{15}$C(=O)O | H<br>— | |

Compounds of formula I where A is CH, forming a piperidine ring; n is 1, forming single bonds from the methyl carbon (α) and its substituents; p, q, and r are 0; m and s are 1; B is a bridging group from the methyl carbon to R, where B is OC(=O)NR$^{15}$; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; and R is phenyl substituted with R$^{17}$, R$^{18}$, R$^{19}$, R$^{20}$, and R$^{21}$; where R$^2$, R$^3$, R$^5$, R$^6$, R$^{15}$, R$^{17}$, R$^{18}$, R$^{20}$, R$^{21}$, R$^{22}$, R$^{23}$, R$^{25}$, R$^{26}$ R$^{27}$, and R$^{28}$ are hydrogen:

I

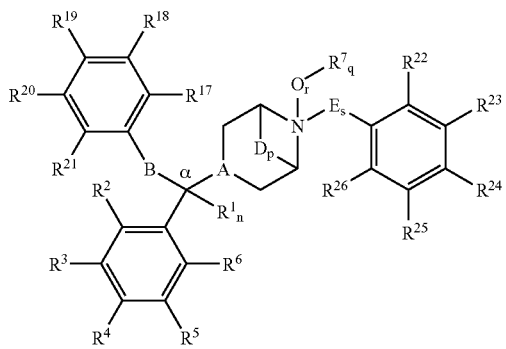

| Cmpd. No. | R$^1$ | R$^4$ | R$^{19}$ | R$^{24}$ |
|---|---|---|---|---|
| 359 | CH$_3$ | CF$_3$ | H | CH=NOC$_2$H$_5$ |
| 360 | CH$_3$ | CF$_3$ | Cl | CH=NOC$_2$H$_5$ |
| 361 | CH$_3$ | OCF$_3$ | Cl | CH=NOC$_2$H$_5$ |
| 362 | CH(CH$_3$)$_2$ | CF$_3$ | H | CH=NOC$_2$H$_5$ |
| 363 | CH(CH$_3$)$_2$ | CF$_3$ | Cl | CH=NOC$_2$H$_5$ |
| 364 | CH(CH$_3$)$_2$ | OCF$_3$ | Cl | CH=NOC$_2$H$_5$ |
| 365 | CH$_2$OCH$_3$ | CF$_3$ | H | CH=NOC$_2$H$_5$ |
| 366 | CH$_2$OCH$_3$ | CF$_3$ | Cl | CH=NOC$_2$H$_5$ |
| 367 | CH$_2$OCH$_3$ | OCF$_3$ | Cl | CH=NOC$_2$H$_5$ |
| 368 | phenyl | CF$_3$ | H | CH=NOC$_2$H$_5$ |
| 369 | phenyl | CF$_3$ | Cl | CH=NOC$_2$H$_5$ |
| 370 | phenyl | OCF$_3$ | Cl | CH=NOC$_2$H$_5$ |
| 371 | CH$_3$ | CF$_3$ | H | pyrid-2-yloxy |
| 372 | CH$_3$ | CF$_3$ | Cl | pyrid-2-yloxy |
| 373 | CH$_3$ | OCF$_3$ | Cl | pyrid-2-yloxy |
| 374 | CH(CH$_3$)$_2$ | CF$_3$ | H | pyrid-2-yloxy |
| 375 | CH(CH$_3$)$_2$ | CF$_3$ | Cl | pyrid-2-yloxy |
| 376 | CH(CH$_3$)$_2$ | OCF$_3$ | Cl | pyrid-2-yloxy |

TABLE 1-continued

| | | | | | |
|---|---|---|---|---|---|
| 377 | CH$_2$OCH$_3$ | CF$_3$ | H | pyrid-2-yloxy | |
| 378 | CH$_2$OCH$_3$ | CF$_3$ | Cl | pyrid-2-yloxy | |
| 379 | CH$_2$OCH$_3$ | OCF$_3$ | Cl | pyrid-2-yloxy | |
| 380 | phenyl | CF$_3$ | H | pyrid-2-yloxy | |
| 381 | phenyl | CF$_3$ | Cl | pyrid-2-yloxy | |
| 382 | phenyl | OCF$_3$ | Cl | pyrid-2-yloxy | |
| 383 | CH$_3$ | CF$_3$ | H | 2-ethyl-2H-tetrazol-5-yl | |
| 384 | CH$_3$ | CF$_3$ | Cl | 2-ethyl-2H-tetrazol-5-yl | |
| 385 | CH$_3$ | OCF$_3$ | Cl | 2-ethyl-2H-tetrazol-5-yl | |
| 386 | CH(CH$_3$)$_2$ | CF$_3$ | H | 2-ethyl-2H-tetrazol-5-yl | |
| 387 | CH(CH$_3$)$_2$ | CF$_3$ | Cl | 2-ethyl-2H-tetrazol-5-yl | |
| 388 | CH(CH$_3$)$_2$ | OCF$_3$ | Cl | 2-ethyl-2H-tetrazol-5-yl | |
| 389 | CH$_2$OCH$_3$ | CF$_3$ | H | 2-ethyl-2H-tetrazol-5-yl | |
| 390 | CH$_2$OCH$_3$ | CF$_3$ | Cl | 2-ethyl-2H-tetrazol-5-yl | |
| 391 | CH$_2$OCH$_3$ | OCF$_3$ | Cl | 2-ethyl-2H-tetrazol-5-yl | |
| 392 | phenyl | CF$_3$ | H | 2-ethyl-2H-tetrazol-5-yl | |
| 393 | phenyl | CF$_3$ | Cl | 2-ethyl-2H-tetrazol-5-yl | |
| 394 | phenyl | OCF$_3$ | Cl | 2-ethyl-2H-tetrazol-5-yl | |

Compounds of formula I where A is CH, forming a piperidine ring; n is 1, forming single bonds from the methyl carbon (α) and its substituents; p is 0; q is 0, and r is 1, forming a N-oxide; m, s, and r are 1; B is a bridging group from the methyl carbon to R, where B is OC(=O)NR$^{15}$; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; and R is phenyl substituted with R$^{17}$, R$^{18}$, R$^{19}$, R$^{20}$, and R$^{21}$; where R$^1$, R$^2$, R$^3$, R$^5$, R$^6$, R$^{15}$, R$^{21}$, R$^{22}$, R$^{23}$, R$^{25}$, R$^{26}$, R$^{27}$ and R$^{28}$ are hydrogen:

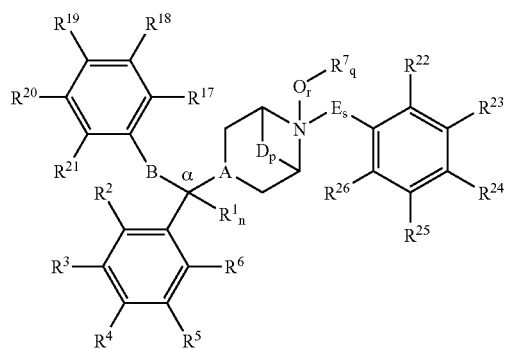

I

| Cmpd. No. | R$^4$ | R$^{17}$ | R$^{18}$ | R$^{19}$ | R$^{20}$ | R$^{24}$ |
|---|---|---|---|---|---|---|
| 395 | CF$_3$ | H | H | Cl | H | pyrid-2-yloxy |
| 396 | CF$_3$ | H | Cl | Cl | H | pyrid-2-yloxy |
| 397 | CF$_3$ | H | F | H | F | pyrid-2-yloxy |
| 398 | CF$_3$ | H | H | CF$_3$ | H | pyrid-2-yloxy |
| 399 | OCF$_3$ | H | H | Cl | H | 2-methyl-2H-tetrazol-5-yl |
| 400 | OCF$_3$ | H | H | F | H | 2-methyl-2H-tetrazol-5-yl |
| 401 | OCF$_3$ | H | H | F | H | 2-ethyl-2H-tetrazol-5-yl |
| 402 | OCF$_3$ | H | H | CF$_3$ | H | 2-methyl-2H-tetrazol-5-yl |
| 403 | OCF$_3$ | H | H | CF$_3$ | H | 2-ethyl-2H-tetrazol-5-yl |
| 404 | OCF$_3$ | H | H | OCF$_3$ | H | 2-methyl-2H-tetrazol-5-yl |
| 405 | OCF$_3$ | H | H | OCF$_3$ | H | 2-ethyl-2H-tetrazol-5-yl |

TABLE 1-continued

Compounds of formula I where A is CH, forming a piperidine ring; n is 1,
forming single bonds from the methyl carbon (α) and its substituents; p, q, and
r are 0; m and s are 1; B is a bridging group from the methyl carbon to R,
where B is O; E is —$(CR^{27}R^{28})_x$—$(CR^{29}R^{30})_y$—, where x is 1, and y is 0; $R^8$ is
phenyl substituted with $R^{22}$, $R^{23}$, $R^{24}$, $R^{25}$, and $R^{26}$; and R is pyrid-2-yl
substituted with $R^{18}$, $R^{19}$, $R^{20}$, and $R^{21}$; where $R^2$, $R^3$, $R^5$, $R^6$, $R^{17}$, $R^{18}$, $R^{21}$, $R^{22}$,
$R^{23}$, $R^{25}$, $R^{26}$, $R^{27}$, and $R^{28}$ are hydrogen:

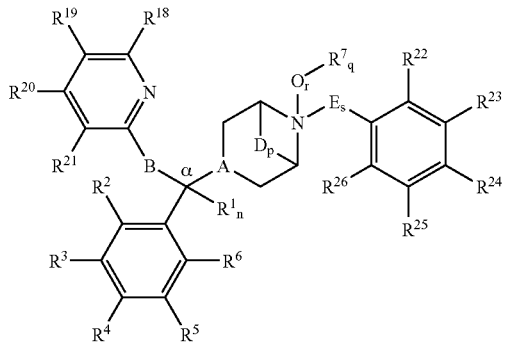

I

| Cmpd. No. | $R^1$ | $R^4$ | $R^{19}$ | $R^{20}$ | $R^{24}$ |
|---|---|---|---|---|---|
| 406 | H | $CF_3$ | $OCF_3$ | H | $OCH(CH_3)_2$ |
| 407 | H | $CF_3$ | $CF_3$ | H | $NHCO_2CH(CH_3)_2$ |
| 408 | H | $CF_3$ | $CF_3$ | H | 2-methyl-2H-tetrazol-5-yl |
| 409 | H | $CF_3$ | $CF_3$ | H | 2-ethyl-2H-tetrazol-5-yl |
| 410 | $CH_3$ | $CF_3$ | $OCF_3$ | $CF_3$ | H | $OC_3H_7$ |
| 411 | $CH_3$ | $CF_3$ | $CF_3$ | H | CH=$NOC_2H_5$ |
| 412 | $CH_3$ | $CF_3$ | H | F | 2-ethyl-2H-tetrazol-5-yl |
| 413 | $CH(CH_3)_2$ | $CF_3$ | Cl | H | $CO_2C_2H_5$ |
| 414 | $CH_2OCH_3$ | $CF_3$ | F | H | pyrid-2-yloxy |
| 415 | phenylmethyl | $CF_3$ | Br | H | $OC_3H_7$ |

Compounds of formula I where A is C, forming a 1,2,5,6-tetrahydropyridyl
ring; n is 1, forming single bonds from the methyl carbon (α) and its
substituents; p, q, and r are 0; m and s are 1; B is a bridging group from the
methyl carbon to R; E is —$(CR^{27}R^{28})_x$—$(CR^{29}R^{30})_y$—, where x is 1, and y is 0; $R^8$ is
phenyl substituted with $R^{22}$, $R^{23}$, $R^{24}$, $R^{25}$, and $R^{26}$; and R is phenyl substituted
with $R^{17}$, $R^{18}$, $R^{19}$, $R^{20}$, and $R^{21}$; where $R^1$, $R^2$, $R^3$, $R^5$, $R^6$, $R^{22}$, $R^{23}$, $R^{25}$, $R^{26}$,
$R^{27}$, and $R^{28}$ are hydrogen:

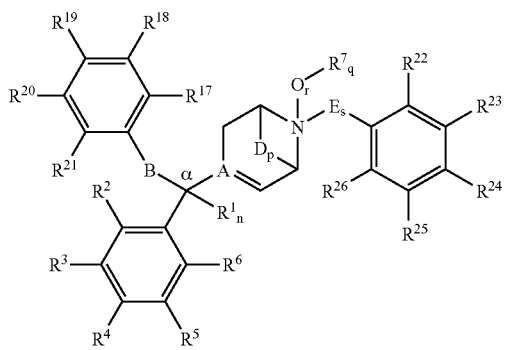

I

| Cmpd. No. | $R^4$ | $R^{19}$ | B | $R^{15}$ | $R^{24}$ |
|---|---|---|---|---|---|
| 416 | $CF_3$ | $CF_3$ | O | — | pyrid-2-yloxy |
| 417 | $CF_3$ | $CF_3$ | S | — | $CO_2C_2H_5$ |
| 418 | $CF_3$ | $CF_3$ | $CH_2$ | — | $OC_3H_7$ |
| 419 | $CF_3$ | $CF_3$ | $CH_2O$ | — | $NHCO_2C_2H_5$ |
| 420 | $CF_3$ | $CF_3$ | $OCH_2$ | — | CH=$NOC_2H_5$ |
| 421 | $CF_3$ | $CF_3$ | $OCH_2CH_2O$ | — | $OC_3H_7$ |
| 422 | Cl | Cl | OC(=O)$NR^{15}$ | H | pyrid-2-yloxy |
| 423 | $CF_3$ | Cl | OC(=O)$NR^{15}$ | H | pyrid-2-yloxy |
| 424 | $OCF_3$ | $CF_3$ | OC(=O)$NR^{15}$ | H | pyrid-2-yloxy |

TABLE 1-continued

| | | | | | |
|---|---|---|---|---|---|
| 425 | CF$_3$ | CF$_3$ | OC(=O)NR$^{15}$ | H | 2-ethyl-2H-tetrazol-5-yl |
| 426 | CF$_3$ | CF$_3$ | NR$^{15}$SO$_2$ | H | pyrid-2-yloxy |

Compounds of formula I where A is CH, forming a piperidine ring; n is 1, forming single bonds from the methyl carbon (α) and its substituents; p, q, and r are 0; m and s are 1; B is a bridging group from the methyl carbon to R; E is —(CR$^{27}$R$^{28}$)$_x$—(CR$^{29}$R$^{30}$)$_y$—, where x is 1, and y is 0; and R$^8$ is phenyl substituted with R$^{22}$, R$^{23}$, R$^{24}$, R$^{25}$, and R$^{26}$; where R$^2$, R$^3$, R$^5$, R$^6$, R$^{22}$, R$^{23}$, R$^{25}$, R$^{26}$ R$^{27}$, and R$^{28}$ are hydrogen:

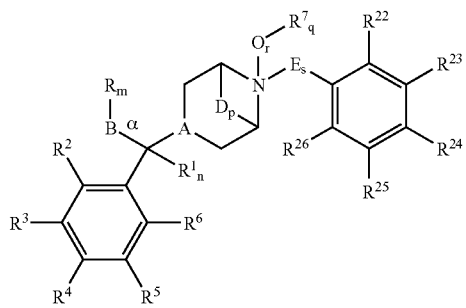

I

| Cmpd. No. | R | R$^4$ | B | R$^{15}$ | R$^{24}$ |
|---|---|---|---|---|---|
| 427 | C$_3$H$_7$ | CF$_3$ | —OC(=O)NR$^{15}$— | H | pyrid-2-yloxy |
| 428 | CH(CH$_3$)$_2$ | Cl | —OC(=O)NR$^{15}$— | H | pyrid-2-yloxy |
| 429 | CH(CH$_3$)$_2$ | CF$_3$ | —OC(=O)NR$^{15}$— | H | pyrid-2-yloxy |
| 430 | CH(CH$_3$)$_2$ | OCF$_3$ | —OC(=O)NR$^{15}$— | H | pyrid-2-yloxy |
| 431 | CH$_2$CH=CH$_2$ | CF$_3$ | —OC(=O)NR$^{15}$— | H | pyrid-2-yloxy |
| 432 | cyclohexyl | CF$_3$ | —OC(=O)NR$^{15}$— | H | pyrid-2-yloxy |
| 433 | C$_3$H$_7$ | OCF$_3$ | —NR$^{15}$SO$_2$— | H | 2-methyl-2H-tetrazol-5-yl |

Compounds of formula I where A is CH, forming a piperidine ring; n is 1, forming single bonds from the methyl carbon (α) and its substituents; p, q, and r are 0; m and s are 1; B is a bridging group from the methyl carbon to R; where R is pyrid-2-yl substituted with R$^{18}$, R$^{19}$, R$^{20}$, and R$^{21}$; E is —(CR$^{27}$R$^{28}$)$_x$—(CR$^{29}$R$^{30}$)$_y$—, where x is 1, and y is 0; and R$^8$ is phenyl substituted with R$^{22}$, R$^{23}$, R$^{24}$, R$^{25}$, and R$^{26}$; where R$^1$, R$^2$, R$^3$, R$^5$, R$^6$, R$^{18}$, R$^{21}$, R$^{22}$, R$^{23}$, R$^{25}$, R$^{26}$ R$^{27}$, and R$^{28}$ are hydrogen:

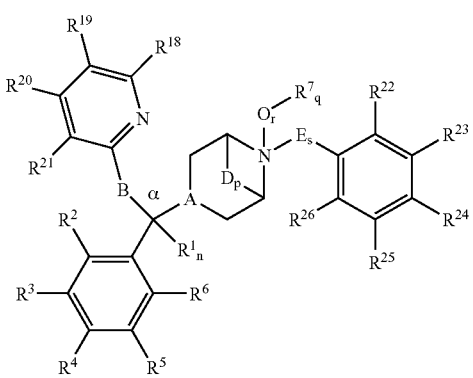

I

| Cmpd. No. | B | R$^4$ | R$^{19}$ | R$^{20}$ | R$^{24}$ |
|---|---|---|---|---|---|
| 434 | O | OCF$_3$ | CF$_3$ | H | 2-methyl-2H-tetrazol-5-yl |
| 435 | O | CF$_3$ | Cl | H | 2-methyl-2H-tetrazol-5-yl |
| 436 | OC(=O)NR$^{15}$* | CF$_3$ | H | H | pyrid-2-yloxy |
| 437 | O | CF$_3$ | CF$_3$ | H | pyrid-2-yloxy |
| 438 | O | CF$_3$ | H | CF$_3$ | pyrid-2-yloxy |
| 439 | OC(=O)NR$^{15}$* | CF$_3$ | Cl | H | pyrid-2-yloxy |
| 440 | O | CF$_3$ | CF$_3$ | H | 6-chloropyridazin-3-yloxy |
| 441 | O | CF$_3$ | H | CF$_3$ | 6-chloropyridazin-3-yloxy |

*R$^{15}$ is hydrogen.

TABLE 1-continued

Compounds of formula I where A is CH, forming a piperidine ring; n is 1,
forming single bonds from the methyl carbon (α) and its substituents; p is 0; m
and s are 1; q is 0 and r is 1, forming an N-oxide; B is a bridging group from
the methyl carbon to R; where R is pyrid-2-yl substituted with $R^{18}$, $R^{19}$, $R^{20}$,
and $R^{21}$; E is —$(CR^{27}R^{28})_x$—$(CR^{29}R^{30})_y$—, where x is 1, and y is 0; and $R^8$ is phenyl
substituted with $R^{22}$, $R^{23}$, $R^{24}$, $R^{25}$, and $R^{26}$; where $R^1$, $R^2$, $R^3$, $R^5$, $R^6$, $R^{18}$, $R^{20}$,
$R^{21}$, $R^{22}$, $R^{23}$, $R^{25}$, $R^{26}$ $R^{27}$, and $R^{28}$ are hydrogen:

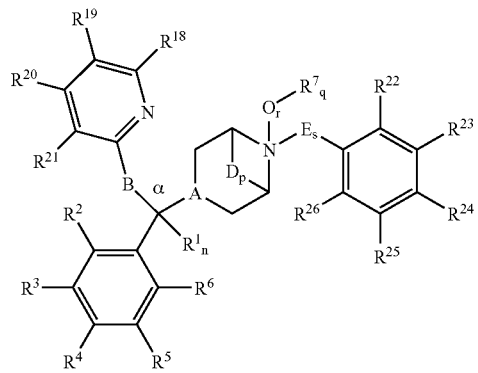

I

| Cmpd. No. | B | $R^4$ | $R^{19}$ | $R^{24}$ |
|---|---|---|---|---|
| 442 | O | $CF_3$ | $CF_3$ | pyrid-2-yloxy |

Compounds of formula I where A is CH, forming a piperidine ring; n is 1,
forming single bonds from the methyl carbon (α) and its substituents; p, q, and
r are 0; m and s are 1; B is a bridging group from the methyl carbon to R;
where R is pyrid-3-yl substituted with $R^{17}$, $R^{19}$, $R^{20}$, and $R^{21}$; E is —$(CR^{27}R^{28})_x$—$(CR^{29}R^{30})_y$—,
where x is 1, and y is 0; and $R^8$ is phenyl substituted with $R^{22}$, $R^{23}$,
$R^{24}$, $R^{25}$, and $R^{26}$; where $R^1$, $R^2$, $R^3$, $R^5$, $R^6$, $R^{21}$, $R^{22}$, $R^{23}$, $R^{25}$, $R^{26}$ $R^{27}$, and $R^{28}$
are hydrogen:

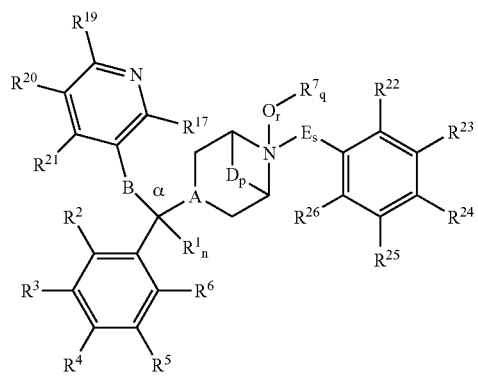

I

| Cmpd. No. | B | $R^4$ | $R^{17}$ | $R^{19}$ | $R^{20}$ | $R^{24}$ |
|---|---|---|---|---|---|---|
| 443 | O | $CF_3$ | H | H | Cl | pyrid-2-yloxy |
| 444 | OC(=O)$NR^{15}$* | $CF_3$ | H | H | H | pyrid-2-yloxy |
| 445 | OC(=O)$NR^{15}$ | $CF_3$ | H | Cl | H | pyrid-2-yloxy |
| 446 | OC(=O)$NR^{15}$ | $CF_3$ | H | CN | H | pyrid-2-yloxy |
| 447 | OC(=O)$NR^{15}$ | $CF_3$ | Cl | H | H | pyrid-2-yloxy |
| 448 | OC(=O)$NR^{15}$ | $CF_3$ | H | $CF_3$ | H | pyrid-2-yloxy |

*$R^{15}$ is hydrogen.

TABLE 1-continued

Compounds of formula I where A is CH, forming a piperidine ring; n is 1,
forming single bonds from the methyl carbon (α) and its substituents; p, q, and
r are 0; m and s are 1; B is a bridging group from the methyl carbon to R;
where R is pyrid-4-yl substituted with $R^{17}$, $R^{18}$, $R^{20}$, and $R^{21}$; E is $-(CR^{27}R^{28})_x-(CR^{29}R^{30})_y-$,
where x is 1, and y is 0; and $R^8$ is phenyl substituted with $R^{22}$, $R^{23}$,
$R^{24}$, $R^{25}$, $R^{26}$; where $R^1$, $R^2$, $R^3$, $R^5$, $R^6$, $R^{17}$, $R^{21}$, $R^{22}$, $R^{23}$, $R^{25}$, $R^{26}$, $R^{27}$, and
$R^{28}$ are hydrogen:

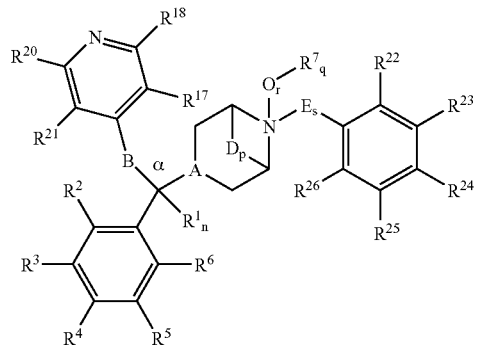

I

| Cmpd. No. | B | $R^4$ | $R^{18}$ | $R^{20}$ | $R^{24}$ |
|---|---|---|---|---|---|
| 449* | O | $OCF_3$ | H | H | 2-methyl-2H-tetrazol-5-yl |
| 450 | $OC(=O)NR^{15}$** | $CF_3$ | H | H | pyrid-2-yloxy |
| 451 | $OC(=O)NR^{15}$ | $CF_3$ | Cl | Cl | pyrid-2-yloxy |

*N-oxide of the pyrid-4-yl moiety.
**$R^{15}$ is hydrogen.

Compounds of formula I where A is CH, forming a piperidine ring; n is 1,
forming single bonds from the methyl carbon (α) and its substituents; p, q, and
r are 0; m and s are 1; B is a bridging group from the methyl carbon to R;
where R is pyridazin-3-yl substituted with $R^{19}$, $R^{20}$, and $R^{21}$; E is $-(CR^{27}R^{28})_x-(CR^{29}R^{30})_y-$,
where x is 1, and y is 0; and $R^8$ is phenyl substituted with $R^{22}$, $R^{23}$,
$R^{24}$, $R^{25}$, and $R^{26}$; where $R^1$, $R^2$, $R^3$, $R^5$, $R^6$, $R^{20}$, $R^{21}$, $R^{22}$, $R^{23}$, $R^{25}$, $R^{26}$ $R^{27}$, and
$R^{28}$ are hydrogen:

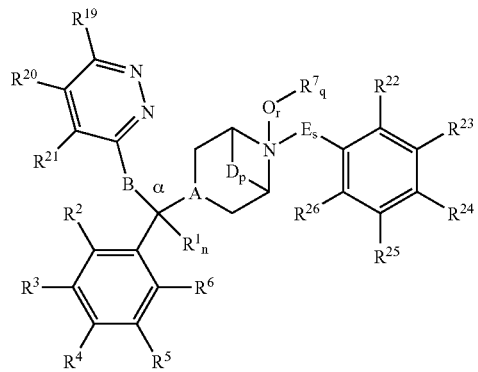

I

| Cmpd. No. | B | $R^4$ | $R^{19}$ | $R^{24}$ |
|---|---|---|---|---|
| 452 | O | $CF_3$ | Cl | pyrid-2-yloxy |
| 453 | O | $OCF_3$ | Cl | 2-methyl-2H-tetrazol-5-yl |

TABLE 1-continued

Compounds of formula I where A is CH, forming a piperidine ring; n is 1, forming single bonds from the methyl carbon (α) and its substituents; p, q, and r are 0; m and s are 1; B is a bridging group from the methyl carbon to R; where R is phenyl substituted with $R^{17}$, $R^{18}$, $R^{19}$, $R^{20}$, and $R^{21}$; E is —$(CR^{27}R^{28})_x$—$(CR^{29}R^{30})_y$—, where x is 1, and y is 0; and $R^8$ is phenyl substituted with $R^{22}$, $R^{23}$, $R^{24}$, $R^{25}$, and $R^{26}$; where $R^1$, $R^2$, $R^3$, $R^6$, $R^{21}$, $R^{22}$, $R^{23}$, $R^{25}$, $R^{26}$, $R^{27}$, and $R^{28}$ are hydrogen:

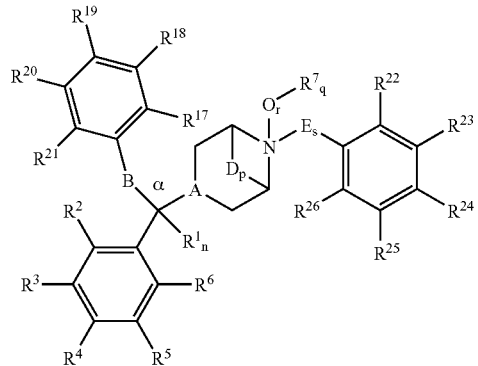

I

| Cmpd. No. | B | $R^{15}/R^{16}$ | $R^2/R^3$ | $R^4/R^5$ | $R^{17}/R^{18}$ | $R^{19}/R^{20}$ | $R^{24}$ |
|---|---|---|---|---|---|---|---|
| 454 | O | — | H/H | $CF_3$/H | H/H | $CF_3$/H | CH=$NOC_2H_5$ |
| 455 | O | — | H/H | $CF_3$/H | H/H | $CF_3$/H | pyrid-2-yloxy |
| 456 | O | — | H/H | $OCF_3$/H | H/H | $CF_3$/H | pyrimidin-2-yloxy |
| 457 | $OCH_2$ | — | H/H | $CF_3$/H | H/H | $NHCO_2CH(CH_3)_2$/H | $NHCO_2CH(CH_3)_2$ |
| 458 | $OC(=O)NR^{15}$ | H/— | H/H | $OCF_3$/H | H/H | F/H | H |
| 459 | $OC(=O)NR^{15}$ | H/— | H/H | $OCF_3$/H | H/H | F/H | Cl |
| 460 | $OC(=O)NR^{15}$ | H/— | H/H | $OCF_3$/H | H/F | H/F | Cl |
| 461 | $OC(=O)NR^{15}$ | H/— | H/H | $OCF_3$/H | H/F | H/F | F |
| 462 | $OC(=O)NR^{15}$ | H/— | H/H | $OCF_3$/H | H/F | H/F | I |
| 463 | $OC(=O)NR^{15}$ | H/— | H/H | $CF_3$/H | H/H | Cl/H | OH |
| 464 | $OC(=O)NR^{15}$ | H/— | H/H | $CF_3$/H | H/F | H/F | OH |
| 465 | $OC(=O)NR^{15}$ | H/— | H/H | $CF_3$/H | H/H | Cl/H | $NH_2$ |
| 466 | $OC(=O)NR^{15}$ | H/— | H/H | $CF_3$/H | H/F | H/F | $NH_2$ |
| 467 | $OC(=O)NR^{15}$ | H/— | H/H | $CF_3$/H | H/F | H/F | $C_5H_{11}$ |
| 468 | $OC(=O)NR^{15}$ | H/— | H/H | $OCF_3$/H | H/H | F/H | $OCH_3$ |
| 469 | $OC(=O)NR^{15}$ | H/— | H/H | $OCF_3$/H | H/F | H/F | $OCH_3$ |
| 470 | $OC(=O)NR^{15}$ | H/— | H/H | Cl/H | H/H | Cl/H | $OC_3H_7$ |
| 471 | $OC(=O)NR^{15}$ | H/— | H/H | Cl/H | H/H | F/H | $OC_3H_7$ |
| 472 | $OC(=O)NR^{15}$ | H/— | H/H | Cl/H | H/$CF_3$ | H/H | $OC_3H_7$ |
| 473 | $OC(=O)NR^{15}$ | H/— | H/H | Cl/H | H/H | $CF_3$/H | $OC_3H_7$ |
| 474 | $OC(=O)NR^{15}$ | H/— | H/H | Cl/H | H/F | H/F | $OC_3H_7$ |
| 475 | $OC(=O)NR^{15}$ | H/— | H/H | F/H | H/H | Cl/H | $OC_3H_7$ |
| 476 | $OC(=O)NR^{15}$ | H/— | H/H | F/H | H/H | F/H | $OC_3H_7$ |
| 477 | $OC(=O)NR^{15}$ | H/— | H/H | F/H | H/$CF_3$ | H/H | $OC_3H_7$ |
| 478 | $OC(=O)NR^{15}$ | H/— | H/H | F/H | H/H | $CF_3$/H | $OC_3H_7$ |
| 479 | $OC(=O)NR^{15}$ | H/— | H/H | F/H | H/F | H/F | $OC_3H_7$ |
| 480 | $OC(=O)NR^{15}$ | H/— | H/Cl | Cl/H | H/H | Cl/H | $OC_3H_7$ |
| 481 | $OC(=O)NR^{15}$ | H/— | H/Cl | Cl/H | H/H | F/H | $OC_3H_7$ |
| 482 | $OC(=O)NR^{15}$ | H/— | H/Cl | Cl/H | H/F | H/F | $OC_3H_7$ |
| 483 | $OC(=O)NR^{15}$ | H/— | H/Cl | Cl/H | H/$CF_3$ | H/H | $OC_3H_7$ |
| 484 | $OC(=O)NR^{15}$ | H/— | H/Cl | Cl/H | H/H | $CF_3$/H | $OC_3H_7$ |
| 485 | $OC(=O)NR^{15}$ | H/— | H/$CF_3$ | H/H | H/H | Cl/H | $OC_3H_7$ |
| 486 | $OC(=O)NR^{15}$ | H/— | H/$CF_3$ | H/H | H/H | F/H | $OC_3H_7$ |
| 487 | $OC(=O)NR^{15}$ | H/— | H/$CF_3$ | H/H | H/F | H/F | $OC_3H_7$ |
| 488 | $OC(=O)NR^{15}$ | H/— | H/$CF_3$ | H/H | H/$CF_3$ | H/H | $OC_3H_7$ |
| 489 | $OC(=O)NR^{15}$ | H/— | H/$CF_3$ | H/H | H/H | $CF_3$/H | $OC_3H_7$ |
| 490 | $OC(=O)NR^{15}$ | H/— | H/H | $CF_3$/H | H/H | Cl/H | $OC_3H_7$ |
| 491 | $OC(=O)NR^{15}$ | H/— | H/H | $CF_3$/H | H/F | H/F | $OC_3H_7$ |
| 492 | $OC(=O)NR^{15}$ | H/— | H/H | $CF_3$/H | H/H | Cl/H | $CO_2CH(CH_3)_2$ |
| 493 | $OC(=O)NR^{15}$ | H/— | H/H | $CF_3$/H | H/F | H/F | $CO_2CH(CH_3)_2$ |
| 494 | $OC(=O)NR^{15}$ | H/— | H/H | $CF_3$/H | H/H | Cl/H | $NHC(=O)CH_3$ |
| 495 | $OC(=O)NR^{15}$ | H/— | H/H | $CF_3$/H | H/F | H/F | $NHC(=O)CH_3$ |
| 496 | $OC(=O)NR^{15}$ | H/— | H/H | $CF_3$/H | H/F | H/F | $NHC(=O)CH(CH_3)_2$ |
| 497 | $OC(=O)NR^{15}$ | H/— | H/H | $CF_3$/H | H/F | H/F | $NHC(=O)C(CH_3)_3$ |
| 498 | $OC(=O)NR^{15}$ | H/— | H/H | $CF_3$/H | H/F | H/F | $NHCO_2CH_3$ |
| 499 | $OC(=O)NR^{15}$ | H/— | H/H | $CF_3$/H | H/F | H/F | $NHCO_2C_2H_5$ |
| 500 | $OC(=O)NR^{15}$ | H/— | H/H | Cl/H | H/H | Cl/H | $NHCO_2CH(CH_3)_2$ |
| 501 | $OC(=O)NR^{15}$ | H/— | H/H | Cl/H | H/F | H/F | $NHCO_2CH(CH_3)_2$ |
| 502 | $OC(=O)NR^{15}$ | H/— | H/H | Cl/H | H/F | H/F | $NHCO_2CH(CH_3)_2$ |

TABLE 1-continued

| | | | | | | | |
|---|---|---|---|---|---|---|---|
| 503 | OC(=O)NR[15] | H/— | H/H | F/H | H/H | Cl/H | NHCO$_2$CH(CH$_3$)$_2$ |
| 504 | OC(=O)NR[15] | H/— | H/H | F/H | H/F | H/H | NHCO$_2$CH(CH$_3$)$_2$ |
| 505 | OC(=O)NR[15] | H/— | H/H | F/H | H/F | H/F | NHCO$_2$CH(CH$_3$)$_2$ |
| 506 | OC(=O)NR[15] | H/— | Cl/H | Cl/H | H/H | Cl/H | NHCO$_2$CH(CH$_3$)$_2$ |
| 507 | OC(=O)NR[15] | H/— | Cl/H | Cl/H | H/F | H/H | NHCO$_2$CH(CH$_3$)$_2$ |
| 508 | OC(=O)NR[15] | H/— | H/Cl | H/Cl | H/H | Cl/H | NHCO$_2$CH(CH$_3$)$_2$ |
| 509 | OC(=O)NR[15] | H/— | H/Cl | H/Cl | H/F | H/H | NHCO$_2$CH(CH$_3$)$_2$ |
| 510 | OC(=O)NR[15] | H/— | H/Cl | H/Cl | H/F | H/F | NHCO$_2$CH(CH$_3$)$_2$ |
| 511 | OC(=O)NR[15] | H/— | H/H | CF$_3$/H | H/H | Cl/H | NHCO$_2$CH(CH$_3$)$_2$ |
| 512 | OC(=O)NR[15] | H/— | H/H | CF$_3$/H | H/F | H/F | NHCO$_2$CH(CH$_3$)$_2$ |
| 513 | OC(=O)NR[15] | H/— | H/H | OCF$_3$/H | H/H | Cl/H | NHCO$_2$CH(CH$_3$)$_2$ |
| 514 | OC(=O)NR[15] | H/— | H/H | OCF$_3$/H | H/F | H/H | NHCO$_2$CH(CH$_3$)$_2$ |
| 515 | OC(=O)NR[15] | H/— | H/H | OCF$_3$/H | H/F | H/F | NHCO$_2$CH(CH$_3$)$_2$ |
| 516 | OC(=O)NR[15] | H/— | H/H | CF$_3$/H | H/F | H/F | N(pyrid-2-yl)CO$_2$CH$_3$) |
| 517 | OC(=O)NR[15] | H/— | H/H | CF$_3$/H | H/F | H/F | NHC(=O)NHC$_2$H$_5$ |
| 518 | OC(=O)NR[15] | H/— | H/H | CF$_3$/H | H/F | H/F | NHC(=S)NHC$_2$H$_5$ |
| 519 | OC(=O)NR[15] | H/— | H/H | CF$_3$/H | H/F | H/F | NHC(=O)N(CH$_3$)$_2$ |
| 520 | OC(=O)NR[15] | H/— | H/H | CF$_3$/H | H/F | H/F | NHC(=O)NP(O)(OC$_2$H$_5$)$_2$ |
| 521 | OC(=O)NR[15] | H/— | H/H | CF$_3$/H | H/H | H/H | OC(=O)NHCH$_3$ |
| 522 | OC(=O)NR[15] | R[15]*/— | H/H | CF$_3$/H | H/F | H/F | OC(=O)NHCH$_3$ |
| 523 | OC(=O)NR[15] | H/— | H/H | Cl/H | H/H | Cl/H | CH=NOC$_2$H$_5$ |
| 524 | OC(=O)NR[15] | H/— | H/H | Cl/H | H/F | H/H | CH=NOC$_2$H$_5$ |
| 525 | OC(=O)NR[15] | H/— | H/H | Cl/H | H/F | H/F | CH=NOC$_2$H$_5$ |
| 526 | OC(=O)NR[15] | H/— | H/H | F/H | H/H | Cl/H | CH=NOC$_2$H$_5$ |
| 527 | OC(=O)NR[15] | H/— | H/H | F/H | H/F | H/H | CH=NOC$_2$H$_5$ |
| 528 | OC(=O)NR[15] | H/— | H/H | F/H | H/F | H/F | CH=NOC$_2$H$_5$ |
| 529 | OC(=O)NR[15] | H/— | Cl/H | Cl/H | H/H | Cl/H | CH=NOC$_2$H$_5$ |
| 530 | OC(=O)NR[15] | H/— | Cl/H | Cl/H | H/F | H/H | CH=NOC$_2$H$_5$ |
| 531 | OC(=O)NR[15] | H/— | Cl/H | Cl/H | H/F | H/F | CH=NOC$_2$H$_5$ |
| 532 | OC(=O)NR[15] | H/— | H/Cl | H/Cl | H/H | Cl/H | CH=NOC$_2$H$_5$ |
| 533 | OC(=O)NR[15] | H/— | H/Cl | H/Cl | H/F | H/H | CH=NOC$_2$H$_5$ |
| 534 | OC(=O)NR[15] | H/— | H/Cl | H/Cl | H/F | H/F | CH=NOC$_2$H$_5$ |
| 535 | OC(=O)NR[15] | H/— | H/H | CF$_3$/H | H/F | H/H | CH=NOC$_2$H$_5$ |
| 536 | OC(=O)NR[15] | CH$_3$/— | H/H | CF$_3$/H | H/H | H/H | CH=NOC$_2$H$_5$ |
| 537 | OC(=O)NR[15] | H/— | H/H | OCF$_3$/H | H/H | Cl/H | CH=NOC$_2$H$_5$ |
| 538 | OC(=O)NR[15] | H/— | H/H | OCF$_3$/H | H/F | H/F | CH=NOC$_2$H$_5$ |
| 539 | OC(=O)NR[15] | H/— | H/H | CF$_3$/H | H/H | Cl/H | CH=NOCH$_2$C≡CH |
| 540 | OC(=O)NR[15] | H/— | H/H | CF$_3$/H | H/F | H/F | CH=NOCH$_2$C≡CH |
| 541 | OC(=O)NR[15] | H/— | H/H | CF$_3$/H | H/F | H/F | SO$_2$N(C$_2$H$_5$)$_2$ |
| 542 | OC(=O)NR[15] | H/— | H/H | CF$_3$/H | H/F | H/F | SO$_2$N-cyclopentyl |
| 543 | OC(=O)NR[15] | H/— | H/H | CF$_3$/H | H/H | Cl/H | Ph |
| 544 | OC(=O)NR[15] | H/— | H/H | CF$_3$/H | H/F | H/F | Ph |
| 545 | OC(=O)NR[15] | H/— | H/H | CF$_3$/H | H/H | Cl/H | OPh |
| 546 | OC(=O)NR[15] | H/— | H/H | CF$_3$/H | H/F | H/F | OPh |
| 547 | OC(=O)NR[15] | H/— | H/H | CF$_3$/H | H/F | H/F | O(2-F—Ph) |
| 548 | OC(=O)NR[15] | H/— | H/H | CF$_3$/H | H/F | H/F | O(2,6-F$_2$—Ph) |
| 549 | OC(=O)NR[15] | H/— | H/H | CF$_3$/H | H/F | H/F | OCH$_2$Ph |
| 550 | OC(=O)NR[15] | H/— | H/H | CF$_3$/H | H/F | H/F | NHC(=O)(2-Cl—Ph) |
| 551 | OC(=O)NR[15] | H/— | H/H | CF$_3$/H | H/F | H/F | NHC(=O)(2,6-Cl$_2$—Ph) |
| 552 | OC(=O)NR[15] | H/— | H/H | CF$_3$/H | H/F | H/F | NHC(=O)(2,6-F$_2$—Ph) |
| 553 | OC(=O)NR[15] | H/— | H/H | CF$_3$/H | H/F | H/F | NHC(=O)(2-OCH$_3$—Ph) |
| 554 | OC(=O)NR[15] | H/— | H/H | CF$_3$/H | H/F | H/F | NHC(=O)(4-OCH$_3$—Ph) |
| 555 | OC(=O)NR[15] | H/— | H/H | CF$_3$/H | H/H | F/H | pyrazol-1-yl |
| 556 | OC(=O)NR[15] | H/— | H/H | CF$_3$/H | H/F | H/F | pyrazol-1-yl |
| 557 | OC(=O)NR[15] | H/— | H/H | CF$_3$/H | H/H | F/H | 1,2,4-triazol-1-yl |
| 558 | OC(=O)NR[15] | H/— | H/H | CF$_3$/H | H/F | H/F | 1,2,4-triazol-1-yl |
| 559 | OC(=O)NR[15] | H/— | H/H | CF$_3$/H | H/H | F/H | 1,2,3-thiadiazol-4-yl |
| 560 | OC(=O)NR[15] | H/— | H/H | CF$_3$/H | H/F | H/F | 1,2,3-thiadiazol-4-yl |
| 561 | OC(=O)NR[15] | H/— | H/H | CF$_3$/H | H/H | Cl/H | 3-Cl-1,2,5-thiadiazol-4-yloxy |
| 562 | OC(=O)NR[15] | H/— | H/H | CF$_3$/H | H/F | H/F | 3-Cl-1,2,5-thiadizol-4-yl |
| 563 | OC(=O)NR[15] | H/— | H/H | CF$_3$/H | H/F | H/F | 1,3-oxazolin-2-ylamino |
| 564 | OC(=O)NR[15] | H/— | H/H | H/H | H/H | Cl/H | 2-ethyl-2H-tetrazol-5-yl |
| 565 | OC(=O)NR[15] | H/— | H/H | H/H | H/H | CF$_3$/H | 2-ethyl-2H-tetrazol-5-yl |
| 566 | OC(=O)NR[15] | H/— | H/H | H/H | H/CF$_3$ | H/F | 2-ethyl-2H-tetrazol-5-yl |
| 567 | OC(=O)NR[15] | H/— | Cl/H | H/H | H/H | Cl/H | 2-ethyl-2H-tetrazol-5-yl |
| 568 | OC(=O)NR[15] | H/— | Cl/H | H/H | H/Cl | Cl/H | 2-ethyl-2H-tetrazol-5-yl |
| 569 | OC(=O)NR[15] | H/— | Cl/H | H/H | H/F | F/H | 2-ethyl-2H-tetrazol-5-yl |
| 570 | OC(=O)NR[15] | H/— | Cl/H | H/H | H/F | H/F | 2-ethyl-2H-tetrazol-5-yl |
| 571 | OC(=O)NR[15] | H/— | Cl/H | H/H | H/H | CF$_3$/H | 2-ethyl-2H-tetrazol-5-yl |
| 572 | OC(=O)NR[15] | H/Cl | Cl/H | H/H | H/H | Cl/H | 2-ethyl-2H-tetrazol-5-yl |
| 573 | OC(=O)NR[15] | H/Cl | Cl/H | H/Cl | H/H | Cl/H | 2-ethyl-2H-tetrazol-5-yl |
| 574 | OC(=O)NR[15] | H/Cl | Cl/H | H/F | F/H | | 2-ethyl-2H-tetrazol-5-yl |
| 575 | OC(=O)NR[15] | H/Cl | Cl/H | H/F | H/F | | 2-ethyl-2H-tetrazol-5-yl |
| 576 | OC(=O)NR[15] | H/Cl | Cl/H | H/H | CF$_3$/H | | 2-ethyl-2H-tetrazol-5-yl |
| 577 | OC(=O)NR[15] | H/Cl | Cl/H | H/H | Cl/H | | 2-ethyl-2H-tetrazol-5-yl |
| 578 | OC(=O)NR[15] | H/Cl | H/Cl | H/Cl | H/H | Cl/H | 2-ethyl-2H-tetrazol-5-yl |
| 579 | OC(=O)NR[15] | H/Cl | H/Cl | H/F | F/H | | 2-ethyl-2H-tetrazol-5-yl |
| 580 | OC(=O)NR[15] | H/Cl | H/Cl | H/F | H/F | | 2-ethyl-2H-tetrazol-5-yl |
| 581 | OC(=O)NR[15] | H/Cl | H/Cl | H/H | CF$_3$/H | | 2-ethyl-2H-tetrazol-5-yl |

TABLE 1-continued

| | | | | | | | |
|---|---|---|---|---|---|---|---|
| 582 | OC(=O)NR$^{15}$ | H/— | H/F | H/H | H/H | Cl/H | 2-ethyl-2H-tetrazol-5-yl |
| 583 | OC(=O)NR$^{15}$ | H/— | H/F | H/H | H/Cl | Cl/H | 2-ethyl-2H-tetrazol-5-yl |
| 584 | OC(=O)NR$^{15}$ | H/— | H/F | H/H | H/F | F/H | 2-ethyl-2H-tetrazol-5-yl |
| 585 | OC(=O)NR$^{15}$ | H/— | H/F | H/H | H/F | H/F | 2-ethyl-2H-tetrazol-5-yl |
| 586 | OC(=O)NR$^{15}$ | H/— | H/F | H/H | H/CF$_3$ | H/H | 2-ethyl-2H-tetrazol-5-yl |
| 587 | OC(=O)NR$^{15}$ | H/— | H/F | H/H | H/H | CF$_3$/H | 2-ethyl-2H-tetrazol-5-yl |
| 588 | OC(=O)NR$^{15}$ | H/— | H/F | F/H | H/H | Cl/H | 2-ethyl-2H-tetrazol-5-yl |
| 589 | OC(=O)NR$^{15}$ | H/— | H/F | F/H | H/F | H/F | 2-ethyl-2H-tetrazol-5-yl |
| 590 | OC(=O)NR$^{15}$ | H/— | H/F | H/F | H/H | Cl/H | 2-ethyl-2H-tetrazol-5-yl |
| 591 | OC(=O)NR$^{15}$ | H/— | H/F | H/F | H/Cl | Cl/H | 2-ethyl-2H-tetrazol-5-yl |
| 592 | OC(=O)NR$^{15}$ | H/— | H/F | H/F | H/F | F/H | 2-ethyl-2H-tetrazol-5-yl |
| 593 | OC(=O)NR$^{15}$ | H/— | H/F | H/F | H/F | H/F | 2-ethyl-2H-tetrazol-5-yl |
| 594 | OC(=O)NR$^{15}$ | H/— | H/F | H/F | H/H | CF$_3$/H | 2-ethyl-2H-tetrazol-5-yl |
| 595 | OC(=O)NR$^{15}$ | H/— | H/H | CH$_3$/H | H/H | Cl/H | 2-ethyl-2H-tetrazol-5-yl |
| 596 | OC(=O)NR$^{15}$ | H/— | H/H | CH$_3$/H | H/Cl | Cl/H | 2-ethyl-2H-tetrazol-5-yl |
| 597 | OC(=O)NR$^{15}$ | H/— | H/H | CH$_3$/H | H/F | F/H | 2-ethyl-2H-tetrazol-5-yl |
| 598 | OC(=O)NR$^{15}$ | H/— | H/H | CH$_3$/H | H/F | H/F | 2-ethyl-2H-tetrazol-5-yl |
| 599 | OC(=O)NR$^{15}$ | H/— | H/H | CH$_3$/H | H/CF$_3$ | H/H | 2-ethyl-2H-tetrazol-5-yl |
| 600 | OC(=O)NR$^{15}$ | H/— | H/H | CH$_3$/H | H/H | CF$_3$/H | 2-ethyl-2H-tetrazol-5-yl |
| 601 | OC(=O)NR$^{15}$ | H/— | H/H | OCH$_3$/H | H/H | Cl/H | 2-ethyl-2H-tetrazol-5-yl |
| 602 | OC(=O)NR$^{15}$ | H/— | H/H | OCH$_3$/H | H/Cl | Cl/H | 2-ethyl-2H-tetrazol-5-yl |
| 603 | OC(=O)NR$^{15}$ | H/— | H/H | OCH$_3$/H | H/F | F/H | 2-ethyl-2H-tetrazol-5-yl |
| 604 | OC(=O)NR$^{15}$ | H/— | H/H | OCH$_3$/H | H/F | H/F | 2-ethyl-2H-tetrazol-5-yl |
| 605 | OC(=O)NR$^{15}$ | H/— | H/H | OCH$_3$/H | H/CF$_3$ | H/H | 2-ethyl-2H-tetrazol-5-yl |
| 606 | OC(=O)NR$^{15}$ | H/— | H/H | OCH$_3$/H | H/H | CF$_3$/H | 2-ethyl-2H-tetrazol-5-yl |
| 607 | OC(=O)NR$^{15}$ | H/— | H/H | OCH$_3$/H | H/H | Ph/H | 2-ethyl-2H-tetrazol-5-yl |
| 608 | OC(=O)NR$^{15}$ | H/— | H/OCH$_3$ | OCH$_3$/H | H/H | Cl/H | 2-ethyl-2H-tetrazol-5-yl |
| 609 | OC(=O)NR$^{15}$ | H/— | H/OCH$_3$ | OCH$_3$/H | H/F | H/F | 2-ethyl-2H-tetrazol-5-yl |
| 610 | OC(=O)NR$^{15}$ | H/— | H/H | CF$_3$/H | H/F | H/F | 2-ethyl-2H-tetrazol-5-yl |
| 611 | OC(=O)NR$^{15}$ | H/— | H/H | Ph/H | H/H | Cl/H | 2-ethyl-2H-tetrazol-5-yl |
| 612 | OC(=O)NR$^{15}$ | H/— | H/H | Ph/H | H/Cl | Cl/H | 2-ethyl-2H-tetrazol-5-yl |
| 613 | OC(=O)NR$^{15}$ | H/— | H/H | Ph/H | H/F | F/H | 2-ethyl-2H-tetrazol-5-yl |
| 614 | OC(=O)NR$^{15}$ | H/— | H/H | Ph/H | H/F | H/F | 2-ethyl-2H-tetrazol-5-yl |
| 615 | OC(=O)NR$^{15}$ | H/— | H/H | Ph/H | H/CF$_3$ | H/H | 2-ethyl-2H-tetrazol-5-yl |
| 616 | OC(=O)NR$^{15}$ | H/— | H/H | OPh/H | H/H | Cl/H | 2-ethyl-2H-tetrazol-5-yl |
| 617 | OC(=O)NR$^{15}$ | H/— | H/H | OPh/H | H/Cl | Cl/H | 2-ethyl-2H-tetrazol-5-yl |
| 618 | OC(=O)NR$^{15}$ | H/— | H/H | OPh/H | H/F | F/H | 2-ethyl-2H-tetrazol-5-yl |
| 619 | OC(=O)NR$^{15}$ | H/— | H/H | OPh/H | H/F | H/F | 2-ethyl-2H-tetrazol-5-yl |
| 620 | OC(=O)NR$^{15}$ | H/— | H/H | OPh/H | H/CF$_3$ | H/H | 2-ethyl-2H-tetrazol-5-yl |
| 621 | OC(=O)NR$^{15}$ | H/— | H/H | OPh/H | H/H | Ph/H | 2-ethyl-2H-tetrazol-5-yl |
| 622 | OC(=O)NR$^{15}$ | H/— | H/H | OPh/H | H/H | OPh/H | 2-ethyl-2H-tetrazol-5-yl |
| 623** | OC(=O)NR$^{15}$ | H/— | H/— | —/H | H/H | Cl/H | 2-ethyl-2H-tetrazol-5-yl |
| 624** | OC(=O)NR$^{15}$ | H/— | H/— | —/H | H/Cl | Cl/H | 2-ethyl-2H-tetrazol-5-yl |
| 625** | OC(=O)NR$^{15}$ | H/— | H/— | —/H | H/F | F/H | 2-ethyl-2H-tetrazol-5-yl |
| 626** | OC(=O)NR$^{15}$ | H/— | H/— | —/H | H/F | H/F | 2-ethyl-2H-tetrazol-5-yl |
| 627 | OC(=O)NR$^{15}$ | H/— | H/H | CF$_3$/H | H/H | Cl/H | pyrid-2-yl |
| 628 | OC(=O)NR$^{15}$ | H/— | H/H | CF$_3$/H | H/F | H/F | pyrid-2-yl |
| 629 | OC(=O)NR$^{15}$ | H/— | H/H | Cl/H | H/H | Cl/H | pyrid-2-yloxy |
| 630 | OC(=O)NR$^{15}$ | H/— | H/H | Cl/H | H/H | F/H | pyrid-2-yloxy |
| 631 | OC(=O)NR$^{15}$ | H/— | H/H | Cl/H | H/F | H/F | pyridi-2-yloxy |
| 632 | OC(=O)NR$^{15}$ | H/— | H/H | Cl/H | H/CH$_3$ | H/CH$_3$ | pyrid-2-yloxy |
| 633 | OC(=O)NR$^{15}$ | H/— | H/H | Cl/H | H/OCH$_3$ | H/OCH$_3$ | pyrid-2-yloxy |
| 634 | OC(=O)NR$^{15}$ | H/— | H/H | Cl/H | H/CF$_3$ | H/H | pyrid-2-yloxy |
| 635 | OC(=O)NR$^{15}$ | H/— | H/H | Cl/H | H/H | CF$_3$/H | pyrid-2-yloxy |
| 636 | OC(=O)NR$^{15}$ | CH$_3$/— | H/H | Cl/H | H/H | CF$_3$/H | pyrid-2-yloxy |
| 637 | OC(=O)NR$^{15}$ | C$_2$H$_5$/— | H/H | Cl/H | H/H | CF$_3$/H | pyrid-2-yloxy |
| 638 | OC(=O)NR$^{15}$ | H/— | H/H | Cl/H | H/CO$_2$CH$_3$ | H/H | pyrid-2-yloxy |
| 639 | OC(=O)NR$^{15}$ | H/— | H/H | F/H | H/H | Cl/H | pyrid-2-yloxy |
| 640 | OC(=O)NR$^{15}$ | H/— | H/H | F/H | H/H | F/H | pyrid-2-yloxy |
| 641 | OC(=O)NR$^{15}$ | H/— | H/H | F/H | H/F | H/F | pyrid-2-yloxy |
| 642 | OC(=O)NR$^{15}$ | H/— | H/H | F/H | H/CF$_3$ | H/H | pyrid-2-yloxy |
| 643 | OC(=O)NR$^{15}$ | H/— | H/H | F/H | H/H | CF$_3$/H | pyrid-2-yloxy |
| 644 | OC(=O)NR$^{15}$SO$_2$ | H/— | H/Cl | Cl/H | H/H | CF$_3$/H | pyrid-2-yloxy |
| 645 | OC(=O)NR$^{15}$ | H/— | H/Cl | Cl/H | H/H | Cl/H | pyrid-2-yloxy |
| 646 | OC(=O)NR$^{15}$ | H/— | H/Cl | Cl/H | H/H | F/H | pyrid-2-yloxy |
| 647 | OC(=O)NR$^{15}$ | H/— | H/Cl | Cl/H | H/F | H/F | pyrid-2-yloxy |
| 648 | OC(=O)NR$^{15}$ | H/— | H/Cl | Cl/H | H/OCH$_3$ | H/H | pyrid-2-yloxy |
| 649 | OC(=O)NR$^{15}$ | H/— | H/Cl | Cl/H | H/OCH$_3$ | H/OCH$_3$ | pyrid-2-yloxy |
| 650 | OC(=O)NR$^{15}$ | H/— | H/Cl | Cl/H | H/CF$_3$ | H/H | pyrid-2-yloxy |
| 651 | OC(=O)NR$^{15}$ | H/— | H/Cl | Cl/H | H/H | CF$_3$/H | pyrid-2-yloxy |
| 652 | OC(=O)NR$^{15}$ | H/— | H/CF$_3$ | H/H | H/H | Cl/H | pyrid-2-yloxy |
| 653 | OC(=O)NR$^{15}$ | H/— | H/CF$_3$ | H/H | H/H | F/H | pyrid-2-yloxy |
| 654 | OC(=O)NR$^{15}$ | H/— | H/CF$_3$ | H/H | H/F | H/F | pyrid-2-yloxy |
| 655 | OC(=O)NR$^{15}$ | H/— | H/CF$_3$ | H/H | H/CF$_3$ | H/H | pyrid-2-yloxy |
| 656 | OC(=O)NR$^{15}$ | H/— | H/CF$_3$ | H/H | H/H | CF$_3$/H | pyrid-2-yloxy |
| 657 | OC(=O)NR$^{15}$ | H/— | H/H | CF$_3$/H | H/H | H/H | pyrid-2-yloxy |
| 658 | OC(=O)NR$^{15}$ | CH$_3$/— | H/H | CF$_3$/H | H/H | H/H | pyrid-2-yloxy |
| 659 | OC(=O)NR$^{15}$CHR$^{16}$ | H/H | H/H | CF$_3$/H | H/H | H/H | pyrid-2-yloxy |
| 660 | OC(=O)NR$^{15}$CHR$^{16}$ | H/CH$_3$ | H/H | CF$_3$/H | H/H | H/H | pyrid-2-yloxy |

TABLE 1-continued

| | | | | | | | |
|---|---|---|---|---|---|---|---|
| 661 | OC(=O)O | — | H/H | CF$_3$/H | H/H | H/H | pyrid-2-yloxy |
| 662 | OC(=O)NR$^{15}$ | H/— | H/H | CF$_3$/H | Cl/H | H/H | pyrid-2-yloxy |
| 663 | OC(=O)NR$^{15}$CHR$^{16}$ | H/H | H/H | CF$_3$/H | Cl/H | H/H | pyrid-2-yloxy |
| 664 | OC(=O)NR$^{15}$ | H/— | H/H | CF$_3$/H | H/Cl | H/H | pyrid-2-yloxy |
| 665 | OC(=O)NR$^{15}$ | H/— | H/H | CF$_3$/H | H/H | Cl/H | pyrid-2-yloxy |
| 666[1] | OC(=O)NR$^{15}$ | H/— | H/H | CF$_3$/H | H/H | Cl/H | pyrid-2-yloxy |
| 667 | OC(=S)NR$^{15}$ | H/— | H/H | CF$_3$/H | H/H | Cl/H | pyrid-2-yloxy |
| 668 | OC(=O)NR$^{15}$SO$_2$ | H/— | H/H | CF$_3$/H | H/H | Cl/H | pyrid-2-yloxy |
| 669 | OC(=O)NR$^{15}$ | H/— | H/H | CF$_3$/H | H/H | Cl/H | pyrid-2-loxy, N-oxide |
| 670 | OC(=O)NR$^{15}$ | H/— | H/H | CF$_3$/H | H/H | Cl/H | 3-cyanopyrid-2-yloxy |
| 671 | OC(=O)NR$^{15}$ | H/— | H/H | CF$_3$/H | H/H | Cl/H | 5-cyanopyrid-2-yloxy |
| 672 | OC(=O)NR$^{15}$ | H/— | H/H | CF$_3$/H | H/Br | H/H | pyrid-2-yloxy |
| 673 | OC(=O)NR$^{15}$ | H/— | H/H | CF$_3$/H | H/H | Br/H | pyrid-2-yloxy |
| 674 | OC(=O)NR$^{15}$ | H/— | H/H | CF$_3$/H | H/F | H/H | pyrid-2-yloxy |
| 675 | OC(=O)NR$^{15}$ | H/— | H/H | CF$_3$/H | H/H | F/H | pyrid-2-yloxy |
| 676 | OC(=O)NR$^{15}$CHR$^{16}$ | H/— | H/H | CF$_3$/H | H/H | F/H | pyrid-2-yloxy |
| 677 | OC(=O)NR$^{15}$ | H/— | H/H | CF$_3$/H | H/H | I/H | pyrid-2-yloxy |
| 678 | OC(=O)NR$^{15}$CHR$^{16}$ | H/— | H/H | CF$_3$/H | Cl/H | Cl/H | pyrid-2-yloxy |
| 679 | OC(=O)NR$^{15}$ | H/— | H/H | CF$_3$/H | F/H | F/H | pyrid-2-yloxy |
| 680 | OC(=O)NR$^{15}$ | H/— | H/H | CF$_3$/H | H/F | H/F | pyrid-2-yloxy |
| 681 | OC(=S)NR$^{15}$ | H/— | H/H | CF$_3$/H | H/F | H/F | pyrid-2-yloxy |
| 682 | OC(=O)NR$^{15}$ | H/— | H/H | CF$_3$/H | H/F | H/F | pyrid-2-yloxy, N-oxide |
| 683 | OC(=O)NR$^{15}$ | H/— | H/H | CF$_3$/H | H/F | H/F | 3-Cl-pyrid-2-yloxy |
| 684 | OC(=O)NR$^{15}$ | H/— | H/H | CF$_3$/H | H/F | H/F | 5-Cl-pyrid-2-yloxy |
| 685 | OC(=O)NR$^{15}$ | H/— | H/H | CF$_3$/H | H/F | H/F | 6-Cl-pyrid-2-yloxy |
| 686 | OC(=O)NR$^{15}$ | H/— | H/H | CF$_3$/H | H/F | H/F | 3,5-Cl$_2$-pyrid-2-yloxy |
| 687 | OC(=O)NR$^{15}$ | H/— | H/H | CF$_3$/H | H/F | H/F | 3-cyanopyrid-2-yloxy |
| 688 | OC(=O)NR$^{15}$ | H/— | H/H | CF$_3$/H | H/F | H/F | 5-cyanopyrid-2-yloxy |
| 689 | OC(=O)NR$^{15}$ | H/— | H/H | CF$_3$/H | H/F | H/F | 3-CF$_3$-pyrid-2-yloxy |
| 690 | OC(=O)NR$^{15}$ | H/— | H/H | CF$_3$/H | H/F | H/F | 4-CF$_3$-pyrid-2-yloxy |
| 691 | OC(=O)NR$^{15}$ | H/— | H/H | CF$_3$/H | H/F | H/F | 5-CF$_3$-pyrid-2-yloxy |
| 692 | OC(=S)NR$^{15}$ | H/— | H/H | CF$_3$/H | H/CF$_3$ | H/H | pyrid-2-yloxy |
| 693 | OC(=S)NR$^{15}$ | H/— | H/H | CF$_3$/H | H/H | CF$_3$/H | pyrid-2-yloxy |
| 694 | OC(=O)NR$^{15}$CHR$^{16}$ | H/— | H/H | CF$_3$/H | H/CH$_3$ | H/H | pyrid-2-yloxy |
| 695 | OC(=O)NR$^{15}$CHR$^{16}$ | H/— | H/H | CF$_3$/H | H/H | CH$_3$/H | pyrid-2-yloxy |
| 696 | OC(=O)NR$^{15}$SO$_2$ | H/— | H/H | CF$_3$/H | H/H | CH$_3$/H | pyrid-2-yloxy |
| 697 | OC(=O)NR$^{15}$ | H/— | H/H | CF$_3$/H | H/F | F/F | pyrid-2-yloxy |
| 698 | OC(=O)NR$^{15}$CHR$^{16}$ | H/— | H/H | CF$_3$/H | H/H | OCH$_3$/H | pyrid-2-yloxy |
| 699 | OC(=O)NR$^{15}$ | H/— | H/H | CF$_3$/H | H/Cl | OCH$_3$/H | pyrid-2-yloxy |
| 700 | OC(=O)NR$^{15}$ | H/— | H/H | CF$_3$/H | H/F | OCH$_3$/H | pyrid-2-yloxy |
| 701 | OC(=O)NR$^{15}$ | H/— | H/H | CF$_3$/H | H/H | OCHF$_2$/H | pyrid-2-yloxy |
| 702 | OC(=O)NR$^{15}$ | H/— | H/H | CF$_3$/H | H/H | SCH$_3$/H | pyrid-2-yloxy |
| 703 | OC(=O)NR$^{15}$ | H/— | H/H | CF$_3$/H | H/H | SCF$_3$/H | pyrid-2-yloxy |
| 704 | OC(=O)NR$^{15}$ | H/— | H/H | CF$_3$/H | H/H | CN/H | pyrid-2-yloxy |
| 705 | OC(=O)NR$^{15}$ | H/— | H/H | CF$_3$/H | H/H | C(=O)CH$_3$/H | pyrid-2-yloxy |
| 706 | OC(=O)NR$^{15}$ | H/— | H/H | OCF$_3$/H | H/H | Cl/H | pyrid-2-yloxy, N-oxide |
| 707 | OC(=O)NR$^{15}$ | H/— | H/H | OCF$_3$/H | H/H | Cl/H | 3-cyanopyrid-2-yloxy |
| 708 | OC(=O)NR$^{15}$ | H/— | H/H | OCF$_3$/H | H/H | Cl/H | 5-cyanopyrid-2-yloxy |
| 709 | OC(=O)NR$^{15}$ | H/— | H/H | OCF$_3$/H | H/F | H/F | pyrid-2-yloxy, N-oxide |
| 710 | OC(=O)NR$^{15}$ | H/— | H/H | OCF$_3$/H | H/F | H/F | 3-cyanopyrid-2-yloxy |
| 711 | OC(=O)NR$^{15}$ | H/— | H/H | OCF$_3$/H | H/F | H/F | 5-cyanopyrid-2-yloxy |
| 712 | OC(=O)NR$^{15}$ | H/— | H/H | Cl/H | H/H | Cl/H | pyrimid-2-yloxy |
| 713 | OC(=O)NR$^{15}$ | H/— | H/H | Cl/H | H/F | H/H | pyrimid-2-yloxy |
| 714 | OC(=O)NR$^{15}$ | H/— | H/H | Cl/H | H/F | H/F | pyrimid-2-yloxy |
| 715 | OC(=O)NR$^{15}$ | H/— | H/H | F/H | H/H | Cl/H | pyrimid-2-yloxy |
| 716 | OC(=O)NR$^{15}$ | H/— | H/H | F/H | H/F | H/H | pyrimid-2-yloxy |
| 717 | OC(=O)NR$^{15}$ | H/— | H/H | F/H | H/F | H/F | pyrimid-2-yloxy |
| 718 | OC(=O)NR$^{15}$ | H/— | Cl/H | Cl/H | H/H | Cl/H | pyrimid-2-yloxy |
| 719 | OC(=O)NR$^{15}$ | H/— | Cl/H | Cl/H | H/F | H/H | pyrimid-2-yloxy |
| 720 | OC(=O)NR$^{15}$ | H/— | Cl/H | Cl/H | H/F | H/F | pyrimid-2-yloxy |
| 721 | OC(=O)NR$^{15}$ | H/— | H/Cl | Cl/H | H/H | Cl/H | pyrimid-2-yloxy |
| 722 | OC(=O)NR$^{15}$ | H/— | H/Cl | Cl/H | H/H | F/H | pyrimid-2-yloxy |
| 723 | OC(=O)NR$^{15}$ | H/— | H/Cl | Cl/H | H/F | H/F | pyrimid-2-yloxy |
| 724 | OC(=O)NR$^{15}$ | H/— | H/Cl | Cl/H | H/CF$_3$ | H/H | pyrimid-2-yloxy |
| 725 | OC(=O)NR$^{15}$ | H/— | H/Cl | Cl/H | H/H | CF$_3$/H | pyrimid-2-yloxy |
| 726 | OC(=O)NR$^{15}$ | H/— | H/Cl | H/Cl | H/H | Cl/H | pyrimid-2-yloxy |
| 727 | OC(=O)NR$^{15}$ | H/— | H/Cl | H/Cl | H/F | H/H | pyrimid-2-yloxy |
| 728 | OC(=O)NR$^{15}$ | H/— | H/Cl | H/Cl | H/F | H/F | pyrimid-2-yloxy |
| 729 | OC(=O)NR$^{15}$ | H/— | H/H | CF$_3$/H | H/H | Cl/H | pyrimid-2-yloxy |
| 730 | OC(=O)NR$^{15}$ | H/— | H/H | CF$_3$/H | F/H | F/H | pyrimid-2-yloxy |
| 731 | OC(=O)NR$^{15}$ | H/— | H/H | CF$_3$/H | H/F | H/F | pyrimid-2-yloxy |
| 732 | OC(=O)NR$^{15}$ | H/— | H/H | CF$_3$/H | H/F | F/H | pyrimid-2-yloxy |
| 733 | OC(=O)NR$^{15}$ | H/— | H/H | OCF$_3$/H | H/H | Cl/H | pyrimid-2-yloxy |
| 734 | OC(=O)NR$^{15}$ | H/— | H/H | OCF$_3$/H | H/F | H/H | pyrimid-2-yloxy |
| 735 | OC(=O)NR$^{15}$ | H/— | H/H | OCF$_3$/H | H/F | H/F | pyrimid-2-yloxy |
| 736 | OC(=O)NR$^{15}$ | H/— | H/H | CF$_3$/H | H/F | H/F | pyridazin-3-yloxy |

TABLE 1-continued

| | | | | | | | |
|---|---|---|---|---|---|---|---|
| 737 | OC(=O)NR$^{15}$ | H/— | H/H | CF$_3$/H | H/H | Cl/H | 6-chloropyridazin-3-yloxy |
| 738 | OC(=O)NR$^{15}$ | H/— | H/H | CF$_3$/H | H/F | H/F | 6-chloropyridazin-3-yloxy |
| 739 | OC(=O)NR$^{15}$ | H/— | H/H | CF$_3$/H | H/F | H/F | 1,3,5-triazin-2-yloxy |
| 740 | OC(=O)NR$^{15}$ | H/— | H/H | CF$_3$/H | H/F | H/F | 4,6-di-OCH$_3$-1,3,5-triazin-2-yloxy |

*R$^{15}$ in Compound 705 is —C(=O)NHCH$_3$
**Cmpd 623, 624, 625 and 626: R$^3$ and R$^4$ are taken together with —CH=CHCH=CH— to form a benzo-fused ring.

Compounds of formula I where A is CH, forming a piperidine ring; n is 1, forming single bonds from the methyl carbon (α) and its substituents; p is 0; and; m and s are 1; B is a bridging group from the methyl carbon to R; where R is phenyl substituted with R$^{17}$, R$^{18}$, R$^{19}$, R$^{20}$, and R$^{21}$; q is 0 and r is 1, forming an N-oxide; E is —(CR$^{27}$R$^{28}$)$_x$—(CR$^{29}$R$^{30}$)$_y$—, where x is 1, and y is 0; and R$^8$ is phenyl substituted with R$^{22}$, R$^{23}$, R$^{24}$, R$^{25}$, and R$^{26}$; where R$^1$, R$^2$, R$^3$, R$^5$, R$^6$, R$^{21}$, R$^{22}$, R$^{23}$, R$^{25}$, R$^{26}$ R$^{27}$, and R$^{28}$ are hydrogen:

I

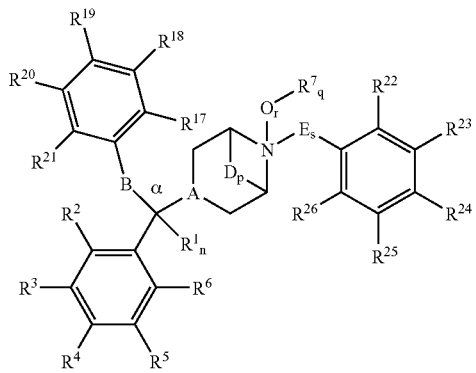

| Cmpd. No. | B | R$^4$ | R$^{17}$/R$^{18}$ | R$^{19}$/R$^{20}$ | R$^{24}$ |
|---|---|---|---|---|---|
| 741 | OC(=O)NR$^{15}$* | CF$_3$ | H/F | H/F | OC$_3$H$_7$ |
| 742 | OC(=O)NR$^{15}$ | CF$_3$ | H/F | H/H | CH=NOC$_2$H$_5$ |
| 743 | OC(=O)NR$^{15}$ | CF$_3$ | H/F | H/F | CH=NOC$_2$H$_5$ |
| 744 | OC(=O)NR$^{15}$ | CF$_3$ | H/F | H/F | CH=NOCH$_2$C≡CH |
| 745 | OC(=O)NR$^{15}$ | CF$_3$ | H/H | Cl/H | CO$_2$CH(CH$_3$)$_2$ |
| 746 | OC(=O)NR$^{15}$ | CF$_3$ | H/F | H/F | NHCO$_2$CH(C$_3$)$_2$ |
| 747 | OC(=O)NR$^{15}$ | CF$_3$ | H/H | Cl/H | Ph |
| 748 | OC(=O)NR$^{15}$ | CF$_3$ | H/F | H/F | Ph |
| 749 | OC(=O)NR$^{15}$ | CF$_3$ | H/F | H/F | OPh |
| 750 | OC(=O)NR$^{15}$ | CF$_3$ | H/F | H/F | O(2-F—Ph) |
| 751 | OC(=O)NR$^{15}$ | CF$_3$ | H/F | H/F | O(2,6-F$_2$—Ph) |
| 752 | OC(=O)NR$^{15}$ | F | H/F | H/F | pyrid-2-yloxy |
| 753 | OC(=O)NR$^{15}$ | CF$_3$ | F/H | F/H | pyrid-2-yloxy |
| 754 | OC(=O)NR$^{15}$ | CF$_3$ | H/F | F/H | pyrid-2-yloxy |
| 755 | OC(=O)NR$^{15}$ | CF$_3$ | H/F | H/F | 3-chloropyrid-2-yloxy |
| 756 | OC(=O)NR$^{15}$ | CF$_3$ | H/F | H/F | 5-chloropyrid-2-yloxy |
| 757 | OC(=O)NR$^{15}$ | CF$_3$ | H/F | H/F | 6-chloropyrid-2-yloxy |
| 758 | OC(=O)NR$^{15}$ | CF$_3$ | H/F | H/F | 3,5-di-Cl$_2$-pyrid-2-yloxy |
| 759 | OC(=O)NR$^{15}$ | CF$_3$ | H/F | H/F | 3-CF$_3$-pyrid-2-yloxy |
| 760 | OC(=O)NR$^{15}$ | CF$_3$ | H/F | H/F | 4-CF$_3$-pyrid-2-yloxy |
| 761 | OC(=O)NR$^{15}$ | CF$_3$ | H/F | H/F | N-(methoxycarbonyl)-pyrid-2-ylamino |
| 762 | OC(=O)NR$^{15}$ | CF$_3$ | H/H | Cl/H | pyrimidin-2-yloxy |
| 763 | OC(=O)NR$^{15}$ | CF$_3$ | F/H | F/H | pyrimidin-2-yloxy |
| 764 | OC(=O)NR$^{15}$ | CF$_3$ | H/F | F/H | pyrimidin-2-yloxy |
| 765 | OC(=O)NR$^{15}$ | CF$_3$ | H/F | H/F | pyrimidin-2-yloxy |
| 766 | O | OCF$_3$ | H/H | CF$_3$/H | pyrimidin-2-yloxy |
| 767 | OC(=O)NR$^{15}$ | CF$_3$ | H/H | Cl/H | 6-chloropyridazin-3-yloxy |
| 768 | OC(=O)NR$^{15}$ | CF$_3$ | H/F | H/F | 6-chloropyridazin-3-yloxy |

*R$^{15}$ is hydrogen in Cmpds 741–765, 767, 768.

TABLE 1-continued

Compounds of formula I where A is CH, forming a piperidine ring; n is 1, forming single bonds from the methyl carbon (α) and its substituents; p, q, and r are 0; m and s are 1; B is a bridging group from the methyl carbon to R; E is —$(CR^{27}R^{28})_x$—$(CR^{29}R^{30})_y$—, where x is 1, and y is 0; and $R^8$ is phenyl substituted with $R^{22}$, $R^{23}$, $R^{24}$, $R^{25}$, and $R^{26}$; where $R^1$, $R^2$, $R^3$, $R^5$, $R^6$, $R^{22}$, $R^{23}$, $R^{25}$, $R^{26}$, $R^{27}$, and $R^{28}$ are hydrogen:

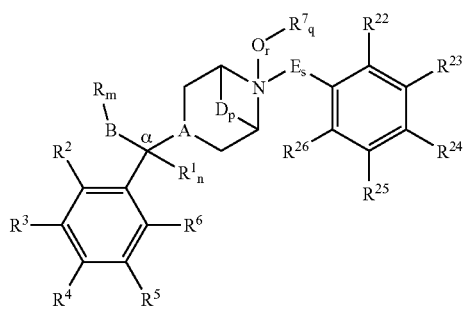

I

| Cmpd. No. | B | $R^{15}$ | $R^{16}$ | R | $R^4$ | $R^{24}$ |
|---|---|---|---|---|---|---|
| 769 | O | — | — | $CH_2CH=CH$ | $CF_3$ | pyrid-2-yloxy |
| 770 | OC(=O)O | — | — | $CH(CH_3)_2$ | $CF_3$ | pyrid-2-yloxy |
| 771 | OC(=O)$NR^{15}$ | H | — | $CH_3$ | $CF_3$ | pyrid-2-yloxy |
| 772 | OC(=S)$NR^{15}$ | H | — | $CH_3$ | $CF_3$ | pyrid-2-yloxy |
| 773 | OC(=O)$NR^{15}$ | $CH_3$ | — | $CH_3$ | $CF_3$ | $CH=NOC_2H_5$ |
| 774 | OC(=O)$NR^{15}$ | H | — | $C_2H_5$ | $CF_3$ | pyrid-2-yloxy |
| 775 | OC(=O)$NR^{15}$ | H | — | $C_3H_7$ | $CF_3$ | pyrid-2-yloxy |
| 776 | OC(=O)$NR^{15}$ | H | — | $CH(CH_3)_2$ | $CF_3$ | pyrid-2-yloxy |
| 777 | OC(=S)$NR^{15}$ | H | — | $CH(CH_3)_2$ | $CF_3$ | pyrid-2-yloxy |
| 778 | OC(=O)$NR^{15}$ | $CH_3$ | — | $CH(CH_3)_2$ | $CF_3$ | pyrid-2-yloxy |
| 779 | OC(=O)$NR^{15}$ | H | — | $C(CH_3)_3$ | $CF_3$ | pyrid-2-yloxy |
| 780 | OC(=O)$NR^{15}$ | H | — | $CH_2CH=CH$ | $CF_3$ | pyrid-2-yloxy |
| 781 | OC(=O)$NR^{15}$ | H | — | cyclopentyl | $CF_3$ | pyrid-2-yloxy |
| 782 | OC(=O)$NR^{15}$ | H | — | cyclohexyl | $CF_3$ | pyrid-2-yloxy |
| 783 | OC(=O)$NR^{15}CHR^{16}$ | H | H | $CO_2C_2H_5$ | $CF_3$ | pyrid-2-yloxy |
| 784 | OC(=O)$NR^{15}CHR^{16}$ | H | $CH(CH_3)_2$ | $CO_2CH_3$ | $CF_3$ | pyrid-2-yloxy |

Compounds of formula I where A is CH, forming a piperidine ring; n is 1, forming single bonds from the methyl carbon (α) and its substituents; p is 0; m and s are 1; B is a bridging group from the methyl carbon to R; q is 0 and r is 1, forming an N-oxide; E is —$(CR^{27}R^{28})_x$—$(CR^{29}R^{30})_y$—, where x is 1, and y is 0; and $R^8$ is phenyl substituted with $R^{22}$, $R^{23}$, $R^{24}$, $R^{25}$, and $R^{26}$; where $R^1$, $R^2$, $R^3$, $R^5$, $R^6$, $R^{22}$, $R^{23}$, $R^{25}$, $R^{26}$ $R^{27}$, and $R^{28}$ are hydrogen:

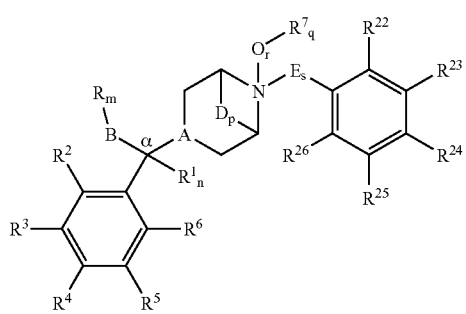

I

| Cmpd. No. | B | $R^{15}$ | R | $R^4$ | $R^{24}$ |
|---|---|---|---|---|---|
| 785 | OC(=O)$NR^{15}$ | H | $CH(CH_3)_2$ | $CF_3$ | pyrid-2-yloxy |

TABLE 1-continued

Compounds of formula I where A is C, forming a 1,2,5,6-tetrahydropyridyl ring; n is 1, forming single bonds from the methyl carbon (α) and its substituents; p, q, and r are 0; m and s are 1; B is a bridging group from the methyl carbon to R; E is —$(CR^{27}R^{28})_x$—$(CR^{29}R^{30})_y$—, where x is 1, and y is 0; $R^8$ is phenyl substituted with $R^{22}$, $R^{23}$, $R^{24}$, $R^{25}$, and $R^{26}$; and R is phenyl substituted with $R^{17}$, $R^{18}$, $R^{19}$, $R^{20}$, and $R^{21}$; where $R^1$, $R^2$, $R^3$, $R^5$, $R^6$, $R^{21}$, $R^{22}$, $R^{23}$, $R^{25}$, $R^{26}$, $R^{27}$, and $R^{28}$ are hydrogen:

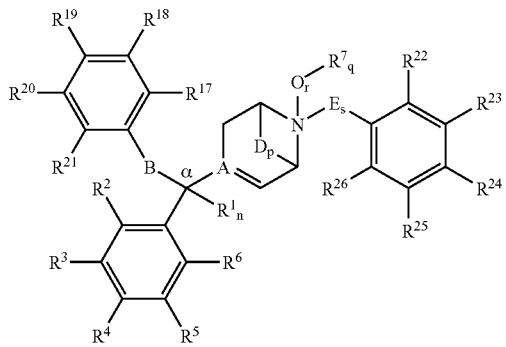

I

| Cmpd. No. | B | $R^4$ | $R^{17}/R^{18}$ | $R^{19}/R^{20}$ | $R^{24}$ |
|---|---|---|---|---|---|
| 786 | OC(=O)NR$^{15}$* | CF$_3$ | H/F | H/F | pyrimidin-2-yloxy |

*$R^{15}$ is hydrogen.

Compounds of formula I where A is C, forming a 1,2,5,6-tetrahydropyridyl ring; n is 1, forming single bonds from the methyl carbon (α) and its substituents; p is 0; m and s are 1; B is a bridging group from the methyl carbon to R; q is 0 and r is 1, forming an N-oxide; E is —$(CR^{27}R^{28})_x$—$(CR^{29}R^{30})_y$—, where x is 1, and y is 0; $R^8$ is phenyl substituted with $R^{22}$, $R^{23}$, $R^{24}$, $R^{25}$, and $R^{26}$; and R is phenyl substituted with $R^{17}$, $R^{18}$, $R^{19}$, $R^{20}$, and $R^{21}$; where $R^1$, $R^2$, $R^3$, $R^5$, $R^6$, $R^{21}$, $R^{22}$, $R^{23}$, $R^{25}$, $R^{26}$, $R^{27}$, and $R^{28}$ are hydrogen:

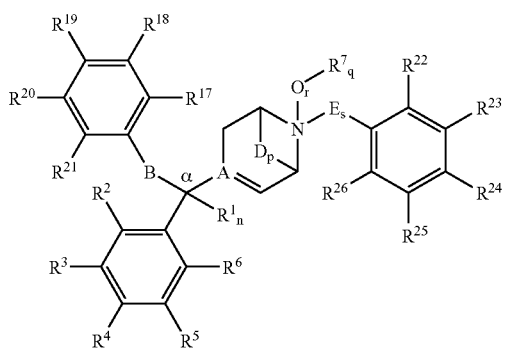

I

| Cmpd. No. | B | $R^4$ | $R^{17}/R^{18}$ | $R^{19}/R^{20}$ | $R^{24}$ |
|---|---|---|---|---|---|
| 787 | OC(=O)NR$^{15}$* | CF$_3$ | H/F | H/F | pyrimidin-2-yloxy |

*$R^{15}$ is hydrogen.

TABLE 1-continued

Compounds of formula I where A is C, forming a piperidine ring; m, p, q, and r are 0; m is 1; n is 0, forming a double bond between the methyl carbon (α) and the 4-position of the piperidine ring; E is —$(CR^{27}R^{28})_x$—$(CR^{29}R^{30})_y$—, where x is 1, and y is 0; $R^8$ is phenyl substituted with $R^{22}$, $R^{23}$, $R^{24}$, $R^{25}$, and $R^{26}$; B is phenyl substituted with $R^9$, $R^{10}$, $R^{11}$, $R^{12}$, and $R^{13}$; where $R^2$, $R^5$, $R^6$, $R^9$, $R^{12}$ $R^{13}$, $R^{22}$, $R^{23}$, $R^{25}$, $R^{26}$ $R^{27}$ and $R^{28}$ are hydrogen;

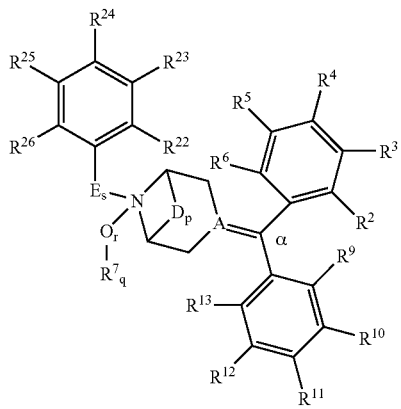

I

| Cmpd. No. | $R^2/R^3/R^4/R^5$ | $R^{10}/R^{11}$ | $R^{24}$ |
|---|---|---|---|
| 788 | H/H/CF$_3$/H | H/CF$_3$ | OC(=O)CH$_3$ |
| 789 | H/H/Cl/H | H/Cl | OC(=O)NHCH$_3$ |
| 790 | H/H/CF$_3$/H | H/CF$_3$ | OC(=O)NHCH$_3$ |
| 791 | H/H/OCF$_3$/H | H/OCF$_3$ | OC(=O)NHCH$_3$ |
| 792 | H/H/CF$_3$/H | H/CF$_3$ | OC(=O)NHCH(CH$_3$)$_2$ |
| 793 | H/H/H/H | H/H | NHCO$_2$CH(CH$_3$)$_2$ |
| 794 | H/H/F/H | H/F | NHCO$_2$CH(CH$_3$)$_2$ |
| 795 | H/Cl/Cl/H | Cl/Cl | NHCO$_2$CH(CH$_3$)$_2$ |
| 796 | H/F/Cl/H | F/Cl | NHCO$_2$CH(CH$_3$)$_2$ |
| 797 | H/H/CF$_3$/H | H/CF$_3$ | NHCO$_2$CH$_2$C=CH$_2$ |
| 798 | H/H/Cl/H | H/Cl | NHCO$_2$CH$_2$C=CHCH$_3$ |
| 799 | H/H/CF$_3$/H | H/CF$_3$ | NHCO$_2$CH$_2$C=CHCH$_3$ |
| 800 | H/H/Cl/H | H/Cl | NHCO$_2$CH$_2$C(CH3)=CH$_2$ |
| 801 | H/H/Cl/H | H/Cl | NHCO$_2$CH$_2$C≡CH |
| 802 | H/H/CF$_3$/H | H/CF$_3$ | NHCO$_2$CH$_2$C≡CH |
| 803 | H/H/CF$_3$/H | H/CF$_3$ | OSO$_2$CH$_3$ |
| 804 | H/H/CF$_3$/H | H/CF$_3$ | OSO$_2$CH(CH$_3$)$_2$ |
| 805 | H/H/CF$_3$/H | H/CF$_3$ | NHSO$_2$CH$_3$ |
| 806 | H/H/CF$_3$/H | H/CF$_3$ | O(2-F—Ph) |
| 807 | H/H/CF$_3$/H | H/CF$_3$ | pyrid-2-yl |
| 808 | H/H/H/H | H/H | pyrid-2-yloxy |
| 809 | H/H/Cl/H | H/Cl | pyrid-2-yloxy |
| 810 | H/H/F/H | H/F | pyrid-2-yloxy |
| 811 | H/H/CF$_3$/H | H/CF$_3$ | pyrid-2-ylamino |
| 812 | H/H/Cl/H | H/Cl | pyrimidin-2-yloxy |
| 813 | H/Cl/Cl/H | Cl/Cl | pyrimidin-2-yloxy |
| 814 | Cl/H/H/H | H/CF$_3$ | pyrimidin-2-yloxy |
| 815 | H/Cl/H/H | H/CF$_3$ | pyrimidin-2-yloxy |
| 816 | H/Cl/H/H | H/CF$_3$ | pyrimidin-2-yloxy |
| 817 | H/F/H/H | H/CF$_3$ | pyrimidin-2-yloxy |
| 818 | H/Cl/Cl/H | H/CF$_3$ | pyrimidin-2-yloxy |
| 819 | H/Cl/H/Cl | H/CF$_3$ | pyrimidin-2-yloxy |
| 820 | H/F/H/F | H/CF$_3$ | pyrimidin-2-yloxy |
| 821 | H/F/Cl/H | H/CF$_3$ | pyrimdiin-2-yloxy |
| 822 | H/CF$_3$/H/H | H/CF$_3$ | pyrimidin-2-yloxy |
| 823 | H/H/CF$_3$/H | H/CF$_3$ | 3,4,5,6-tetrahydropyrimidin-2-yloxy |
| 824 | H/H/CF$_3$/H | H/CF$_3$ | pyrimidin-2-yloxy |
| 825 | H/H/CF$_3$/H | H/CF$_3$ | pyrazin-2-yloxy |
| 826 | H/H/CF$_3$/H | H/CF$_3$ | 6-chloropyridazin-3-yloxy |

TABLE 1-continued

Compounds of formula I where A is C, forming a piperidine ring; s is 1; n is 0, forming a double bond between the methyl carbon (α) and the 4-position of the piperidine ring; m and p are 0; q is 0 and r is 1, forming an N-oxide; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; B is phenyl substituted with R$^9$, R$^{10}$, R$^{11}$, R$^{12}$, and R$^{13}$; where R$^6$, R$^9$, R$^{12}$ R$^{13}$, R$^{22}$, R$^{23}$, R$^{25}$, R$^{26}$ R$^{27}$ and R$^{28}$ are hydrogen;

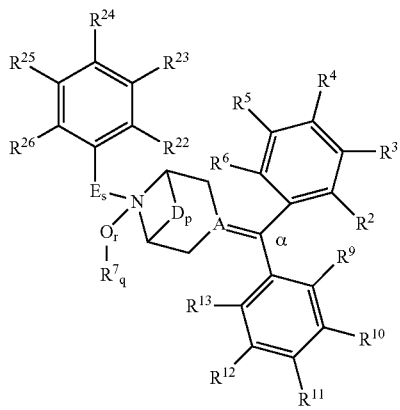

I

| Cmpd. No. | R$^2$/R$^3$/R$^4$/R$^5$ | R$^{10}$/R$^{11}$ | R$^{24}$ |
|---|---|---|---|
| 827 | H/H/Cl/H | H/Cl | OC(=O)NHCH$_3$ |
| 828 | H/H/CF$_3$/H | H/CF$_3$ | OC(=O)NHCH$_3$ |
| 829 | H/H/OCF$_3$/H | H/OCF$_3$ | OC(=O)NHCH$_3$ |
| 830 | H/H/CF$_3$/H | H/CF$_3$ | OC(=O)NHCH(CH$_3$)$_2$ |
| 831 | H/H/Cl/H | H/Cl | NHCO$_2$CH(CH$_3$)$_2$ |
| 832 | H/H/F/H | H/F | NHCO$_2$CH(CH$_3$)$_2$ |
| 833 | H/Cl/Cl/H | Cl/Cl | NHCO$_2$CH(CH$_3$)$_2$ |
| 834 | H/F/Cl/H | F/Cl | NHCO$_2$CH(CH$_3$)$_2$ |
| 835 | H/H/OCH$_3$/H | H/OCH$_3$ | NHCO$_2$CH(CH$_3$)$_2$ |
| 836 | H/H/CF$_3$/H | H/CF$_3$ | NHCO$_2$CH$_2$CH=CH$_2$ |
| 837 | H/H/CF$_3$/H | H/CF$_3$ | NHCO$_2$CH$_2$CH=CHCH$_3$ |
| 838 | H/H/CF$_3$/H | H/CF$_3$ | NHCO$_2$CH$_2$C≡CH |
| 839 | H/H/CF$_3$/H | H/CF$_3$ | O(2-F—Ph) |
| 840 | H/H/CF$_3$/H | H/CF$_3$ | pyrid-2-yl |
| 841 | H/H/Cl/H | H/Cl | pyrid-2-yloxy |
| 842 | H/H/F/H | H/F | pyrid-2-yloxy |
| 843 | H/H/CF$_3$/H | H/CF$_3$ | pyrid-2-ylamino |
| 844 | H/H/Cl/H | H/Cl | pyrimidin-2-yloxy |
| 845 | Cl/H/H/H | H/CF$_3$ | pyrimidin-2-yloxy |
| 846 | H/Cl/H/H | H/CF$_3$ | pyrimidin-2-yloxy |
| 847 | H/H/Cl/H | H/CF$_3$ | pyrimidin-2-yloxy |
| 848 | H/F/H/H | H/CF$_3$ | pyrimidin-2-yloxy |
| 849 | H/Cl/Cl/H | Cl/Cl | pyrimidin-2-yloxy |
| 850 | H/Cl/Cl/H | H/CF$_3$ | pyrimidin-2-yloxy |
| 851 | H/Cl/H/Cl | H/CF$_3$ | pyrimidin-2-yloxy |
| 852 | H/F/Cl/H | H/CF$_3$ | pyrimidin-2-yloxy |
| 853 | H/CF$_3$/H/H | H/CF$_3$ | pyrimidin-2-yloxy |
| 854 | H/H/CF$_3$/H | H/CF$_3$ | pyrimidin-2-yloxy |
| 855 | H/H/CF$_3$/H | H/CF$_3$ | 6-chloropyridazin-3-yloxy |

TABLE 1-continued

Compounds of formula I where A is C, forming a piperidine ring; s is 1; n is 0, forming a double bond between the methyl carbon (α) and the 4-position of the piperidine ring; m and p are 0; q is 0 and r is 1, forming an N-oxide; E is —(CR$^{27}$R$^{28}$)$_x$—(CR$^{29}$R$^{30}$)$_y$—, where x is 1, and y is 0; R$^8$ is phenyl substituted with R$^{22}$, R$^{23}$, R$^{24}$, R$^{25}$, and R$^{26}$; B is phenyl substituted with R$^9$, R$^{10}$, R$^{11}$, R$^{12}$, and R$^{13}$; where R$^6$, R$^9$, R$^{11}$ R$^{13}$, R$^{22}$, R$^{23}$, R$^{25}$, R$^{26}$ R$^{27}$ and R$^{28}$ are hydrogen;

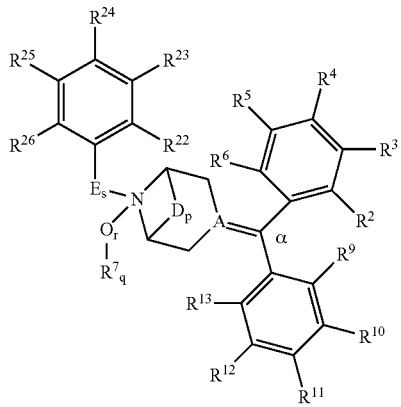

I

| Cmpd. No. | R$^3$/R$^4$ | R$^9$ | R$^{10}$ | R$^{12}$ | R$^{24}$ |
|---|---|---|---|---|---|
| 856 | H/CF$_3$ | H | Cl | Cl | pyrimidin-2-yloxy |
| 857 | H/CF$_3$ | Cl | H | H | pyrimidin-2-yloxy |

Compounds of formula I where A is C, forming a piperidine ring; m, p, q, and r are 0; s is 1; n is 0, forming a double bond between the methyl carbon (α) and the 4-position of the piperidine ring; R$^8$ is pyrid-3-yl substituted with R$^{22}$, R$^{24}$, R$^{25}$, and R$^{26}$; E is —(CR$^{27}$R$^{28}$)$_x$—(CR$^{29}$R$^{30}$)$_y$—, where x is 1, and y is 0; B is phenyl substituted with R$^9$, R$^{10}$, R$^{11}$, R$^{12}$, and R$^{13}$; where R$^2$, R$^3$, R$^5$, R$^6$, R$^9$, R$^{10}$, R$^{12}$, R$^{13}$, R$^{22}$, R$^{25}$, R$^{26}$, R$^{27}$, and R$^{28}$ are hydrogen;

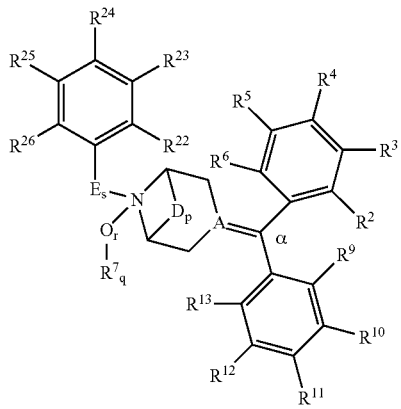

I

| Cmpd. No. | R$^4$ | R$^{11}$ | R$^{24}$ |
|---|---|---|---|
| 858 | CF$_3$ | CF$_3$ | phenoxy |
| 859 | CF$_3$ | CF$_3$ | pyrimidin-2-ylamino |

TABLE 1-continued

Compounds of formula I where A is CH, forming a piperidine ring; n is 1,
forming single bonds from the methyl carbon (α) and its substituents; p is 0; q,
and r are 1, forming a N-substituted oxy derivative; m and s are 1; B is a
bridging group from the methyl carbon to R; where R is phenyl substituted
with $R^{17}$, $R^{18}$, $R^{19}$, $R^{20}$, and $R^{21}$; E is —$(CR^{27}R^{28})_x$—$(CR^{29}R^{30})_y$—, where x is 1, and
y is 0; and $R^8$ is phenyl substituted with $R^{22}$, $R^{23}$, $R^{24}$, $R^{25}$, and $R^{26}$; where $R^1$,
$R^2$, $R^3$, $R^6$, $R^{21}$, $R^{22}$, $R^{23}$, $R^{25}$, $R^{26}$, $R^{27}$, and $R^{28}$ are hydrogen:

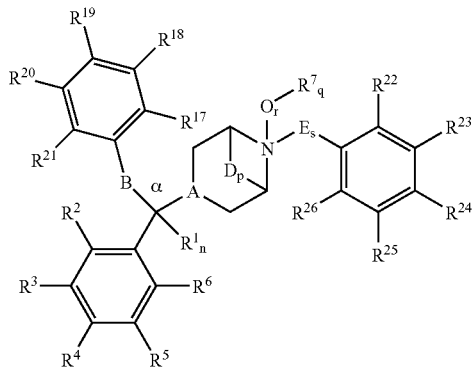

I

| Cmpd. No. | B | $R^{15}$ | $R^4$ | $R^7$ | $R^{19}$ | $R^{24}$ |
|---|---|---|---|---|---|---|
| 860[9] | OC(=O)$NR^{15}$ | H | $CF_3$ | $C_2H_5$ | Cl | pyrid-2-yloxy |

Compounds of formula I where A is CH, forming a piperidine ring; n is 1,
forming single bonds from the methyl carbon (α) and its substituents; p is 0;
and; m and s are 1; B is a bridging group from the methyl carbon to R; where R
is phenyl substituted with $R^{17}$, $R^{18}$, $R^{19}$, $R^{20}$, and $R^{21}$; q is 0 and r is 1, forming
an N-oxide; E is —$(CR^{27}R^{28})_x$—$(CR^{29}R^{30})_y$—, where x is 1, and y is 0; and $R^8$ is
phenyl substituted with $R^{22}$, $R^{23}$, $R^{24}$, $R^{25}$, and $R^{26}$; where $R^1$, $R^2$, $R^3$, $R^5$, $R^6$,
$R^{21}$, $R^{22}$, $R^{23}$, $R^{25}$, $R^{26}$ $R^{27}$, and $R^{28}$ are hydrogen:

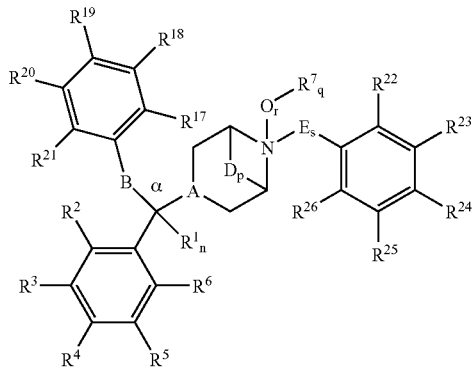

I

| Cmpd. No. | B | $R^4$ | $R^{17}/R^{18}$ | $R^{19/R20}$ | $R^{24}$ |
|---|---|---|---|---|---|
| 861 | OC(=O)$NR^{15}$* | $CF_3$ | H/F | H/F | 6-chloropyrid-3-yloxy |
| 862 | OC(=O)$NR^{15}$ | $CF_3$ | H/H | Cl/H | CH=$NOC_2H_5$ |
| 863 | OC(=O)$NR^{15}$ | Cl | H/H | $OCF_3$/H | pyrid-2-yloxy |

*$R^{15}$ in Cmpds 861–863 is hydrogen.
[1] chloride salt,
[2] trifluoroacetate salt,
[3] succinate salt,
[4] tartarate salt,
[5] bromide salt,
[6] oxalate salt,
[7] chloride salt, monohydrate,
[8] ethanesulfonate salt,
[9] ethyl sulfate salt The following table sets forth physical characterizing data for compounds of formula I of the present invention:

TABLE 2

Physical Characteristics

| Cmpd No. | Emperical Formula | Physical State/ Melting Point (° C.) |
|---|---|---|
| 1 | $C_{18}H_{19}N$ | — |
| 2 | $C_{18}H_{19}N \cdot HCl$ | — |
| 3 | $C_{18}H_{19}N \cdot HBr$ | Solid, 200 |
| 4 | $C_{18}H_{18}ClN \cdot HCl$ | — |
| 5 | $C_{18}H_{18}ClN \cdot HCl$ | — |
| 6 | $C_{18}H_{18}ClN \cdot HCl$ | — |
| 7 | $C_{18}H_{17}F_2N \cdot C_2H_2O_4 \cdot H_2O$ | — |
| 8 | $C_{20}H_{17}F_3N_6$ | Solid, 93–95 |
| 9 | $C_{20}H_{17}F_6NO_2$ | Oil |
| 10 | $C_{22}H_{27}N$ | Oil |
| 11 | $C_{19}H_{20}ClN \cdot HCl$ | — |
| 12 | $C_{21}H_{19}F_6NO_2$ | Oil |
| 13 | $C_{31}H_{33}FN_2$ | Oil |
| 14 | $C_{28}H_{28}N_2$ | Flakes, 105–107 |
| 15 | $C_{28}H_{25}F_2N_3OS$ | Solid, 228–230 |
| 16 | $C_{27}H_{26}FN_3OS$ | Solid, 153–155 |
| 17 | $C_{27}H_{25}F_2N_3OS$ | Solid, 134–137 |
| 18 | $C_{28}H_{32}F_6N_2 \cdot HCl$ | — |
| 19 | $C_{30}H_{34}N_2 \cdot HCl \cdot H_2O$ | — |
| 20 | $C_{22}H_{28}N_2$ | Liquid |
| 21 | $C_{30}H_{30}N_2O_2$ | Solid, 105–107 |
| 22 | $C_{25}H_{30}N_2O_2$ | — |
| 23 | $C_{25}H_{31}N_2O_2S_2$ | Solid, 136–137 |
| 24 | $C_{18}H_{18}ClN \cdot HCl$ | — |
| 25 | $C_{30}H_{33}N_3O$ | Solid, 159–160 |
| 26 | $C_{31}H_{35}N_3O$ | Solid, 134–135 |
| 27 | $C_{22}H_{22}N_2S$ | — |
| 28 | $C_{25}H_{23}ClFN$ | Oil |
| 29 | $C_{25}H_{23}F_2N$ | Oil |
| 30 | $C_{26}H_{24}F_3N$ | Oil |
| 31 | $C_{26}H_{23}F_4N$ | Oil |
| 32 | $C_{26}H_{24}F_3NO$ | Oil |
| 33 | $C_{27}H_{22}BrF_6N$ | Solid |
| 34 | $C_{26}H_{23}F_4N$ | Viscous oil |
| 35 | $C_{26}H_{23}F_4NO$ | Oil |
| 36 | $C_{25}H_{22}ClF_2N$ | Viscous oil |
| 37 | $C_{25}H_{22}F_3N$ | Viscous oil |
| 38 | $C_{26}H_{22}F_5N$ | Viscous oil |
| 39 | $C_{26}H_{26}ClNO$ | Viscous oil |
| 40 | $C_{26}H_{26}FNO$ | Solid, 87–89 |
| 41 | $C_{27}H_{26}F_3NO$ | Viscous oil |
| 42 | $C_{28}H_{25}F_6NO_3$ | Oil |
| 43 | $C_{30}H_{35}NO$ | Solid, 86–89 |
| 44 | $C_{28}H_{31}NO_3$ | Solid, 114–115 |
| 45 | $C_{30}H_{29}F_6NO$ | Solid |
| 46 | $C_{29}H_{27}F_6NO$ | Solid |
| 47 | $C_{30}H_{29}F_6NO_3$ | Solid |
| 48 | $C_{30}H_{29}F_6NO_3$ | Oil |
| 49 | $C_{31}H_{31}F_6NO_4$ | Oil |
| 50 | $C_{30}H_{27}F_6NO_2$ | Sticky solid |
| 51 | $C_{31}H_{29}F_6NO_2$ | Sticky solid |
| 52 | $C_{29}H_{26}F_6N_2O$ | Solid |
| 53 | $C_{29}H_{23}F_9N_2O$ | Solid |
| 54 | $C_{29}H_{26}F_6N_2O_2$ | Solid |
| 55 | $C_{30}H_{28}F_6N_2O_2$ | Solid |
| 56 | $C_{31}H_{30}F_6N_2O_2$ | Sticky solid |
| 57 | $C_{31}H_{30}F_6N_2O_2$ | Solid |
| 58 | $C_{31}H_{30}F_6N_2O_2$ | Solid, 60–65 |
| 59 | $C_{32}H_{32}F_6N_2O_2$ | Solid |
| 60 | $C_{30}H_{28}F_6N_2O$ | Solid |
| 61 | $C_{31}H_{26}F_6N_2OS$ | Sticky solid |
| 62 | $C_{32}H_{26}F_6N_2O$ | Solid |
| 63 | $C_{32}H_{25}ClF_6N_2O$ | Solid |
| 64 | $C_{32}H_{25}ClF_6N_2O_3$ | Solid |
| 65 | $C_{32}H_{25}ClF_6N_2O$ | Solid |
| 66 | $C_{32}H_{25}ClF_6N_2O$ | Solid |
| 67 | $C_{33}H_{25}F_9N_2O$ | Solid |
| 68 | $C_{33}H_{25}F_9N_2O_3$ | Solid |
| 69 | $C_{33}H_{25}F_9N_2O$ | Solid |
| 70 | $C_{33}H_{25}F_6N_3O$ | Solid |
| 71 | $C_{33}H_{25}F_6N_3O$ | Solid |
| 72 | $C_{32}H_{25}F_6N_3O_3$ | Solid |
| 73 | $C_{34}H_{29}F_6N_3O_3$ | Solid |
| 74 | $C_{28}H_{25}ClF_3N_5$ | Oil |
| 75 | $C_{29}H_{25}F_6N_5$ | Solid, 58–63 |
| 76 | $C_{28}H_{28}ClN_5$ | Solid |
| 77 | $C_{28}H_{27}Cl_2N_5$ | Oil |
| 78 | $C_{28}H_{27}F_2N_5$ | Oil |
| 79 | $C_{28}H_{27}ClFN_5$ | Solid |
| 80 | $C_{29}H_{28}F_3N_5$ | Oil |
| 81 | $C_{29}H_{27}F_4N_5$ | Oil |
| 82 | $C_{30}H_{27}F_6N_5$ | Solid, 104–106 |
| 83 | $C_{30}H_{25}F_4N_5O_4$ | Solid |
| 84 | $C_{26}H_{25}ClN_2S$ | — |
| 85 | $C_{27}H_{28}NO$ | — |
| 86 | $C_{27}H_{22}BrF_6NO$ | Solid |
| 87 | $C_{27}H_{21}BrF_7NO$ | Solid |
| 88 | $C_{25}H_{22}ClF_2NO$ | Solid, 90–96 |
| 89 | $C_{25}H_{22}F_3NO_2$ | Solid, 159–160 |
| 90 | $C_{26}H_{22}F_5NO$ | Solid, 162–167 |
| 91 | $C_{26}H_{26}ClNO_2$ | Solid, 155–163 |
| 92 | $C_{26}H_{26}FNO_2$ | Solid, 179–183 |
| 93 | $C_{27}H_{26}F_3NO_2$ | Solid, 158–162 |
| 94 | $C_{29}H_{27}F_6NO_2$ | Sticky solid |
| 95 | $C_{30}H_{29}F_6NO_2$ | Solid |
| 96 | $C_{30}H_{31}F_6NO_4$ | Solid, 76–80 |
| 97 | $C_{32}H_{27}F_8NO_4$ | Solid |
| 98 | $C_{31}H_{29}F_6NO_2$ | Sticky solid |
| 99 | $C_{30}H_{27}F_6NO_3$ | Solid |
| 100 | $C_{31}H_{29}F_6NO_3$ | Solid |
| 101 | $C_{30}H_{28}F_6N_2O_3$ | Solid |
| 102 | $C_{31}H_{30}F_6N_2O_3$ | Solid |
| 103 | $C_{31}H_{30}F_6N_2O_3$ | Solid |
| 104 | $C_{32}H_{32}F_6N_2O_3$ | Solid |
| 105 | $C_{31}H_{26}F_6N_2O_2S$ | Sticky solid |
| 106 | $C_{32}H_{26}F_6N_2O_2$ | Solid |
| 107 | $C_{32}H_{25}ClF_6N_2O_2$ | Solid |
| 108 | $C_{32}H_{25}ClF_6N_2O_2$ | Solid |
| 109 | $C_{33}H_{25}F_9N_2O_2$ | Solid |
| 110 | $C_{33}H_{25}F_9N_2O_2$ | Solid |
| 111 | $C_{33}H_{25}F_6N_3O_2$ | Solid |
| 112 | $C_{29}H_{25}F_6N_5O$ | Solid, 90–95 |
| 113 | $C_{28}H_{27}Cl_2N_5O$ | Solid |
| 114 | $C_{30}H_{27}F_6N_5O$ | Sticky solid |
| 115 | $C_{30}H_{25}F_4N_5O_5$ | Solid |
| 116 | $C_{40}H_{43}F_4NO_4 \cdot HBr$ | Solid, 121–123 |
| 117 | $C_{35}H_{30}F_6N_2O$ | Solid |
| 118 | $C_{40}H_{38}F_6N_2O_4 \cdot HBr$ | Solid |
| 181 | $C_{34}H_{30}F_5N_3O_5$ | Solid, 98–103 |
| 182 | $C_{30}H_{31}ClF_3N_3O_3$ | Solid foam |
| 183 | $C_{30}H_{31}BrF_3N_3O_3$ | — |
| 184 | $C_{29}H_{29}F_4N_3O_4$ | Oil |
| 185 | $C_{30}H_{31}F_4N_3O_4$ | Oil |
| 186 | $C_{29}H_{29}F_4N_3O_4$ | Oil |
| 187 | $C_{30}H_{31}F_4N_3O_4$ | Oil |
| 188 | $C_{30}H_{30}Cl_2F_3N_3O_3$ | — |
| 189 | $C_{30}H_{30}Cl_2F_3N_3O_3$ | — |
| 190 | $C_{30}H_{30}Cl_2F_3N_3O_3$ | — |
| 191 | $C_{30}H_{30}Cl_2F_3N_3O_3$ | — |
| 192 | $C_{30}H_{29}Cl_3F_3N_3O_3$ | — |
| 193 | $C_{30}H_{30}F_5N_3O_3$ | — |
| 194 | $C_{29}H_{28}F_5N_3O_4$ | Sticky solid |
| 195 | $C_{30}H_{30}F_5N_3O_4$ | Oil |
| 196 | $C_{30}H_{30}F_5N_3O_3$ | — |
| 197 | $C_{32}H_{34}F_5N_3O_3$ | — |
| 198 | $C_{30}H_{30}F_5N_3O_3$ | — |
| 199 | $C_{30}H_{30}F_5N_3O_3$ | — |
| 200 | $C_{30}H_{30}F_5N_3O_3$ | — |
| 201 | $C_{30}H_{29}F_6N_3O_3$ | — |
| 202 | $C_{30}H_{27}F_8N_3O_3$ | — |
| 203 | $C_{31}H_{31}F_6N_3O_3$ | — |
| 204 | $C_{31}H_{31}F_6N_3O_3$ | — |
| 205 | $C_{31}H_{31}F_6N_3O_3$ | — |
| 206 | $C_{31}H_{30}ClF_6N_3O_3$ | — |
| 207 | $C_{31}H_{30}ClF_6N_3O_3$ | — |

TABLE 2-continued

Physical Characteristics

| Cmpd No. | Emperical Formula | Physical State/ Melting Point (° C.) |
|---|---|---|
| 208 | $C_{31}H_{30}BrF_6N_3O_3$ | — |
| 209 | $C_{31}H_{34}F_3N_3O_4$ | — |
| 210 | $C_{32}H_{35}ClF_3N_3O_5$ | — |
| 211 | $C_{31}H_{31}F_6N_3O_4$ | — |
| 212 | $C_{36}H_{36}F_3N_3O_3$ | — |
| 213 | $C_{36}H_{36}F_3N_3O_3$ | — |
| 214 | $C_{34}H_{34}F_3N_3O_3$ | — |
| 227 | $C_{32}H_{29}ClF_3N_3O_3$ | — |
| 228 | $C_{32}H_{28}Cl_2F_3N_3O_3$ | — |
| 229 | $C_{32}H_{28}Cl_2F_3N_3O_3$ | — |
| 230 | $C_{32}H_{28}Cl_2F_3N_3O_3$ | — |
| 231 | $C_{32}H_{28}Cl_2F_3N_3O_3$ | — |
| 232 | $C_{32}H_{28}Cl_2F_3N_3O_3$ | — |
| 233 | $C_{32}H_{28}Cl_2F_3N_3O_3$ | — |
| 234 | $C_{32}H_{27}Cl_3F_3N_3O_3$ | — |
| 235 | $C_{32}H_{29}F_4N_3O_4$ | Solid, 73–78 |
| 236 | $C_{32}H_{29}F_4N_3O_4$ | Solid, 75–80 |
| 237 | $C_{32}H_{28}F_5N_3O_3$ | — |
| 238 | $C_{32}H_{28}F_5N_3O_4$ | Solid, 65–70 |
| 239 | $C_{32}H_{28}F_5N_3O_3$ | — |
| 240 | $C_{32}H_{28}F_5N_3O_3$ | — |
| 241 | $C_{32}H_{28}F_5N_3O_3$ | — |
| 242 | $C_{32}H_{27}F_6N_3O_3$ | — |
| 243 | $C_{32}H_{25}F_8N_3O_3$ | — |
| 244 | $C_{33}H_{29}F_6N_3O_3$ | — |
| 245 | $C_{33}H_{29}F_6N_3O_3$ | Solid foam |
| 246 | $C_{33}H_{29}F_6N_3O_4$ | Solid, 75–80 |
| 247 | $C_{33}H_{28}ClF_6N_3O_3$ | — |
| 248 | $C_{34}H_{28}F_9N_3O_3$ | — |
| 249 | $C_{33}H_{29}F_6N_3O_4$ | — |
| 250 | $C_{38}H_{34}F_3N_3O_3$ | — |
| 251 | $C_{38}H_{34}F_3N_3O_3$ | — |
| 261 | $C_{30}H_{31}F_3N_6O_3$ | Solid foam, 70–75 |
| 262 | $C_{29}H_{28}ClF_3N_6O_3$ | Solid foam, 65–69 |
| 263 | $C_{29}H_{28}ClF_3N_6O_3$ | Solid foam, 79–83 |
| 264 | $C_{28}H_{28}Cl_2N_6O_2$ | Solid |
| 265 | $C_{30}H_{30}ClF_3N_6O_2$ | — |
| 267 | $C_{29}H_{28}ClF_3N_6O_3$ | Solid foam, 85–89 |
| 267 | $C_{30}H_{30}ClF_3N_6O_3$ | Solid foam, 85–89 |
| 268 | $C_{30}H_{30}BrF_3N_6O_2$ | — |
| 269 | $C_{30}H_{30}BrF_3N_6O_2$ | — |
| 270 | $C_{30}H_{30}BrF_3N_6O_3$ | Solid foam, 93–97 |
| 271 | $C_{30}H_{30}F_3IN_6O_3$ | Solid foam, 89–92 |
| 272 | $C_{29}H_{28}F_4N_6O_3$ | Solid foam, 66–70 |
| 273 | $C_{29}H_{28}F_4N_6O_3$ | Solid foam, 80–84 |
| 274 | $C_{28}H_{28}ClFN_6O_2$ | Solid |
| 275 | $C_{29}H_{28}F_4N_6O_3$ | Solid foam, 78–81 |
| 276 | $C_{29}H_{29}F_4N_6O_3 \cdot C_2H_5O_3S$ | Solid |
| 277 | $C_{30}H_{30}F_4N_6O_3$ | Semi-solid |
| 278 | $C_{30}H_{30}F_4N_6O_3$ | — |
| 279 | $C_{30}H_{29}Cl_2F_3N_6O_2$ | — |
| 280 | $C_{30}H_{29}Cl_2F_3N_6O_2$ | — |
| 281 | $C_{30}H_{29}Cl_2F_3N_6O_2$ | — |
| 282 | $C_{30}H_{29}Cl_2F_3N_6O_2$ | — |
| 283 | $C_{30}H_{29}Cl_2F_3N_6O_2$ | — |
| 284 | $C_{30}H_{29}Cl_2F_3N_6O_2$ | — |
| 285 | $C_{31}H_{33}F_3N_6O_3$ | Solid foam, 81–83 |
| 286 | $C_{33}H_{37}F_3N_6O_3$ | Solid foam, 76–79 |
| 287 | $C_{31}H_{33}F_3N_6O_4$ | Solid foam, 76–79 |
| 288 | $C_{31}H_{30}F_6N_6O_2$ | — |
| 289 | $C_{31}H_{30}F_6N_6O_2$ | Solid foam |
| 290 | $C_{30}H_{28}F_6N_6O_3$ | Solid, 70–80 |
| 291 | $C_{31}H_{30}F_6N_6O_3$ | Gum |
| 292 | $C_{31}H_{29}ClF_6N_6O_2$ | — |
| 293 | $C_{32}H_{29}F_9N_6O_2$ | — |
| 294 | $C_{30}H_{28}F_6N_6O_4$ | Solid, 70–80 |
| 295 | $C_{31}H_{30}F_6N_6O_4$ | Gum |
| 296 | $C_{30}H_{30}F_3N_7O_5$ | — |
| 297 | $C_{36}H_{35}F_3N_6O_2$ | — |
| 298 | $C_{36}H_{35}F_3N_6O_3$ | — |
| 302 | $C_{31}H_{30}F_6N_6O_2S$ | Semi-solid |
| 304 | $C_{31}H_{31}F_6N_5O_2$ | Gum |
| 305 | $C_{31}H_{31}F_6N_5O_3$ | Gum |
| 306 | $C_{31}H_{32}F_3N_9O_2$ | Solid, 148–155 |
| 307 | $C_{31}H_{29}F_6N_5O_3$ | Gum |
| 308 | $C_{31}H_{29}F_6N_5O_4$ | Gum |
| 309 | $C_{29}H_{30}ClF_3N_6O$ | Syrup |
| 310 | $C_{29}H_{30}ClF_3N_6O$ | Syrup |
| 311 | $C_{29}H_{30}ClF_3N_6O$ | Syrup |
| 312 | $C_{29}H_{30}BrF_3N_6O$ | Semi-solid, 56–61 |
| 313 | $C_{29}H_{30}F_4N_6O$ | Syrup |
| 314 | $C_{29}H_{30}F_4N_6O$ | — |
| 315 | $C_{29}H_{30}F_4N_6O$ | Syrup |
| 316 | $C_{29}H_{30}F_3IN_6O$ | Semi-solid, 58–62 |
| 317 | $C_{30}H_{33}F_3N_6O$ | Syrup |
| 318 | $C_{30}H_{33}F_3N_6O_2$ | Syrup |
| 319 | $C_{30}H_{30}F_6N_6O_2$ | Syrup |
| 320 | $C_{29}H_{30}F_3N_7O_3$ | Semi-solid, 57–62 |
| 321 | $C_{29}H_{29}F_3N_6O_2$ | Solid, 180–184 |
| 322 | $C_{29}H_{28}ClF_3N_6O_2$ | Solid, 173–175 |
| 323 | $C_{29}H_{28}ClF_3N_6O_2$ | Solid, 143–146 |
| 324 | $C_{29}H_{28}ClF_3N_6O_2$ | Solid, 217–220 |
| 325 | $C_{29}H_{28}BrF_3N_6O_2$ | Solid, 217–220 |
| 326 | $C_{29}H_{28}F_4N_6O_2$ | Solid, 141–144 |
| 327 | $C_{29}H_{28}F_4N_6O_2$ | Solid, 151–159 |
| 328 | $C_{29}H_{28}F_4N_6O_2$ | Solid, 195–198 |
| 329 | $C_{29}H_{28}F_3IN_6O_2$ | Solid, 225–229 |
| 330 | $C_{30}H_{31}F_3N_6O_2$ | Solid, 215–218 |
| 331 | $C_{30}H_{31}F_3N_6O_3$ | Solid, 204–209 |
| 332 | $C_{30}H_{28}F_6N_6O_3$ | Solid, 210–213 |
| 333 | $C_{29}H_{28}F_3N_7O_4$ | Solid, 232–236 |
| 334 | $C_{29}H_{29}ClF_3N_7O_2$ | Solid foam, 86–90 |
| 335 | $C_{29}H_{29}ClF_3N_7O_2$ | Solid foam, 75–78 |
| 336 | $C_{29}H_{29}ClF_3N_7O_2$ | Solid foam, 89–93 |
| 337 | $C_{29}H_{29}BrF_3N_7O_2$ | Solid foam, 94–99 |
| 338 | $C_{29}H_{29}F_4N_7O_2$ | Solid foam, 84–88 |
| 339 | $C_{29}H_{29}F_4N_7O_2$ | Solid foam, 89–92 |
| 340 | $C_{29}H_{29}F_4N_7O_2$ | Solid foam, 74–78 |
| 341 | $C_{29}H_{29}F_3IN_7O_2$ | Solid foam, 142–149 |
| 342 | $C_{30}H_{32}F_3N_7O_2$ | Solid foam, 198–200 |
| 343 | $C_{30}H_{32}F_3N_7O_3$ | Solid foam, 83–87 |
| 344 | $C_{30}H_{29}F_6N_7O_2$ | Solid foam, 93–98 |
| 345 | $C_{30}H_{29}F_6N_7O_3$ | Solid foam, 83–88 |
| 346 | $C_{29}H_{29}F_3N_8O_4$ | Solid foam, 105–110 |
| 347 | $C_{29}H_{28}ClF_3N_6O_3$ | Solid foam, 76–79 |
| 348 | $C_{29}H_{28}ClF_3N_6O_3$ | Solid foam, 58–61 |
| 349 | $C_{29}H_{28}ClF_3N_6O_3$ | Solid foam, 153–156 |
| 350 | $C_{29}H_{28}BrF_3N_6O_3$ | Solid foam, 73–76 |
| 351 | $C_{29}H_{28}F_4N_6O_3$ | Solid foam, 76–80 |
| 352 | $C_{29}H_{28}F_4N_6O_3$ | Solid foam, 63–69 |
| 353 | $C_{29}H_{28}F_4N_6O_3$ | Solid foam, 92–95 |
| 354 | $C_{29}H_{28}F_3IN_6O_3$ | Solid foam, 73–75 |
| 355 | $C_{30}H_{31}F_3N_6O_3$ | Solid foam, 73–76 |
| 356 | $C_{30}H_{31}F_3N_6O_4$ | Solid foam, 73–75 |
| 357 | $C_{30}H_{28}F_6N_6O_4$ | Solid foam, 69–72 |
| 358 | $C_{29}H_{28}F_3N_7O_5$ | Solid, 143–146 |
| 395 | $C_{32}H_{29}ClF_3N_3O_4$ | — |
| 396 | $C_{32}H_{28}Cl_2F_3N_3O_4$ | — |
| 397 | $C_{32}H_{28}F_5N_3O_4$ | — |
| 398 | $C_{33}H_{29}F_6N_3O_4$ | — |
| 399 | $C_{29}H_{28}ClF_3N_6O_4$ | Solid |
| 400 | $C_{29}H_{28}F_4N_6O_4$ | Solid |
| 401 | $C_{30}H_{30}F_4N_6O_4$ | Solid, 130–137 |
| 402 | $C_{30}H_{28}F_6N_6O_4$ | Solid, 138–142 |
| 403 | $C_{31}H_{30}F_6N_6O_5$ | Solid foam, 118–122 |
| 404 | $C_{29}H_{28}F_6N_6O_5$ | Solid, 136–140 |
| 405 | $C_{31}H_{30}F_6N_6O_5$ | Solid foam, 120–125 |
| 427 | $C_{29}H_{32}F_3N_3O_3$ | Oil |
| 429 | $C_{29}H_{32}F_3N_3O_3$ | Oil |
| 432 | $C_{32}H_{36}F_3N_3O_3$ | Oil |
| 433 | $C_{25}H_{31}F_3N_6O_3S$ | Oil |
| 434 | $C_{28}H_{26}F_6N_6O_2$ | Oil |
| 435 | $C_{27}H_{26}ClF_3N_6O$ | Liquid |
| 436 | $C_{31}H_{29}F_3N_4O_3$ | White solid |
| 437 | $C_{31}H_{27}F_6N_3O_2$ | Paste |
| 438 | $C_{31}H_{27}F_6N_3O_2$ | Pasty solid |
| 439 | $C_{31}H_{28}ClF_3N_4O_3$ | Solid |
| 440 | $C_{30}H_{25}ClF_6N_4O_2$ | Solid |

TABLE 2-continued

Physical Characteristics

| Cmpd No. | Emperical Formula | Physical State/ Melting Point (° C.) |
|---|---|---|
| 441 | $C_{30}H_{25}ClF_6N_4O_2$ | Solid |
| 442 | $C_{31}H_{27}F_6N_3O_3$ | Solid |
| 443 | $C_{30}H_{27}ClF_3N_3O_2$ | Sticky solid |
| 444 | $C_{31}H_{29}F_3N_4O_3$ | White solid |
| 445 | $C_{31}H_{28}ClF_3N_4O_3$ | White solid |
| 446 | $C_{32}H_{28}F_3N_5O_3$ | Solid |
| 447 | $C_{31}H_{28}ClF_3N_4O_3$ | White solid |
| 448 | $C_{32}H_{28}F_6N_4O_3$ | Solid |
| 449 | $C_{27}H_{27}F_3N_6O_3$ | Solid |
| 450 | $C_{31}H_{29}F_3N_4O_3$ | White solid |
| 451 | $C_{31}H_{27}Cl_2F_3N_4O_3$ | — |
| 452 | $C_{29}H_{26}ClF_3N_4O_2$ | Sticky solid |
| 453 | $C_{26}H_{25}ClF_3N_7O_2$ | Solid |
| 454 | $C_{30}H_{30}F_6N_2O_2$ | Gooey solid |
| 455 | $C_{32}H_{28}F_6N_2O_2$ | Gooey solid |
| 456 | $C_{31}H_{27}F_6N_3O_3$ | Solid |
| 457 | $C_{35}H_{42}F_3N_3O_5$ | Solid |
| 458 | $C_{27}H_{26}F_4N_2O_3$ | Solid |
| 459 | $C_{27}H_{25}ClF_4N_2O_3$ | Solid |
| 460 | $C_{27}H_{24}ClF_5N_2O_3$ | Solid |
| 461 | $C_{27}H_{24}F_6N_2O_3$ | Solid |
| 462 | $C_{27}H_{24}F_5IN_2O_3$ | Solid |
| 463 | $C_{27}H_{26}ClF_3N_2O_3$ | Solid |
| 464 | $C_{27}H_{25}F_5N_2O_3$ | Solid |
| 465 | $C_{27}H_{27}ClF_3N_3O_2$ | Solid |
| 466 | $C_{27}H_{26}F_5N_3O_2$ | Solid |
| 467 | $C_{32}H_{35}F_5N_2O_2$ | Solid |
| 468 | $C_{28}H_{28}F_4N_2O_4$ | Solid |
| 469 | $C_{28}H_{27}F_5N_2O_4$ | Solid |
| 470 | $C_{29}H_{32}Cl_2N_2O_3$ | — |
| 471 | $C_{29}H_{32}ClFN_2O_3$ | — |
| 474 | $C_{30}H_{32}ClF_3N_2O_3$ | — |
| 473 | $C_{30}H_{32}ClF_3N_2O_3$ | — |
| 474 | $C_{29}H_{31}ClF_2N_2O_3$ | — |
| 475 | $C_{29}H_{32}ClFN_2O_3$ | — |
| 476 | $C_{29}H_{32}F_2N_2O_3$ | — |
| 477 | $C_{30}H_{32}F_4N_2O_3$ | — |
| 478 | $C_{30}H_{32}F_4N_2O_3$ | — |
| 479 | $C_{29}H_{31}F_3N_2O_3$ | — |
| 480 | $C_{29}H_{31}Cl_3N_2O_3$ | — |
| 481 | $C_{29}H_{31}Cl_2FN_2O_3$ | — |
| 482 | $C_{29}H_{30}Cl_2F_2N_2O_3$ | — |
| 483 | $C_{30}H_{31}Cl_2F_3N_2O_3$ | — |
| 484 | $C_{30}H_{31}Cl_2F_3N_2O_3$ | — |
| 485 | $C_{30}H_{32}ClF_3N_2O_3$ | — |
| 486 | $C_{30}H_{32}F_4N_2O_3$ | — |
| 487 | $C_{30}H_{31}F_5N_2O_3$ | — |
| 488 | $C_{31}H_{32}F_6N_2O_3$ | — |
| 489 | $C_{31}H_{32}F_6N_2O_3$ | — |
| 490 | $C_{30}H_{32}ClF_3N_2O_3$ | Solid |
| 491 | $C_{30}H_{31}F_5N_2O_3$ | Solid |
| 492 | $C_{31}H_{32}ClF_3N_2O_4$ | Solid |
| 493 | $C_{31}H_{31}F_5N_2O_4$ | Solid |
| 494 | $C_{29}H_{29}ClF_3N_3O_3$ | Solid |
| 495 | $C_{29}H_{28}F_5N_3O_3$ | Solid |
| 496 | $C_{31}H_{32}F_5N_3O_3$ | Solid |
| 497 | $C_{32}H_{34}F_5N_3O_3$ | Solid |
| 498 | $C_{29}H_{28}F_5N_3O_4$ | Solid |
| 499 | $C_{30}H_{30}F_5N_3O_4$ | Solid |
| 500 | $C_{30}H_{33}Cl_2N_3O_4$ | — |
| 501 | $C_{30}H_{33}ClFN_3O_4$ | — |
| 502 | $C_{30}H_{32}ClF_2N_3O_4$ | — |
| 503 | $C_{30}H_{33}ClFN_3O_4$ | — |
| 504 | $C_{30}H_{33}F_2N_3O_4$ | — |
| 505 | $C_{30}H_{32}F_3N_3O_4$ | — |
| 506 | $C_{30}H_{32}Cl_3N_3O_4$ | — |
| 507 | $C_{30}H_{31}Cl_2F_2N_3O_4$ | — |
| 508 | $C_{30}H_{32}Cl_3N_3O_4$ | — |
| 509 | $C_{30}H_{32}Cl_2FN_3O_4$ | — |
| 510 | $C_{30}H_{31}Cl_2F_2N_3O_4$ | — |
| 511 | $C_{31}H_{25}F_6N_3O$ | Solid |
| 512 | $C_{31}H_{32}F_5N_3O_4$ | Solid |
| 513 | $C_{31}H_{33}ClF_3N_3O_5$ | — |
| 514 | $C_{31}H_{33}F_4N_3O_5$ | — |
| 515 | $C_{31}H_{32}F_5N_3O_5$ | — |
| 516 | $C_{34}H_{31}F_5N_4O_4$ | Solid, 95–110 |
| 517 | $C_{30}H_{31}F_5N_4O_3$ | Solid |
| 518 | $C_{30}H_{31}F_5N_4O_2S$ | Solid |
| 519 | $C_{30}H_{31}F_5N_4O_3$ | Solid |
| 520 | $C_{32}H_{36}F_5N_4O_6P$ | Solid |
| 521 | $C_{29}H_{30}F_3N_3O_4$ | Solid |
| 522 | $C_{31}H_{31}F_5N_4O_5$ | Solid |
| 523 | $C_{29}H_{31}Cl_2N_3O_3$ | — |
| 524 | $C_{29}H_{31}ClFN_3O_3$ | — |
| 525 | $C_{29}H_{30}ClF_2N_3O_3$ | — |
| 526 | $C_{29}H_{31}ClFN_3O_3$ | — |
| 527 | $C_{29}H_{31}F_2N_3O_3$ | — |
| 528 | $C_{29}H_{30}F_3N_3O_3$ | — |
| 529 | $C_{29}H_{30}Cl_3N_3O_3$ | — |
| 530 | $C_{29}H_{30}Cl_2FN_3O_3$ | — |
| 531 | $C_{29}H_{29}Cl_2F_2N_3O_3$ | — |
| 532 | $C_{29}H_{30}Cl_3N_3O_3$ | — |
| 533 | $C_{29}H_{30}Cl_2FN_3O_3$ | — |
| 534 | $C_{29}H_{29}Cl_2F_2N_3O_3$ | — |
| 535 | $C_{30}H_{31}F_4N_3O_3$ | Solid, 63–73 |
| 536 | $C_{31}H_{34}F_3N_3O_3$ | Solid |
| 537 | $C_{30}H_{31}ClF_3N_3O_4$ | — |
| 538 | $C_{30}H_{30}F_5N_3O_4$ | — |
| 539 | $C_{31}H_{29}ClF_3N_3O_3$ | Solid |
| 540 | $C_{31}H_{28}F_5N_3O_3$ | Solid |
| 541 | $C_{31}H_{34}F_5N_3O_4S$ | — |
| 542 | $C_{32}H_{34}F_5N_3O_4S$ | — |
| 543 | $C_{33}H_{30}ClF_3N_2O_2$ | Solid |
| 544 | $C_{33}H_{29}F_5N_2O_2$ | Solid |
| 545 | $C_{33}H_{30}ClF_3N_2O_3$ | Solid |
| 546 | $C_{33}H_{29}F_5N_2O_3$ | Solid |
| 547 | $C_{33}H_{28}F_6N_2O_3$ | Solid, 58–67 |
| 548 | $C_{33}H_{27}F_7N_2O_3$ | Solid, 72–81 |
| 549 | $C_{34}H_{31}F_5N_2O_3$ | Solid |
| 550 | $C_{34}H_{29}ClF_5N_3O_3$ | Solid |
| 551 | $C_{34}H_{28}Cl_2F_5N_3O_3$ | Solid |
| 552 | $C_{34}H_{28}F_7N_3O_3$ | Solid |
| 553 | $C_{35}H_{32}F_5N_3O_4$ | Solid |
| 554 | $C_{35}H_{32}F_5N_3O_4$ | Solid |
| 555 | $C_{30}H_{28}F_4N_4O_2$ | Solid |
| 556 | $C_{30}H_{27}F_5N_4O_2$ | Solid |
| 557 | $C_{29}H_{27}F_4N_5O_2$ | Solid |
| 558 | $C_{29}H_{26}F_5N_5O_2$ | Solid |
| 559 | $C_{29}H_{26}F_4N_4O_2S$ | Solid |
| 560 | $C_{29}H_{25}F_5N_4O_2S$ | Solid |
| 561 | $C_{29}H_{25}Cl_2F_3N_4O_3S$ | Solid |
| 562 | $C_{29}H_{24}ClF_5N_4O_3S$ | Solid |
| 563 | $C_{30}H_{29}F_5N_4O_3$ | Solid |
| 564 | $C_{29}H_{31}ClN_6O_2$ | — |
| 565 | $C_{30}H_{31}F_3N_6O_2$ | — |
| 566 | $C_{30}H_{30}F_4N_6O_2$ | — |
| 567 | $C_{29}H_{30}Cl_2N_6O_2$ | — |
| 568 | $C_{29}H_{29}Cl_3N_6O_2$ | — |
| 569 | $C_{29}H_{29}ClF_2N_6O_2$ | — |
| 570 | $C_{29}H_{29}ClF_2N_6O_2$ | — |
| 571 | $C_{30}H_{30}ClF_3N_6O_2$ | — |
| 572 | $C_{29}H_{29}Cl_3N_6O_2$ | — |
| 573 | $C_{29}H_{28}Cl_4N_6O_2$ | — |
| 574 | $C_{29}H_{28}Cl_2F_2N_6O_2$ | — |
| 575 | $C_{29}H_{28}Cl_2F_2N_6O_2$ | — |
| 576 | $C_{30}H_{29}Cl_2F_3N_6O_2$ | — |
| 577 | $C_{29}H_{29}Cl_3N_6O_2$ | — |
| 578 | $C_{29}H_{28}Cl_4N_6O_2$ | — |
| 579 | $C_{29}H_{28}Cl_2F_2N_6O_2$ | — |
| 580 | $C_{29}H_{28}Cl_2F_2N_6O_2$ | — |
| 581 | $C_{30}H_{29}Cl_2F_3N_6O_2$ | — |
| 582 | $C_{29}H_{30}ClFN_6O_2$ | — |
| 583 | $C_{29}H_{29}Cl_2FN_6O_2$ | — |
| 584 | $C_{29}H_{29}F_3N_6O_2$ | — |
| 585 | $C_{29}H_{29}F_3N_6O_2$ | — |
| 586 | $C_{30}H_{30}F_4N_6O_2$ | — |
| 587 | $C_{30}H_{30}F_4N_6O_2$ | — |
| 588 | $C_{29}H_{29}ClF_2N_6O_2$ | — |

TABLE 2-continued

Physical Characteristics

| Cmpd No. | Emperical Formula | Physical State/ Melting Point (° C.) |
|---|---|---|
| 589 | $C_{29}H_{28}F_4N_6O_2$ | — |
| 590 | $C_{29}H_{29}ClF_2N_6O_2$ | — |
| 591 | $C_{29}H_{28}Cl_2F_2N_6O_2$ | — |
| 592 | $C_{29}H_{28}F_4NO_2$ | — |
| 593 | $C_{29}H_{28}F_4N_6O_2$ | — |
| 594 | $C_{30}H_{29}F_5N_6O_2$ | — |
| 595 | $C_{30}H_{33}ClN_6O_2$ | — |
| 596 | $C_{30}H_{32}Cl_2N_6O_2$ | — |
| 597 | $C_{30}H_{32}F_2N_6O_2$ | — |
| 598 | $C_{30}H_{32}F_2N_6O_2$ | — |
| 599 | $C_{31}H_{33}F_3N_6O_2$ | — |
| 600 | $C_{31}H_{33}F_3N_6O_2$ | — |
| 601 | $C_{30}H_{33}ClN_6O_3$ | — |
| 602 | $C_{30}H_{32}Cl_2N_6O_3$ | — |
| 603 | $C_{30}H_{32}F_2N_6O_3$ | — |
| 604 | $C_{30}H_{32}F_2N_6O_3$ | — |
| 605 | $C_{31}H_{33}F_3N_6O_3$ | — |
| 606 | $C_{31}H_{33}F_3N_6O_3$ | — |
| 607 | $C_{36}H_{38}N_6O_3$ | — |
| 608 | $C_{31}H_{35}ClN_6O_4$ | — |
| 609 | $C_{31}H_{34}F_2N_6O_4$ | — |
| 610 | $C_{30}H_{29}F_5N_6O_2$ | — |
| 611 | $C_{35}H_{35}ClN_6O_2$ | — |
| 612 | $C_{35}H_{34}Cl_2N_6O_2$ | — |
| 613 | $C_{35}H_{34}F_2N_6O_2$ | — |
| 614 | $C_{35}H_{34}F_2N_6O_2$ | — |
| 615 | $C_{36}H_{35}F_3N_6O_2$ | — |
| 616 | $C_{35}H_{35}ClN_6O_3$ | — |
| 617 | $C_{35}H_{34}Cl_2N_6O_3$ | — |
| 618 | $C_{35}H_{34}F_2N_6O_3$ | — |
| 619 | $C_{35}H_{34}F_2N_6O_3$ | — |
| 620 | $C_{36}H_{35}F_3N_6O_3$ | — |
| 621 | $C_{41}H_{40}N_6O_3$ | — |
| 622 | $C_{41}H_{40}N_6O_4$ | — |
| 623 | $C_{33}H_{33}ClN_6O_2$ | — |
| 624 | $C_{33}H_{32}Cl_2N_6O_2$ | — |
| 625 | $C_{33}H_{32}F_2N_6O_2$ | — |
| 626 | $C_{33}H_{32}F_2N_6O_2$ | — |
| 627 | $C_{32}H_{29}ClF_3N_3O_2$ | Solid |
| 628 | $C_{32}H_{28}F_5N_3O_2$ | Solid |
| 629 | $C_{31}H_{29}Cl_2N_3O_3$ | — |
| 630 | $C_{31}H_{29}ClFN_3O_3$ | — |
| 631 | $C_{31}H_{28}ClF_2N_3O_3$ | — |
| 632 | $C_{33}H_{34}ClN_3O_3$ | — |
| 633 | $C_{33}H_{34}ClN_3O_5$ | — |
| 634 | $C_{32}H_{29}ClF_3N_3O_3$ | — |
| 635 | $C_{32}H_{29}ClF_3N_3O_3$ | — |
| 636 | $C_{33}H_{31}ClF_3N_3O_3$ | White solid |
| 637 | $C_{34}H_{33}ClF_3N_3O_3$ | White solid |
| 638 | $C_{33}H_{32}ClN_3O_5$ | — |
| 639 | $C_{31}H_{29}ClFN_3O_3$ | — |
| 640 | $C_{31}H_{29}F_2N_3O_3$ | — |
| 641 | $C_{31}H_{28}F_3N_3O_3$ | — |
| 642 | $C_{32}H_{29}F_4N_3O_3$ | — |
| 643 | $C_{32}H_{29}F_4N_3O_3$ | — |
| 644 | $C_{31}H_{29}Cl_2N_3O_5S$ | — |
| 645 | $C_{31}H_{28}Cl_3N_3O_3$ | — |
| 646 | $C_{31}H_{28}Cl_2FN_3O_3$ | — |
| 647 | $C_{31}H_{27}Cl_2F_2N_3O_3$ | — |
| 648 | $C_{32}H_{31}Cl_2N_3O_4$ | — |
| 649 | $C_{33}H_{33}Cl_2N_3O_5$ | — |
| 650 | $C_{32}H_{28}Cl_2F_3N_3O_3$ | — |
| 651 | $C_{32}H_{28}Cl_2F_3N_3O_3$ | — |
| 652 | $C_{32}H_{29}ClF_3N_3O_3$ | — |
| 653 | $C_{32}H_{29}F_4N_3O_3$ | — |
| 654 | $C_{32}H_{28}F_5N_3O_3$ | — |
| 655 | $C_{33}H_{29}F_6N_3O_3$ | — |
| 656 | $C_{33}H_{29}F_6N_3O_3$ | — |
| 657 | $C_{32}H_{30}F_3N_3O_3$ | — |
| 658 | $C_{33}H_{32}F_3N_3O_3$ | White solid |
| 659 | $C_{33}H_{32}F_3N_3O_3$ | Oil |
| 660 | $C_{34}H_{34}F_3N_3O_3$ | Oil |
| 661 | $C_{32}H_{29}F_3N_2O_4$ | White solid |
| 662 | $C_{32}H_{29}ClF_3N_3O_3$ | Tan solid |
| 663 | $C_{33}H_{31}ClF_3N_3O_3$ | Oil |
| 664 | $C_{32}H_{29}ClF_3N_3O_3$ | Yellow solid |
| 665 | $C_{32}H_{29}ClF_3N_3O_3$ | Solid |
| 666 | $C_{32}H_{29}ClF_3N_3O_3.HCl$ | — |
| 667 | $C_{32}H_{29}ClF_3N_3O_2S$ | — |
| 668 | $C_{32}H_{29}ClF_3N_3O_5S$ | — |
| 669 | $C_{32}H_{29}ClF_3N_3O_4$ | Solid |
| 670 | $C_{33}H_{28}ClF_3N_4O_3$ | White solid |
| 671 | $C_{33}H_{28}ClF_3N_4O_3$ | White solid |
| 672 | $C_{32}H_{29}BrF_3N_3O_3$ | Thick oil |
| 673 | $C_{32}H_{29}BrF_3N_3O_3$ | Tan solid |
| 674 | $C_{32}H_{29}F_4N_3O_3$ | Yellow paste |
| 675 | $C_{32}H_{29}F_4N_3O_3$ | — |
| 676 | $C_{33}H_{31}F_4N_3O_3$ | Oil |
| 677 | $C_{32}H_{29}F_3IN_3O_3$ | Solid, 85–99 |
| 678 | $C_{33}H_{30}Cl_2F_3N_3O_3$ | Oil |
| 679 | $C_{32}H_{28}F_5N_3O_3$ | Solid |
| 680 | $C_{32}H_{28}F_5N_3O_3$ | Solid |
| 681 | $C_{32}H_{28}F_5N_3O_2S$ | — |
| 682 | $C_{32}H_{28}F_5N_3O_4$ | White solid |
| 683 | $C_{32}H_{27}ClF_5N_3O_3$ | Solid, 81–91 |
| 684 | $C_{32}H_{27}ClF_5N_3O_3$ | Solid, 61–77 |
| 685 | $C_{32}H_{27}ClF_5N_3O_3$ | Solid, 76–83 |
| 686 | $C_{32}H_{26}Cl_2F_5N_3O_3$ | Solid, 78–90 |
| 687 | $C_{33}H_{27}F_5N_4O_3$ | White solid |
| 688 | $C_{33}H_{27}F_5N_4O_3$ | White solid |
| 689 | $C_{33}H_{27}F_8N_3O_3$ | Solid, 75–86 |
| 690 | $C_{33}H_{27}F_8N_3O_3$ | Solid, 77–86 |
| 691 | $C_{33}H_{27}F_8N_3O_3$ | Solid, 80–88 |
| 692 | $C_{33}H_{29}F_6N_3O_2S$ | — |
| 693 | $C_{33}H_{29}F_6N_3O_2S$ | — |
| 694 | $C_{34}H_{34}F_3N_3O_3$ | Oil |
| 695 | $C_{34}H_{34}F_3N_3O_3$ | Oil |
| 696 | $C_{33}H_{32}F_3N_3O_5S$ | — |
| 697 | $C_{32}H_{27}F_6N_3O_3$ | White solid |
| 698 | $C_{34}H_{34}F_3N_3O_4$ | Oil |
| 699 | $C_{33}H_{31}ClF_3N_3O_4$ | Solid |
| 700 | $C_{33}H_{31}F_4N_3O_4$ | Solid |
| 701 | $C_{33}H_{30}F_5N_3O_4$ | — |
| 702 | $C_{33}H_{32}F_3N_3O_3S$ | — |
| 703 | $C_{33}H_{29}F_6N_3O_3S$ | — |
| 704 | $C_{33}H_{29}F_3N_4O_3$ | — |
| 705 | $C_{34}H_{32}F_3N_3O_4$ | — |
| 706 | $C_{32}H_{29}ClF_3N_3O_5$ | Solid |
| 707 | $C_{33}H_{28}ClF_3N_4O_4$ | White solid |
| 708 | $C_{33}H_{28}ClF_3N_4O_4$ | White solid |
| 709 | $C_{32}H_{28}F_5N_3O_5$ | Solid |
| 710 | $C_{33}H_{27}F_5N_4O_4$ | White solid |
| 711 | $C_{33}H_{27}F_5N_4O_4$ | White solid |
| 712 | $C_{30}H_{28}Cl_2N_4O_3$ | — |
| 713 | $C_{30}H_{28}ClFN_4O_3$ | — |
| 714 | $C_{30}H_{27}ClF_2N_4O_3$ | — |
| 715 | $C_{30}H_{28}ClFN_4O_3$ | — |
| 716 | $C_{30}H_{28}F_2N_4O_3$ | — |
| 717 | $C_{30}H_{27}F_3N_4O_3$ | — |
| 718 | $C_{30}H_{27}Cl_3N_4O_3$ | — |
| 719 | $C_{30}H_{27}Cl_2FN_4O_3$ | — |
| 720 | $C_{30}H_{26}Cl_2F_2N_4O_3$ | — |
| 721 | $C_{30}H_{27}Cl_3N_4O_3$ | Solid |
| 722 | $C_{30}H_{27}Cl_2FN_4O_3$ | Solid |
| 723 | $C_{30}H_{26}Cl_2F_2N_4O_3$ | Solid |
| 724 | $C_{31}H_{27}Cl_2F_3N_4O_3$ | Solid |
| 725 | $C_{31}H_{27}Cl_2F_3N_4O_3$ | Solid |
| 726 | $C_{30}H_{27}Cl_3N_4O_3$ | — |
| 727 | $C_{30}H_{27}Cl_2FN_4O_3$ | — |
| 728 | $C_{30}H_{26}Cl_2F_2N_4O_3$ | — |
| 729 | $C_{31}H_{28}ClF_3N_4O_3$ | Solid, 94–104 |
| 730 | $C_{31}H_{27}F_5N_4O_3$ | Solid |
| 731 | $C_{31}H_{27}F_5N_4O_3$ | Solid, 92–102 |
| 732 | $C_{31}H_{27}F_5N_4O_3$ | Solid |
| 733 | $C_{31}H_{28}ClF_3N_4O_4$ | — |
| 734 | $C_{31}H_{28}F_4N_4O_4$ | — |
| 735 | $C_{31}H_{27}F_5N_4O_4$ | — |
| 736 | $C_{31}H_{27}F_5N_4O_3$ | Solid |

TABLE 2-continued

Physical Characteristics

| Cmpd No. | Emperical Formula | Physical State/ Melting Point (° C.) |
|---|---|---|
| 737 | $C_{31}H_{27}Cl_2F_3N_4O_3$ | Solid |
| 738 | $C_{31}H_{26}ClF_5N_4O_3$ | Solid |
| 739 | $C_{30}H_{26}F_5N_5O_3$ | — |
| 740 | $C_{32}H_{30}F_5N_5O_5$ | — |
| 741 | $C_{30}H_{31}F_5N_2O_4$ | Solid |
| 742 | $C_{30}H_{31}F_4N_3O_4$ | Solid, 136–142 |
| 743 | $C_{30}H_{30}F_5N_3O_4$ | Solid, 138–143 |
| 744 | $C_{31}H_{28}F_5N_3O_4$ | Solid |
| 745 | $C_{31}H_{32}ClF_3N_2O_5$ | Solid |
| 746 | $C_{31}H_{32}F_5N_3O_5$ | Solid |
| 747 | $C_{33}H_{30}ClF_3N_2O_3$ | Solid |
| 748 | $C_{33}H_{29}F_5N_2O_3$ | Solid |
| 749 | $C_{33}H_{29}F_5N_2O_4$ | Solid |
| 750 | $C_{33}H_{28}F_6N_2O_4$ | Solid, 135–144 |
| 751 | $C_{33}H_{27}F_7N_2O_4$ | Solid, 141–146 |
| 752 | $C_{31}H_{28}F_3N_3O_4$ | — |
| 753 | $C_{32}H_{28}F_5N_3O_4$ | Solid |
| 754 | $C_{32}H_{28}F_5N_3O_4$ | Solid |
| 755 | $C_{32}H_{27}ClF_5N_3O_4$ | Solid, 145–148 |
| 756 | $C_{32}H_{27}ClF_5N_3O_4$ | Solid, 157–161 |
| 757 | $C_{32}H_{27}ClF_5N_3O_4$ | Solid, 137–142 |
| 758 | $C_{32}H_{26}Cl_2F_5N_3O_4$ | Solid, 172–174 |
| 759 | $C_{33}H_{27}F_8N_3O_4$ | Solid, 142–144 |
| 760 | $C_{33}H_{27}F_8N_3O_4$ | Solid, 159–161 |
| 761 | $C_{34}H_{31}F_5N_4O_5$ | Solid, 149–153 |
| 762 | $C_{31}H_{28}ClF_3N_4O_4$ | Solid, 171–175 |
| 763 | $C_{31}H_{27}F_5N_4O_4$ | Solid |
| 764 | $C_{31}H_{27}F_5N_4O_4$ | Solid |
| 765 | $C_{31}H_{27}F_5N_4O_4$ | Solid, 150–153 |
| 766 | $C_{31}H_{27}F_6N_3O_4$ | Solid |
| 767 | $C_{31}H_{27}Cl_2F_3N_4O_4$ | Solid, 152–154 |
| 768 | $C_{31}H_{26}ClF_5N_4O_4$ | Solid, 151–154 |
| 769 | $C_{28}H_{29}F_3N_2O_2$ | Solid |
| 770 | $C_{29}H_{31}F_3N_2O_4$ | Gum |
| 771 | $C_{27}H_{28}F_3N_3O_3$ | White solid |
| 772 | $C_{27}H_{28}F_3N_3O_2S$ | Yellow solid |
| 773 | $C_{26}H_{32}F_3N_3O_3$ | Solid |
| 774 | $C_{28}H_{30}F_3N_3O_3$ | Tan solid |
| 775 | $C_{29}H_{32}F_3N_3O_3$ | Oil |
| 776 | $C_{29}H_{32}F_3N_3O_3$ | Oily solid |
| 777 | $C_{29}H_{32}F_3N_3O_2S$ | Yellow solid |
| 778 | $C_{30}H_{34}F_3N_3O_3$ | Yellow solid |
| 779 | $C_{30}H_{34}F_3N_3O_3$ | Solid |
| 780 | $C_{29}H_{30}F_3N_3O_3$ | Oil |
| 781 | $C_{31}H_{34}F_3N_3O_3$ | Solid |
| 782 | $C_{32}H_{36}F_3N_3O_3$ | Oil |
| 783 | $C_{30}H_{32}F_3N_3O_5$ | Solid |
| 784 | $C_{32}H_{36}F_3N_3O_5$ | Oil |
| 785 | $C_{29}H_{32}F_3N_3O_4$ | Solid |
| 786 | $C_{31}H_{25}F_5N_4O_3$ | Solid, 85–92 |
| 787 | $C_{31}H_{25}F_5N_4O_4$ | Solid, 137–141 |
| 788 | $C_{29}H_{25}F_6NO_2$ | Solid |
| 789 | $C_{27}H_{26}Cl_2N_2O_2$ | Solid |
| 790 | $C_{29}H_{26}F_6N_2O_2$ | Solid |
| 791 | $C_{29}H_{26}F_6N_2O_4$ | Solid |
| 792 | $C_{31}H_{30}F_6N_2O_2$ | Solid |
| 793 | $C_{29}H_{32}N_2O_2$ | Solid |
| 794 | $C_{29}H_{30}F_2N_2O_2$ | Solid |
| 795 | $C_{29}H_{28}Cl_4N_2O_2$ | Solid |
| 796 | $C_{29}H_{28}Cl_2F_2N_2O_2$ | Solid |
| 797 | $C_{31}H_{28}F_6N_2O_2$ | Solid |
| 798 | $C_{30}H_{30}Cl_2N_2O_2$ | Solid |
| 799 | $C_{32}H_{30}F_6N_2O_2$ | Solid |
| 800 | $C_{30}H_{30}Cl_2N_2O_2$ | Solid |
| 801 | $C_{29}H_{26}Cl_2N_2O_2$ | Solid |
| 802 | $C_{31}H_{26}F_6N_2O_2$ | Solid |
| 803 | $C_{28}H_{25}F_6NO_3S$ | Solid |
| 804 | $C_{30}H_{29}F_6NO_3S$ | Solid |
| 805 | $C_{28}H_{26}F_6N_2O_2S$ | Solid |
| 806 | $C_{33}H_{26}F_7NO$ | Solid, 50–59 |
| 807 | $C_{32}H_{26}F_6N_2$ | Solid |
| 808 | $C_{30}H_{28}N_2O$ | Solid |
| 809 | $C_{30}H_{26}Cl_2N_2O$ | Solid |
| 810 | $C_{30}H_{26}F_2N_2O$ | Solid |
| 811 | $C_{32}H_{27}F_6N_3$ | Paste |
| 812 | $C_{29}H_{25}Cl_2N_3O$ | Paste |
| 813 | $C_{29}H_{23}Cl_4N_3O$ | Solid |
| 814 | $C_{30}H_{25}ClF_3N_3O$ | Solid |
| 815 | $C_{30}H_{25}ClF_3N_3O$ | Solid |
| 816 | $C_{30}H_{25}ClF_3N_3O$ | Solid |
| 817 | $C_{30}H_{25}F_4N_3O$ | Solid |
| 818 | $C_{30}H_{24}Cl_2F_3N_3O$ | Solid |
| 819 | $C_{30}H_{24}Cl_2F_3N_3O$ | Solid |
| 820 | $C_{30}H_{24}F_5N_3O$ | Solid |
| 821 | $C_{30}H_{24}ClF_4N_3O$ | Solid |
| 822 | $C_{31}H_{25}F_6N_3O$ | Solid |
| 823 | $C_{31}H_{29}F_6N_3O$ | Paste |
| 824 | $C_{31}H_{25}F_6N_3O$ | Solid |
| 825 | $C_{31}H_{25}F_6N_3O$ | Solid |
| 826 | $C_{31}H_{24}ClF_6N_3O$ | Solid, 68–77 |
| 827 | $C_{27}H_{26}Cl_2N_2O_3$ | Solid |
| 828 | $C_{29}H_{26}F_6N_2O_3$ | Solid |
| 829 | $C_{29}H_{26}F_6N_2O_5$ | Solid |
| 830 | $C_{31}H_{30}F_6N_2O_3$ | Solid |
| 831 | $C_{29}H_{30}Cl_2N_2O_3$ | Solid |
| 832 | $C_{29}H_{30}F_2N_2O_3$ | Solid |
| 833 | $C_{29}H_{28}Cl_4N_2O_3$ | Solid |
| 834 | $C_{29}H_{28}Cl_2F_2N_2O_3$ | Solid |
| 835 | $C_{31}H_{36}N_2O_5$ | Solid |
| 836 | $C_{31}H_{28}F_6N_2O_3$ | Solid |
| 837 | $C_{32}H_{30}F_6N_2O_3$ | Solid |
| 838 | $C_{31}H_{26}F_6N_2O_3$ | Solid |
| 839 | $C_{33}H_{26}F_7NO_2$ | Solid, 171–173 |
| 840 | $C_{32}H_{26}F_6N_2O$ | Solid |
| 841 | $C_{30}H_{26}Cl_2N_2O_2$ | Solid |
| 842 | $C_{30}H_{26}F_2N_2O_2$ | Solid |
| 843 | $C_{32}H_{27}F_6N_3O$ | Paste |
| 844 | $C_{29}H_{25}Cl_2N_3O_2$ | Solid |
| 845 | $C_{30}H_{25}ClF_3N_3O_2$ | Solid |
| 846 | $C_{30}H_{25}ClF_3N_3O_2$ | Solid |
| 847 | $C_{30}H_{25}ClF_3N_3O_2$ | Solid |
| 848 | $C_{30}H_{25}F_4N_3O_2$ | Solid |
| 849 | $C_{29}H_{23}Cl_4N_3O_2$ | Solid |
| 850 | $C_{30}H_{24}Cl_2F_3N_3O_2$ | Solid |
| 851 | $C_{30}H_{24}Cl_2F_3N_3O_2$ | Solid |
| 852 | $C_{30}H_{24}ClF_4N_3O_2$ | Solid |
| 853 | $C_{31}H_{25}F_6N_3O_2$ | Solid |
| 854 | $C_{31}H_{25}F_6N_3O_2$ | Solid |
| 955 | $C_{31}H_{24}ClF_6N_3O_2$ | Solid, 128–135 |
| 856 | $C_{30}H_{24}Cl_2F_3N_3O_2$ | Solid |
| 857 | $C_{30}H_{25}ClF_3N_3O_2$ | Solid |
| 858 | $C_{32}H_{26}F_6N_2O$ | Solid |
| 859 | $C_{30}H_{25}F_6N_5$ | Solid |
| 860 | $C_{34}H_{34}ClF_3N_3O_4C_2H_5O_4S$ | Solid |
| 861 | $C_{32}H_{27}ClF_5N_3O_4$ | Solid, 158–161 |
| 862 | $C_{30}H_{31}ClF_3N_3O_4$ | Solid |
| 863 | $C_{32}H_{29}ClF_3N_3O_5$ | Solid |

Candidate insecticides were evaluated for activity against the tobacco budworm (*Heliothis virescens* [Fabricius]) in a surface-treated diet test.

In this test one mL of molten (65–70° C.) wheat germ-based artificial diet was pipetted into each well of a four by six (24 well) multi-well plate (ID# 430345-15.5 mm dia.× 17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Test Compounds Applied to the Surface of the Diet of Tobacco Budworm

| | Cmpd. No | | | | | | | | |
|---|---|---|---|---|---|---|---|---|---|
| | 30 | 31 | 42 | 44 | 45 | 46 | 47 | 48 | 50 |
| Percent Mortality | 100 | 17 | 100 | 67 | 0 | 100 | 0 | 100 | 67 |
| Percent Growth Inhibition | 54 | 99 | 100 | 100 | 24 | 100 | 11 | 100 | 96 |

| | Cmpd. No | | | | | | | | |
|---|---|---|---|---|---|---|---|---|---|
| | 51 | 52 | 53 | 54 | 55 | 56 | 57 | 58 | 59 |
| Percent Mortality | 0 | 33 | 0 | 100 | 100 | 100 | 100 | 100 | 0 |
| Percent Growth Inhibition | 26 | 100 | 100 | 100 | 100 | 100 | 100 | 100 | 59 |

| | Cmpd. No | | | | | | | |
|---|---|---|---|---|---|---|---|---|
| | 60 | 61 | 62 | 63 | 64 | 65 | 66 | 67 | 68 |
| Percent Mortality | 100 | 100 | 100 | 33 | 100 | 100 | 100 | 0 | 100 |
| Percent Growth Inhibition | 100 | 100 | 100 | 100 | 100 | 100 | 100 | 98 | 100 |

| | Cmpd. No | | | | | | | |
|---|---|---|---|---|---|---|---|---|
| | 70 | 71 | 72 | 74 | 75 | 76 | 77 | 78 | 79 |
| Percent Mortality | 100 | 100 | 100 | 100 | 100 | 0 | 100 | 67 | 83 |
| Percent Growth Inhibition | 100 | 100 | 100 | 100 | 96 | 91 | 100 | 100 | 100 |

| | Cmpd. No | | | | | | | |
|---|---|---|---|---|---|---|---|---|
| | 80 | 81 | 82 | 83 | 85 | 87 | 93 | 94 | 95 |
| Percent Mortality | 33 | 100 | 100 | 100 | 100 | 100 | 33 | 100 | 100 |
| Percent Growth Inhibition | 100 | 100 | 100 | 100 | 100 | 100 | 97 | 100 | 100 |

| | Cmpd. No | | | | | | | |
|---|---|---|---|---|---|---|---|---|
| | 98 | 99 | 100 | 101 | 102 | 103 | 104 | 105 | 106 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | |
|---|---|---|---|---|---|---|---|---|
| | 107 | 108 | 109 | 111 | 112 | 113 | 114 | 115 | 117 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

TABLE 3-continued

Insecticidal Activity of Test Compounds Applied to the
Surface of the Diet of Tobacco Budworm

| | Cmpd. No | | | | | | | | |
|---|---|---|---|---|---|---|---|---|---|
| | 118 | 181 | 182 | 183 | 184 | 185 | 186 | 187 | 188 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 189 | 190 | 191 | 192 | 193 | 194 | 195 | 196 | 197 |
| Percent Mortality | 100 | 100 | 100 | 67 | 100 | 100 | 100 | 100 | 0 |
| Percent Growth Inhibition | 100 | 100 | 100 | 98 | 100 | 100 | 100 | 100 | 94 |

| | Cmpd. No | | | | | | | | |
|---|---|---|---|---|---|---|---|---|---|
| | 199 | 200 | 201 | 202 | 203 | 204 | 205 | 206 | 207 |
| Percent Mortality | 100 | 100 | 100 | 100 | 100 | 100 | 33 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 208 | 209 | 210 | 211 | 212 | 213 | 214 | 227 | 228 |
| Percent Mortality | 100 | 100 | 0 | 100 | 100 | 100 | 0 | 100 | 100 |
| Percent Growth Inhibition | 100 | 100 | 67 | 100 | 100 | 100 | 100 | 100 | 100 |

| | Cmpd. No | | | | | | | | |
|---|---|---|---|---|---|---|---|---|---|
| | 229 | 230 | 231 | 232 | 233 | 234 | 235 | 236 | 237 |
| Percent Mortality | 100 | 100 | 100 | 100 | 33 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 238 | 239 | 240 | 241 | 242 | 243 | 244 | 245 | 246 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 247 | 248 | 249 | 250 | 251 | 261 | 262 | 263 | 264 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 265 | 266 | 267 | 268 | 269 | 270 | 271 | 272 | 273 |
| Percent Mortality | 100 | 100 | 100 | 100 | 100 | 100 | 100 | 99 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 274 | 275 | 276 | 277 | 279 | 280 | 281 | 282 | 283 |
| Percent Mortality | 100 | 100 | 17 | 100 | 100 | 100 | 100 | 0 | 100 |
| Percent Growth Inhibition | 100 | 100 | 79 | 100 | 100 | 100 | 100 | 95 | 100 |

| | Cmpd. No | | | | | | | | |
|---|---|---|---|---|---|---|---|---|---|
| | 284 | 285 | 286 | 287 | 288 | 289 | 290 | 291 | 292 |
| Percent Mortality | 100 | 100 | 50 | 100 | 100 | 100 | 100 | 100 | 100 |
| Percent Growth Inhibition | 100 | 100 | 94 | 100 | 100 | 100 | 100 | 95 | 100 |

TABLE 3-continued

Insecticidal Activity of Test Compounds Applied to the
Surface of the Diet of Tobacco Budworm

| | \multicolumn{9}{c}{Cmpd. No} |
|---|---|---|---|---|---|---|---|---|---|
| | 293 | 294 | 295 | 297 | 298 | 302 | 304 | 305 | 306 |
| Percent Mortality | 17 | 100 | 100 | 100 | 100 | 100 | 100 | 100 | 33 |
| Percent Growth Inhibition | 93 | 100 | 92 | 100 | 100 | 100 | 95 | 95 | 59 |

| | \multicolumn{9}{c}{Cmpd. No} |
|---|---|---|---|---|---|---|---|---|---|
| | 307 | 308 | 309 | 310 | 311 | 312 | 313 | 314 | 315 |
| Percent Mortality | 100 | 100 | 100 | 100 | 100 | 100 | 100 | 100 | 100 |
| Percent Growth Inhibition | 92 | 92 | 100 | 100 | 100 | 100 | 100 | 100 | 100 |

| | \multicolumn{9}{c}{Cmpd. No} |
|---|---|---|---|---|---|---|---|---|---|
| | 316 | 317 | 318 | 319 | 320 | 321 | 322 | 323 | 324 |
| Percent Mortality | 50 | 100 | 100 | 100 | 100 | 17 | 0 | 67 | 83 |
| Percent Growth Inhibition | 100 | 100 | 100 | 100 | 100 | 95 | 78 | 98 | 99 |

| | \multicolumn{9}{c}{Cmpd. No} |
|---|---|---|---|---|---|---|---|---|---|
| | 325 | 326 | 327 | 328 | 329 | 330 | 331 | 332 | 333 |
| Percent Mortality | 50 | 0 | 0 | 0 | 50 | 33 | 67 | 100 | 17 |
| Percent Growth Inhibition | 100 | 93 | 99 | 95 | 99 | 89 | 98 | 100 | 99 |

| | \multicolumn{9}{c}{Cmpd. No} |
|---|---|---|---|---|---|---|---|---|---|
| | 334 | 335 | 336 | 337 | 338 | 339 | 340 | 341 | 342 |
| Percent Mortality | 100 | 100 | 100 | 100 | 100 | 50 | 83 | 100 | 100 |
| Percent Growth Inhibition | 100 | 100 | 100 | 100 | 100 | 100 | 100 | 100 | 100 |

| | \multicolumn{9}{c}{Cmpd. No} |
|---|---|---|---|---|---|---|---|---|---|
| | 343 | 344 | 345 | 346 | 347 | 348 | 349 | 350 | 351 |
| Percent Mortality | 100 | 100 | 100 | 100 | 83 | 100 | 100 | 100 | 50 |
| Percent Growth Inhibition | 100 | 100 | 100 | 100 | 100 | 100 | 100 | 100 | 100 |

| | \multicolumn{9}{c}{Cmpd. No} |
|---|---|---|---|---|---|---|---|---|---|
| | 352 | 353 | 354 | 355 | 356 | 357 | 358 | 395 | 396 |
| Percent Mortality | 83 | 17 | 100 | 100 | 100 | 100 | 83 | 100 | 100 |
| Percent Growth Inhibition | 100 | 87 | 100 | 100 | 100 | 100 | 99 | 100 | 100 |

| | \multicolumn{9}{c}{Cmpd. No} |
|---|---|---|---|---|---|---|---|---|---|
| | 397 | 398 | 399 | 400 | 401 | 402 | 403 | 404 | 405 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | \multicolumn{9}{c}{Cmpd. No} |
|---|---|---|---|---|---|---|---|---|---|
| | 427 | 429 | 432 | 433 | 434 | 435 | 436 | 437 | 438 |
| Percent Mortality | 33 | 100 | 100 | 100 | 100 | 100 | 50 | 100 | 100 |
| Percent Growth Inhibition | 100 | 100 | 100 | 100 | 100 | 100 | 100 | 100 | 100 |

| | \multicolumn{9}{c}{Cmpd. No} |
|---|---|---|---|---|---|---|---|---|---|
| | 439 | 440 | 441 | 442 | 443 | 444 | 445 | 446 | 447 |
| Percent Mortality | 100 | 100 | 100 | 100 | 33 | 0 | 100 | 17 | 100 |
| Percent Growth Inhibition | 100 | 100 | 100 | 100 | 100 | 96 | 100 | 100 | 100 |

TABLE 3-continued

Insecticidal Activity of Test Compounds Applied to the
Surface of the Diet of Tobacco Budworm

| | Cmpd. No | | | | | | | | |
|---|---|---|---|---|---|---|---|---|---|
| | 448 | 450 | 451 | 452 | 453 | 454 | 455 | 456 | 457 |
| Percent Mortality | 100 | 0 | 100 | 67 | 83 | 100 | 100 | 17 | 0 |
| Percent Growth Inhibition | 100 | 62 | 100 | 100 | 100 | 100 | 100 | 100 | 16 |

| | Cmpd. No | | | | | | | | |
|---|---|---|---|---|---|---|---|---|---|
| | 458 | 459 | 460 | 461 | 462 | 463 | 464 | 465 | 466 |
| Percent Mortality | 0 | 0 | 0 | 0 | 83 | 0 | 0 | 0 | 17 |
| Percent Growth Inhibition | 94 | 99 | 100 | 98 | 100 | 65 | 63 | 92 | 77 |

| | Cmpd. No | | | | | | | | |
|---|---|---|---|---|---|---|---|---|---|
| | 467 | 468 | 469 | 470 | 471 | 472 | 473 | 474 | 475 |
| Percent Mortality | 0 | 33 | 17 | 100 | 100 | 100 | 100 | 100 | 100 |
| Percent Growth Inhibition | 68 | 100 | 100 | 100 | 100 | 100 | 100 | 100 | 100 |

| | Cmpd. No | | | | | | | | |
|---|---|---|---|---|---|---|---|---|---|
| | 476 | 477 | 478 | 479 | 480 | 481 | 482 | 483 | 484 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 485 | 486 | 487 | 488 | 489 | 490 | 491 | 492 | 493 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 494 | 495 | 496 | 497 | 498 | 499 | 501 | 501 | 502 |
| Percent Mortality | 0 | 0 | 100 | 17 | 100 | 100 | 100 | 100 | 100 |
| Percent Growth Inhibition | 77 | 98 | 100 | 100 | 100 | 100 | 100 | 100 | 100 |

| | Cmpd. No | | | | | | | | |
|---|---|---|---|---|---|---|---|---|---|
| | 503 | 504 | 505 | 506 | 507 | 508 | 509 | 510 | 511 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 512 | 513 | 514 | 515 | 516 | 517 | 518 | 519 | 520 |
| Percent Mortality | 100 | 100 | 100 | 100 | 100 | 0 | 17 | 17 | 17 |
| Percent Growth Inhibition | 100 | 100 | 100 | 100 | 100 | 86 | 96 | 93 | 99 |

| | Cmpd. No | | | | | | | | |
|---|---|---|---|---|---|---|---|---|---|
| | 521 | 522 | 523 | 524 | 525 | 526 | 527 | 528 | 529 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 530 | 531 | 532 | 533 | 534 | 535 | 536 | 537 | 538 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

TABLE 3-continued

Insecticidal Activity of Test Compounds Applied to the
Surface of the Diet of Tobacco Budworm

| | Cmpd. No | | | | | | | | |
|---|---|---|---|---|---|---|---|---|---|
| | 539 | 540 | 541 | 542 | 543 | 544 | 545 | 546 | 547 |
| Percent Mortality | 100 | 100 | 0 | 0 | 100 | 100 | 100 | 100 | 100 |
| Percent Growth Inhibition | 100 | 100 | 59 | 43 | 100 | 100 | 100 | 100 | 100 |

| | Cmpd. No | | | | | | | | |
|---|---|---|---|---|---|---|---|---|---|
| | 548 | 549 | 550 | 551 | 552 | 553 | 554 | 555 | 556 |
| Percent Mortality | 100 | 0 | 100 | 100 | 100 | 100 | 0 | 33 | 100 |
| Percent Growth Inhibition | 100 | 98 | 100 | 100 | 100 | 100 | 99 | 100 | 100 |

| | Cmpd. No | | | | | | | | |
|---|---|---|---|---|---|---|---|---|---|
| | 557 | 558 | 559 | 560 | 561 | 562 | 563 | 564 | 565 |
| Percent Mortality | 0 | 17 | 17 | 33 | 50 | 33 | 0 | 100 | 100 |
| Percent Growth Inhibition | 86 | 99 | 97 | 96 | 100 | 100 | 96 | 100 | 100 |

| | Cmpd. No | | | | | | | | |
|---|---|---|---|---|---|---|---|---|---|
| | 566 | 567 | 568 | 569 | 570 | 571 | 572 | 573 | 574 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 575 | 576 | 577 | 578 | 579 | 580 | 581 | 582 | 583 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 584 | 585 | 586 | 587 | 588 | 589 | 590 | 591 | 592 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 593 | 594 | 595 | 596 | 597 | 598 | 599 | 600 | 601 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 602 | 603 | 604 | 605 | 606 | 607 | 608 | 609 | 610 |
| Percent Mortality | 100 | 100 | 100 | 100 | 100 | 100 | 83 | 33 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 611 | 612 | 613 | 614 | 615 | 616 | 617 | 618 | 619 |
| Percent Mortality | 83 | 0 | 83 | 16 | 17 | 100 | 0 | 100 | 17 |
| Percent Growth Inhibition | 100 | 48 | 100 | 99 | 72 | 100 | 14 | 100 | 100 |

| | Cmpd. No | | | | | | | | |
|---|---|---|---|---|---|---|---|---|---|
| | 620 | 621 | 622 | 623 | 624 | 625 | 626 | 627 | 628 |
| Percent Mortality | 0 | 0 | 0 | 100 | 100 | 100 | 100 | 100 | 100 |
| Percent Growth Inhibition | 29 | 4 | 4 | 100 | 100 | 100 | 100 | 100 | 100 |

TABLE 3-continued

Insecticidal Activity of Test Compounds Applied to the
Surface of the Diet of Tobacco Budworm

| | Cmpd. No | | | | | | | | |
|---|---|---|---|---|---|---|---|---|---|
| | 629 | 630 | 631 | 632 | 633 | 634 | 635 | 636 | 637 |
| Percent Mortality | 100 | 100 | 100 | 100 | 50 | 100 | 100 | 100 | 100 |
| Percent Growth Inhibition | 100 | 100 | 100 | 100 | 100 | 100 | 100 | 100 | 100 |
| | Cmpd. No | | | | | | | | |
| | 638 | 639 | 640 | 641 | 642 | 643 | 644 | 645 | 646 |
| Percent Mortality | 100 | 100 | 100 | 100 | 100 | 100 | 0 | 100 | 100 |
| Percent Growth Inhibition | 100 | 100 | 100 | 100 | 100 | 100 | 0 | 100 | 100 |
| | Cmpd. No | | | | | | | | |
| | 647 | 648 | 648 | 650 | 651 | 652 | 653 | 654 | 655 |
| Percent Mortality | 100 | 100 | 83 | 100 | 100 | 100 | 100 | 100 | 100 |
| Percent Growth Inhibition | 100 | 100 | 100 | 100 | 100 | 100 | 100 | 100 | 100 |
| | Cmpd. No | | | | | | | | |
| | 656 | 657 | 658 | 659 | 660 | 661 | 662 | 663 | 664 |
| Percent Mortality | 100 | 100 | 0 | 50 | 0 | 0 | 100 | 50 | 100 |
| Percent Growth Inhibition | 100 | 100 | 100 | 100 | 98 | 91 | 100 | 100 | 100 |
| | Cmpd. No | | | | | | | | |
| | 665 | 666 | 667 | 668 | 669 | 670 | 671 | 672 | 673 |
| Percent Mortality | 0 | 100 | 100 | 0 | 100 | 100 | 100 | 100 | 100 |
| Percent Growth Inhibition | 100 | 100 | 100 | 25 | 100 | 100 | 100 | 100 | 100 |
| | Cmpd. No | | | | | | | | |
| | 674 | 675 | 676 | 677 | 678 | 679 | 680 | 681 | 682 |
| Percent Mortality | 100 | 100 | 100 | 100 | 100 | 100 | 17 | 100 | 100 |
| Percent Growth Inhibition | 100 | 100 | 100 | 100 | 100 | 100 | 100 | 100 | 100 |
| | Cmpd. No | | | | | | | | |
| | 683 | 684 | 685 | 686 | 687 | 688 | 689 | 690 | 691 |
| Percent Mortality | 100 | 100 | 100 | 17 | 100 | 100 | 100 | 100 | 100 |
| Percent Growth Inhibition | 100 | 100 | 100 | 98 | 100 | 100 | 100 | 100 | 100 |
| | Cmpd. No | | | | | | | | |
| | 692 | 693 | 694 | 695 | 696 | 697 | 698 | 699 | 700 |
| Percent Mortality | 100 | 100 | 50 | 100 | 0 | 100 | 100 | 100 | 100 |
| Percent Growth Inhibition | 100 | 100 | 100 | 100 | 32 | 100 | 100 | 100 | 100 |
| | Cmpd. No | | | | | | | | |
| | 701 | 702 | 703 | 704 | 705 | 706 | 707 | 708 | 709 |
| Percent Mortality | 100 | 100 | 100 | 100 | 17 | 100 | 100 | 100 | 100 |
| Percent Growth Inhibition | 100 | 100 | 100 | 100 | 100 | 100 | 100 | 100 | 100 |
| | Cmpd. No | | | | | | | | |
| | 710 | 711 | 712 | 713 | 714 | 715 | 716 | 717 | 718 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

TABLE 3-continued

Insecticidal Activity of Test Compounds Applied to the
Surface of the Diet of Tobacco Budworm

| | Cmpd. No | | | | | | | | |
|---|---|---|---|---|---|---|---|---|---|
| | 719 | 720 | 721 | 722 | 723 | 724 | 725 | 726 | 727 |
| Percent Mortality | 100 | 100 | 100 | 83 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 728 | 729 | 730 | 731 | 732 | 733 | 734 | 735 | 736 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 737 | 738 | 739 | 740 | 741 | 742 | 743 | 744 | 745 |
| Percent Mortality | 100 | 100 | 0 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 746 | 747 | 748 | 749 | 750 | 751 | 752 | 753 | 754 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 755 | 756 | 757 | 758 | 759 | 760 | 761 | 762 | 763 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 764 | 765 | 767 | 768 | 769 | 770 | 771 | 772 | 773 |
| Percent Mortality | 100 | 100 | 100 | 100 | 0 | 0 | 17 | 0 | 100 |
| Percent Growth Inhibition | 100 | 100 | 100 | 100 | 13 | 76 | 72 | 78 | 100 |

| | Cmpd. No | | | | | | | | |
|---|---|---|---|---|---|---|---|---|---|
| | 774 | 775 | 776 | 777 | 778 | 779 | 780 | 781 | 782 |
| Percent Mortality | 0 | 33 | 100 | 67 | 0 | 100 | 0 | 100 | 100 |
| Percent Growth Inhibition | 98 | 100 | 100 | 100 | 100 | 100 | 98 | 100 | 100 |

| | Cmpd. No | | | | | | | | |
|---|---|---|---|---|---|---|---|---|---|
| | 783 | 784 | 785 | 786 | 787 | 788 | 789 | 790 | 791 |
| Percent Mortality | 0 | 100 | 100 | 100 | 100 | 33 | 100 | 100 | 100 |
| Percent Growth Inhibition | 70 | 100 | 100 | 100 | 100 | 87 | 100 | 100 | 100 |

| | Cmpd. No | | | | | | | | |
|---|---|---|---|---|---|---|---|---|---|
| | 792 | 793 | 794 | 795 | 796 | 797 | 798 | 799 | 800 |
| Percent Mortality | 100 | 0 | 83 | 50 | 100 | 100 | 0 | 0 | 0 |
| Percent Growth Inhibition | 100 | 76 | 100 | 94 | 100 | 100 | 59 | 83 | 86 |

| | Cmpd. No | | | | | | | | |
|---|---|---|---|---|---|---|---|---|---|
| | 801 | 802 | 803 | 804 | 805 | 806 | 807 | 808 | 809 |
| Percent Mortality | 100 | 100 | 100 | 100 | 33 | 0 | 100 | 0 | 100 |
| Percent Growth Inhibition | 100 | 100 | 100 | 100 | 100 | 100 | 100 | 64 | 100 |

TABLE 3-continued

Insecticidal Activity of Test Compounds Applied to the
Surface of the Diet of Tobacco Budworm

| | Cmpd. No | | | | | | | | |
|---|---|---|---|---|---|---|---|---|---|
| | 810 | 811 | 812 | 813 | 814 | 815 | 816 | 817 | 818 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 819 | 820 | 821 | 822 | 823 | 824 | 825 | 826 | 827 |
| Percent Mortality | 50 | 50 | 100 | 100 | 67 | 100 | 83 | 100 | 100 |
| Percent Growth Inhibition | 100 | 92 | 100 | 100 | 100 | 100 | 100 | 100 | 100 |

| | Cmpd. No | | | | | | | | |
|---|---|---|---|---|---|---|---|---|---|
| | 828 | 829 | 830 | 831 | 832 | 833 | 834 | 835 | 836 |
| Percent Mortality | 100 | 100 | 100 | 100 | 83 | 100 | 100 | 0 | 100 |
| Percent Growth Inhibition | 100 | 100 | 100 | 100 | 100 | 100 | 100 | 80 | 100 |

| | Cmpd. No | | | | | | | | |
|---|---|---|---|---|---|---|---|---|---|
| | 837 | 838 | 839 | 840 | 841 | 842 | 843 | 844 | 845 |
| Percent Mortality | 100 | 100 | 100 | 100 | 100 | 100 | 100 | 100 | 83 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 846 | 847 | 848 | 849 | 850 | 851 | 852 | 853 | 854 |
| Percent Mortality | 100 | 100 | 83 | 100 | 100 | 50 | 100 | 100 | 100 |
| Percent Growth Inhibition | 100 | 100 | 100 | 100 | 100 | 100 | 100 | 100 | 100 |

| | Cmpd. No | | | | | | | |
|---|---|---|---|---|---|---|---|---|
| | 855 | 856 | 857 | 858 | 859 | 860 | 861 | 862 |
| Percent Mortality | 100 | 50 | 83 | 17 | 0 | 100 | 100 | 100 |
| Percent Growth Inhibition | 100 | 100 | 100 | 99 | 46 | 100 | 100 | 100 |

These tests were conducted with 0.25 millimoles of candidate insecticide on the surface of the diet.

As set forth in the foregoing Table 3, most of the compounds therein provided 100% mortality and 100% growth inhibition of tobacco budworm.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I

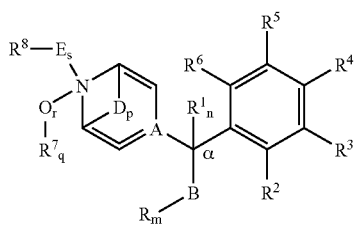

I wherein;

m=1, n=1, q=0, s=1, r=0 or 1, and p is 0;

A is selected from C and CH, forming a six-membered azine ring selected from piperidine, 1,4-dihydropyridine, and 1,2,5,6-tetrahydropyridine;

$R^2$, $R^3$, $R^4$, $R^5$, and $R^6$ are independently selected from hydrogen, halogen, alkyl, haloalkyl, hydroxyl, alkoxy, haloalkoxy, pentahalothio, alkylthio, cyano, nitro, alkylcarbonyl, alkoxycarbonyl, aryl, or aryloxy, provided that at least one of $R^2$, $R^3$, $R^4$, $R^5$, and $R^6$ are other than hydrogen; and either of $R^2$ and $R^3$, or $R^3$ and $R^4$ may be taken together with —OCF$_2$O—, —OCF$_2$CF$_2$—, —C$_2$F$_2$CO—, or —CH═CHCH═CH—, forming a benzo-fused ring;

where a single bond between methyl carbon α and the 4-position of the six-membered azine ring is formed;

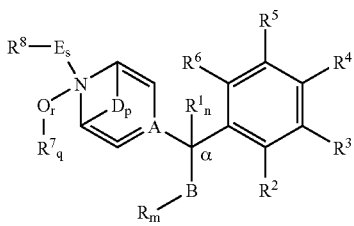

B is a bridging group from methyl carbon α to R;
where
B is selected from O, *OCH$_2$, *OC(=O)NR$^{15}$, where the asterisk denotes attachment to the methyl carbon α; where R$^{15}$ is H;
and,
R is phenyl substituted with R$^{17}$, R$^{18}$, R$^{19}$, R$^{20}$, and R$^{21}$; pyrid-2-yl substituted with R$^{18}$, R$^{19}$, R$^{20}$, and R$^{21}$; pyrid-3-yl substituted with R$^{17}$, R$^{19}$, R$^{20}$, and R$^{21}$; pyrid4-yl substituted with R$^{17}$, R$^{18}$, R$^{20}$, and R$^{21}$; or pyridazin-3-yl substituted with R$^{19}$, R$^{20}$ and R$^{21}$; where R$^{17}$, R$^{18}$, R$^{19}$, R$^{20}$, and R$^{21}$ are described above;
R$^1$ is
when q is 0, and r is 1, an N-oxide derivative of the six-membered azine ring nitrogen is formed;
R$^8$ is phenyl substituted with R$^{22}$, R$^{23}$, R$^{24}$, R$^{25}$, and R$^{26}$,

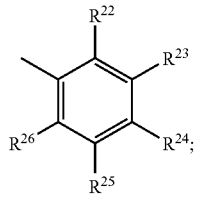

where
R$^{22}$, R$^{23}$, R$^{24}$, R$^{25}$, and R$^{26}$ are independently selected from hydrogen, halogen, alkyl, hydroxy, alkoxy, alkoxyalkyl, dialkoxyalkyl, trialkoxyalkyl, alkoxyiminoalkyl, alkenyloxyiminoalkyl, alkynyloxyiminoalkyl, cycloalkylalkoxy, alkoxyalkoxy, alkylthio, dithioalkoxyalkyl, trithioalkoxyalkyl, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted arylalkoxy, cyano, nitro, amino, alkylamino, alkylcarbonylamino, alkoxycarbonylamino, alkenyloxycarbonylamino, alkynyloxycarbonylamino, haloalkylcarbonylamino, alkoxyalkoxycarbonylamino, (alkyl)(alkoxycarbonyl)amino, alkylsulfonylamino, optionally substituted (heteroaryl)(alkoxycarbonyl)amino, optionally substituted arylcarbonylamino, formyl, optionally substituted 1,3-dioxolan-2-yl, optionally substituted 1,3-dioxan-2-yl, optionally substituted 1,3-oxazolidin-2-yl, optionally substituted 1,3-oxazaperhydroin-2-yl, optionally substituted 1,3-dithiolan-2-yl, optionally substituted 1,3-dithian-2-yl, alkoxycarbonyl, alkylaminocarbonyloxy, alkylaminocarbonylamino, dialkylaminocarbonylamino, alkylamino(thiocarbonyl)amino, dialkylphosphoroureidyl, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted heteroaryl, optionally substituted heteroaryloxy, optionally substituted pyrrolyl, optionally substituted pyrazolyl, optionally substituted pyrazinyloxy, optionally substituted 1,3-oxazolinyl, optionally substituted 1,3-oxazolinyloxy, optionally substituted 1,3-oxazolinylamino, optionally substituted 1,2,4-triazolyl, optionally substituted 1,2,3-thiadiazolyl, optionally substituted 1,2,5-thiadiazolyl, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahydropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, dialkoxyalkyl, dithioalkoxyalkyl, cyano, nitro, amino, or alkoxycarbonylamino, provided that at least one of R$^{22}$, R$^{23}$, R$^{24}$, R$^{25}$, and R$^{26}$ is other than hydrogen;
when s is 1;
E is a bridging group selected from (CR$^{27}$R$^{28}$)$_x$—(CR$^{29}$R$^{30}$)$_y$—,
where
x is 1; y is 0,
and,
where R$^{27}$, R$^{28}$, R$^{29}$, and R$^{30}$ are independently selected from hydrogen, alkyl, and aryl optionally substituted with alkoxy;
N-oxides;
and
agriculturally-acceptable salts thereof.

2. A compound of claim 1, wherein p and q are 0; r is 0 or 1; and s is 1; R$^2$, R$^3$, R$^4$, R$^5$, and R$^6$ are independently selected from hydrogen, halogen, alkyl, haloalkyl, hydroxyl, alkoxy, haloalkoxy, pentahalothio, alkylthio, nitro, aryl, and aryloxy; E is the bridging group —(CR$^{27}$R$^{28}$)$_x$—(CR$^{29}$R$^{30}$)$_y$—, where x is 1 and y is 0, R$^{27}$ and R$^{28}$ are hydrogen; and R$^8$ is phenyl substituted with R$^{22}$, R$^{23}$, R$^{25}$, and R$^{26}$, where R$^{22}$, R$^{23}$, R$^{25}$, and R$^{26}$ are independently selected from hydrogen, alkoxy, dialkoxyalkyl, dithioalkoxyalkyl, alkoxyiminoalkyl, alkenyloxyiminoalkyl, alkynyloxyiminoalkyl, alkoxycarbonylamino, optionally substituted arylcarbonylamino, alkoxycarbonyl, alkylaminocarbonyloxy, optionally substituted 1,3-dioxolane-2-yl, optionally substituted 1,3-dioxan-2-yl, optionally substituted 1,3-dithiolan-2-yl, optionally substituted 1,3-dithian-2-yl, optionally substituted aryl, optionally substituted aryloxy, optionally substituted 2H-tetrazole, optionally substituted pyridyl, optionally substituted pyridyloxy, optionally substituted pyrimidinyl, optionally substituted pyrimidinyloxy, and optionally substituted pyridazinyloxy.

3. A compound of claim 2, wherein A is CH, forming said piperidine ring;
m and n are 1, forming a single bond between methyl carbon α and the 4-position of said rings;
R$^1$ is hydrogen;
B is said bridging group selected from O and *OC(=O)NR$^{15}$, where R$^{15}$, is hydrogen;
and
R is phenyl substituted with R$^{17}$, R$^{18}$, R$^{19}$, R$^{20}$, and R$^{21}$ where R$^{17}$, R$^{18}$, R$^{19}$, R$^{20}$, and R$^{21}$ are independently selected from hydrogen, halogen, alkyl, haloalkyl, alkoxy, haloalkoxy, nitro, aryl, aryloxy, and 2-alkyl-2H-tetrazole.

4. A compound of claim 3, wherein R$^2$, R$^3$, R$^4$, R$^5$, and R$^6$ are independently selected from hydrogen, halogen, haloalkyl, and haloalkoxy; and R$^{22}$, R$^{23}$, R$^{24}$, R$^{25}$, and R$^{26}$ are independently selected from hydrogen, dialkoxyalkyl, dithioalkoxyalkyl, alkoxyiminoalkyl, alkylaminocarbonyloxy, optionally substituted 1,3-dioxolan-2-yl, optionally substituted aryloxy, optionally substituted 2H-tetrazole, optionally substituted pyridyloxy, and optionally substituted pyridyloxy.

5. A compound of claim 4, wherein B is the bridging group O or *OC(=O)NR$^{15}$; R$^{17}$, R$^{18}$, R$^{19}$, R$^{20}$, and R$^{21}$ are independently selected from hydrogen, halogen, haloalkyl, and haloalkoxy.

6. A compound of claim 5, wherein $R^2$, $R^3$, $R^5$, $R^6$, $R^7$, $R^{18}$, $R^{20}$, $R^{21}$, $R^{22}$, $R^{23}$, $R^{24}$, $R^{25}$, and $R^{26}$ are hydrogen; $R^4$ and $R^{19}$ are difluoromethyl, trifluoromethyl or trifluoromethoxy; and $R^{24}$ is pyrid-2-yloxy or pyrimidin-2-yloxy.

7. A composition containing an insecticidally effective amount of a compound of claim 1 in admixture with at least one agriculturally acceptable extender or adjuvant.

8. A composition containing an insecticidally effective amount of a compound of claim 2 in admixture with at least one agriculturally acceptable extender or adjuvant.

9. A composition containing an insecticidally effective amount of a compound of claim 3 in admixture with at least one agriculturally acceptable extender or adjuvant.

10. A composition containing an insecticidally effective amount of a compound of claim 4 in admixture with at least one agriculturally acceptable extender or adjuvant.

11. A composition containing an insecticidally effective amount of a compound of claim 5 in admixture with at least one agriculturally acceptable extender or adjuvant.

12. A composition containing an insecticidally effective amount of a compound of claim 6 in admixture with at least one agriculturally acceptable extender or adjuvant.

13. The insecticidal composition of claim 7, further comprising one or more second compounds.

14. The insecticidal composition of claim 8, further comprising one or more second compounds.

15. The insecticidal composition of claim 9, further comprising one or more second compounds.

16. The insecticidal composition of claim 10, further comprising one or more second compounds.

17. The insecticidal composition of claim 11, further comprising one or more second compounds.

18. The insecticidal composition of claim 12, further comprising one or more second compounds.

19. A method of controlling tobacco budworm, comprising applying an insecticidally effective amount of a composition of claim 7 to a locus where tobacco budworm are present or are expected to be present.

20. A method of controlling tobacco budworm, comprising applying an insecticidally effective amount of a composition of claim 8 to a locus where tobacco budworm are present or are expected to be present.

21. A method of controlling tobacco budworm, comprising applying an insecticidally effective amount of a composition of claim 9 to a locus where tobacco budworm are present or are expected to be present.

22. A method of controlling tobacco budworm, comprising applying an insecticidally effective amount of a composition of claim 10 to a locus where tobacco budworm are present or are expected to be present.

23. A method of controlling tobacco budworm, comprising applying an insecticidally effective amount of a composition of claim 11 to a locus where tobacco budworm are present or are expected to be present.

24. A method of controlling tobacco budworm, comprising applying an insecticidally effective amount of a composition of claim 12 to a locus where insects are present or are expected to be present.

25. A method of controlling tobacco budworm, comprising applying an insecticidally effective amount of a composition of claim 13 to a locus where tobacco budworm are present or are expected to be present.

26. A method of controlling tobacco budworm, comprising applying an insecticidally effective amount of a composition of claim 14 to a locus where tobacco budworm are present or are expected to be present.

27. A method of controlling tobacco budworm, comprising applying an insecticidally effective amount of a composition of claim 15 to a locus where tobacco budworm are present or are expected to be present.

28. A method of controlling tobacco budworm, comprising applying an insecticidally effective amount of a composition of claim 16 to a locus where tobacco budworm are present or are expected to be present.

29. A method of controlling tobacco budworm, comprising applying an insecticidally effective amount of a composition of claim 17 to a locus where tobacco budworm are present or are expected to be present.

30. A method of controlling tobacco budworm, comprising applying an insecticidally effective amount of a composition of claim 18 to a locus where tobacco budworm are present or are expected to be present.

* * * * *